(12) United States Patent
Wood et al.

(10) Patent No.: US 8,008,006 B2
(45) Date of Patent: Aug. 30, 2011

(54) SYNTHETIC NUCLEIC ACID MOLECULE COMPOSITIONS AND METHODS OF PREPARATION

(75) Inventors: Keith V. Wood, Mt. Horeb, WI (US);
Monika G. Wood, Mt. Horeb, WI (US);
Brian Almond, Fitchburg, WI (US);
Aileen Paguio, Madison, WI (US);
Frank Fan, Madison, WI (US)

(73) Assignee: Promega Corporation, Madison, WI (US)

( * ) Notice: Subject to any disclaimer, the term of this patent is extended or adjusted under 35 U.S.C. 154(b) by 396 days.

(21) Appl. No.: 11/825,304

(22) Filed: Jul. 5, 2007

(65) Prior Publication Data

US 2008/0070299 A1 Mar. 20, 2008

Related U.S. Application Data

(63) Continuation of application No. 10/943,508, filed on Sep. 17, 2004, now Pat. No. 7,728,118.

(51) Int. Cl.
*C12N 15/53* (2006.01)
*C12Q 1/68* (2006.01)

(52) U.S. Cl. ............ 435/6; 435/8; 435/325; 435/252.3; 435/320.1; 435/189; 536/23.2

(58) Field of Classification Search .................. None
See application file for complete search history.

(56) References Cited

U.S. PATENT DOCUMENTS

| | | |
|---|---|---|
| 4,246,340 A | 1/1981 | Lundin et al. |
| 4,412,001 A | 10/1983 | Baldwin et al. |
| 4,503,142 A | 3/1985 | Berman et al. |
| 4,581,335 A | 4/1986 | Baldwin et al. |
| 4,968,613 A | 11/1990 | Masuda et al. |
| 5,096,825 A | 3/1992 | Barr et al. |
| 5,106,732 A | 4/1992 | Kondo et al. |
| 5,168,062 A | 12/1992 | Stinski |
| 5,182,202 A | 1/1993 | Kajiyama et al. |
| 5,196,524 A | 3/1993 | Gustafson et al. |
| 5,219,737 A | 6/1993 | Kajiyama et al. |
| 5,221,623 A | 6/1993 | Legocki et al. |
| 5,229,285 A | 7/1993 | Kajiyama et al. |
| 5,283,179 A | 2/1994 | Wood |
| 5,292,658 A | 3/1994 | Cormier et al. |
| 5,330,906 A | 7/1994 | Kajiyama et al. |
| 5,352,598 A | 10/1994 | Kajiyama et al. |
| 5,418,155 A | 5/1995 | Cormier et al. |
| 5,567,862 A | 10/1996 | Adang et al. |
| 5,583,024 A | 12/1996 | McElroy et al. |
| 5,604,123 A | 2/1997 | Kazami et al. |
| 5,605,793 A | 2/1997 | Stemmer |
| 5,618,682 A | 4/1997 | Scheirer |
| 5,629,168 A | 5/1997 | Kricka |
| 5,641,641 A | 6/1997 | Wood |
| 5,650,289 A | 7/1997 | Wood |
| 5,670,356 A | 9/1997 | Sherf et al. |
| 5,674,713 A | 10/1997 | McElroy et al. |
| 5,700,673 A | 12/1997 | McElroy et al. |
| 5,744,307 A | 4/1998 | Kuroda et al. |
| 5,744,320 A | 4/1998 | Sherf et al. |
| 5,786,464 A | 7/1998 | Seed |
| 5,795,737 A | 8/1998 | Seed et al. |
| 5,814,471 A | 9/1998 | Wood |
| 5,874,304 A | 2/1999 | Zolotukhin et al. |
| 5,952,547 A | 9/1999 | Cornelissen et al. |
| 5,968,750 A | 10/1999 | Zolotukhin et al. |
| 5,976,796 A | 11/1999 | Szalay et al. |
| 6,020,192 A | 2/2000 | Muzyczka et al. |
| 6,074,859 A | 6/2000 | Hirokawa et al. |
| 6,114,148 A | 9/2000 | Seed et al. |
| 6,130,313 A | 10/2000 | Li et al. |
| 6,169,232 B1 | 1/2001 | Hey et al. |
| 6,306,600 B1 | 10/2001 | Kain et al. |
| 6,602,677 B1 | 8/2003 | Wood et al. |
| 6,700,038 B1 | 3/2004 | Dasgputa et al. |
| 6,878,531 B1 | 4/2005 | Seyfang |
| 2002/0100076 A1 | 7/2002 | Garcon et al. |
| 2003/0157643 A1 | 8/2003 | Almond et al. |
| 2004/0146987 A1* | 7/2004 | Zdanovsky et al. .......... 435/69.7 |
| 2005/0032085 A1 | 2/2005 | Labas et al. |
| 2006/0068395 A1 | 3/2006 | Wood et al. |
| 2006/0127988 A1 | 6/2006 | Wood et al. |
| 2006/0183212 A1 | 8/2006 | Wood et al. |
| 2008/0070299 A1 | 3/2008 | Wood et al. |
| 2008/0090291 A1 | 4/2008 | Wood et al. |
| 2009/0191622 A1 | 7/2009 | Almond et al. |

FOREIGN PATENT DOCUMENTS

| | | |
|---|---|---|
| EP | 0337349 | 10/1989 |
| EP | 0364707 A1 | 4/1990 |
| EP | 0437013 | 7/1991 |
| EP | 0449621 | 10/1991 |
| EP | 0524448 | 1/1993 |
| EP | 0353464 B1 | 10/1993 |
| JP | 3-167288 | 7/1991 |
| JP | 7-67696 | 3/1995 |
| JP | 8-510837 | 11/1996 |

(Continued)

OTHER PUBLICATIONS

"U.S. Appl. No. 09/645,706, Record of Oral Hearing held Aug. 13, 2008", 15 pgs.
"U.S. Appl. No. 09/645,706, Examiner's Answer mailed Dec. 12, 2007", 67 pgs.
"U.S. Appl. No. 09/645,706, Reply Brief filed Feb. 12, 2008", 17 pgs.
"U.S. Appl. No. 09/645,706, Decision on Appeal mailed Sep. 3, 2008", 26 pgs.
"U.S. Appl. No. 09/645,706, Request to Reopen Prosecution filed Nov. 3, 2008", 21 pgs.
"U.S. Appl. No. 09/645,706, Final Office Action mailed Feb. 3, 2009", 24 pgs.
"U.S. Appl. No. 10/314,827, Amendment filed Nov. 25, 2008 to Office Communication mailed Oct. 28, 2008", 6 pgs.
"U.S. Appl. No. 10/314,827, Communication mailed Aug. 5, 2008 including Transcript of Oral Hearing held Jun. 17, 2008", 23 pgs.
"U.S. Appl. No. 10/314,827, Decision on Appeal dated Jul. 22, 2008", 23 pgs.

(Continued)

*Primary Examiner* — Rebecca Prouty
(74) *Attorney, Agent, or Firm* — Michael Best & Friedrich LLP

(57) ABSTRACT

A method to prepare synthetic nucleic acid molecules having reduced inappropriate or unintended transcriptional characteristics when expressed in a particular host cell.

23 Claims, 2 Drawing Sheets

FOREIGN PATENT DOCUMENTS

| | | |
|---|---|---|
| JP | 9-294600 | 11/1997 |
| JP | 10-087621 | 4/1998 |
| JP | 2000-503536 | 3/2000 |
| JP | 2004-180561 | 2/2004 |
| WO | WO-9001542 A1 | 2/1990 |
| WO | WO-9116432 A1 | 10/1991 |
| WO | WO-9215673 A1 | 9/1992 |
| WO | WO-95/18853 | 7/1995 |
| WO | WO-95/25798 | 9/1995 |
| WO | WO-96/22376 | 7/1996 |
| WO | WO-9708320 A1 | 3/1997 |
| WO | WO-97/26366 | 7/1997 |
| WO | WO-9726333 | 7/1997 |
| WO | WO-9747358 A1 | 12/1997 |
| WO | WO 98/13487 | 4/1998 |
| WO | WO 98/46729 | 10/1998 |
| WO | WO-99/14336 | 3/1999 |
| WO | WO-0123541 A2 | 4/2001 |
| WO | WO-0127150 A2 | 4/2001 |
| WO | WO-0216944 A2 | 2/2002 |
| WO | WO-02/090535 A1 | 11/2002 |
| WO | WO 02/094992 | 11/2002 |
| WO | WO 03/042401 | 5/2003 |
| WO | WO-2004025264 A2 | 3/2004 |
| WO | WO-2004042010 A2 | 5/2004 |
| WO | WO-2006034061 A2 | 3/2006 |

OTHER PUBLICATIONS

"U.S. Appl. No. 10/314,827, Office Communication mailed Oct. 28, 2008", 15 pgs.

"U.S. Appl. No. 10/314,827, Request to Reopen Prosecution and Amendment filed Sep. 22, 2008", 21 pgs.

"U.S. Appl. No. 10/943,508, Non-Final Office Action mailed Aug. 6, 2007", 24 pgs.

"U.S. Appl. No. 10/943,508, Amendment and Response filed Nov. 2, 2007 to Office Action mailed Aug. 6, 2007", 18 pgs.

"U.S. Appl. No. 10/943,508, Non Final Office Action mailed Feb. 27, 2007", 15 pgs.

"U.S. Appl. No. 10/943,508, Notice of Allowance mailed Sep. 29, 2008", 9 pgs.

"U.S. Appl. No. 10/943,508, Preliminary Amendment filed Feb. 2, 2005", 4 pgs.

"U.S. Appl. No. 10/943,508, Response filed May 24, 2007 to Non Final Office Action mailed Feb. 27, 2007", 21 pgs.

"U.S. Appl. No. 10/943,508, Amendment and Response filed Apr. 17, 2008 to Final Office Action mailed Jan. 24, 2008", 17 pgs.

"U.S. Appl. No. 10/943,508, Office Communication mailed Jul. 10, 2008", 2 pgs.

"U.S. Appl. No. 10/943,508, Response filed Aug. 7, 2008 to Office Communication mailed Jul. 10, 2008", 10 pgs.

"U.S. Appl. No. 10/943,508, Final Office Action Mailed Jan. 24, 2008", 25 pgs.

"U.S. Appl. No. 11/316,042, Non-Final Office Action mailed Jun. 11, 2008", 11 pgs.

"U.S. Appl. No. 11/316,042, Preliminary Amendment filed Dec. 22, 2005", 8 pgs.

"U.S. Appl. No. 11/316,042, Restriction Requirement mailed Mar. 18, 2008", 5 pgs.

"U.S. Appl. No. 11/316,042, Response filed Dec. 11, 2008 to Non-Final Office Action mailed Jun. 11, 2008", 14 pgs.

"U.S. Appl. No. 11/316,042, Response filed Apr. 15, 2008 to Restriction Requirement mailed Mar. 18, 2008", 7 pgs.

"U.S. Appl. No. 11/786,785, Preliminary Amendment filed Apr. 12, 2007", 11 pgs.

"U.S. Appl. No. 12/323,270, Preliminary Amendment filed Dec. 2, 2008", 10 pgs.

"Australian Patent Application No. 2001285278, Examiner's First Report mailed Oct. 16, 2006", 2 pgs.

"Australian Patent Application No. 2001285278, Examiner's Second Report mailed Dec. 19, 2007", 2 pgs.

"Australian Patent Application No. 2001285278, Response filed Apr. 21, 2008 to Examiner's Report mailed Dec. 19, 2007", 34 pgs.

"Australian Patent Application No. 2001285278, Response filed Dec. 10, 2007 to Examiner's First Report mailed Oct. 16, 2006", 31 pgs.

"Australian Patent Application No. 2003297293, Examiner's Report No. 2 mailed Jun. 18, 2007", 2 pgs.

"Australian Patent Application No. 2003297293, Examiner's First Report mailed Oct. 5, 2006", 2 pgs.

"Australian Patent Application No. 2003297293, Response filed May 30, 2007 to Examiner's First Report mailed Oct. 5, 2006", 19 pgs.

"Australian Patent Application No. 2003297293, Response filed Aug. 29, 2007 to Examiner's Report No. 2 mailed Jun. 18, 2007", 27 pgs.

"BIOBASE", [online]. [retrieved Jul. 31, 2007]. Retrieved from the Internet: <URL: www.gene-regulation.com/pub/databases/html>,(2007), 1 pg.

"Canadian Application Serial No. 2,420,328, Office Action mailed Feb. 4, 2008", 3 pgs.

"Canadian Application Serial No. 2,420,328 Response filed Jul. 31, 2008 to Office Action mailed Feb. 4, 2008", 77 pgs.

"Canadian Application Serial No. 2,525,582, Examiner's Report mailed Jan. 2, 2008", 5 pgs.

"Canadian Application Serial No. 2,525,582, Response filed Jun. 20, 2008 to Examiner's Report mailed Jan. 2, 2008", 21 pgs.

"European Application Serial Application No. 01964425.1, Communication Noting Loss of Rights (R. 69(1) EPC mailed Feb. 10, 2006", 1 pg.

"European Application Serial No. 01964425.1, Communication Pursuant to Article 96(2) EPC mailed Nov. 23, 2006", 13 pgs.

"European Application Serial No. 01964425.1, Communication Pursuant to Article 96(2) EPC mailed Jun. 27, 2005", 12 pgs.

"European Application Serial No. 01964425.1, Office Action mailed Jun. 9, 2008", 9 pgs.

"European Application Serial No. 01964425.1, Response filed Oct. 20, 2008 to Office Action mailed Jun. 9, 2008", 25 pgs.

"European Application Serial No. 01964425.1, Response filed Apr. 6, 2006 to Communication mailed Jun. 27, 2005", 20 pgs.

"European Application Serial No. 03819255.5, Communication Pursuant to Article 96(2) EPC mailed May 18, 2007", 5 pgs.

"European Application Serial No. 03819255.5, Response filed Nov. 27, 2007 to Communication mailed May 18, 2007", 12 pgs.

"Japanese Application Serial No. 2005-513754, Decision on Rejection mailed May 13, 2008", 3 pgs.

"Japanese Application Serial No. 2005-513754, Reasons for Appeal filed on Sep. 5, 2008", (w/ English Translation),30 pgs.

"Japanese Application Serial No. 2005-513754, Argument and Amendment filed Feb. 29, 2008 to Office Action mailed Nov. 13, 2007", (w/ English Translation),33 pgs.

"Japanese Application Serial No. 2005-513754, Office Action mailed Nov. 13, 2007", (w/ English Translation),7 pgs.

"Japanese Patent Application No. 2002-521985, Amendment and Appeal Brief filed Jul. 12, 2007", (w/ English Translation),27 pgs.

"Japanese Patent Application No. 2002-521985, Notice of Reasons for Rejection mailed Jun. 7, 2006", (English Translation),6 pgs.

"Japanese Patent Application No. 2002-521985, Official Action on Formalities mailed Jul. 19, 2007", 3 pgs.

"Japanese Patent Application No. 2002-521985, Response filed Oct. 23, 2006 to Notice of Reasons for Rejection mailed Jun. 7, 2006", 54 pgs.

"Monstastrea cavernosa mcavFP_6 mRNa, complete cds", *Accession: AY037769* (gi: 19982568).. (2001), 2 pgs.

"Montastraea cavernosa clone 7.7 green fluorescent protein-like protein mRNA, Complete cds", *Accession: AY037768* (gi: 21303777), (2001), 2 pgs.

"Montastraea cavernosa green fluorescent proten mRNA, complete cds", *Accession: AF406766*(gi: 15425964), (2001), 2 pgs.

"Montastraea faveolata green fluorescent protein mRNA, complete cds", *Accession: AF401282*(gi: 15081471), (2001), 2 pgs.

"PCT Application No. PCT/US03/37117, International Preliminary Examination Report mailed Mar. 15, 2007", 10 pgs.

"PCT Application No. PCT/US03/37117, International Search Report mailed Oct. 31, 2005", 5 pgs.

"PCT Application No. PCT/US2005/033218, International Preliminary Report on Patentability mailed Mar. 29, 2007", 10 pgs.

"Prosecution File History for U.S. Appl. No. 10/314,827", 259 pgs.

"Prosecution File History for U.S. Appl. No. 09/645,706", (as of Nov. 5, 2007), 387 pgs.

"Prosecution File History for U.S. Patent No. 5,670,356", 105 pgs.

Franklin, S., et al., "Development of a GFP reporter gene for *Chlamydomonas reinhardtii* chloroplast", *The Plant Journal*, 30(6), (Jun. 2002), 733-744.

Kappel, C. A., et al., "Regulating Gene Expression in Transgenic Animals", *Current Opinion in Biotechnology*, 3, (1992), 548-553.

LeClerc, G. M., et al., "Development of a Destabilized Firefly Luciferase Enzyme for Measurement of Gene Expression", *590 Biotechniques*: vol. 29(3), (2000), 590-601.

Mullins, John J., et al., "Transgenesis in Nonmurine Species", *Hypertension*, 22, No. 4, (1993),630-633.

Mullins, Linda J., et al., "Transgenesis in the Rat and Larger Mammals", *Journal of Clinical Investigation*, 97(7), (Apr. 1996), 1557-1560.

Voss, S. D., et al., "The Role of Enhancers in the Regulation of Cell-Type-Specific Transcriptional Control", *Trends Biochem. Sci.*, 11, (1986), 287-289.

"U.S. Appl. No. 10/943,508, Notice of Allowance mailed Mar. 11, 2009", 8 pgs.

"U.S. Appl. No. 11/316,042, Final Office Action mailed Apr. 2, 2009", 8 pgs.

"European Application Serial No. 03819255.5, Office Action mailed on Mar. 17, 2009", 4 pgs.

"European Application Serial No. 05797929.6, Office Action mailed Apr. 2, 2009", 4 pgs.

*CloneTech Catalog*, (1996/97),96.

*CloneTech document* PT2038-5, (1996/97),1-2, pGFP-1 Vector Information.

"Aminoglycoside 3'-phosphotransferase mutant [synthetic construct]", *GenBank Accession No. AAD50549*, (Aug. 1999).

"Cloning vector PGFP-1 green fluorescent protein, complete cds", *GenBank Accession No. U19276.1*, (Jul. 1995).

"Cloning Vector pGL3—Control", *GenBank Accession No. U47296*, 4 pgs.

"Cloning Vector psiSTRIKE Puromycin, Complete Sequence", *GenBank Accession No. AY497507*, 3 pgs.

"Dual-Luciferase tm Reporter Assay System", (1998),2 pgs.

"International Search Report for corresponding PCT Application No. PCT/US2005/033218", (Mar. 31, 2006),9 pgs.

"Partial International Search Report for corresponding PCT Application No. PCT/US2005/033218",(Jan. 12, 2006),1 pg.

"Promega Technical Bulletin No. 161—Luciferase Assay System With Reporter Lysis Buffer", (Mar. 1998),9 pgs.

"Promega Technical Bulletin No. 101—Luciferase Assay System", (Mar. 1998),9 pgs.

"Promega Technical Manual—Dual-Luciferase tm Reporter Assay System", (Feb. 1999),26 pgs.

"Promega Technical Manual—Steady-Glo tm Luciferase Assay System", (Oct. 1998),19 pgs.

"Sequence 1 from Patent WO9529245", *GenBank Accession No. A47120*, 2 pgs.

"Synthetic construct aminoglycoside 3'-phosphotransferase mutant (mNeo) gene, complete cds", *GenBank Accession No. AF081957.1*, (Aug. 1999).

"TESS—Filtered String Search Page", http://www.cbil.upenn.edu/cgi-bin/tess/tess?RQ=SEA-FR-QueryF,(Jun. 2006),6 pgs.

Alam, J., et al., "Reporter Genes: Application to the Study of Mammalian Gene Transcription", *Analytical Biochemistry*, 188(2), (1990),245-254.

Andrews, E. M., et al., "Hierarchy of Polyadenylation Site Usage by Bovine Papillomavirus in Transformed Mouse Cells", *Journal of Virology*, 67(12), (1993),7705-7710.

Aota, S, "Codon Usage Tabulated from the GenBank Genetic Sequence Data", *Nucleic Acids Research*, 16, A Supplement to Nucleic Acids Research vol. 16,(1988),r315-r402.

Bachmair, A., "In vivo Half-Life of a Protein is a Function of its Amino Terminal Residue", *Science*, 234(4773), (1986),179-186.

Batt, David B., "Polyadenylation and Transcription Termination in Gene Constructs Containing Multiple Tandem Polyadenylation Signals", *Nucleic Acids Research*, 22(14), (Jul. 15, 1994),2811-2816.

Benzakour, O, "Evaluation of the Use of the Luciferase-Reporter-Gene System for Gene-Regulation Studies Involving Cyclic AMP-Elevating Agents.", *Biochem. J*, 309 (Pt 2), (Jul. 15, 1995),385-387.

Benardi, G., "Codon Usage and Genome Composition", *J. Mol. Evol.*, 22(4), (1985),363-365.

Bonin, A. L., "Photinus Pyralis Luciferase: Vectors that Contain a Modified luc Coding Sequence Allowing Convenient Transfer into Other Systems", *Gene*, 141(1), (1994),75-77.

Bouthors, A.-T., et al., "Site-Directed Mutagenesis of Residues 164, 170, 171, 179, 220, 237 and 242 in PER-1 beta-Lactamase Hydrolysing Expanded-Spectrum Cephalosporins", *Protein Engineering*, 12(4), (Apr. 1999),313-318.

Bronstein, Irena, et al., "Chemiluminescent and Bioluminescent Reporter Gene Assays", *Analytical Biochemistry*, 219(2), (1994),169-181.

Bulmer, M, "Codon usage and secondary structure of MS2 phage RNA", *Nucleic Acids Res.*, 17(5), (Mar. 11, 1989),1839-1843.

Bulmer, M, "Coevolution of codon usage and transfer RNA abundance", *Nature*, 325(6106), (1987),728-730.

Carswell, S., et al., "Efficiency of Utilization of the Simian Virus 40 Late Polyadenylation Site: Effects of Upsteam Sequences", *Molecular and Cellular Biology*, 9(10), (1989),4248-4258.

Chen, H., "Gene transfer and expression in oligodendrocytes under the control of myelin basic protein transcriptional control region mediated by adeno-associated virus", *Gene Therapy*, 5, (Jan. 14, 1998),50-58.

Cheng, X., et al., "Agrobacterium-transformed Rice Plants Expressing Synthetic crylA(b) and CrylA(c) Genes are Highly Toxic to Striped Stem Borer and Yellow Stem Borer", *Proceedings of the National Academy of Sciences of the USA*, 95(6), (Mar. 17, 1998),2767-2772.

Coker, G T., "8-Br-cAMP Inhibits the Transient Expression of Firefly Luciferase", *FEBS Letters*, 249, (1989),183-185.

De Wet, Jeffrey R., "Cloning of Firefly Luciferase cDNA and the Expression of Active Luciferase in *Escherichia coli*", *Proc. Natl. Acad. Sci. USA*, 82, (1985),7870-7873.

De Wet, J. R., "Firefly Luciferase Gene: Structure and Expression in Mammalian Cells", *Molecular and Cellular Biology*, 7(2), (1987),725-737.

Dean, Caroline, "mRNA Transcripts of Several Plant Genes are Polyadenylated at multiple sites in vivo", *Nucleic Acids Research*, vol. 14(5), (1986),2229-2240.

Dementieva, E. I., "Physicochemical Properties of Recombinant Luciolo mingrelica luciferase and its Mutant Forms", *Biochemistry*, 61 (1), (1996),115-119.

Faisst, S, "Compilation of Vertebrate-Encoded Transcription Factors", *Nucleic Acids Research*, 20(1), (Jan. 11, 1992),3-26.

Ferbitz, L., "A Synthetic Gene Coding for Renilla luciferase is a versatile expression marker in green algae", *GenBank Accession No. AAF93166*, (Aug. 8, 2000),1 pg.

Fiers, W, et al., "On Codon Usage (letter)", *Nature*, 277(5694), (1979),328.

Fleer, R., "High-Level Secretion of Correctly Processed Recombinant Human interleukin-1 beta in *Kluyveromyces lactis*", *Gene*, 107(2), (1991),285-295.

Frampton, J., et al., "Synergy Between the NF-E1 Erythroid-Specific Transcription Factor and the CACCC Factor in the Erythroid-Specific Promotor of the Human Porphobilinogen Deaminase Gene", *Molecular and Cellular Biology*, 10(7), (1990),3838-3842.

Fuerst, Thomas R., "Structure and stability of mRNA synthesized by vaccinia virus-encoded bacteriophage T7 RNA polymerase in mammalian cells Importance of teh 5' untranslated leader", *J. Mol. Biol.*, 206, (1989),333-348.

Gould, S. J., "A Conserved Tripeptide Sorts Proteins to Peroxisomes", *The Journal of Cell Biology*, 108, (1989),1657-1664.

Gould, S. J., "Antibodies Directed Against the Peroxisomal Targeting Signal of Firefly Luciferase Recognize Multiple Mammalian Peroxisomal Proteins", *The Journal of Cell Biology*, 110, (1990),27-34.

Gould, S. J., "Identification and Characterization of a Peroxisomal Targeting Signal", *Dissertation Abstracts International*, vol. 50/07-B, (1989),2 pgs.

Gouy, M, "Codon usage in bacteria: correlation with gene expressivity", *Nucleic Acids Res.*, 10(22), (1982),7055-7074.

Green, Pamela J., "Control of mRNA Stability in Higher Plants", *Plant Physiol.*, vol. 102, (1993),1065-1070.

Gruber, M G., "Design Strategy for Synthetic Luciferase Reporter Genes", *11th International Symposium on Bioluminescence and Chemiluminescence*, An abstract,(May 2000).

Henning, K. A., "Humanizing the yeast telomerase template", *Proceedings of the National Academy of Sciences of USA*, 95(10), (May 12, 1998),5667-5671.

Holm, L , "Codon usage and gene expression", *Nucleic Acids Res.*, 14(7), (1986),3075-3087.

Hsieh, C. J., et al., "Nucleotide Sequence, Transcriptional Analysis, and Glucose Regulation of the Phenoxazinone Synthase Gene (phsA) from *Streptomyces antibioticus*", *Journal of Bacteriology*, 177(20), (1995),5740-5747.

Iannacone, Rina , "Specific sequence modifications os a cry3B endotoxin gene result in high levels of expression and insect resistance", *Plant Melecular Biology 34*, (Jun. 1997),485-496.

Ikemura, T , "Codon usage and tRNA content in unicellular and multicellular organisms", *Molecular Biology and Evolution*, 2(1), (1985), 13-34.

Jensen, P. R., et al., "The Sequence of Spacers Between the Consensus Sequences Modulates the Strength of Prokaryotic Promoters", *Applied and Environmental Microbiology*, 64(1), (1998),82-87.

Johnson, L R., "Role of the transcription factor Sox-2 in the expression of the FGF-4 gene in embryonal carcinoma cells", *Molecular Reproduction and Development.*, 50(4), (1998),377-386.

Jones, P L., "Tumor Necrosis Factor Alpha and Iinterleukin-1beta Regulate the Murine Manganese Superoxide Dismutase Gene Through a Complex Intronic Enhancer Involving C/EBP-Beta and NF-KappaB", *Mol. Cell. Biol.*, 17(12), (1997),6970-6981.

Keller, G.-A. , "Firefly luciferase is targeted to peroxisomes in mammalian cells", *Proc. Natl. Acad. Sci. USA*, 84, (1987),3264-3268.

Kim, C. H., et al., "Codon Optimization for High-level Expression of Human Erythropoietin (EPO) in Mammalian Cells", *Gene*, vol. 199, No. 1-2, XP004126394, (Oct. 15, 1997),293-301.

Kimura, A , et al., "Detailed analysis of the mouse H-2Kb promoter: enhancer-like sequences and their role in the regulation of class I gene expression", *Cell*, 44(2), (Jan. 31, 1986),261-272.

Kuprash, D V., "Conserved kappa B Element Located Downstream of the Tumor Necrosis Factor alpha Gene: Distinct NF-kappa B Binding Pattern and Enhancer Activity in LPS Activated Murine Macrophages", *Oncogene*, 11(1), (1995),97-106.

Lamb, K A., "Effects of Differentiation on the Transcriptional Regulation of the FGF-4 Gene: Critical Roles Played by a Distal Enhancer", *Molecular Reproduction and Development*, 51(2), (1998),218-224.

Lewis, M. K., et al., "Efficient Site Directed in vitro Mutagenesis Using Ampicillin Selection", *Nucleic Acids Research*, 18(12), (1990), 3439-3443.

Liljenstrom, H , "Translation rate modification by preferential codon usage: intragenic position effects", *J. Theor. Biol.*, 124(1), (1987),43-55.

Liu, J., "Improved assay sensitivity of an engineered secreted *Renilla* luciferase", *Gene*, 237(1), (Sep. 3, 1999),153-159.

Magari, S. R., "Pharmacologic Control of a Humanized Gene Therapy System Implanted into Nude Mice", *Journal of Clinical Investigation*, 100(11), (Dec. 1, 1997),2865-2872.

Malter, James S., "Identification of an AUUUA-Specific Messenger RNA Binding Protein", *Science*, vol. 246, (1989),664-666.

Maranville, E. , et al., "Assessment of Amino-Acid Substutions at Tryptophan 16 in alpha-galactosidase", *European Journal of Biochemistry*, 267(5), (2000),1495-1501.

Matsumura, I. , et al., "Directed Evolution of the surface Chemistry of the Reporter Enzyme Beta-glucuronidase", *Nature Biotechnology*, 17(7), (1999),696-701.

McWherter, C. A., et al., "Scanning Alanine Mutagenesis and De-Peptidization of a Candate albicans myristoyl-CoA: Protein N-myristoyltransferase Octapeptide Substrate Reveals Three Elements Critical for Molecular Recognition", *Journal of Biological Chemistry*, 272(18), (1997),11874-11880.

Mount, S. M., "Genomic Sequence, Splicing, and Gene Annotation", *American Journal of Human Genetics*, 67(4), (2000),788-792.

Murray, E. E., "Codon Usage in Plant Genes", *Nucleic Acids Research*, 17(2), (Jan. 25, 1989),477-498.

Nibu, Y , "A Cell Type-Dependent Enhancer Core Element is Located in Exon 5 of the Human Angiotensinogen Gene", *Biochemical Biophysical Research Communications*, 205(2), (1994),1102-1108.

Pan, W. , et al., "Vaccine Candidate MSP-1 from *Plasmodium falciparum*: a Redesigned 4917 bp polynucleotide enables ynthesis and isolation of full-length Protein from *Escherichia coli* and Mammalian cells", *Nucleic Acids Research*, 27(4), DDBJ/EMBL/GenBank accession No. AJ131294,(Feb. 15, 1999), 1094-1103.

Peers, B , "Regulatory Elements Controlling Pituitary-Specific Expression of the Human Prolactin Gene", *Molecular and Cellular Biology*, 10(9), (Sep. 1990),4690-4700.

Perlak, Frederick J., "Modification of the coding sequence enhances plant expression of insect control protein genes", *Proc. Natl. Acad. Sci.*, 88, (1991),3324-3328.

Reese, M G., "Large Scale Sequencing Specific Neural Networks for Promoter and Splice Site Recognition", *Biocomputing: Proceedings of the 1996 Pacific Symposium, Lawrence Hunter et al., ed., World Publishing Co.*, Singapore, Abstract Only, (1996), 1 pg.

Reese, M G., et al., "New Neural Network Algorithms for Improved Eukaryotic Promoter Site Recognition", *The Seventh International Genome Sequencing and Analysis Conference*, Hilton Head Island, South Carolina, (Abstract Only),(1995),1 pg.

Riggs, J. , et al., "Common Factor 1 is a Transcriptional Activator Which Binds in the c-myc Promoter, the Skeletal alpha-Actin Provider, and the Immunoglobulin Heavy-Chain Enhancer", *Molecular and Cellular Biology*, 11(3), (1991),1765-1769.

Robinson, M , "Codon usage can affect efficiency of translation of genes in *Eshcerichia coli*", *Nucleic Acids Res.*, 12(17), (1984),6663-6671.

Saisanit, S , "A Novel Enhancer, the Pro-B Enhancer, Regulates Id1 Gene Expression in Progenitor B Cells", *Mol. Cell. Biol.*, 15(3), (1995),1513-1521.

Sala-Newby, G. , "Engineering a Bioluminescent Indicator for Cyclic AMP-Dependent Protein Kinase", *Biochemical. Journal*, 279(Part 3), (Nov. 1991),727-732.

Sala-Newby, G. , "Engineering firefly luciferase as an indicator cyclic AMP-dependent protein kinase in living cells", *FEBS Letters*, 307 (2), (Jul. 1992),pp. 241-244.

Sala-Newby, G. B., "Stepwise Removal of the C-Terminal 12 Amino Acids of Firefly Luciferase Results in Graded Loss of Activity", *Biochimica et Biophysica Acta (BBA)—Protein Structure and Molecular Enzymology*, 1206(1), (1994),155-160.

Schatt, M D., "A Single DNA-Binding Transcription Factor is Sufficient for Activation from a Distant Enhancer and/or from a Promoter Position", *The EMBO Journal*, 9(2), (Feb. 1990),481-487.

Senapathy, P. , et al., "Splice Junctions, Branch Point Sites, and Exons: Sequence Statistics, Identification, and Applications to Genome Project", *Methods in Enzymology*, 183, (1990),252.

Sharp, P M., "Codon usage patterns in *Escherichia coli, Bacillus subtilis, Saccharomyces cerevisiae, Schizosaccharomyces pombe, Drosophila melanogaster* and *Homo sapiens*; a review of the considerable within-species diversity", *Nucleic Acids Research*, 16(17), (Sep. 12, 1988),8207-8211.

Sharp, P M., "The Codon Adaptation Index—A Measure of Directional Synonymous Codon Usage Bias, and Its Potential Applications", *Nucleic Acids Research*, 15(3), (Feb. 11, 1987),1281-95.

Shaw, Gray , "A Conserved AU Sequenced from the 3' Untranslated Region of GM-CSF mRNA Mediates Selective mRNA Degradation", *Cell*, vol. 46, (1986),659-667.

Sherf, B. A., et al., "Dual-Luciferase tm Reporter Assay: An Advanced Co-Reporter Technology Integrating Firefly and *Renilla* luciferase Assays", *Promega Notes Magazine*, No. 57, (1996),7 pgs.

Sherf, B. A., "Firefly Luciferase Engineered for Improved Genetic Reporting", *Promega Notes Magazine* No. 49, (1994),8 pgs.

Shim, J. , et al., "Canonical 3'-deoxyribonucleotides as a chain terminator for HCV NS5B RNA-dependent RNA polymerase", *Antiviral Research*, 58, (May 2003),243-251.

Simpson, Craig G., "Efficient Splicing of an AU-Rich Antisense Intron Sequence", *Plant Molecular Biology*, vol. 21, (1993),205-211.

Sirot, D. , et al., "A Complex Mutant of TEM-1 Beta-Lactamase With Mutations Encountered in Both IRT-4 and Extended-Spectrum TEM-15, Produced by *Escherichia coli* Clnical Isolate", *Antimicrobial Agents and Chemotherapy*, 41(6), (Jun. 1997),1322-1325.

Sommer, Jurg M., "In vivo import of firefly luciferase into the glycosomes of *Trypanosoma brucei* and mutational analysis of the C-terminal targeting signal", *Mol. Biol. of the Cell*, 3, (1992),749-759.

Sorensen, M A., "Codon usage determines translatin rate in *Escherichia coli*", *J. Mol. Biol.*, 207(2), (1989),365-377.

Stapleton, P. D., et al., "Construction and Characterization of Mutants of the TEM-1 beta-Lactamase Containing Amino Acid Substitutions Associated With Both Extended=Spectrum Resistance and Resistance to beta-Lactamase Inhibitors", *Antimicrobial Agents and Chemotherapy*, 43(8), (Aug. 1999),1881-1887.

Strauss, E. C., et al., "In Vivo Protein-DNA Interactions of Hypersensitive Site 3 of the Human Beta-Globin Locus Control Region", *Proc. Natl. Acad. Sci. USA*, 89(13), (Jul. 1992),5809-5813.

Tanaka, M , "Synonymous codon usage and cost of genetic information", *Bull. Osaka Med. Coll.*, 34(1-2), (3-12),1988.

Ticher, A , "Nucleic acid compositions, codon usage, and the rate of synonymous substitution in protein-coding genes", *J. Mol. Evol.*, 28(4), (1989),286-298.

Turkel, S , "GCR-1-Dependent Transcriptional Activation of Yeast Retrotransposon Ty2-917", *Yeast*, 13(10), (1997),917-930.

Van Aarssen, Roel, et al., "cryIA(b) Transcript Formation in Tobacco is Inefficient", *Plant Molecular Biology*, vol. 28, (1995),513-524.

Viviani, V. R., "Bioluminescence Color Determinants of Phrixothrix Railroad-worm Luciferases: Chimeric Luciferases, Site-directed Mutagenesis of Arg 215 and Guanidine effect", *Photochemistry and Photobiology*, 72(2), (Aug. 2000),267-271.

Voladri, R. K., et al., "Structure-Function Relationships Among Wild-Type Variants of Staphylococcus aureu beta-Lactamase: Importance of Amino Acids 128 and 216", *Journal of Bacteriology*, 178(24), (Dec. 1996),7248-7253.

Wada, Ken-Nosuke , "Codon Usage Tabulated from GenBank Genetic Sequence Data", *Nucleic Acids Research*, 18 Suppl, (Apr. 25, 1990),2367-2411.

Wada, K.-N. , et al., "Codon Usage Tabulated From the GenBank Genetic Sequence Data", *Nucleic Acids Research*, 20(Suppl.), (1992),2111-2118.

Wain-Hobson, S , "Preferential codon usage in genes", *Gene*, 13(4), (1981),355-364.

Wells, K. D., et al., "Codon optimization, genetic insulation, and an rtTA reporter improve performance of the tetracycline swittch", *Transgenic Research*, 8, (1999),371-381.

Wilson, Tim, "Removal of poly(A) and Consequence Degradation of c-fos mRNA Facilitated by 3' AU-Rich Sequences", *Nature*, vol. 336, (1988),396-399.

Wood, Keith V., "Bioluminescent click beetles revisited", *Journal of Bioluminescence and Chemiluminescence*, 4(1), (Jul. 1989),31-39.

Wood, Keith V., "Complementary DNA Coding Click Beetle luciferases can elicit bioluminescence of different colors", *Science*, 244(4905), (May 12, 1989),700-702.

Wood, Keith V., "Introduction to beetle luciferases and their applications", *Journal of Bioluminescence and Chemiluminescence*, 4, (Jul. 1989),289-301.

Wood, K V., "Luc Genes: Introduction of Colour Into Bioluminescence Assays", *Journal of Bioluminescence and Chemiluminescence*, vol. 5, (Apr. 1990),107-114.

Wood, K. V., "Photographic Detection of Luminescence in *Escherichia coli* Containing the Gene for Firefly Luciferase", *Analytical Biochemistry*, 161(2), (Mar. 1987),501-507.

Wood, K. V., "The Chemical Mechanism and Evolutionary Development of Beetle Bioluminescence", *Photochemistry and Photobiology*, 62 (4), (1995),662-673.

Yanai, K , et al., "A cis-acting DNA element located between TATA box and transcription initiation site is critical in response to regulatory sequences in human angiotensinogen gene", *J. Biol. Chem.*, 271(27), (1996),15981-15986.

Yang, J K., "Human Dihydrofolate Reductase Gene Organization. Extensive Conservation of the G + C-rich 5' Non-Coding Sequence and Strong Intron Size Divergence From Homologous Mammalian Genes", *Journal of Molecular Biology*, 176(2), (Jun. 25, 1984),169-187.

Zhuang, Y. , et al., "Co-Reporter vector phRG-B, complete sequence", *Database EMBL*, (Accession No. EMBL:AF362550),(May 15, 2001),3 pgs.

"U.S. Appl. No. 09/645,706 Final Office Action Mailed Sep. 3, 2009", 15.

"U.S. Appl. No. 10/943,508 Notice of Allowance Mailed Aug. 31, 2009", 6 pgs.

"U.S. Appl. No. 09/645,706, Response filed Jul. 31, 2009 to Final Office Action mailed Feb. 3, 2009", 10 pgs.

"U.S. Appl. No. 10/314,827, Notice of Allowance mailed Jul. 13, 2009", 21 Pgs.

"U.S. Appl. No. 11/316,042 , Final Office Action mailed Sep. 4, 2009", 16.

"U.S. Appl. No. 11/316,042, Response filed Aug. 3, 2009 to Final Office Action mailed Apr. 2, 2009", 11 pgs.

"U.S. Appl. No. 11/786,785, Non Final Office Action mailed Aug. 4, 2009", 16 pgs.

"Sequence of pcdna3.1/Hygro," [Retrieved from the Internet http://www.invitrogen.com/content/sfs/vectors/pcdna3.1hygro_seq.txt] (2005) 2 pages).

Alberts, "Intron sequences are removed as lariat-shaped RNA molecules," Mol. Cell Biol. (1994) 3:373-374.

Arnold, F.H., "Directed evolution: creating biocatalysts for the future," Chem. Eng. Sci. (1996) 51:5091-5102.

Borovkov, A.Y. et al., "Xcm-I-containing vector for direct cloning of PCR products," BioTechniques (1997) 22(5):812-814.

Bothwell, A.L. et al., "Heavy chain variable region contribution to the NP b family of antibodies: somatic mutation evident in a y2a variable region," Cell (1981) 24(3):625-637.

Bowie, J.U. et al., "Deciphering the message in protein sequences: tolerance to amino acid substitutions," Science (1990) 247(4948):1306-1310.

Branchini, B.R., "Naphtyl- and quinolylluciferin: green and red light emitting firefly luciferin analogues," Photochem. Photobiol. (1989) 49(5):689-695.

Cadwell, R.C. et al., "Randomization of genes by PCR mutagenesis," PCR Methods and Apps. (1992) 2:28-33.

Cameron, "Recent advances in transgenic technology," Mol. Biol. (1997) 7:253-265.

Chen, C-Y., et al., "Interplay of two functionally and structurally distinct domains of the c-fos Au-rich element specifies its mRNA-destabilizing function," Mol. Cell. Biol. (1994) 14(1):416-426.

Corish, P. et al., "Attenuation of green fluorescent protein half-life in mammalian cells," Protein Engin. (1999) 12(12):1035-1040.

Deluca, M. et al., "Role of sulfhydryl groups in firefly luciferase," Biochem. (1964) 3(7):935-939.

Deluca, M. et al., "The hydrolase properties of firefly luciferase," Biochem. Biophys. Res. Comm. (1965) 18(5-6):836-842.

Deluca, M. et al., "The role of 1,N6-ethenoadenosine triphosphate and 1, N6-ethenoadenosine," Proc. Natl. Acad. Sci. (1973) 70(6):1664-1666.

Devine, J.H. et al., "Luciferase from the East European firefly *Luciola mingrelica*: cloning and nucleotide sequence of the cDNA, overexpression in *Escherichia coli* and purification of the enzyme," Biochim. et Biophys. Acta (1993) 1173:121-132.

Dorsky, R.I. et al., "A transgenic Lef1/beta-catenin-dependent reporter is expressed in spatially restricted domains throughout zebrafish development," Dev. Biol. (2002) 241:229-237.

Farr, A. et al., "A pitfall of using a second plasmid to determine transfection efficiency," Nuc. Acids Res. (1992) 20(4):920.

Ford, S.R. et al., "Enhancement of firefly luciferase activity by cytidine nucleotides," Anal. Biochem. (1992) 204(2):283-291.

Fromant, M. et al., "Direct random utagenesis of gene-sized DNA fragments using polymerase chain reaction," Anal. Biochem. (1995) 224:347-353.

Genbank Deposit Accession No. AF384683, "*Montastraea cavernosa* green fluorescent protein mRNA," Complete cds, Version AF384683.2 GI: 15298095, Aug. 2001, 1 page.

Genbank Deposit Accession No. AY037770, "*Montastraea cavernosa* meavFP_7.5 mRNA," Complete cds, Version AY037770.1 GI:19982596, Apr. 2002, 1 page.

Genbank Deposit Accession No. AY056460, "*Montastraea cavernosa* cyan fluorescent protein mRNA," Complete cds, Version AY056460.1 GI:16508124, Oct. 2001, 1 page.

Gilon, T. et al., "Degradation signals for ubiquitin system proteolysis in *Saccharomyces cerevisiae*," EMBO J. (1998) 17(10):2759-2766.

Glass, R.E. et al., "Gene function: *E.coli* and its heritable elements," University of California Press (1982) 95.

Gluzman, Y., "SV40-transformed cells support the replication of early SV40 mutants," Cell (1981) 23(1):175-182.

Gould, S.J. et al., "Firefly luciferase as a tool in molecular and cell biology," Anal. Biochem. (1988) 175:5-13.

Hanahan, D., "Techniques for Transformation of *E. coli*," in DNA Cloning: A Practical Approach, Chapter 6, D.W. Glover, editor, IRL Press, Oxford (1985) 1:109-135.

Hastings, J.W., "Biological diversity, chemical mechanisms, and the evolutionary origins of bioluminescent systems," J. Mol. Evolution (1983) 19(3/4):309-321.

Hofte, H. et al., "Structural and functional analysis of a cloned delta endotoxin of *Bacillus thuringiensis* berliner 1715," Eur. J. Biochem. (1986) 161:273-280.

Holcik, M. et al., "Four highly stable eukaryotic mRNAs assemble 3' untranslated region RNA-protein complexes sharing cis and trans components," Proc. Natl. Acad. Sci. USA (1997) 94(6):2410-2414.

Janowski, M., "Ras proteins and the Ras-related signal transduction pathway," Rad. Environ. Biophys. (1991) 30(3):185-189.

Kajiyama, N. et al., "Enhancement of thermostability of firefly luciferase from *Luciola lateralis* by a single amino acid substitution," Biosci. Biotechnol. Biochem. (1994) 58(6):1170-1171.

Kajiyama, N. et al., "Isolation and characterization of mutants of firefly luciferase which produce different colors of light," Protein Engineering (1991) 4(6):691-693.

Kajiyama, N. et al., "Thermostabilization of firefly luciferase by a single amino acid substitution at position 217," Biochem. (1993) 32(50):13795-13799.

Kao, R. et al., "Single amino acid substitutions affecting the specificity of the fungal ribotoxin mitogillin" FEBS Lett. (2001) 466(1):87-90.

Kay, S.A. et al., "Video imaging of regulating firefly luciferase activity in transgenic plants and *Drosophila*," Promega Notes Magazine (1994) No. 49, 7 pages.

Kitts, P.A., "Neomycin phosphotransferase," GenBank Accession No. AAA69543 (Jul. 1995) 2 pages.

Kozak, M., "An analysis of 5'-noncoding sequences from 699 vertebrate messenger RNAs," Nucl. Acids Res. (1987) 15(20):8125-8132.

Kutuzova, G.D. et al., "Bioluminescence color variation and kinetic behavior relationships among beetle luciferases," in Bioluminescence and Chemiluminescence, Molecular Reporting with Photons, J.W. Hastings et al., eds., John Wiley & Sons, Chinchester, England (1996) 248-252.

Lathe, R., "Synthetic oligonucleotide probes deduced from amino acid sequence data theoretical and practical considerations" J. Mol. Biol. (1985) 183(1):1-12.

Lee, R.T. et al., "Substrate-binding properties of firefly luciferase," Arch. Biochem. Biophys. (1970) 141(1):38-52.

Lisser, S. et al., "Compilation of *E.coli* MRNA promoter sequences," Nucl. Acids Res. (1993) 21(7):1507-1516.

Lodish et al., "Splicesomes, assembled from snRNPs and a pre-mRNA, carry out splicing," Chapter 11, RNA Processing, Nuclear Transport, and Post-Transcriptional Control, Mol. Cell Biol. (2000) 4:416-418.

Lorenz, W.W. et al., "Isolation and expression of a cDNA encoding *Renilla reniformis* luciferase," Proc. Natl. Acad. Sci. USA (1991) 88(10):4438-4442.

Lucas, M. et al., "Coelenterazine is a superoxide anion-sensitive chemiluminescent probe: its usefulness in the assay of respiratory burst in neutrophils," Anal. Biochem. (1992) 206(2):273-277.

Matthews, J. et al., "Purification and properties of *Renilla reinformis* luciferase," Biochem. (1977) 16(1):85-91.

Matz, "Amplification of representative cDNA samples from microscopic amounts of invertebrate tissue to search for new genes," Institute of Bioorganic Chemistry RAS (2002) 1-21.

Matz, M.V. et al., "Fluorescent proteins from nonbioluminescent anthozoa species," Nat. Biotech. (1999) 17(10):969-973.

Maukhov, I.V. et al., "Cloning of the *Vibrio harveyi* luxA and luxB genes and the expression of bioluminescnece in *Escherichia coli* and *Bacillus subtills*," Russ. Bioech. (1996) 1:1-6.

McElroy, W.D. et al., "Function of adenosine triphosphate in the activation of luciferin," Archives of Biochem. Biophys. (1956) 64:257-271.

McElroy, W.D. et al., "Mechanisms of bioluminescent reactions," in A Symposium on Light and Life, edited by W.D. McElroy and B. Glass, John Hopkins Press (1961) 219-257.

McElroy, W.D., "Factors influencing the response of the bioluminescent reaction to adenosine triphosphate," Archives of Biochem. Biophys (1949) 22:420-433.

Moyer, J.D. et al., "Nucleoside triphosphate specificity of firefly luciferase," Anal. Biochem. (1983) 131(1):187-189.

Murakami, S. et al., "Bioluminescent enzyme immunoassay using thermostable mutant luciferase and acetate kinase as a labelled enzyme," Analytica Chimica (1998) 361:19-26.

Murray, I.A., et al., "Steroid recognition by chloramphenicol acetyltransferase: engineering and structural analysis of a high affinity fusidic acid binding site," J. Mol. Biol. (1995) 254:993-1005.

Ow, D.W., "Transient and stable expression of the firefly luciferase gene in plant cells and transgenic plants," Science (1986) 234(4778):856-859.

Petit, T. et al., "A mutation Ser 213/Asn in the hexokinase 1 from *Schizosaccharomyces pombe* increases its affinity for cluesses," Biochem. Biophys. Res. Comm. (1998) 251(3):714-719.

Pinto, M. et al., "Denaturation of proteins during heat shock," J. Biol. Chem. (1991) 266(21):13941-13946.

Promega Corporation "Luciferase Reporter Gene Technology" brochure (1996) 4 pages.

Promega Corporation, "Steady-Glo™ Luciferase Assay System" brochure (1998) 2 pages.

Purdy, D. et al., "Heterologous gene expression in *Campylobacter coli*: the use of bacterial luciferase in a promoter probe vector," FEMS Microbiol. Lett. (1993) 111(2-3):233-237.

Quandt, K. et al., "MatInd and MatInspector: new fast and versatile tools for detection of consensus matches in nucleotide sequence data," Nucl. Acids Res. (1995) 23(23):4878-4884.

Rhodes, W.C. et al., "The synthesis and function of luciferyl-adenylate and oxyluciferyl-adenylate," J. Biol. Chem. (1958) 233(6):1528-1537.

Ringquist, S. et al., "Translation initiation in *Escherichia coli*: sequences within the ribosome-binding site," Mol. Microbiol. (1992) 1219-1229.

Rommens, J.M. et al., "cAMP-inducible chloride conductance in mouse fibroblast lines stably expressing the human cystic fibrosis transmembrance conductance regulator," Proc. Natl. Acad. Sci. (1991) 88:7500-7504.

Rosendahl, M.S. et al., "Dimensional probing of the ATP binding site on firefly luciferase," Photochem. Photobiol. (1982) 35(6):857-861.

Saiki, R.K. et al., "Primer-directed enzymatic amplification of DNA with a thermostable DNA polymerase," Science (1988) 239(4839):487-491.

Sala-Newby, G.B. et al., "Expression of recombinant firefly luciferase in prokaryotic and eukaryotic cells," Biochem. Soc. Trans. (1992) 20:143S.

Schmidt, E.V. et al., "The cytomegalovirus enhancer: a pan-active control element in transgenic mice," Mol. Cell Biol. (1990) 10(8):4406-4411.

Schutte, B.C. et al., "Optimized conditions for cloning PCR products into an Xclm T-vector," BioTechniques (1997) 22(1):40-43.

Seliger, H.H. et al., "The colors of firefly bioluminescence: enzyme configuration and species specificity," Proc. Natl. Acad. Sci. (1964) 52(1):75-81.

Seol, J.H. et al., "Site-directed mutagenesis of the Cys residues in ClpA, the ATPase component of protease Ti (SlpAP) in *Escherichia coli*," Biol. Chem. (1997) 378(10):1205-1209.

Stemmer, W.P.C., "DNA shuffling by random fragmentation and reassembly: in vitro recombination for molecular evolution," Proc. Natl. Acad. Sci. USA (1994) 91(22):10747-10751.

Stewart, C.L. et al., "Expression of retroviral vectors in transgenic mice obtain by embryo infection," EMBO J. (1987) 6(2):383-388.

Szittner, R. et al., "Nucleotide sequence, expression, and properties of luciferase coded by lux genes from a terrestrial bacterium," J. Biol. Chem. (1990) 265(27):16581-16587.

Tabaska, J.E. et al., "Detection of polyadenylation signals in human DNA sequences," Gene (1999) 77-86.

Tarpey, M.M. et al., "Chemiluminescent detection of oxidants in vascular tissue. Lucigenin but not coelenterazine enhances superoxide formation," Circ. Res. (1999) 84(1):1203-1211.

Teranishi, K. et al., "Coelenterazine analogs as chemiluminescent probe for superoxide anion," Anal. Biochem. (1997) 249(1):37-43.

Wagner, E.F. et al., "Transfer of genes into embryonal carcinoma cells by retrovirus infection: efficient expression from an internal promoter," EMBO J. (1985) 4(3):663-666.

Walker, D.E. et al., "An aspartic acid at amino acid 108 is required to rescue infectious virus after transfection of a poliovirus cDNA containing a CGDD but not SGDD amino acid motif in 3D pol," J. Virol. (1995) 69(12):8173-8177.

White, P.J. et al., "Generation and characterisation of a thermostable mutant of luciferase from photinus pyralis, in Bioluminescence and Chemiluminescence, Fundamentals and Applied Aspects," Proceedings of the 8th International Symposium on Bioluminescence and Chemiluminescence, John Wiley & Sons, Cambridge (Sep. 1994) 419-422.

White, P.J., et al., "Improved thermostability of the North American firefly luciferase: saturation mutagenesis at position 354," Biochem. J. (1996) 319(Pt. 2):343-350.

Wigley, P. et al., "Site-specific transgene insertion: an approach," Reprod. Fertil. Dev. (1994) 585-588.

Wood, K.V. et al., "Synthesis of active firefly luciferase by in vitro translation of RNA obtained from adult lanters," Biochem. Biophys. Res. Commun. (1984) 124(2):592-596.

Wood, K.V., "Luciferases of luminous beetles: evolution, color variation, and applications," Dissertation (1989), submitted as two parts, Part 1 and Part 2.

Yang, F. et al., "The molecular structure of green fluorescent protein," Nature Biotech. (1996) 14(10):1246-1251.

Ye, L. et al., "Cloning and sequencing of a cDNA for firefly luciferase from *Photuris pennsylvanica*," Biochimica et Biophysica Acta (1997) 1339(1):39-52.

Yotov, W.V. et al., GenBank Accession No. AAD50549 (Aug. 1999) 2 pages.

Zhang, J-H. et al., "Directed evolution of a fucosidase from a galactosidase by DNA shuffling and screening," Proc. Natl. Acad. Sci. USA (1997) 94(9):4504-4509.

Zhao, H. et al., "Functional and nonfunctional mutations distinguished by random recombination of homologous genes," Proc. Natl. Acad. Sci. USA (1997) 94(15):7997-8000.

Canadian Patent Office Action for Application No. 2,420,328 dated Dec. 7, 2009 (3 pages).

Canadian Patent Office Action for Application No. 2,525,582 dated Dec. 30, 2009 (3 pages).

Chinese Patent Office Action for Application No. 200580039282.5 dated Aug. 7, 2009 (10 pages) with English translation.

European Patent Office Summons to Attend Oral Proceedings for Application No. 01964425.1 dated Feb. 8, 2008 (11 pages).

European Patent Office Action for Application No. 05797929.6 dated Mar. 8, 2010 (4 pages).

Written Opinion for Application No. PCT/US2005/033218 dated Mar. 31, 2006 (8 pages).

Japanese Patent Office Action for Application No. 2002-521985 mailed Mar. 16, 2007 (11 pages) with English translation.

Japanese Patent Office Action for Application No. 2002-521985 mailed Jan. 5, 2009(8 pages).

Japanese Patent Office Action and Dentcritical of Entry of Amendment for Application No. 2002-521985 mailed Aug. 3, 2010 (65 pages) with English translation.

Japanese Patent Office Action for Application No. 2006-288147 mailed Dec. 3, 2008 (7 pages) with English translation.

United States Patent Office Action for U.S. Appl. No. 09/645,706 dated Feb. 14, 2003 (16 pages).

United States Patent Office Action for U.S. Appl. No. 09/645,706 dated Jan. 6, 2004 (12 pages).

United States Patent Office Action for U.S. Appl. No. 09/645,706 dated Apr. 29, 2004 (6 pages).

United States Patent Office Action for U.S. Appl. No. 09/645,706 dated Sep. 13, 2004 (19 pages).

United States Patent Office Action for U.S. Appl. No. 09/645,706 dated Mar. 22, 2005 (15 pages).

United States Patent Office Action for U.S. Appl. No. 09/645,706 dated Dec. 19, 2005 (29 pages).

United States Patent Office Action for U.S. Appl. No. 09/645,706 dated Sep. 13, 2006 (21 pages).

United States Patent Office Advisory Action for U.S. Appl. No. 09/645,706 dated Mar. 1, 2007 (16 pages).

United States Patent Office Notice of Allowance for U.S. Appl. No. 09/645,706 dated Jun. 4, 2010 (4 pages).

United States Patent Office Action for U.S. Appl. No. 11/786,785 dated May 12, 2010 (12 pages).

United States Patent Office Notice of Allowance/Office Action for U.S. Appl. No. 10/943,508 dated Sep. 29, 2008 (7 pages).

United States Patent Office Notice of Allowance for U.S. Appl. No. 10/943,508 dated Dec. 23, 2009 (4 pages).

United States Patent Office Action for U.S. Appl. No. 10/314,827 dated Jul. 2, 2007 (45 pages).

United States Patent Office Action for U.S. Appl. No. 10/314,827 dated Oct. 16, 2006 (8 pages).

United States Patent Office Action for U.S. Appl. No. 10/314,827 dated May 8, 2006 (23 pages).

United States Patent Office Action for U.S. Appl. No. 10/314,827 dated Sep. 12, 2005 (23 pages).

Japanese Patent Office Action for Application No. 2007-532513 dated Feb. 28, 2011 (11 pages) with English translation.

* cited by examiner

Figure 1

| Amino Acid | Codon |
|---|---|
| Phe | UUU, UUC |
| Ser | UCU, UCC, UCA, UCG, AGU, AGC |
| Tyr | UAU, UAC |
| Cys | UGU, UGC |
| Leu | UUA, UUG, CUU, CUC, CUA, CUG |
| Trp | UGG |
| Pro | CCU, CCC, CCA, CCG |
| His | CAU, CAC |
| Arg | CGU, CGC, CGA, CGG, AGA, AGG |
| Gln | CAA, CAG |
| Ile | AUU, AUC, AUA |
| Thr | ACU, ACC, ACA, ACG |
| Asn | AAU, AAC |
| Lys | AAA, AAG |
| Met | AUG |
| Val | GUU, GUC, GUA, GUG |
| Ala | GCU, GCC, GCA, GCG |
| Asp | GAU, GAC |
| Gly | GGU, GGC, GGA, GGG |
| Glu | GAA, GAG |

SEQUENCE LISTING

<160> NUMBER OF SEQ ID NOS: 97

<210> SEQ ID NO 1
<211> LENGTH: 795
<212> TYPE: DNA
<213> ORGANISM: Unknown
<220> FEATURE:
<223> OTHER INFORMATION: Neo from neomycin gene from Promega's pCI-neo.

<400> SEQUENCE: 1

```
atgattgaac aagatggatt gcacgcaggt tctccggccg cttgggtgga gaggctattc      60
ggctatgact gggcacaaca gacaatcggc tgctctgatg ccgccgtgtt ccggctgtca     120
gcgcaggggc gcccggttct ttttgtcaag accgacctgt ccggtgccct gaatgaactg     180
caggacgagg cagcgcggct atcgtggctg gccacgacgg gcgttccttg cgcagctgtg     240
```

```
ctcgacgttg tcactgaagc gggaagggac tggctgctat tgggcgaagt gccggggcag    300
gatctcctgt catctcacct tgctcctgcc gagaaagtat ccatcatggc tgatgcaatg    360
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgcg catgcccgac    540
ggcgaggatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctacccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                     795
```

```
<210> SEQ ID NO 2
<211> LENGTH: 264
<212> TYPE: PRT
<213> ORGANISM: Unknown
<220> FEATURE:
<223> OTHER INFORMATION: Neo from neomycin gene from Promega's pCI-neo.

<400> SEQUENCE: 2
```

```
Met Ile Glu Gln Asp Gly Leu His Ala Gly Ser Pro Ala Ala Trp Val
 1               5                  10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260
```

<210> SEQ ID NO 3
<211> LENGTH: 825
<212> TYPE: DNA
<213> ORGANISM: Artificial Sequence
<220> FEATURE:
<223> OTHER INFORMATION: A synthetic construct.

<400> SEQUENCE: 3

```
ccactcagtg gccaccatga tcgagcagga cggcctgcac gccggcagcc ccgccgcctg      60
ggtggagcgc ctgttcggct acgactgggc ccagcagacc atcggctgca gcgacgccgc     120
cgtgttccgc ctgagcgccc agggccgccc cgtgctgttc gtgaagaccg acctgagcgg     180
cgccctgaac gagctgcagg acgaggccgc ccgcctgagc tggctggcca ccaccggcgt     240
gccctgcgcc gccgtgctgg acgtggtgac cgaggccggc cgcgactggc tgctgctggg     300
cgaggtgccc ggccaggacc tgctgagcag ccacctggcc ccgccgaga aggtgagcat      360
catggccgac gccatgcgcc gcctgcacac cctggacccc gccacctgcc ccttcgacca     420
ccaggccaag caccgcatcg agcgcgcccg cacccgcatg gaggccggcc tggtggacca     480
ggacgacctg gacgaggagc accagggcct ggccccgcc gagctgttcg cccgcctgaa      540
ggcccgcatg cccgacggcg aggacctggt ggtgacccac ggcgacgcct gcctgcccaa     600
catcatggtg gagaacggcc gcttcagcgg cttcatcgac tgcggccgcc tgggcgtggc     660
cgaccgctac caggacatcg ccctggccac ccgcgacatc gccgaggagc tgggcggcga     720
gtgggccgac cgcttcctgg tgctgtacgg catcgccgcc ccgacagcc agcgcatcgc      780
cttctaccgc ctgctggacg agttcttcta ataaccagtc tctgg                    825
```

<210> SEQ ID NO 4
<211> LENGTH: 825
<212> TYPE: DNA
<213> ORGANISM: Artificial Sequence
<220> FEATURE:
<223> OTHER INFORMATION: A synthetic construct.

<400> SEQUENCE: 4

```
ccactcagtg gccaccatga tcgagcagga cggcctgcac gccggcagcc ccgccgcctg      60
ggtggagcgc ctgttcggct acgactgggc ccagcagacc atcggctgca gcgacgccgc     120
cgtgttccgc ctgagcgccc agggccgccc cgtgctgttc gtgaagaccg acctgagcgg     180
cgccctgaac gagctgcagg acgaggccgc ccgcctgagc tggctggcca ccaccggcgt     240
gccctgcgcc gccgtgctgg acgtggtgac cgaggccggc cgcgactggc tgctgctggg     300
cgaggtgccc ggccaggacc tgctgagcag ccacctggcc ccgccgaga aggtgagcat      360
catggccgac gccatgcgcc gcctgcacac cctggacccc gccacctgcc ccttcgacca     420
ccaggccaag caccgcatcg agcgcgcccg cacccgcatg gaggccggcc tggtggacca     480
ggacgacctg gacgaggagc accagggcct ggccccgcc gagctgttcg cccgcctgaa      540
ggcccgcatg cccgacggcg aggacctggt ggtgacccac ggcgacgcct gcctgcccaa     600
catcatggtg gagaacggcc gcttcagcgg cttcatcgac tgcggccgcc tgggcgtggc     660
cgaccgctac caggacatcg ccctggccac ccgcgacatc gccgaggagc tgggcggcga     720
gtgggccgac cgcttcctgg tgctgtacgg catcgccgcc ccgacagcc agcgcatcgc      780
cttctaccgc ctgctggacg agttcttcta ataaccagtc tctgg                    825
```

<210> SEQ ID NO 5
<211> LENGTH: 818

```
<212> TYPE: DNA
<213> ORGANISM: Artificial Sequence
<220> FEATURE:
<223> OTHER INFORMATION: A synthetic construct.

<400> SEQUENCE: 5
cctgcaggcc accatgatcg aacaagacgg cctccatgct ggcagtcccg cagcttgggt      60
cgaacgcttg ttcgggtacg actgggccca gcagaccatc ggatgtagcg atgcggccgt     120
gttccgtcta agcgctcaag gccggcccgt gctgttcgtg aagaccgacc tgagcggcgc     180
cctgaacgag cttcaagacg aggctgcccg cctgagctgg ctggccacca ccggtgtacc     240
ctgcgccgct gtgttggatg ttgtgaccga agccggccgg gactggctgc tgctgggcga     300
ggtccctggc caggatctgc tgagcagcca ccttgccccc gctgagaagg tttccatcat     360
ggccgatgca atgcggcgcc tgcacaccct ggaccccgct acatgcccct cgaccacca     420
ggctaagcat cggatcgagc gtgctcggac ccgcatggag gccggcctgg tggaccagga     480
cgacctggac gaggagcatc agggcctggc ccccgctgaa ctgttcgccc gcctgaaagc     540
ccgcatgccg gacggtgagg acctggttgt gacacatggt gatgcctgcc tccctaacat     600
catggtcgag aatggccgct tctccggctt catcgactgc ggtcgcctag gagttgccga     660
ccgctaccag gacatcgccc tggccacccg cgacatcgct gaggagcttg gcggcgagtg     720
ggccgaccgc ttcttagtct tgtacggcat cgcagctccc gacagccagc gcatcgcctt     780
ctaccgcctg ctcgacgagt cttttaatg agcttaag                              818

<210> SEQ ID NO 6
<211> LENGTH: 1024
<212> TYPE: DNA
<213> ORGANISM: Escherichia coli

<400> SEQUENCE: 6
atgaaaaagc ctgaactcac cgcgacgtct gtcgagaagt ttctgatcga aaagttcgac      60
agcgtctccg acctgatgca gctctcggag ggcgaagaat ctcgtgcttt cagcttcgat     120
gtaggagggc gtggatatgt cctgcgggta aatagctgcg ccgatggttt ctacaaagat     180
cgttatgttt atcggcactt tgcatcggcc gcgctcccga ttccggaagt gcttgacatt     240
ggggaattca gcgagagcct gacctattgc atctcccgcc gtgcacaggg tgtcacgttg     300
caagacctgc ctgaaaccga actgcccgct gttctgcagc cggtcgcgga ggccatggat     360
gcgatcgctg cggccgatct tagccagacg agcgggttcg cccattcgg accgcaagga     420
atcggtcaat acactacatg gcgtgatttc atatgcgcga ttgctgatcc ccatgtgtat     480
cactggcaaa ctgtgatgga cgacaccgtc agtgcgtccg tcgcgcaggc tctcgatgag     540
ctgatgcttt gggccgagga ctgccccgaa gtccggcacc tcgtgcacgc ggatttcggc     600
tccaacaatg tcctgacgga caatggccgc ataacagcgg tcattgactg gagcgaggcg     660
atgttcgggg attcccaata cgaggtcgcc aacatcttct tctggaggcc gtggttggct     720
tgtatggagc agcagacgcg ctacttcgag cggaggcatc cggagcttgc aggatcgccg     780
cggctccggg cgtatatgct ccgcattggt cttgaccaac tctatcagag cttggttgac     840
ggcaatttcg atgatgcagc ttgggcgcag ggtcgatgcg acgcaatcgt ccgatccgga     900
gccgggactg tcgggcgtac acaaatcgcc cgcagaagcg cggccgtctg gaccgatggc     960
tgtgtagaag tactcgccga tagtggaaac cgacgcccca gcactcgtcc gagggcaaag    1020
gaat                                                                 1024
```

<210> SEQ ID NO 7
<211> LENGTH: 341
<212> TYPE: PRT
<213> ORGANISM: Escherichia coli

<400> SEQUENCE: 7

Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
    290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Arg Ala Lys Glu
            340

<210> SEQ ID NO 8
<211> LENGTH: 1056
<212> TYPE: DNA
<213> ORGANISM: Artificial Sequence
<220> FEATURE:
<223> OTHER INFORMATION: A synthetic construct.

```
<400> SEQUENCE: 8
ccactcagtg gccaccatga agaagcccga gctgaccgcc accagcgtgg agaagttcct      60
gatcgagaag ttcgacagcg tgagcgacct gatgcagctg agcgagggcg aggagagccg     120
cgccttcagc ttcgacgtgg gcggccgcgg ctacgtgctg cgcgtgaaca gctgcgccga     180
cggcttctac aaggaccgct acgtgtaccg ccacttcgcc agcgccgccc tgcccatccc     240
cgaggtgctg gacatcggcg agttcagcga gagcctgacc tactgcatca gccgccgcgc     300
ccagggcgtg accctgcagg acctgcccga gaccgagctg cccgccgtgc tgcagcccgt     360
ggccgaggcc atggacgcca tcgccgccgc cgacctgagc cagaccagcg gcttcggccc     420
cttcggcccc cagggcatcg ccagtacac  cacctggcgc gacttcatct gcgccatcgc     480 cgaccccac gtgtaccact ggcagaccgt gatggacgac accgtgagcg ccagcgtggc     540
ccaggccctg gacgagctga tgctgtgggc cgaggactgc cccgaggtgc gccacctggt     600
gcacgccgac ttcggcagca caacgtgct gaccgacaac ggccgcatca ccgccgtgat      660
cgactggagc gaggccatgt tcggcgacag ccagtacgag gtggccaaca tcttcttctg     720
gcgcccctgg ctggcctgca tggagcagca gacccgctac ttcgagcgcc gccaccccga     780
gctggccggc agccccgcc tgcgcgccta catgctgcgc atcggcctgg accagctgta      840
ccagagcctg gtggacggca acttcgacga cgccgcctgg gcccagggcc gctgcgacgc     900
catcgtgcgc agcggcgccg gcaccgtggg ccgcacccag atcgcccgcc gcagcgccgc     960
cgtgtggacc gacggctgcg tggaggtgct ggccgacagc ggcaaccgcc gccccagcac    1020 ccgccccgc gccaaggagt aataaccagc tcttgg                                1056

<210> SEQ ID NO 9
<211> LENGTH: 1056
<212> TYPE: DNA
<213> ORGANISM: Artificial Sequence
<220> FEATURE:
<223> OTHER INFORMATION: A synthetic construct.

<400> SEQUENCE: 9
ccactccgtg gccaccatga agaagcccga gctgaccgct accagcgttg aaaaatttct      60
catcgagaag ttcgacagtg tgagcgacct gatgcagttg tcggagggcg aagagagccg     120
agccttcagc ttcgatgtcg gcggacgcgg ctatgtactg cgggtgaata gctgcgctga     180
tggcttctac aaagaccgct acgtgtaccg ccacttcgcc agcgctgcac tacccatccc     240
cgaagtgttg gacatcggcg agttcagcga gagcctgaca tactgcatca gtagacgcgc     300
ccaaggcgtt actctccaag acctccccga aacagagctg cctgctgtgt tacagcctgt     360
cgccgaagct atggatgcta ttgccgccgc cgacctcagt caaaccagcg gcttcggccc     420
attcggcccc caaggcatcg ccagtacac  aacctggcgg gatttcattt gcgccattgc     480
tgatccccat gtctaccact ggcagaccgt gatggacgac accgtgtccg ccagcgtagc     540
tcaagccctg gacgaactga tgctgtgggc cgaagactgt cccgaggtgc gccacctcgt     600
ccatgccgac ttcggcagca caacgtcct gaccgacaac ggccgcatca ccgccgtaat      660
cgactggtcc gaagctatgt tcggggacag tcagtacgag gtggccaaca tcttcttctg     720 gcggcccctgg ctggcttgca tggagcagca gactcgctac ttcgagcgcc ggcatcccga    780
gctggccggc agccctcgtc tgcgagccta catgctgcgc atcggcctgg atcagctcta     840
ccagagcctc gtggacggca acttcgacga tgctgcctgg gctcaaggcc gctgcgatgc     900
catcgtccgc agcggggccg gcaccgtcgg tcgcacacaa atcgctcgcc ggagcgccgc     960
```

```
cgtatggacc gacggctgcg tcgaggtgct ggccgacagc ggcaaccgcc ggcccagtac    1020
acgaccgcgc gctaaggagt agtaaccagg ctctgg                              1056
```

<210> SEQ ID NO 10
<211> LENGTH: 1048
<212> TYPE: DNA
<213> ORGANISM: Artificial Sequence
<220> FEATURE:
<223> OTHER INFORMATION: A synthetic construct.

<400> SEQUENCE: 10

```
cctgcaggcc accatgaaga agcccgagct gaccgctacc agcgttgaaa aatttctcat      60
cgagaagttc gacagtgtga gcgacctgat gcagttgtcg gagggcgaag agagccgagc     120
cttcagcttc gatgtcggcg gacgcggcta tgtactgcgg gtgaatagct gcgctgatgg     180
cttctacaaa gaccgctacg tgtaccgcca cttcgccagc gctgcactac ccatccccga     240
agtgttggac atcggcgagt tcagcgagag cctgacatac tgcatcagta gacgcgccca     300
aggcgttact ctccaagacc tccccgaaac agagctgcct gctgtgttac agcctgtcgc     360
cgaagctatg gatgctattg ccgccgccga cctcagtcaa accagcggct cggcccatt     420 cgggccccaa ggcatcggcc agtacacaac ctggcgggat ttcatttgcg ccattgctga     480
tccccatgtc taccactggc agaccgtgat ggacgacacc gtgtccgcca gcgtagctca     540
agccctggac gaactgatgc tgtgggccga agactgtccc gaggtgcgcc acctcgtcca     600
tgccgacttc ggcagcaaca acgtcctgac cgacaacggc cgcatcaccg ccgtaatcga     660
ctggtccgaa gctatgttcg gggacagtca gtacgaggtg gccaacatct tcttctggcg     720
gccctggctg gcttgcatgg agcagcagac tcgctacttc gagcgccggc atcccgagct     780
ggccggcagc cctcgtctgc gagcctacat gctgcgcatc ggcctggatc agctctacca     840
gagcctcgtg gacggcaact tcgacgatgc tgcctgggct caaggccgct gcgatgccat     900
cgtccgcagc ggggccggca ccgtcggtcg cacacaaatc gctcgccgga gcgccgccgt     960
atggaccgac ggctgcgtcg aggtgctggc cgacagcggc aaccgccggc ccagtacacg    1020
accgcgcgct aaggagtagt aacttaag                                       1048
```

<210> SEQ ID NO 11
<211> LENGTH: 1174
<212> TYPE: DNA
<213> ORGANISM: Artificial Sequence
<220> FEATURE:
<223> OTHER INFORMATION: A synthetic construct.

<400> SEQUENCE: 11

```
ggatccgttt gcgtattggg cgctcttccg ctgatctgcg cagcaccatg gcctgaaata      60
acctctgaaa gaggaacttg gttagctacc ttctgaggcg gaaagaacca gctgtggaat     120
gtgtgtcagt tagggtgtgg aaagtcccca ggctccccag caggcagaag tatgcaaagc     180
atgcatctca attagtcagc aaccaggtgt ggaaagtccc caggctcccc agcaggcaga     240
agtatgcaaa gcatgcatct caattagtca gcaaccatag tcccgcccct aactccgccc     300
atcccgcccc taactccgcc cagttccgcc cattctccgc cccatggctg actaattttt     360
tttatttatg cagaggccga ggcgcctctg cctctgagc tattccagaa gtagtgagga     420
ggcttttttg gaggcctagg cttttgcaaa aagctcgatt cttctgacac tagcgccacc     480
atgaccgagt acaagcctac cgtgcgcctg gccactcgcg atgatgtgcc ccgcgccgtc     540
cgcactctgg ccgccgcttt cgccgactac cccgctaccc ggcacaccgt ggaccccgac     600
```

```
cggcacatcg agcgtgtgac agagttgcag gagctgttcc tgacccgcgt cgggctggac      660
atcggcaagg tgtgggtagc cgacgacggc gcggccgtgg ccgtgtggac taccccgag       720 agcgttgagg ccggcgccgt gttcgccgag atcggccccc gaatggccga gctgagcggc      780
agccgcctgg ccgcccagca gcaaatggag ggcctgcttg cccccatcg tcccaaggag       840 cctgcctggt ttctggccac tgtaggagtg agccccgacc accagggcaa gggcttgggc      900
agcgccgtcg tgttgcccgg cgtagaggcc gccgaacgcg ccggtgtgcc cgcctttctc      960
gaaacaagcg caccaagaaa ccttccattc tacgagcgcc tgggcttcac cgtgaccgcc     1020
gatgtcgagg tgcccgaggg acctaggacc tggtgtatga cacgaaaacc tggcgcctaa     1080
tgatctagaa ccggtcatgg ccgcaataaa atatctttat tttcattaca tctgtgtgtt     1140
ggttttttgt gtgttcgaac tagatgctgt cgac                                 1174

<210> SEQ ID NO 12
<211> LENGTH: 1776
<212> TYPE: DNA
<213> ORGANISM: Artificial Sequence
<220> FEATURE:
<223> OTHER INFORMATION: A synthetic construct.

<400> SEQUENCE: 12
atggcttcca aggtgtacga ccccgagcaa cgcaaacgca tgatcactgg gcctcagtgg       60
tgggctcgct gcaagcaaat gaacgtgctg gactccttca tcaactacta tgattccgag      120
aagcacgccg agaacgccgt gattttctg catggtaacg ctgcctccag ctacctgtgg       180
aggcacgtcg tgcctcacat cgagcccgtg gctagatgca tcatccctga tctgatcgga      240
atgggtaagt ccggcaagag cgggaatggc tcatatcgcc tcctggatca ctacaagtac      300
ctcaccgctt ggttcgagct gctgaacctt ccaaagaaaa tcatctttgt gggccacgac      360
tggggggctt gtctggcctt tcactactcc tacgagcacc aagacaagat caaggccatc      420
gtccatgctg agagtgtcgt ggacgtgatc gagtcctggg acgagtggcc tgacatcgag      480
gaggatatcg ccctgatcaa gagcgaagag ggcgagaaaa tggtgcttga aataacttc      540 ttcgtcgaga ccatgctccc aagcaagatc atgcggaaac tggagcctga ggagttcgct      600
gcctacctgg agccattcaa ggagaagggc gaggttagac ggcctaccct ctcctggcct      660
cgcgagatcc ctctcgttaa gggaggcaag cccgacgtcg tccagattgt ccgcaactac      720
aacgcctacc ttcgggccag cgacgatctg cctaagatgt catcgagtc cgaccctggg      780 ttcttttcca acgctattgt cgagggagct aagaagttcc ctaacaccga gttcgtgaag      840
gtgaagggcc tccacttcag ccaggaggac gctccagatg aaatgggtaa gtacatcaag      900
agcttcgtgg agcgcgtgct gaagaacgag cagaccggtg tgggagcgg aggtggcgga      960 tcaggtggcg gaggctccgg agggattgaa caagatggat tgcacgcagg ttctccggcc     1020
gcttgggtgg agaggctatt cggctatgac tgggcacaac agacaatcgg ctgctctgat     1080
gccgccgtgt tccggctgtc agcgcagggg cgcccggttc tttttgtcaa gaccgacctg     1140
tccggtgccc tgaatgaact gcaggacgag gcagcgcggc tatcgtggct ggccacgacg     1200
ggcgttcctt gcgcagctgt gctcgacgtt gtcactgaag cgggaaggga ctggctgcta     1260
ttgggcgaag tgcggggcca ggatctcctg tcatctcacc ttgctcctgc cgagaaagta     1320
tccatcatgg ctgatgcaat gcggcggctg catacgcttg atccggctac ctgcccattc     1380
gaccaccaag cgaaacatcg catcgagcga gcacgtactc ggatggaagc cggtcttgtc     1440
gatcaggatg atctggacga agagcatcag gggctcgcgc cagccgaact gttcgccagg     1500
```

```
ctcaaggcgc gcatgcccga cggcgaggat ctcgtcgtga cccatggcga tgcctgcttg    1560
ccgaatatca tggtggaaaa tggccgcttt tctggattca tcgactgtgg ccggctgggt    1620
gtggcggacc gctatcagga catagcgttg gctacccgtg atattgctga agagcttggc    1680
ggcgaatggg ctgaccgctt cctcgtgctt tacggtatcg ccgctcccga ttcgcagcgc    1740
atcgccttct atcgccttct tgacgagttc ttctaa                              1776
```

<210> SEQ ID NO 13
<211> LENGTH: 1776
<212> TYPE: DNA
<213> ORGANISM: Artificial Sequence
<220> FEATURE:
<223> OTHER INFORMATION: A synthetic construct.

<400> SEQUENCE: 13

```
atgattgaac aagatggatt gcacgcaggt tctccggccg cttgggtgga gaggctattc      60
ggctatgact gggcacaaca gacaatcggc tgctctgatg ccgccgtgtt ccggctgtca     120
gcgcaggggc gcccggttct ttttgtcaag accgacctgt ccggtgccct gaatgaactg     180
caggacgagg cagcgcggct atcgtggctg gccacgacgg gcgttccttg cgcagctgtg     240
ctcgacgttg tcactgaagc gggaagggac tggctgctat tgggcgaagt gccggggcag     300
gatctcctgt catctcacct tgctcctgcc gagaaagtat ccatcatggc tgatgcaatg     360
cggcggctgc atacgcttga tccggctacc tgcccattcg accaccaagc gaaacatcgc     420
atcgagcgag cacgtactcg gatggaagcc ggtcttgtcg atcaggatga tctggacgaa     480
gagcatcagg ggctcgcgcc agccgaactg ttcgccaggc tcaaggcgcg catgcccgac     540
ggcgaggatc tcgtcgtgac ccatggcgat gcctgcttgc cgaatatcat ggtggaaaat     600
ggccgctttt ctggattcat cgactgtggc cggctgggtg tggcggaccg ctatcaggac     660
atagcgttgg ctacccgtga tattgctgaa gagcttggcg gcgaatgggc tgaccgcttc     720
ctcgtgcttt acggtatcgc cgctcccgat tcgcagcgca tcgccttcta tcgccttctt     780
gacgagttct tcaccggtgg tgggagcgga ggtggcggat caggtggcgg aggctccgga     840
ggggcttcca aggtgtacga ccccgagcaa cgcaaacgca tgatcactgg gcctcagtgg     900
tgggctcgct gcaagcaaat gaacgtgctg gactccttca tcaactacta tgattccgag     960
aagcacgccg agaacgccgt gattttctg catggtaacg ctgcctccag ctacctgtgg    1020
aggcacgtcg tgcctcacat cgagcccgtg gctagatgca tcatccctga tctgatcgga    1080
atgggtaagt ccggcaagag cgggaatggc tcatatcgcc tcctggatca ctacaagtac    1140
ctcaccgctt ggttcgagct gctgaacctt ccaaagaaaa tcatctttgt gggccacgac    1200 tgggggggctt gtctggcctt tcactactcc tacgagcacc aagacaagat caaggccatc    1260
gtccatgctg agagtgtcgt ggacgtgatc gagtcctggg acgagtggcc tgacatcgag    1320
gaggatatcg ccctgatcaa gagcgaagag ggcgagaaaa tggtgcttga ataacttc     1380 ttcgtcgaga ccatgctccc aagcaagatc atgcggaaac tggagcctga ggagttcgct    1440
gcctacctgg agccattcaa ggagaagggc gaggttagac ggcctaccct ctcctggcct    1500
cgcgagatcc ctctcgttaa gggaggcaag cccgacgtcg tccagattgt ccgcaactac    1560
aacgcctacc tcgggccag cgacgatctg cctaagatgt catcgagtc cgaccctggg     1620 ttcttttcca acgctattgt cgagggagct aagaagttcc ctaacaccga gttcgtgaag    1680
gtgaagggcc tccacttcag ccaggaggac gctccagatg aaatgggtaa gtacatcaag    1740
agcttcgtgg agcgcgtgct gaagaacgag cagtaa                              1776
```

<210> SEQ ID NO 14
<211> LENGTH: 1653
<212> TYPE: DNA
<213> ORGANISM: Artificial Sequence
<220> FEATURE:
<223> OTHER INFORMATION: A synthetic construct.

<400> SEQUENCE: 14

| | | | | | |
|---|---|---|---|---|---|
| atggccgatg | ctaagaacat | taagaagggc | cctgctccct | tctaccctct | ggaggatggc | 60 |
| accgctggcg | agcagctgca | caaggccatg | aagaggtatg | ccctggtgcc | tggcaccatt | 120 |
| gccttcaccg | atgcccacat | tgaggtggac | atcacctatg | ccgagtactt | cgagatgtct | 180 |
| gtgcgcctgg | ccgaggccat | gaagaggtac | ggcctgaaca | ccaaccaccg | catcgtggtg | 240 |
| tgctctgaga | actctctgca | gttcttcatg | ccagtgctgg | gcgccctgtt | catcggagtg | 300 |
| gccgtggccc | tgctaacga | catttacaac | gagcgcgagc | tgctgaacag | catgggcatt | 360 |
| tctcagccta | ccgtggtgtt | cgtgtctaag | aagggcctgc | agaagatcct | gaacgtgcag | 420 |
| aagaagctgc | ctatcatcca | gaagatcatc | atcatggact | ctaagaccga | ctaccagggc | 480 |
| ttccagagca | tgtacacatt | cgtgacatct | catctgcctc | ctggcttcaa | cgagtacgac | 540 |
| ttcgtgccag | agtctttcga | cagggacaaa | accattgccc | tgatcatgaa | cagctctggg | 600 |
| tctaccggcc | tgcctaaggg | cgtggccctg | cctcatcgca | ccgcctgtgt | gcgcttctct | 660 |
| cacgcccgcg | accctatttt | cggcaaccag | atcatccccg | acaccgctat | tctgagcgtg | 720 |
| gtgccattcc | accacggctt | cggcatgttc | accaccctgg | gctacctgat | tgcggctttt | 780 |
| cgggtggtgc | tgatgtaccg | cttcgaggag | gagctgttcc | tgcgcagcct | gcaagactac | 840 |
| aaaattcagt | ctgccctgct | ggtgccaacc | ctgttcagct | tcttcgctaa | gagcaccctg | 900 |
| atcgacaagt | acgacctgtc | taacctgcac | gagattgcct | ctggcggcgc | ccactgtct | 960 |
| aaggaggtgg | cgaagccgt | ggccaagcgc | tttcatctgc | caggcatccg | ccagggctac | 1020 |
| ggcctgaccg | agacaaccag | cgccattctg | attaccccag | agggcgacga | caagcctggc | 1080 |
| gccgtgggca | aggtggtgcc | attcttcgag | gccaaggtgg | tggacctgga | caccggcaag | 1140 |
| accctgggag | tgaaccagcg | cggcgagctg | tgtgtgcgcg | ccctatgat | tatgtccggc | 1200 |
| tacgtgaata | accctgaggc | cacaaacgcc | ctgatcgaca | aggacggctg | gctgcactct | 1260 |
| ggcgacattg | cctactggga | cgaggacgag | cacttcttca | tcgtggaccg | cctgaagtct | 1320 |
| ctgatcaagt | acaagggcta | ccaggtggcc | cagccgagc | tggagtctat | cctgctgcag | 1380 |
| cacccctaaca | ttttcgacgc | cggagtggcc | ggcctgcccg | acgacgatgc | cggcgagctg | 1440 |
| cctgccgccg | tcgtcgtgct | ggaacacggc | aagaccatga | ccgagaagga | gatcgtggac | 1500 |
| tatgtggcca | gccaggtgac | aaccgccaag | aagctgcgcg | gcggagtggt | gttcgtggac | 1560 |
| gaggtgccca | agggcctgac | cggcaagctg | gacgcccgca | agatccgcga | gatcctgatc | 1620 |
| aaggctaaga | aaggcggcaa | gatcgccgtg | taa | | | 1653 |

<210> SEQ ID NO 15
<211> LENGTH: 597
<212> TYPE: DNA
<213> ORGANISM: Streptomyces sp.

<400> SEQUENCE: 15

| | | | | | |
|---|---|---|---|---|---|
| atgaccgagt | acaagcccac | ggtgcgcctc | gccacccgcg | acgacgtccc | ccgggccgta | 60 |
| cgcacccctcg | ccgccgcgtt | cgccgactac | cccgccacgc | gccacaccgt | cgacccggac | 120 |
| cgccacatcg | agcgggtcac | cgagctgcaa | gaactcttcc | tcacgcgcgt | cgggctcgac | 180 |

```
atcggcaagg tgtgggtcgc ggacgacggc gccgcggtgg cggtctggac cacgccggag    240
agcgtcgaag cggggcggt gttcgccgag atcggcccgc gcatggccga gttgagcggt    300
tcccggctgg ccgcgcagca acagatggaa ggcctcctgg cgccgcaccg gcccaaggag    360
cccgcgtggt tcctggccac cgtcggcgtg tcgcccgacc accagggcaa gggtctgggc    420
agcgccgtcg tgctccccgg agtggaggcg gccgagcgcg ccggggtgcc cgccttcctg    480
gagacctccg cgccccgcaa cctccccttc tacgagcggc tcggcttcac cgtcaccgcc    540
gacgtcgagg tgcccgaagg accgcgcacc tggtgcatga cccgcaagcc cggtgcc     597
```

<210> SEQ ID NO 16
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 16

```
aaagccacca tggaggacgc caagaacatc aagaagggcc ccgccccctt ctaccccctg     60
gaggacggca ccgccggcga gcagctgcac aaggccatga gcgctacgc cctggtgccc    120 ggcaccatcg ccttcaccga cgcccacatc gaggtggaca tcacctacgc cgagtacttc    180
gagatgagcg tgcgcctggc cgaggccatg aagcgctacg gcctgaacac caaccaccgc    240
atcgtggtgt gcagcgagaa cagcctgcag ttcttcatgc ccgtgctggg cgccctgttc    300
atcggcgtgg ccgtggcccc cgccaacgac atctacaacg agcgcgagct gctgaacagc    360
atgggcatca gccagcccac cgtggtgttc gtgagcaaga agggcctgca gaagatcctg    420
aacgtgcaga gaagctgcc catcatccag aagatcatca tcatggacag caagaccgac    480
taccagggct tccagagcat gtacaccttc gtgaccagcc acctgccccc cggcttcaac    540
gagtacgact tcgtgcccga gagcttcgac cgcgacaaga ccatcgccct gatcatgaac    600
agcagcggca gcaccggcct gcccaagggc gtggccctgc ccaccgcac cgcctgcgtg    660 cgcttcagcc acgcccgcga ccccatcttc ggcaaccaga tcatccccga caccgccatc    720
ctgagcgtgg tgcccttcca ccacggcttc ggcatgttca ccaccctggg ctacctgatc    780
tgcggcttcc gcgtggtgct gatgtaccgc ttcgaggagg agctgttcct gcgcagcctg    840
caggactaca agatccagag cgccctgctg gtgcccaccc tgttcagctt cttcgccaag    900
agcaccctga tcgacaagta cgacctgagc aacctgcacg agatcgccag cggcggcgcc    960
cccctgagca aggaggtggg cgaggccgtg gccaagcgct ccaccctgcc cggcatccgc   1020
cagggctacg gcctgaccga gaccaccagc gccatcctga tcacccccga gggcgacgac   1080
aagcccggcg ccgtgggcaa ggtggtgccc ttcttcgagg ccaaggtggt ggacctggac   1140
accggcaaga ccctgggcgt gaaccagcgc ggcgagctgt gcgtgcgcgg ccccatgatc   1200
atgagcggct acgtgaacaa ccccgaggcc accaacgccc tgatcgacaa ggacggctgg   1260
ctgcacagcg gcgacatcgc ctactgggac gaggacgagc acttcttcat cgtggaccgc   1320
ctgaagagcc tgatcaagta caagggctac caggtggccc ccgccgagct ggagagcatc   1380
ctgctgcagc accccaacat cttcgacgcc ggcgtggccg gcctgcccga cgacgacgcc   1440
ggcgagctgc ccgccgccgt ggtggtgctg gagcacggca gaccatgac cgagaaggag   1500 atcgtggact acgtggccag ccaggtgacc accgccaaga gctgcgcgg cggcgtggtg   1560 ttcgtggacg aggtgcccaa gggcctgacc ggcaagctgg acgcccgcaa gatccgcgag   1620
atcctgatca aggccaagaa gggcggcaag atcgccgtgt aataattcta ga          1672
```

<210> SEQ ID NO 17
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 17

| | | | | | |
|---|---|---|---|---|---|
| aaagccacca | tggaggacgc | caagaacatc | aagaagggcc | cagcgccatt | ctaccccctg | 60 |
| gaggacggca | ccgccggcga | gcagctgcac | aaggccatga | agcgctacgc | cctggtgccc | 120 |
| ggcaccatcg | ccttcaccga | cgcacatatc | gaggtggaca | tcacctacgc | cgagtacttc | 180 |
| gagatgagcg | ttcggctggc | agaggctatg | aagcgctatg | gctgaacac | caaccatcgc | 240 |
| atcgtggtgt | gcagcgagaa | cagcttgcag | ttcttcatgc | ccgtgttggg | tgccctgttc | 300 |
| atcggcgtgg | ctgtggcccc | agctaacgac | atctacaacg | agcgcgagct | gctgaacagc | 360 |
| atgggcatca | gccagcccac | cgtcgtattc | gtgagcaaga | aagggctgca | aaagatcctg | 420 |
| aacgtgcaaa | agaagctgcc | catcatccaa | aagatcatca | tcatggacag | caagaccgac | 480 |
| taccagggct | tccaaagcat | gtacaccttc | gtgaccagcc | atttgccgcc | cggcttcaac | 540 |
| gagtacgact | tcgtgcccga | gagcttcgac | cgcgacaaga | ccatcgccct | gatcatgaac | 600 |
| agtagtggca | gtaccggctt | acctaagggc | gtggccctac | cgcaccgcac | cgcctgtgtc | 660 |
| cgattcagtc | atgcccgcga | ccccatcttc | ggcaaccaga | tcatccccga | caccgctatc | 720 |
| ctgagcgtgg | tgccatttca | ccacggcttc | ggcatgttca | ccaccctggg | ctacttgatc | 780 |
| tgcggcttcc | gggtcgtgct | gatgtaccgc | ttcgaggagg | agctattctt | gcgcagcttg | 840 |
| caagactaca | agattcaaag | cgccctgctg | gtgcccaccc | tgttcagttt | cttcgccaag | 900 |
| agcaccctga | tcgacaagta | cgacctgagc | aacctgcacg | agatcgccag | cggcggcgcc | 960 |
| ccgctcagca | aggaggtggg | cgaggccgtg | gccaagcgct | ccacctgcc | aggcatccgc | 1020 |
| cagggctacg | gcctgaccga | gacaaccagc | gccattctga | tcaccccga | ggggacgac | 1080 |
| aagcctggcg | cagtaggcaa | ggtggtgccc | ttcttcgagg | ctaaggtggt | ggacctggac | 1140 |
| accggtaaaa | ccctgggtgt | gaaccagcgc | ggcgagctgt | gcgtccgtgg | ccccatgatc | 1200 |
| atgagcggct | acgttaacaa | ccccgaggct | acaaacgccc | tgatcgacaa | ggacggctgg | 1260 |
| ctgcacagcg | gcgacatcgc | ctactgggac | gaggacgagc | acttcttcat | cgtggaccgg | 1320 |
| ctgaagagcc | tgatcaaata | caagggctac | caggtagccc | cagccgaact | ggagagcatc | 1380 |
| ctgctgcagc | accccaacat | cttcgacgcc | ggggtcgccg | gcctgcccga | cgacgatgcc | 1440 |
| ggcgagctgc | ccgccgcagt | cgtggtgctg | gagcacggta | aaaccatgac | cgagaaggag | 1500 |
| atcgtggact | atgtggccag | ccaggttaca | accgccaaga | agctgcgcgg | cggcgtggtg | 1560 |
| ttcgtggacg | aggtgcctaa | aggcctgacg | ggcaagttgg | acgcccgcaa | gatccgcgag | 1620 |
| attctgatca | aggccaagaa | gggcggcaag | atcgccgtgt | aataattcta | ga | 1672 |

<210> SEQ ID NO 18
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 18

| | | | | | |
|---|---|---|---|---|---|
| aaagccacca | tggaagatgc | caaaaacatt | aagaagggcc | cagcgccatt | ctaccccactg | 60 |
| gaggacggca | ccgccggcga | gcagctgcac | aaagccatga | agcgctacgc | cctggtgccc | 120 |

```
ggcaccatcg cctttaccga cgcacatatc gaggtggaca tcacctacgc cgagtacttc    180
gagatgagcg ttcggctggc agaggctatg aagcgctatg gctgaatac caaccatcgc    240 atcgtggtgt gcagcgagaa tagcttgcag ttcttcatgc ccgtgttggg tgccctgttc    300
atcggtgtgg ctgtggcccc agctaacgac atctacaacg agcgcgagct gctgaacagc    360
atgggcatca gccagcccac cgtcgtattc gtgagcaaga aagggctgca aaagatcctc    420
aacgtgcaaa agaagctacc gatcatacaa aagatcatca tcatggatag caagaccgac    480
taccagggct ccaaaagcat gtacaccttc gtgaccagcc atttgccacc cggcttcaac    540
gagtacgact tcgtgcccga gagcttcgac cgggacaaaa ccatcgccct gatcatgaac    600
agtagtggca gtaccggatt gcccaagggc gtagccctac cgcaccgcac cgcctgtgtc    660
cgattcagtc atgcccgcga ccccatcttc ggcaaccaga tcatccccga caccgctatc    720
ctcagcgtgg tgccatttca ccacggcttc ggcatgttca ccacgctggg ctacttgatc    780
tgcggctttc gggtcgtgct catgtaccgc ttcgaggagg agctattctt gcgcagcttg    840
caagactata agattcaaag cgccctgctg gtgcccacac tgttcagctt cttcgccaag    900
agcactctca tcgacaagta cgacctgagc aacctgcacg agatcgccag cggcggggcg    960
ccgctcagca aggaggtggg cgaggccgtg gccaagcgct ccacctacc aggcatccgc   1020 cagggctacg gcctgacaga acaaccagc gccattctga tcacccccga aggggacgac   1080
aagcctggcg cagtaggcaa ggtggtgccc ttcttcgagg ctaaggtggt ggacttggac   1140
accggtaaga ccctgggtgt gaaccagcgc ggcgagctgt gcgtccgtgg ccccatgatc   1200
atgagcggct acgttaacaa ccccgaggct acaaacgctc tcatcgacaa ggacggctgg   1260
ctgcacagcg gcgacatcgc ctactgggac gaggacgagc acttcttcat cgtggaccgg   1320
ctgaagagcc tgatcaaata caagggctac caggtagccc cagccgaact ggagagcatc   1380
ctgctgcaac accccaacat cttcgacgcc ggggtcgccg gcctgcccga cgacgatgcc   1440
ggcgagctgc ccgccgcagt cgtcgtgctg gagcacggta aaaccatgac cgagaaggag   1500
atcgtggact atgtggccag ccaggttaca accgccaaga gctgcgcgg tggtgttgtg   1560 ttcgtggacg aggtgcctaa aggcctgacg ggcaagttgg acgcccgcaa gatccgcgag   1620
attctcatta aggccaagaa gggcggcaag atcgccgtgt aataattcta ga           1672
```

<210> SEQ ID NO 19
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 19

```
aaagccacca tggaagatgc caaaaacatt aagaagggcc cagcgccatt ctacccactc     60
gaagacggca ccgccggcga gcagctgcac aaagccatga agcgctacgc cctggtgccc    120
ggcaccatcg cctttaccga cgcacatatc gaggtggaca ttacctacgc cgagtacttc    180
gagatgagcg ttcggctggc agaagctatg aagcgctatg gctgaacac caaccatcgc    240 atcgtggtgt gcagcgagaa tagcttgcag ttcttcatgc ccgtgttggg tgccctgttc    300
atcggtgtgg ctgtggcccc agctaacgac atctacaacg agcgcgagct gctgaacagc    360
atgggcatca gccagcccac cgtcgtattc gtgagcaaga aagggctgca aaagatcctc    420
aacgtgcaaa agaagctacc gatcatacaa aagatcatca tcatggatag caagaccgac    480
taccagggct ccaaaagcat gtacaccttc gtgacttccc atttgccacc cggcttcaac    540
```

```
gagtacgact tcgtgcccga gagcttcgac cgggacaaaa ccatcgccct gatcatgaac      600
agtagtggca gtaccggatt gcccaagggc gtagccctac cgcaccgcac cgcttgtgtc      660
cgattcagtc atgcccgcga ccccatcttc ggcaaccaga tcatccccga caccgctatc      720
ctcagcgtgg tgccatttca ccacggcttc ggcatgttca ccacgctggg ctacttgatc      780
tgcggctttc gggtcgtgct catgtaccgc ttcgaggagg agctattctt gcgcagcttg      840
caagactata agattcaaag cgccctgctg gtgcccacac tgttcagttt cttcgccaag      900
agcactctca tcgacaagta cgacctaagc aacttgcacg agatcgccag cggcggggcg      960
ccgctcagca aggaggtggg cgaggccgtg gccaaacgct tccacctacc aggcatccgc     1020
cagggctacg gcctgacaga aacaaccagc gccattctga tcacccccga aggggacgac     1080
aagcctggcg cagtaggcaa ggtggtgccc ttcttcgagg ctaaggtggt ggacttggac     1140
accggtaaga cactgggtgt gaaccagcgc ggcgagctgt gcgtccgtgg ccccatgatc     1200
atgagcggct acgttaacaa ccccgaggct acaaacgctc tcatcgacaa ggacggctgg     1260
ctgcacagcg gcgacatcgc ctactgggac gaggacgagc acttcttcat cgtggaccgg     1320
ctgaagagcc tgatcaaata caagggctac caggtagccc cagccgaact ggagagcatc     1380
ctgctgcaac accccaacat cttcgacgcc ggggtcgccg gcctgcccga cgacgatgcc     1440
ggcgagctgc ccgccgcagt cgtcgtgctg aacacggta aaaccatgac cgagaaggag      1500
atcgtggact atgtggccag ccaggttaca accgccaaga agctgcgcgg tggtgttgtg     1560
ttcgtggacg aggtgcctaa aggcctgacg ggcaagttgg acgcccgcaa gatccgcgag     1620
attctcatta aggccaagaa gggcggcaag atcgccgtgt aataattcta ga             1672

<210> SEQ ID NO 20
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 20
aaagccacca tggaagatgc caaaaacatt aagaagggcc cagcgccatt ctacccactc       60
gaagacggca ccgccggcga gcagctgcac aaagccatga gcgctacgc cctggtgccc      120 ggcaccatcg cctttaccga cgcacatatc gaggtggaca ttacctacgc cgagtacttc      180
gagatgagcg ttcggctggc agaagctatg aagcgctatg gactgaacac caaccatcgg      240
atcgtggtgt gcagcgagaa tagcttgcag ttcttcatgc ccgtgttggg tgccctgttc      300
atcggtgtgg ctgtggcccc agctaacgac atctacaacg agcgcgagct gctgaacagc      360
atgggcatca gccagcccac cgtcgtattc gtgagcaaga aagggctgca aaagatcctc      420
aacgtgcaaa agaagctacc gatcatacaa aagatcatca tcatggatag caagaccgac      480
taccagggct tccaaagcat gtacaccttc gtgacttccc atttgccacc cggcttcaac      540
gagtacgact tcgtgcccga gagcttcgac cgggacaaaa ccatcgccct gatcatgaac      600
agtagtggca gtaccggatt gcccaagggc gtagccctac cgcaccgcac cgcttgtgtc      660
cgattcagtc atgcccgcga ccccatcttc ggcaaccaga tcatccccga caccgctatc      720
ctcagcgtgg tgccatttca ccacggcttc ggcatgttca ccacgctggg ctacttgatc      780
tgcggctttc gggtcgtgct catgtaccgc ttcgaggagg agctattctt gcgcagcttg      840
caagactata agattcaaag cgccctgctg gtgcccacac tgttcagttt cttcgctaag      900
agcactctca tcgacaagta cgacctaagc aacttgcacg agatcgccag cggcggggcg      960
```

```
ccgctcagca aggaggtggg cgaggccgtg gccaaacgct tccacctacc aggcatccgc    1020
cagggctacg gcctgacaga acaaccagc gccattctga tcaccccga aggggacgac    1080 aagcctggcg cagtaggcaa ggtggtgccc ttcttcgagg ctaaggtggt ggacttggac    1140
accggtaaga cactgggtgt gaaccagcgc ggcgagctgt gcgtccgtgg ccccatgatc    1200
atgagcggct acgttaacaa ccccgaggct acaaacgctc tcatcgacaa ggacggctgg    1260
ctgcacagcg gcgacatcgc ctactgggac gaggacgagc acttcttcat cgtggaccgg    1320
ctgaagagcc tgatcaaata caagggctac caggtagccc cagccgaact ggagagcatc    1380
ctgctgcaac accccaacat cttcgacgcc ggggtcgccg gcctgcccga cgacgatgcc    1440
ggcgagctgc ccgccgcagt cgtcgtgctg gaacacggta aaaccatgac cgagaaggag    1500
atcgtggact atgtggccag ccaggttaca accgccaaga agctgcgcgg tggtgttgtg    1560
ttcgtggacg aggtgcctaa aggcctgacg ggcaagttgg acgcccgcaa gatccgcgag    1620
attctcatta aggccaagaa gggcggcaag atcgccgtgt aataattcta ga    1672

<210> SEQ ID NO 21
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 21
aaagccacca tggaagatgc caaaaacatt aagaagggc cagcgccatt ctacccactc      60
gaagacggca ccgccggcga gcagctgcac aaagccatga gcgctacgc cctggtgccc     120 ggcaccatcg cctttaccga cgcacatatc gaggtggaca ttacctacgc cgagtacttc     180
gagatgagcg ttcggctggc agaagctatg aagcgctatg gctgaatac aaaccatcgg     240 atcgtggtgt gcagcgagaa tagcttgcag ttcttcatgc ccgtgttggg tgccctgttc     300
atcggtgtgg ctgtggcccc agctaacgac atctacaacg agcgcgagct gctgaacagc     360
atgggcatca gccagcccac cgtcgtattc gtgagcaaga agggctgca aaagatcctc     420 aacgtgcaaa agaagctacc gatcatacaa aagatcatca tcatggatag caagaccgac     480
taccagggct ccaaaagcat gtacaccttc gtgacttccc atttgccacc cggcttcaac     540
gagtacgact tcgtgcccga gagcttcgac cgggacaaaa ccatcgccct gatcatgaac     600
agtagtggca gtaccggatt gcccaagggc gtagccctac cgcaccgcac cgcttgtgtc     660
cgattcagtc atgcccgcga ccccatcttc ggcaaccaga tcatcccga caccgctatc     720 ctcagcgtgg tgccatttca ccacggcttc ggcatgttca ccacgctggg ctacttgatc     780
tgcggctttc gggtcgtgct catgtaccgc ttcgaggagg agctattctt gcgcagcttg     840
caagactata agattcaaag cgccctgctg gtgcccacac tgttcagttt cttcgctaag     900
agcactctca tcgacaagta cgacctaagc aacttgcacg agatcgccag cggcggggcg     960
ccgctcagca aggaggtagg tgaggccgtg gccaaacgct tccacctacc aggcatccgc    1020
cagggctacg gcctgacaga acaaccagc gccattctga tcaccccga aggggacgac    1080 aagcctggcg cagtaggcaa ggtggtgccc ttcttcgagg ctaaggtggt ggacttggac    1140
accggtaaga cactgggtgt gaaccagcgc ggcgagctgt gcgtccgtgg ccccatgatc    1200
atgagcggct acgttaacaa ccccgaggct acaaacgctc tcatcgacaa ggacggctgg    1260
ctgcacagcg gcgacatcgc ctactgggac gaggacgagc acttcttcat cgtggaccgg    1320
ctgaagagcc tgatcaaata caagggctac caggtagccc cagccgaact ggagagcatc    1380
```

```
ctgctgcaac accccaacat cttcgacgcc ggggtcgccg gcctgcccga cgacgatgcc    1440
ggcgagctgc ccgccgcagt cgtcgtgctg gaacacggta aaaccatgac cgagaaggag    1500
atcgtggact atgtgccag ccaggttaca accgccaaga agctgcgcgg tggtgttgtg    1560
ttcgtggacg aggtgcctaa aggcctgacg ggcaagttgg acgcccgcaa gatccgcgag    1620
attctcatta aggccaagaa gggcggcaag atcgccgtgt aataattcta ga    1672
```

<210> SEQ ID NO 22
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 22

```
aaagccacca tggaagatgc caaaaacatt aagaagggcc cagcgccatt ctacccactc     60
gaagacggga ccgccggcga gcagctgcac aaagccatga gcgctacgc cctggtgccc    120 ggcaccatcg cctttaccga cgcacatatc gaggtggaca ttacctacgc cgagtacttc    180
gagatgagcg ttcggctggc agaagctatg aagcgctatg gctgaatac aaaccatcgg    240 atcgtggtgt gcagcgagaa tagcttgcag ttcttcatgc ccgtgttggg tgccctgttc    300
atcggtgtgg ctgtggcccc agctaacgac atctacaacg agcgcgagct gctgaacagc    360
atgggcatca gccagcccac cgtcgtattc gtgagcaaga aggggctgca aaagatcctc    420
aacgtgcaaa agaagctacc gatcatacaa aagatcatca tcatggatag caagaccgac    480
taccagggct tccaaagcat gtacaccttc gtgacttccc atttgccacc cggcttcaac    540
gagtacgact tcgtgcccga gagcttcgac cgggacaaaa ccatcgccct gatcatgaac    600
agtagtggca gtaccggatt gcccaagggc gtagccctac cgcaccgcac cgcttgtgtc    660
cgattcagtc atgcccgcga ccccatcttc ggcaaccaga tcatcccga caccgctatc    720 ctcagcgtgg tgccatttca ccacggcttc ggcatgttca ccacgctggg ctacttgatc    780
tgcggctttc gggtcgtgct catgtaccgc ttcgaggagg agctattctt gcgcagcttg    840
caagactata agattcaatc tgccctgctg gtgcccacac tatttagctt cttcgctaag    900
agcactctca tcgacaagta cgacctaagc aacttgcacg agatcgccag cggcggggcg    960
ccgctcagca aggaggtagg tgaggccgtg gccaaacgct tccacctacc aggcatccgc   1020
cagggctacg gcctgacaga aacaaccagc gccattctga tcaccccga aggggacgac   1080 aagcctggcg cagtaggcaa ggtggtgccc ttcttcgagg ctaaggtggt ggacttggac   1140
accggtaaga cactgggtgt gaaccagcgc ggcgagctgt gcgtccgtgg ccccatgatc   1200
atgagcggct acgttaacaa ccccgaggct acaaacgctc tcatcgacaa ggacggctgg   1260
ctgcacagcg gcgacatcgc ctactgggac gaggacgagc acttcttcat cgtggaccgg   1320
ctgaagagcc tgatcaaata caagggctac caggtagccc cagccgaact ggagagcatc   1380
ctgctgcaac accccaacat cttcgacgcc ggggtcgccg gcctgcccga cgacgatgcc   1440
ggcgagctgc ccgccgcagt cgtcgtgctg gaacacggta aaaccatgac cgagaaggag   1500
atcgtggact atgtgccag ccaggttaca accgccaaga agctgcgcgg tggtgttgtg   1560
ttcgtggacg aggtgcctaa aggcctgacg ggcaagttgg acgcccgcaa gatccgcgag   1620
attctcatta aggccaagaa gggcggcaag atcgccgtgt aataattcta ga          1672
```

<210> SEQ ID NO 23
<211> LENGTH: 1672

<212> TYPE: DNA
<213> ORGANISM: Artificial Sequence
<220> FEATURE:
<223> OTHER INFORMATION: A synthetic construct.

<400> SEQUENCE: 23

```
aaagccacca tggaagatgc caaaaacatt aagaagggcc cagcgccatt ctacccactc      60
gaagacggga ccgccggcga gcagctgcac aaagccatga agcgctacgc cctggtgccc     120
ggcaccatcg cctttaccga cgcacatatc gaggtggaca ttacctacgc cgagtacttc     180
gagatgagcg ttcggctggc agaagctatg aagcgctatg gctgaataca aaaccatcgg     240
atcgtggtgt gcagcgagaa tagcttgcag ttcttcatgc ccgtgttggg tgccctgttc     300
atcggtgtgg ctgtgccccc agctaacgac atctacaacg agcgcgagct gctgaacagc     360
atgggcatca gccagcccac cgtcgtattc gtgagcaaga aagggctgca aaagatcctc     420
aacgtgcaaa agaagctacc gatcatacaa aagatcatca tcatggatag caagaccgac     480
taccagggct tccaaagcat gtacaccttc gtgacttccc atttgccacc cggcttcaac     540
gagtacgact tcgtgcccga gagcttcgac cgggacaaaa ccatcgccct gatcatgaac     600
agtagtggca gtaccggatt gcccaagggc gtagccctac cgcaccgcac cgcttgtgtc     660
cgattcagtc atgcccgcga ccccatcttc ggcaaccaga tcatccccga caccgctatc     720
ctcagcgtgg tgccatttca ccacggcttc ggcatgttca ccacgctggg ctacttgatc     780
tgcggctttc gggtcgtgct catgtaccgc ttcgaggagg agctattctt gcgcagcttg     840
caagactata agattcaatc tgccctgctg gtgcccacac tatttagctt cttcgctaag     900
agcactctca tcgacaagta cgacctaagc aacttgcacg agatcgccag cggcggggcg     960
ccgctcagca aggaggtagg tgaggccgtg gccaaacgct ccacctacc aggcatccgc    1020
cagggctacg gcctgacaga aacaaccagc gccattctga tcacccccga aggggacgac    1080
aagcctggcg cagtaggcaa ggtggtgccc ttcttcgagg ctaaggtggt ggacttggac    1140
accggtaaga cactgggtgt gaaccagcgc ggcgagctgt gcgtccgtgg ccccatgatc    1200
atgagcggct acgttaacaa ccccgaggct acaaacgctc tcatcgacaa ggacggctgg    1260
ctgcacagcg gcgacatcgc ctactgggac gaggacgagc acttcttcat cgtggaccgg    1320
ctgaagagcc tgatcaaata caagggctac caggtagccc cagccgaact ggagagcatc    1380
ctgctgcaac accccaacat cttcgacgcc ggggtcgccg gctgcccga cgacgatgcc    1440
ggcgagctgc ccgccgcagt cgtcgtgctg aacacggta aaaccatgac cgagaaggag    1500
atcgtggact atgtggccag ccaggttaca accgccaaga agctgcgcgg tggtgttgtg    1560
ttcgtggacg aggtgcctaa aggactgacc ggcaagttgg acgcccgcaa gatccgcgag    1620
attctcatta aggccaagaa gggcggcaag atcgccgtgt aataattcta ga            1672
```

<210> SEQ ID NO 24
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 24

```
aaagccacca tggaggatgc taagaatatt aagaagggc ctgctccttt ttatcctctg      60
gaggatggga cagctgggga gcagctgcat aaggctatga agagatatgc tctggtgcct    120
gggacaattc ttttacaga tgctcatatt gaggtggata ttacatatgc tgagtattt     180
gagatgtctg tgagactggc tgaggctatg aagagatatg gctgaataca aaatcataga    240
```

```
attgtggtgt gttctgagaa ttctctgcag tttttatgc ctgtgctggg ggctctgttt    300
attggggtgg ctgtggctcc tgctaatgat atttataatg agagagagct gctgaattct   360
atggggattt ctcagcctac agtggtgttt gtgtctaaga aggggctgca gaagattctg   420
aatgtgcaga agaagctgcc tattattcag aagattatta ttatggattc taagacagat   480
tatcaggggt tcagtctat gtatacattt gtgacatctc atctgcctcc tgggttaat    540
gagtatgatt ttgtgcctga gtcttttgat agagataaga caattgctct gattatgaat   600
tcttctgggt ctacagggct gcctaagggg gtggctctgc tcatagaac agcttgtgtg    660
agattttctc atgctagaga tcctattttt gggaatcaga ttattcctga tacagctatt   720
ctgtctgtgg tgccttttca tcatgggttt gggatgttta caacactggg gtatctgatt   780
tgtgggttta gagtggtgct gatgtataga tttgaggagg agctgtttct gagatctctg   840
caggattata agattcagtc tgctctgctg gtgcctacac tgttttcttt ttttgctaag   900
tctacactga ttgataagta tgatctgtct aatctgcatg agattgcttc tgggggggct   960
cctctgtcta aggaggtggg ggaggctgtg gctaagagat tcatctgcc tgggattaga   1020
caggggtatg ggctgacaga gacaacatct gctattctga ttacacctga ggggatgat   1080
aagcctgggg ctgtggggaa ggtggtgcct ttttttgagg ctaaggtggt ggatctggat   1140
acagggaaga cactggggt gaatcagaga ggggagctgt gtgtgagagg gcctatgatt   1200
atgtctgggt atgtgaataa tcctgaggct acaaatgctc tgattgataa ggatgggtgg   1260
ctgcattctg gggatattgc ttattgggat gaggatgagc atttttttat tgtggataga   1320
ctgaagtctc tgattaagta taaggggtat caggtggctc ctgctgagct ggagtctatt   1380
ctgctgcagc atcctaatat ttttgatgct ggggtggctg ggctgcctga tgatgatgct   1440
ggggagctgc ctgctgctgt ggtggtgctg gagcatggga agacaatgac agagaaggag   1500
attgtggatt atgtggcttc tcaggtgaca acagctaaga agctgagagg ggggggtggtg  1560
tttgtggatg aggtgcctaa ggggctgaca gggaagctgg atgctagaaa gattagagag   1620
attctgatta aggctaagaa gggggggaag attgctgtgt aataattcta ga            1672
```

<210> SEQ ID NO 25
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 25

```
aaagccacca tggaagatgc taaaaacatt aagaagggc ctgctccttt ctaccctctg     60
gaggatggga ctgccgggga gcagctgcat aaagctatga gcggtatgc tctggtgcca    120
ggcacaattg cgttcacgga tgctcacatt gaggtggaca ttacatacgc tgagtatttt   180
gagatgtcgg tgcggctggc tgaggctatg aagcgatatg gctgaatac aaaccataga    240
attgtagtgt gctctgagaa ctcgttgcag tttttatgc ctgtgctggg ggctctcttc    300
atcggggtgg ctgtggctcc tgctaacgac atttacaatg agagagagct tttgaactcg   360
atggggattt ctcagcctac agtggtgttt gtgagtaaga aagggcttca aaagattctc   420
aatgtgcaaa agaagctgcc tattattcaa aagattatta ttatggactc taagacagac   480
taccaggggt tcagtctat gtatacattt gtgacatctc atctgcctcc tgggttcaac   540
gagtatgact ttgtgcccga gtctttcgac agagataaga caattgctct gattatgaat   600
tcatctgggt ctaccgggct gcctaagggt gtagctctgc cacatagaac agcttgtgtg   660
```

```
agattttctc atgctaggga ccctattttt gggaatcaga ttattcctga tactgctatt    720
ctgtcggttg tgcccttcca tcatgggttt gggatgttta caacactggg ctacctgata    780
tgtgggttta gagtggtgct catgtatagg tttgaggagg agcttttttt gcgctctctg    840
caagattata agattcagtc tgctctgctg gtgcctacac tgttttcttt ttttgctaag    900
tctaccctga tcgataagta tgatctgtcc aacctgcacg agattgcttc tggggggggct    960 cctctgtcta aggaggtagg tgaggctgtg gctaagcgct ttcatctgcc tggaatcaga   1020
caggggtatg ggctaacaga aacaacatct gctattctga ttacaccaga ggggatgat    1080 aagcccgggg ctgtagggaa agtggtgccc ttttttgaag ctaaagtagt tgatcttgat   1140
accggtaaga cactggggggt gaatcagcga ggggaactgt gtgtgagagg gcctatgatt   1200
atgtcggggt atgtgaacaa ccctgaggct acaaatgctc tgattgataa ggatgggtgg   1260
ctgcattcgg gcgatattgc ttactgggat gaggatgagc atttcttcat cgtggacaga   1320
ctgaagtcgt tgatcaaata taaggggtat caagtagctc ctgctgagct ggagtccatt   1380
ctgcttcaac atcctaacat tttcgatgct ggggtggctg gctgcctga tgatgatgct    1440 ggggagctgc ctgctgctgt agtggtgctg gagcacggta agacaatgac agagaaggag   1500
attgtggatt atgtggcttc acaagtgaca acagctaaga aactgagagg tggcgttgtg   1560
tttgtggatg aggtgcctaa agggctgaca ggcaagctgg atgctagaaa aattcgagag   1620
attctgatta aggctaagaa gggtggaaag attgctgtgt aatagttcta ga             1672
```

<210> SEQ ID NO 26
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 26

```
aaagccacca tggaagatgc taaaaacatt aagaaggggc ctgctccttt ctaccctctt     60
gaagatggga ctgctggcga gcaacttcac aaagctatga agcggtatgc tcttgtgcca    120
ggcacaattg cgttcacgga tgctcacatt gaggtggaca tcacatacgc tgagtatttt    180
gagatgtcgg tgcggctggc agaagctatg aagcgctatg gctgaatac aaaccataga     240 attgtagtgt gcagtgagaa ctcgttgcag ttctttatgc ccgtgctggg ggctctcttc    300
atcggggtgg ctgtggctcc tgctaacgac atctacaacg agcgagagct gttgaactcg    360
atggggattt ctcagcctac agtggtgttt gtgagtaaga aagggcttca aaagattctc    420
aatgtgcaaa agaagctgcc tattattcaa aagattatta ttatgactc taagaccgac    480 taccagggt ttcagtctat gtatacattt gtgacatctc atctgcctcc tggcttcaac    540
gagtacgact tcgtgcccga gtctttcgac agagataaga caattgctct gatcatgaat   600
tcatcccggt ctaccgggct gcctaagggt gtagctctgc cccatagaac agcttgtgtg    660
agattttctc atgctaggga cctatttttt gggaatcaga ttattcctga cactgctatt    720
ctgtcggtgg tgcccttcca tcatgggttt gggatgttta caacactggg ctacctaata    780
tgtgggttta gagtggtgct catgtatagg tttgaagaag agctgttctt acgctctttg    840
caagattata agattcagtc tgctctgctg gtgccaacac tattctcttt ttttgctaag    900
tctacgctca tagacaagta tgacttgtcc aacttgcacg agattgcttc tggcggagca    960
cctctgtcta aggaggtagg tgaggctgtg gctaagcgct ttcatctgcc tggtatcaga   1020
caggggtatg ggctaacaga aacaacatct gctattctga ttacaccaga ggggatgat    1080
```

```
aagcccgggg ctgtagggaa agtggtgccc ttttttgaag ccaaagtagt tgatcttgat   1140
accggtaaga cactaggggt gaaccagcgt ggtgaactgt gtgtgagagg gcctatgatt   1200
atgtcggggt acgttaacaa ccccgaagct acaaatgctc tgattgataa ggatggctgg   1260
ctgcattcgg gcgacattgc ttactgggat gaggatgagc atttcttcat cgtggacaga   1320
ctgaagtcgt tgatcaaata caaggggtat caagtagctc ctgctgagct ggaatccatt   1380
ctgcttcaac atcccaacat tttcgatgct ggggtggctg ggctgcctga tgatgatgct   1440
ggggagttgc ctgctgctgt agtggtgctt gagcacggta agacaatgac agagaaggag   1500
atcgtggatt atgtggcttc acaagtgaca acagctaaga aactgagagg tggcgttgtg   1560
tttgtggatg aggtgcctaa agggctcact ggcaagctgg atgctagaaa aattcgagag   1620
attctgatta aggctaagaa gggtggaaag attgctgtgt aatagttcta ga           1672

<210> SEQ ID NO 27
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 27
aaagccacca tggaagatgc taaaaacatt aagaaggggc tgctcccctt ctaccctctt     60
gaagatggga ctgctggcga gcaacttcac aaagctatga agcggtatgc tcttgtgcca    120
ggcacaattg cgttcacgga tgctcacatt gaggtggaca tcacatacgc tgagtatttt    180
gagatgtcgg tgcggctggc agaagctatg aagcgctatg gctgaataca aaaccataga    240
attgtagtgt gcagtgagaa ctcgttgcag ttctttatgc ccgtgctggg ggctctcttc    300
atcggggtgg ctgtggctcc tgctaacgac atctacaacg agcgagagct gttgaactcg    360
atggggatct ctcagcctac agtggtgttt gtgagtaaga aagggcttca aaagattctc    420
aatgtgcaaa agaagctgcc tattattcaa aagattatta ttatggactc taagacagac    480
taccaggggt tcagtccatg tatacattt gtgacatctc atctgcctcc tggcttcaac    540
gagtacgact tcgtgcccga gtctttcgac agagataaga caattgctct gatcatgaat    600
tcatccgggt ctaccgggct gcctaagggt gtagctctgc cccatcgaac agcttgtgtg    660
agattctctc atgccaggga cccgatcttt gggaatcaga ttattcctga cactgctatt    720
ctgtcggtgg tgcccttca tcatgggttt gggatgttta caacactggg ataccctaata   780 tgtgggttta gagtggtgct catgtatagg tttgaagaag aactgttctt acgctctttg    840
caagattata agattcagtc tgctctgctg gtgccaacac tattctcttt ttttgctaag    900
tctacgctca tagacaagta tgacttgtcc aacttgcacg agattgcttc tggcggagca    960
cctctgtcta aggaggtagg tgaggctgtg gctaagcgct tcatctgcc tggtatcaga   1020 cagggggtacg gctaacaga aacaacttct gctattctga ttacaccaga gggcgatgac   1080
aagcccgggg ctgtagggaa agtggtgccc ttttttgaag ccaaagtagt tgatcttgat   1140
accggtaaga cactaggggt gaaccagcgt ggtgaactgt gtgtgcgggg ccctatgatt   1200
atgtcggggt acgttaacaa ccccgaagct acaaatgctc ttattgataa ggatggctgg   1260
ttgcattcgg gcgacattgc ctactgggat gaggatgagc atttcttcat cgtggacaga   1320
ctgaagtcgt tgatcaaata caaggggtat caagtagctc ctgctgagct ggaatccatt   1380
ctgcttcaac atcccaaacat tttcgatgct ggggtggctg ggctgcctga tgatgatgct   1440
ggagagttgc ctgctgctgt agtagtgctt gagcacggta agacaatgac agagaaggag   1500
```

| | |
|---|---|
| atcgtggatt atgtggcttc acaagtgaca acagctaaga aactgagagg tggcgttgtg | 1560 |
| tttgtggatg aggtgcctaa agggctcact ggcaagctgg atgccagaaa aattcgagag | 1620 |
| attctcatta aggctaagaa gggtggaaag attgctgtgt aatagttcta ga | 1672 |

<210> SEQ ID NO 28
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 28

| | |
|---|---|
| aaagccacca tggaagatgc taaaaacatt aagaaggggc tgctcccctt ctaccctctt | 60 |
| gaagatggga ctgctggcga gcaacttcac aaagctatga agcggtatgc tcttgtgcca | 120 |
| ggcacaattg cgttcacgga tgctcacatt gaggtggaca tcacatacgc tgagtatttt | 180 |
| gagatgtcgg tgcggctggc agaagctatg aagcgctatg gctgaatac aaaccataga | 240 |
| attgtagtgt gcagtgagaa ctcgttgcag ttctttatgc ccgtgctggg ggctctcttc | 300 |
| atcggggtgg ctgtggctcc tgctaacgac atctacaacg agcgagagct gttgaactcg | 360 |
| atggggatct ctcagcctac agtggtgttt gtgagtaaga aagggcttca aaagattctc | 420 |
| aatgtgcaaa agaagctgcc tattatacaa aagattatta ttatggactc taagaccgac | 480 |
| taccaggggt ttcagtccat gtacacattt gtaacctctc atctgcctcc tggcttcaac | 540 |
| gagtacgact tcgtgcccga gtctttcgac agggacaaaa cgattgctct gatcatgaac | 600 |
| tcatccgggt ctaccgggct gcctaagggt gtagctctgc cccatcgaac agcttgtgtg | 660 |
| agattctctc atgccaggga cccgatcttt gggaatcaga ttattcctga cactgctatt | 720 |
| ctgtcggtgg tgcccttca tcatgggttt gggatgttca caacactggg atacctcatt | 780 |
| tgcgggttta gagtggtgct catgtatagg tttgaagaag aactattcct acgctctttg | 840 |
| caagattata agattcagtc tgctctgctg gtgccaacac tattctcttt ttttgctaag | 900 |
| tctacgctca tagacaagta tgacttgtcc aacttgcacg agattgcttc tggcggagca | 960 |
| cctctgtcta aggaggtagg tgaggctgtg gctaagcgct tcatctgcc tggtatcaga | 1020 |
| caggggtacg gctaacaga acaacttct gctattctga ttacaccaga gggcgatgac | 1080 |
| aaacccgggg ctgtagggaa agtggtgccc tttttgaag ccaaagtagt tgatcttgat | 1140 |
| accggtaaga cactaggggt gaaccagcgt ggtgaactgt gtgtgcgggg ccctatgatt | 1200 |
| atgtcggggt acgttaacaa ccccgaagct acaaatgctc ttattgataa ggatggctgg | 1260 |
| ttgcattcgg gcgacattgc ctactgggat gaggatgagc atttcttcat cgtggacaga | 1320 |
| ctgaagtcgt tgatcaaata caaggggtat caagtagctc ctgctgagct ggaatccatt | 1380 |
| ctgcttcaac atcctaacat tttcgatgct ggggtggctg gctgcctga tgatgatgct | 1440 |
| ggagagttgc ctgctgctgt agtagtgctt gagcacggta agacaatgac agagaaggag | 1500 |
| atcgtggatt atgtggcttc acaagtgaca acagctaaga aactgagagg tggcgttgtg | 1560 |
| tttgtggatg aggtgcctaa agggctcact ggcaagctgg atgccagaaa aattcgagag | 1620 |
| attctcatta aggctaagaa gggtggaaag attgctgtgt aatagttcta ga | 1672 |

<210> SEQ ID NO 29
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 29

```
aaagccacca tggaagatgc caaaaacatt aagaaggggc tgctcccctt ctaccctctt      60
gaagatggga ctgctggcga gcaacttcac aaagctatga agcggtatgc tcttgtgcca     120
ggcacaattg cgttcacgga tgctcacatt gaagtagaca tcacatacgc tgagtatttt     180
gagatgtcgg tgcggctggc agaagctatg aagcgctatg gctgaataca aaaccataga     240
attgtagtgt gcagtgagaa ctcgttgcag ttctttatgc ccgtgctggg ggctctcttc     300
atcggggtgg ctgtggctcc tgctaacgac atctacaacg agcgagagct gttgaactcg     360
atggggatct ctcagcctac agtggtgttt gtgagtaaga aagggcttca aaagattctc     420
aatgtgcaaa agaagctgcc tattatacaa aagattatta ttatggactc taagaccgac     480
taccaggggt ttcagtccat gtacacattt gtaacctctc atctgcctcc tggcttcaac     540
gagtacgact tcgtgcccga gtctttcgac agggacaaaa cgattgctct gatcatgaac     600
agctccgggc tccgggct gcctaagggt gtagctctgc ccatcgaac agcttgtgtg         660
agattctctc atgccaggga cccgatcttt ggaaaccaga tcatccctga cactgctatt     720
ctgtcggtgg tgcccttca tcatgggttt gggatgttca caacactggg atacctcatt     780
tgcgggttta gagtggtgct catgtatagg tttgaagaag aactattcct acgctctttg     840
caagattata agattcagtc tgctctgctg gtgccaacac tattctcttt ttttgctaag     900
tctacgctca tagacaagta tgacttgtcc aacttgcacg agattgcttc tggcggagca     960
cctctgtcta aggaggtagg tgaggctgtg gctaagcgct tcatctgcc tggtatcaga    1020
cagggggtacg gctaacaga aacaacttct gctattctga ttacaccaga gggcgatgac    1080
aaacccgggg ctgtagggaa agtggtgccc tttttttgaag ccaaagtagt tgatcttgat   1140
accggtaaga cactaggggt gaaccagcgt ggtgaactgt gtgtgcgggg ccctatgatt    1200
atgtcgggt acgttaacaa ccccgaagct acaaatgctc tcatagacaa ggacgggtgg    1260
cttcatagcg gcgacattgc ctactgggac gaggatgagc atttcttcat cgtggacaga    1320
ctgaagtcgt tgatcaaata caaggggtat caagtagctc ctgctgagct ggaatccatt    1380
ctgcttcaac accccaatat cttcgatgct ggggtggctg gctgcctga tgatgatgct      1440
ggagagctgc ctgctgctgt agtagtgctt gagcacggta agacaatgac agagaaggag    1500
atcgtggatt atgtggcttc acaagtgaca acagctaaga aactgagagg tggcgttgtg    1560
tttgtggatg aggtgcctaa agggctcact ggcaagctgg atgccagaaa aattcgagag    1620
attctcatta aggctaagaa gggtggaaag attgctgtgt aatagttcta ga            1672
```

<210> SEQ ID NO 30
<211> LENGTH: 1056
<212> TYPE: DNA
<213> ORGANISM: Artificial Sequence
<220> FEATURE:
<223> OTHER INFORMATION: A synthetic construct.

<400> SEQUENCE: 30

```
ccactcagtg gccaccatga agaagcccga gctgaccgct accagcgttg agaagttcct      60
gatcgagaag ttcgacagcg tgagcgacct gatgcagtta agcgagggcg aggaaagccg    120
cgccttcagc ttcgatgtcg gcggacgcgg ctatgtactc cgggtgaata gctgcgctga    180
tggcttctac aaagaccgct acgtgtaccg ccacttcgcc agcgctgcac tgcccatccc    240
cgaggtgctg gacatcggcg agttcagcga gagcctgaca tactgcatca gccgccgcgc    300
tcaaggcgtg actctccaag acctgcccga gacagagctg cccgctgtgc tacagcctgt    360
```

| | |
|---|---|
| cgccgaggct atggacgcta ttgccgccgc cgacctgagc cagaccagcg gcttcggccc | 420 |
| attcgggccc caaggcatcg gccagtacac cacctggcgc gacttcatct gcgccattgc | 480 |
| tgatccccat gtctaccact ggcagaccgt gatggacgac accgtgagcg ccagcgtagc | 540 |
| tcaagccctg gacgagctga tgctgtgggc cgaggactgc cccgaggtgc gccatctcgt | 600 |
| ccatgccgac ttcggcagca acaacgtcct gaccgacaac ggccgcatca ccgccgtaat | 660 |
| cgactggagc gaggccatgt tcggggacag tcagtacgag gtggccaaca tcttcttctg | 720 |
| gcggccctgg ctggcctgca tggagcagca aacccgctac ttcgagcgcc gccatcccga | 780 |
| gctggccggc agccccgtc tgcgagccta catgctgcgc atcggcctgg atcagctcta | 840 |
| ccagagcctc gtggacggca acttcgacga tgctgcctgg gctcaaggcc gctgcgatgc | 900 |
| catcgtccgc agcggggccg gcaccgtcgg tcgcacacaa atcgctcgcc ggagcgccgc | 960 |
| cgtatggacc gacggctgcg tcgaggtgct ggccgacagc ggcaaccgcc ggcccagtac | 1020 |
| acgaccgcgc gctaaggagt agtaaccagc tcttgg | 1056 |

<210> SEQ ID NO 31
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 31

| | |
|---|---|
| aaagccacca tggaagatgc caaaaacatt aagaaggggc tgctcccctt ctaccctctt | 60 |
| gaagatggga ctgctggcga gcaacttcac aaagctatga gcggtatgc tcttgtgcca | 120 |
| gggacaattg cgttcacgga tgctcacatt gaagtagaca tcacatacgc tgagtatttt | 180 |
| gagatgtcgg tgcggctggc agaagctatg aagcgctatg gctgaatac aaaccataga | 240 |
| attgtagtgt gcagtgagaa ctcgttcag ttctttatgc ccgtgctggg ggctctcttc | 300 |
| atcggggtgg ctgtggctcc tgctaacgac atctacaacg agcgagagct gttgaactcg | 360 |
| atggggatct ctcagcctac agtggtgttt gtgagtaaga aagggcttca aaagattctc | 420 |
| aatgtgcaaa agaagctacc gatcatacaa aagatcatca tcatggatag caagaccgac | 480 |
| taccaggggt tcagtccat gtacacattt gtaacctctc atctgcctcc tggcttcaac | 540 |
| gagtacgact tcgtgcccga gtctttcgac agggacaaaa cgattgctct gatcatgaac | 600 |
| agctccgggc taccgggct gcctaagggt gtagctctgc cccatcgaac agcttgtgtg | 660 |
| agattctctc atgccaggga cccgatcttt ggaaaccaga tcatccctga cactgctatt | 720 |
| ctgtcggtgg tgcccttca tcatgggttt gggatgttca caacactggg atacctcatt | 780 |
| tgcgggttta gagtggtgct catgtatagg tttgaagaag aactattcct acgctctttg | 840 |
| caagattata agattcagtc tgctctgctg gtgccaacac tattctcttt ttttgctaag | 900 |
| tctacgctca tagacaagta tgacttgtcc aacttgcacg agattgcttc tggcggagca | 960 |
| cctctgtcta aggaggtagg tgaggctgtg gctaagcgct tcatctgcc tggtatcaga | 1020 |
| cagggggtacg ggctaacaga aacaacttct gctattctga ttacaccaga gggcgatgac | 1080 |
| aaacctgggg ctgtagggaa agtggtgccc ttttttgaag ccaaagtagt tgatcttgat | 1140 |
| accggtaaga cactagggt gaaccagcgt ggtgaactgt gtgtgcgggg ccctatgatt | 1200 |
| atgtcggggt acgttaacaa ccccgaagct acaaatgctc tcatagacaa ggacgggtgg | 1260 |
| cttcatagcg gcgacattgc ctactgggac gaggatgagc atttcttcat cgtggacaga | 1320 |
| ctgaagtcgt tgatcaaata caaggggtat caagtagctc ctgccgagct tgagtccatt | 1380 |

| | | |
|---|---|---|
| ctgcttcaac accccaatat cttcgatgct ggggtggctg ggctgcctga tgatgatgct | 1440 | |
| ggagagctgc ctgctgctgt agtagtgctt gagcatggta agacaatgac agagaaggag | 1500 | |
| atcgtggatt atgtggcttc acaagtgaca acagctaaga aactccgagg tggcgttgtg | 1560 | |
| tttgtggatg aggtgcctaa agggctcact ggcaagctgg atgccagaaa aattcgagag | 1620 | |
| attctcatta aggctaagaa gggtggaaag attgctgtgt aatagttcta ga | 1672 | |

<210> SEQ ID NO 32
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 32

| | | |
|---|---|---|
| aaagccacca tggaagatgc caaaaacatt aagaagggc ctgctccctt ctaccctctt | 60 | |
| gaagatggga ctgctggcga gcaacttcac aaagctatga agcggtatgc tcttgtgcca | 120 | |
| gggacaattg cgttcacgga tgctcacatt gaagtagaca tcacatacgc tgagtatttt | 180 | |
| gagatgtcgg tgcggctggc agaagctatg aagcgctatg gctgaatac aaaccataga | 240 | |
| attgtagtgt gcagtgagaa ctcgttgcag ttctttatgc ccgtgctggg ggctctcttc | 300 | |
| attggggtgg ctgtggctcc tgctaatgac atctacaacg agcgagagct gttgaacagt | 360 | |
| atggggatct ctcagcctac agtggtgttt gtgagtaaga aagggcttca aaagattctc | 420 | |
| aatgtgcaaa agaagctacc gatcatacaa aagatcatca tcatggatag caagaccgac | 480 | |
| taccaggggt ttcagtccat gtacacattt gtaacctctc atctgcctcc tggcttcaat | 540 | |
| gagtatgact tcgtgcccga gtctttcgac agggacaaaa cgattgctct gatcatgaac | 600 | |
| agcagtgggt ctaccgggct gcctaagggt gtagctctgc cccatcgaac agcttgtgtg | 660 | |
| agattctctc atgccaggga cccgatcttt ggaaaccaga tcatccctga cactgctatt | 720 | |
| ctgtcggtgg tgcccttca tcatgggttt gggatgttca acactgggg atacctcatt | 780 | |
| tgcgggttta gagtggtgct catgtatagg tttgaagaag aactattcct acgctctttg | 840 | |
| caagattata agattcagtc tgctctgctg gtgccaacac tattctcttt ttttgctaag | 900 | |
| tctacgctca tagacaagta tgacttgtcc aacttgcacg agattgcttc tggcggagca | 960 | |
| cctctgtcta aggaggtagg tgaggctgtg gctaagcgct tcatctgcc tggtatcaga | 1020 | |
| caggggtacg gctaacaga aacaacttct gctattctga ttacaccaga gggcgatgac | 1080 | |
| aaacctgggg ctgtagggaa agtggtgccc ttttttgaag ccaaagtagt tgatcttgat | 1140 | |
| accggtaaga cactagggt gaaccagaga ggtgaattgt gtgtgagggg ccctatgatt | 1200 | |
| atgtcgggt acgttaacaa ccccgaagct acaaatgctc tcatagacaa ggacgggtgg | 1260 | |
| cttcatagtg gagatattgc ctactgggat gaagatgagc atttcttcat cgtggacaga | 1320 | |
| ctgaagtcgt tgatcaaata caaggggtat caagtagctc ctgccgagct tgagtccatt | 1380 | |
| ctgcttcaac accccaatat cttcgatgct ggggtggctg gctgcctga tgatgatgct | 1440 | |
| ggagagctgc ctgctgctgt agtagtgctt gagcatggta agacaatgac agagaaggag | 1500 | |
| atcgtggatt atgtggcttc acaagtgaca acagctaaga aactccgagg tggcgttgtg | 1560 | |
| tttgtggatg aggtgcctaa agggctcact ggcaagctgg atgccagaaa aattcgagag | 1620 | |
| attctcatta aggctaagaa gggtggaaag attgctgtgt aatagttcta ga | 1672 | |

<210> SEQ ID NO 33
<211> LENGTH: 1672

<212> TYPE: DNA
<213> ORGANISM: Artificial Sequence
<220> FEATURE:
<223> OTHER INFORMATION: A synthetic construct.

<400> SEQUENCE: 33

| | | | | | |
|---|---|---|---|---|---|
| aaagccacca | tggaagatgc | caaaaacatt | aagaaggggc | ctgctcccctt | ctaccctctt | 60 |
| gaagatggga | ctgctggcga | gcaacttcac | aaagctatga | agcggtatgc | tcttgtgcca | 120 |
| gggacaattg | cgttcacgga | tgctcacatt | gaagtagaca | tcacatacgc | tgagtatttt | 180 |
| gagatgtcgg | tgcggctggc | agaagctatg | aagcgctatg | ggctgaatac | aaaccataga | 240 |
| attgtagtgt | gcagtgagaa | ctcgttgcag | ttctttatgc | ccgtgctggg | ggctctcttc | 300 |
| attggggtgg | ctgtggctcc | tgctaatgac | atctacaacg | agcgagagct | gttgaacagt | 360 |
| atggggatct | ctcagcctac | agtggtgttt | gtgagtaaga | aagggcttca | aaagattctc | 420 |
| aatgtgcaaa | agaagctacc | gatcatacaa | aagatcatca | tcatggatag | caagaccgac | 480 |
| taccaggggt | ttcagtccat | gtacacattt | gtaacctctc | atctgcctcc | tggcttcaat | 540 |
| gagtatgact | tcgtgcccga | gtctttcgac | agggacaaaa | cgattgctct | gatcatgaac | 600 |
| agcagtgggg | ctaccgggct | gcctaagggt | gtagctctgc | cccatcgaac | agcttgtgtg | 660 |
| agattctctc | atgccaggga | cccgatcttt | ggaaaccaga | tcatccctga | cactgctatt | 720 |
| ctgtcggtgg | tgcccttca | tcatgggttt | gggatgttca | aacactggg | atacctcatt | 780 |
| tgcgggttta | gagtggtgct | catgtatagg | tttgaagaag | aactattcct | acgctctttg | 840 |
| caagattata | agattcagtc | tgctctgctg | gtgccaacac | tattctcttt | ttttgctaag | 900 |
| tctacgctca | tagacaagta | tgacttgtcc | aacttgcacg | agattgcttc | tggcggagca | 960 |
| cctctgtcta | aggaggtagg | tgaggctgtg | gctaagcgct | tcatctgcc | tggtatcaga | 1020 |
| caggggtacg | ggctaacaga | aacaacttct | gctattctga | ttacaccaga | gggcgatgac | 1080 |
| aaacctgggg | ctgtagggaa | agtggtgccc | tttttgaag | ccaaagtagt | tgatcttgat | 1140 |
| accggtaaga | cactaggggt | gaaccagaga | ggtgaattgt | gtgtgagggg | ccctatgatt | 1200 |
| atgtcgggt | acgttaacaa | ccccgaagct | acaaatgctc | tcatagacaa | ggacgggtgg | 1260 |
| cttcatagtg | gagatattgc | ctactgggat | gaagatgagc | atttcttcat | cgtggacaga | 1320 |
| ctgaagtcgt | tgatcaaata | caaggggtat | caagtagctc | ctgccgagct | tgagtccatt | 1380 |
| ctgcttcaac | accccaatat | cttcgatgct | ggggtggctg | ggctgcctga | tgatgatgct | 1440 |
| ggagagctgc | ctgctgctgt | agtagtgctt | gagcatggta | agacaatgac | agagaaggag | 1500 |
| atcgtggatt | atgtggcttc | acaagtgaca | acagctaaga | aactccgagg | tggcgttgtg | 1560 |
| tttgtggatg | aggtgcctaa | aggactcact | ggcaagctgg | atgccagaaa | aattcgagag | 1620 |
| attctcatta | aggctaagaa | gggtggaaag | attgctgtgt | aatagttcta | ga | 1672 |

<210> SEQ ID NO 34
<211> LENGTH: 10
<212> TYPE: DNA
<213> ORGANISM: Artificial Sequence
<220> FEATURE:
<223> OTHER INFORMATION: A synthetic construct.

<400> SEQUENCE: 34
gccaccatga        10

<210> SEQ ID NO 35
<211> LENGTH: 11
<212> TYPE: DNA
<213> ORGANISM: Artificial Sequence

```
<220> FEATURE:
<223> OTHER INFORMATION: A synthetic construct.
<220> FEATURE:
<221> NAME/KEY: misc_feature
<222> LOCATION: 4, 5, 6, 7, 8
<223> OTHER INFORMATION: n = A,T,C or G

<400> SEQUENCE: 35
ccannnnntg g                                                             11

<210> SEQ ID NO 36
<211> LENGTH: 25
<212> TYPE: DNA
<213> ORGANISM: Artificial Sequence
<220> FEATURE:
<223> OTHER INFORMATION: A synthetic construct.
<220> FEATURE:
<221> NAME/KEY: misc_feature
<222> LOCATION: 1, 2, 3, 4, 5, 9, 10, 11, 12, 13
<223> OTHER INFORMATION: n = A,T,C or G

<400> SEQUENCE: 36
nnnnnccann nnntggccac catgg                                              25

<210> SEQ ID NO 37
<211> LENGTH: 20
<212> TYPE: DNA
<213> ORGANISM: Artificial Sequence
<220> FEATURE:
<223> OTHER INFORMATION: A synthetic construct.
<220> FEATURE:
<221> NAME/KEY: misc_feature
<222> LOCATION: 10, 11, 12, 13, 14, 18, 19, 20
<223> OTHER INFORMATION: n = A,T,C or G

<400> SEQUENCE: 37
taataaccan nnnntggnnn                                                    20

<210> SEQ ID NO 38
<211> LENGTH: 825
<212> TYPE: DNA
<213> ORGANISM: Artificial Sequence
<220> FEATURE:
<223> OTHER INFORMATION: A synthetic construct.

<400> SEQUENCE: 38
ccactcagtg gccaccatga tcgagcagga cggcctccat gctggcagtc ccgcagcctg        60
ggtcgagcgc ttgttcgggt acgactgggc ccagcagacc atcggatgta gcgatgccgc       120
agtgttccgc ctgagcgctc aaggccggcc cgtgctgttc gtgaagaccg acctgagcgg       180
cgccctgaac gagcttcaag acgaggctgc ccgcctgagc tggctggcca ccaccggtgt       240
accctgcgcc gctgtgttgg atgttgtgac cgaagccggc cgcgactggc tgctgctggg       300
cgaggtgcct ggccaggacc tgctgagcag ccacctggcc cccgctgaga aggtgagcat       360
catggccgac gccatgcggc gcctgcacac cctggacccc gctacatgcc ccttcgacca       420
ccaggctaag caccgcatcg agcgggctcg acccgcatg gaggccggcc tggtggacca       480
ggacgacctg gacgaggagc accagggcct ggccccgct gaactgttcg cccgcctgaa       540
agcccgcatg ccggacggtg aggacctggt tgtgacacac ggcgacgcct gcctccctaa       600
catcatggtc gagaacgggc gcttctccgg cttcatcgac tgcggccgcc tgggcgttgc       660
cgaccgctac caggacatcg ccctggccac ccgcgacatc gccgaggagc tgggcggcga       720
gtgggccgac cgcttcctgg tcttgtacgg catcgcagct cccgacagcc agcgcatcgc       780
cttctaccgc ctgctggacg agttcttcta gtaaccaggc tctgg                      825
```

<210> SEQ ID NO 39
<211> LENGTH: 825
<212> TYPE: DNA
<213> ORGANISM: Artificial Sequence
<220> FEATURE:
<223> OTHER INFORMATION: A synthetic construct.

<400> SEQUENCE: 39

| | | | | | |
|---|---|---|---|---|---|
| ccactccgtg | gccaccatga | tcgaacaaga | cggcctccat | gctggcagtc | ccgcagcttg | 60 |
| ggtcgaacgc | ttgttcgggt | acgactgggc | ccagcagacc | atcggatgta | gcgatgcggc | 120 |
| cgtgttccgt | ctaagcgctc | aaggccggcc | cgtgctgttc | gtgaagaccg | acctgagcgg | 180 |
| cgccctgaac | gagcttcaag | acgaggctgc | ccgcctgagc | tggctggcca | ccaccggtgt | 240 |
| accctgcgcc | gctgtgttgg | atgttgtgac | cgaagccggc | cgggactggc | tgctgctggg | 300 |
| cgaggtccct | ggccaggatc | tgctgagcag | ccaccttgcc | ccgctgaga | aggtttccat | 360 |
| catggccgat | gcaatgcggc | gcctgcacac | cctggacccc | gctacatgcc | ccttcgacca | 420 |
| ccaggctaag | catcggatcg | agcgtgctcg | gacccgcatg | gaggccggcc | tggtggacca | 480 |
| ggacgacctg | gacgaggagc | atcagggcct | ggccccgct | gaactgttcg | cccgcctgaa | 540 |
| agcccgcatg | ccggacggtg | aggacctggt | tgtgacacat | ggagatgcct | gcctccctaa | 600 |
| catcatggtc | gagaatggcc | gcttctccgg | cttcatcgac | tgcggtcgcc | taggagttgc | 660 |
| cgaccgctac | caggacatcg | ccctggccac | ccgcgacatc | gctgaggagc | ttggcggcga | 720 |
| gtgggccgac | cgcttcttag | tcttgtacgg | catcgcagct | cccgcacagcc | agcgcatcgc | 780 |
| cttctaccgc | ctgctcgacg | agttcttta | atgaccaggc | tctgg | | 825 |

<210> SEQ ID NO 40

<400> SEQUENCE: 40

000

<210> SEQ ID NO 41
<211> LENGTH: 861
<212> TYPE: DNA
<213> ORGANISM: Escherichia coli

<400> SEQUENCE: 41

| | | | | | |
|---|---|---|---|---|---|
| atgagtattc | aacatttccg | tgtcgccctt | attcccttt | ttgcggcatt | ttgccttcct | 60 |
| gtttttgctc | acccagaaac | gctggtgaaa | gtaaaagatg | ctgaagatca | gttgggtgca | 120 |
| cgagtgggtt | acatcgaact | ggatctcaac | agcggtaaga | tccttgagag | ttttcgcccc | 180 |
| gaagaacgtt | ttccaatgat | gagcactttt | aaagttctgc | tatgtggcgc | ggtattatcc | 240 |
| cgtattgacg | ccgggcaaga | gcaactcggt | cgccgcatac | actattctca | gaatgacttg | 300 |
| gttgagtact | caccagtcac | agaaaagcat | cttacggatg | gcatgacagt | aagagaatta | 360 |
| tgcagtgctg | ccataaccat | gagtgataac | actgcggcca | acttacttct | gacaacgatc | 420 |
| ggaggaccga | aggagctaac | cgcttttttg | cacaacatgg | gggatcatgt | aactcgcctt | 480 |
| gatcgttggg | aaccggagct | gaatgaagcc | ataccaaacg | acgagcgtga | ccacacgatg | 540 |
| cctgtagcaa | tggcaacaac | gttgcgcaaa | ctattaactg | gcgaactact | tactctagct | 600 |
| tcccggcaac | aattaataga | ctggatggag | gcggataaag | ttgcaggacc | acttctgcgc | 660 |
| tcggcccttc | cggctggctg | gtttattgct | gataaatctg | gagccggtga | gcgtgggtct | 720 |
| cgcggtatca | ttgcagcact | ggggccagat | ggtaagccct | cccgtatcgt | agttatctac | 780 |

| | |
|---|---|
| acgacgggga gtcaggcaac tatggatgaa cgaaatagac agatcgctga gataggtgcc | 840 |
| tcactgatta agcattggta a | 861 |

<210> SEQ ID NO 42
<211> LENGTH: 1056
<212> TYPE: DNA
<213> ORGANISM: Artificial Sequence
<220> FEATURE:
<223> OTHER INFORMATION: A synthetic construct.

<400> SEQUENCE: 42

| | |
|---|---|
| ccactccgtg gccaccatga agaagcccga gctgaccgct accagcgttg aaaaatttct | 60 |
| catcgagaag ttcgacagtg tgagcgacct gatgcagttg tcggagggcg aagagagccg | 120 |
| agccttcagc ttcgatgtcg gcggacgcgg ctatgtactg cgggtgaata gctgcgctga | 180 |
| tggcttctac aaagaccgct acgtgtaccg ccacttcgcc agcgctgcac tacccatccc | 240 |
| cgaagtgttg gacatcggcg agttcagcga gagcctgaca tactgcatca gtagacgcgc | 300 |
| ccaaggcgtt actctccaag acctccccga aacagagctg cctgctgtgt tacagcctgt | 360 |
| cgccgaagct atggatgcta ttgccgccgc cgacctcagt caaaccagcg gcttcggccc | 420 |
| attcgggccc caaggcatcg gccagtacac aacctggcgg gatttcattt gcgccattgc | 480 |
| tgatccccat gtctaccact ggcagaccgt gatggacgac accgtgtccg ccagcgtagc | 540 |
| tcaagccctg gacgaactga tgctgtgggc cgaagactgt cccgaggtgc gccacctcgt | 600 |
| ccatgccgac ttcggcagca caacgtcct gaccgacaac ggccgcatca ccgccgtaat | 660 |
| cgactggagc gaggctatgt tcggggacag tcagtacgag gtggccaaca tcttcttctg | 720 |
| gcggccctgg ctggcttgca tggagcagca gactcgctac ttcgagcgcc ggcatcccga | 780 |
| gctggccggc agccctcgtc tgcgagccta catgctgcgc atcggcctgg atcagctcta | 840 |
| ccagagcctc gtggacggca acttcgacga tgctgcctgg gctcaaggcc gctgcgatgc | 900 |
| catcgtccgc agcggggccg gcaccgtcgg tcgcacacaa atcgctcgcc ggagcgccgc | 960 |
| cgtatggacc gacggctgcg tcgaggtgct ggccgacagc ggcaaccgcc ggcccagtac | 1020 |
| acgaccgcgc gctaaggagt agtaaccagc tcttgg | 1056 |

<210> SEQ ID NO 43
<211> LENGTH: 1653
<212> TYPE: DNA
<213> ORGANISM: Artificial Sequence
<220> FEATURE:
<223> OTHER INFORMATION: A synthetic construct.

<400> SEQUENCE: 43

| | |
|---|---|
| atggaagacg ccaaaaacat aaagaaaggc ccggcgccat tctatccgct ggaagatgga | 60 |
| accgctggag agcaactgca taaggctatg aagagatacg ccctggttcc tggaacaatt | 120 |
| gcttttacag atgcacatat cgaggtggac atcacttacg ctgagtactt cgaaatgtcc | 180 |
| gttcggttgg cagaagctat gaaacgatat gggctgaata caaatcacag aatcgtcgta | 240 |
| tgcagtgaaa actctcttca attctttatg ccggtgttgg gcgcgttatt tatcggagtt | 300 |
| gcagttgcgc ccgcgaacga catttataat gaacgtgaat tgctcaacag tatgggcatt | 360 |
| tcgcagccta ccgtggtgtt cgtttccaaa aaggggttgc aaaaaatttt gaacgtgcaa | 420 |
| aaaaagctcc caatcatcca aaaaattatt atcatggatt ctaaaacgga ttaccaggga | 480 |
| tttcagtcga tgtacacgtt cgtcacatct catctacctc ccggttttaa tgaatacgat | 540 |
| tttgtgccag agtccttcga tagggacaag acaattgcac tgatcatgaa ctcctctgga | 600 |

-continued

```
tctactggtc tgcctaaagg tgtcgctctg cctcatagaa ctgcctgcgt gagattctcg      660
catgccagag atcctatttt tggcaatcaa atcattccgg atactgcgat tttaagtgtt      720
gttccattcc atcacggttt tggaatgttt actacactcg atatttgat atgtggattt       780 cgagtcgtct taatgtatag atttgaagaa gagctgtttc tgaggagcct tcaggattac      840
aagattcaaa gtgcgctgct ggtgccaacc ctattctcct tcttcgccaa aagcactctg      900
attgacaaat acgatttatc taatttacac gaaattgctt ctggtggcgc tcccctctct      960
aaggaagtcg gggaagcggt tgccaagagg ttccatctgc caggtatcag gcaaggatat     1020
gggctcactg agactacatc agctattctg attacacccg aggggatga taaaccgggc      1080 gcggtcggta agttgttcc attttttgaa gcgaaggttg tggatctgga taccgggaaa      1140
acgctgggcg ttaatcaaag aggcgaactg tgtgtgagag gtcctatgat tatgtccggt     1200
tatgtaaaca atccggaagc gaccaacgcc ttgattgaca aggatggatg ctacattct      1260 ggagacatag cttactggga cgaagacgaa cacttcttca tcgttgaccg cctgaagtct     1320
ctgattaagt acaaaggcta tcaggtggct cccgctgaat tggaatccat cttgctccaa    1380 cacccaaca tcttcgacgc aggtgtcgca ggtcttcccg acgatgacgc cggtgaactt     1440
cccgccgccg ttgttgtttt ggagcacgga aagacgatga cggaaaaaga gatcgtggat    1500
tacgtcgcca gtcaagtaac aaccgcgaaa aagttgcgcg gaggagttgt gtttgtggac    1560
gaagtaccga aggtcttac cggaaaaactc gacgcaagaa aaatcagaga gatcctcata   1620
aaggccaaga agggcggaaa gatcgccgtg taa                                 1653
```

<210> SEQ ID NO 44
<211> LENGTH: 1369
<212> TYPE: DNA
<213> ORGANISM: Artificial Sequence
<220> FEATURE:
<223> OTHER INFORMATION: A synthetic construct.

<400> SEQUENCE: 44

```
ggatccgttt gcgtattggg cgctcttccg ctgatctgcg cagcaccatg gcctgaaata      60
acctctgaaa gaggaacttg gttagctacc ttctgaggcg gaaagaacca gctgtggaat    120
gtgtgtcagt tagggtgtgg aaagtcccca ggctccccag caggcagaag tatgcaaagc    180
atgcatctca attagtcagc aaccaggtgt ggaaagtccc caggctcccc agcaggcaga    240
agtatgcaaa gcatgcatct caattagtca gcaaccatag tcccgcccct aactccgccc    300
atcccgcccc taactccgcc cagttccgcc cattctccgc cccatggctg actaattttt    360
tttatttatg cagaggccga ggccgcctct gcctctgagc tattccagaa gtagtgagga    420
ggcttttttg gaggcctagg cttttgcaaa aagctcgatt cttctgacac tagcgccacc    480
atgatcgaac aagacggcct ccatgctggc agtcccgcag cttgggtcga acgcttgttc    540
gggtacgact gggcccagca gaccatcgga tgtagcgatg cggccgtgtt ccgtctaagc    600
gctcaaggcc ggcccgtgct gttcgtgaag accgacctga gcggcgccct gaacgagctt    660
caagacgagg ctgcccgcct gagctggctg gccaccaccg cgtaccctg cgccgctgtg    720 ttggatgttg tgaccgaagc cggccgggac tggctgctgc tgggcgaggt ccctggccag    780
gatctgctga gcagccacct tgcccccgct gagaaggttt ctatcatggc cgatgcaatg    840
cggcgcctgc acaccctgga ccccgctacc tgcccttcg accaccaggc taagcatcgg    900
atcgagcgtg ctcggacccg catggaggcc ggctggtgg accaggacga cctggacgag    960
gagcatcagg gcctggcccc cgctgaactg ttcgcccgac tgaaagcccg catgccggac   1020
```

```
ggtgaggacc tggttgtcac acacggagat gcctgcctcc ctaacatcat ggtcgagaat    1080
ggccgcttct ccggcttcat cgactgcggt cgcctaggag ttgccgaccg ctaccaggac    1140
atcgccctgg ccacccgcga catcgctgag gagcttggcg gcgagtgggc cgaccgcttc    1200
ttagtcttgt acggcatcgc agctcccgac agccagcgca tcgccttcta ccgcttgctc    1260
gacgagttct tttaatgatc tagaaccggt catggccgca ataaaatatc tttattttca    1320
ttacatctgt gtgttggttt tttgtgtgtt cgaactagat gctgtcgac                1369

<210> SEQ ID NO 45
<211> LENGTH: 1214
<212> TYPE: DNA
<213> ORGANISM: Artificial Sequence
<220> FEATURE:
<223> OTHER INFORMATION: A synthetic construct.

<400> SEQUENCE: 45
gcggccgcaa atgctaaacc actgcagtgg ttaccagtgc ttgatcagtg aggcaccgat      60
ctcagcgatc tgcctatttc gttcgtccat agtggcctga ctcccgtcg tgtagatcac     120 tacgattcgt gagggcttac catcaggccc cagcgcagca atgatgccgc gagagccgcg    180
ttcaccggcc cccgatttgt cagcaatgaa ccagccagca gggagggccg agcgaagaag    240
tggtcctgct actttgtccg cctccatcca gtctatgagc tgctgtcgtg atgctagagt    300
aagaagttcg ccagtgagta gttccgaag agttgtggcc attgctactg gcatcgtggt     360
atcacgctcg tcgttcggta tggcttcgtt caactctggt tcccagcggt caagccgggt    420
cacatgatca cccatattat gaagaaatgc agtcagctcc ttagggcctc cgatcgttgt    480
cagaagtaag ttggccgcgg tgttgtcgct catggtaatg gcagcactac acaattctct    540
taccgtcatg ccatccgtaa gatgcttttc cgtgaccggc gagtactcaa ccaagtcgtt    600
ttgtgagtag tgtatacggc gaccaagctg ctcttgcccg gcgtctatac gggacaacac    660
cgcgccacat agcagtactt tgaaagtgct catcatcggg aatcgttctt cggggcggaa    720
agactcaagg atcttgccgc tattgagatc cagttcgata tagcccactc ttgcacccag    780
ttgatcttca gcatctttta ctttcaccag cgtttcgggg tgtgcaaaaa caggcaagca    840
aaatgccgca agaagggaa tgagtgcgac acgaaaatgt tggatgctca tactcttcct    900
ttttcaatat gttgcagca tttgtcaggg ttactagtac gtctctcttg agagaccgcg    960
atcgccacca tgtctaggta ggtagtaaac gaaagggctt aaaggcctaa gtggccctcg    1020
agtccagcct tgagttggtt gagtccaagt cacgtttgga gatctggtac cttacgcgta    1080
tgagggttga gtccaagtca cgtttggaga tctggtacct tacgcgtatg agctctacgt    1140
agctagcggc ctcggcggcc gaattcttgc gttcgaagct tggcaatccg gtactgttgg    1200
taaagccacc atgg                                                     1214

<210> SEQ ID NO 46
<211> LENGTH: 1522
<212> TYPE: DNA
<213> ORGANISM: Artificial Sequence
<220> FEATURE:
<223> OTHER INFORMATION: A synthetic construct.

<400> SEQUENCE: 46
gcggccgcaa atgctaaacc actgcagtgg ttaccagtgc ttgatcagtg aggcaccgat      60
ctcagcgatc tgcctatttc gttcgtccat agtggcctga ctcccgtcg tgtagatcac     120 tacgattcgt gagggcttac catcaggccc cagcgcagca atgatgccgc gagagccgcg    180
```

| | |
|---|---|
| ttcaccggcc cccgatttgt cagcaatgaa ccagccagca gggagggccg agcgaagaag | 240 |
| tggtcctgct actttgtccg cctccatcca gtctatgagc tgctgtcgtg atgctagagt | 300 |
| aagaagttcg ccagtgagta gtttccgaag agttgtggcc attgctactg gcatcgtggt | 360 |
| atcacgctcg tcgttcggta tggcttcgtt caactctggt tcccagcggt caagccgggt | 420 |
| cacatgatca cccatattat gaagaaatgc agtcagctcc ttagggcctc cgatcgttgt | 480 |
| cagaagtaag ttggccgcgg tgttgtcgct catggtaatg gcagcactac acaattctct | 540 |
| taccgtcatg ccatccgtaa gatgcttttc cgtgaccggc gagtactcaa ccaagtcgtt | 600 |
| ttgtgagtag tgtatacggc gaccaagctg ctcttgcccg gcgtctatac gggacaacac | 660 |
| cgcgccacat agcagtactt tgaaagtgct catcatcggg aatcgttctt cggggcggaa | 720 |
| agactcaagg atcttgccgc tattgagatc cagttcgata tagcccactc ttgcacccag | 780 |
| ttgatcttca gcatctttta cttttaccag cgtttcgggg tgtgcaaaaa caggcaagca | 840 |
| aaatgccgca agaagggaa tgagtgcgac acgaaaatgt tggatgctca tactcttcct | 900 |
| ttttcaatat gtttgcagca tttgtcaggg ttactagtac gtctctcaag agatttgtgc | 960 |
| atacacagtg actcatactt tcaccaatac tttgcatttt ggataaatac tagacaactt | 1020 |
| tagaagtgaa ttatttatga ggttgtctta aaattaaaaa ttacaaagta ataaatcaca | 1080 |
| ttgtaatgta ttttgtgtga tacccagagg tttaaggcaa cctattactc ttatgctcct | 1140 |
| gaagtccaca attcacagtc ctgaactata atcttatctt tgtgattgct gagcaaattt | 1200 |
| gcagtataat ttcagtgctt ttaaattttg tcctgcttac tattttcctt ttttatttgg | 1260 |
| gtttgatatg cgtgcacaga atggggcttc tattaaaata ttcttgagag accgcgatcg | 1320 |
| ccaccatgtc taggtaggta gtaaacgaaa gggcttaaag gcctaagtgg ccctcgagtc | 1380 |
| cagccttgag ttggttgagt ccaagtcacg tttggagatc tggtacctta cgcgtatgag | 1440 |
| ctctacgtag ctagcggcct cggcggccga attcttgcgt tcgaagcttg gcaatccggt | 1500 |
| actgttggta aagccaccat gg | 1522 |

<210> SEQ ID NO 47
<211> LENGTH: 1134
<212> TYPE: DNA
<213> ORGANISM: Artificial Sequence
<220> FEATURE:
<223> OTHER INFORMATION: A synthetic construct.

<400> SEQUENCE: 47

| | |
|---|---|
| gcggccgcaa atgctaaacc actgcagtgg ttaccagtgc ttgatcagtg aggcaccgat | 60 |
| ctcagcgatc tgcctatttc gttcgtccat agtggcctga ctccccgtcg tgtagatcac | 120 |
| tacgattcgt gagggcttac catcaggccc cagcgcagca atgatgccgc gagagccgcg | 180 |
| ttcaccggcc cccgatttgt cagcaatgaa ccagccagca gggagggccg agcgaagaag | 240 |
| tggtcctgct actttgtccg cctccatcca gtctatgagc tgctgtcgtg atgctagagt | 300 |
| aagaagttcg ccagtgagta gtttccgaag agttgtggcc attgctactg gcatcgtggt | 360 |
| atcacgctcg tcgttcggta tggcttcgtt caactctggt tcccagcggt caagccgggt | 420 |
| cacatgatca cccatattat gaagaaatgc agtcagctcc ttagggcctc cgatcgttgt | 480 |
| cagaagtaag ttggccgcgg tgttgtcgct catggtaatg gcagcactac acaattctct | 540 |
| taccgtcatg ccatccgtaa gatgcttttc cgtgaccggc gagtactcaa ccaagtcgtt | 600 |
| ttgtgagtag tgtatacggc gaccaagctg ctcttgcccg gcgtctatac gggacaacac | 660 |
| cgcgccacat agcagtactt tgaaagtgct catcatcggg aatcgttctt cggggcggaa | 720 |

| | |
|---|---|
| agactcaagg atcttgccgc tattgagatc cagttcgata tagcccactc ttgcacccag | 780 |
| ttgatcttca gcatcttta ctttcaccag cgtttcgggg tgtgcaaaaa caggcaagca | 840 |
| aaatgccgca agaagggaa tgagtgcgac acgaaaatgt tggatgctca tactcgtcct | 900 |
| ttttcaatat tattgaagca tttatcaggg ttactagtac gtctctcaag agatttgtgc | 960 |
| atacacagtg actcatactt tcaccaatac tttgcatttt ggataaatac tagacaactt | 1020 |
| tagaagtgaa ttatttatga ggttgtctta aaattaaaaa ttacaaagta ataaatcaca | 1080 |
| ttgtaatgta ttttgtgtga tacccagagg tttaaggcaa cctattactc ttat | 1134 |

```
<210> SEQ ID NO 48
<211> LENGTH: 319
<212> TYPE: DNA
<213> ORGANISM: Artificial Sequence
<220> FEATURE:
<223> OTHER INFORMATION: A synthetic construct.

<400> SEQUENCE: 48
```

| | |
|---|---|
| actagtacgt ctctcaagga taagtaagta atattaaggt acgggaggta cttggagcgg | 60 |
| ccgcaataaa atatctttat tttcattaca tctgtgtgtt ggttttttgt gtgaatcgat | 120 |
| agtactaaca tacgctctcc atcaaaacaa aacgaaacaa acaaactag caaaataggc | 180 |
| tgtccccagt gcaagtgcag gtgccagaac atttctctgg cctaagtggc cggtaccgag | 240 |
| ctcgctagcc tcgaggatat cagatctggc ctcggcggcc aagcttggca atccggtact | 300 |
| gttggtaaag ccaccatgg | 319 |

```
<210> SEQ ID NO 49
<211> LENGTH: 320
<212> TYPE: DNA
<213> ORGANISM: Artificial Sequence
<220> FEATURE:
<223> OTHER INFORMATION: A synthetic construct.

<400> SEQUENCE: 49
```

| | |
|---|---|
| actagtacgt ctctcaagga taagtaagta atattaaggt acgggaggta ttggacaggc | 60 |
| cgcaataaaa tatctttatt ttcattacat ctgtgtgttg gttttttgtg tgaatcgata | 120 |
| gtactaacat acgctctcca tcaaaacaaa acgaaacaaa acaaactagc aaaataggct | 180 |
| gtccccagtg caagtgcagg tgccagaaca tttctctggc taactggcc ggtacctgag | 240 |
| ctcgctagcc tcgaggatat caagatctgg cctcggcggc caagcttggc aatccggtac | 300 |
| tgttggtaaa gccaccatgg | 320 |

```
<210> SEQ ID NO 50
<211> LENGTH: 5
<212> TYPE: DNA
<213> ORGANISM: Artificial Sequence
<220> FEATURE:
<223> OTHER INFORMATION: A synthetic construct.

<400> SEQUENCE: 50
```

| | |
|---|---|
| tataa | 5 |

```
<210> SEQ ID NO 51
<211> LENGTH: 6
<212> TYPE: DNA
<213> ORGANISM: Artificial Sequence
<220> FEATURE:
<223> OTHER INFORMATION: A synthetic construct.

<400> SEQUENCE: 51
```

```
stratg                                                              6

<210> SEQ ID NO 52
<211> LENGTH: 9
<212> TYPE: DNA
<213> ORGANISM: Artificial Sequence
<220> FEATURE:
<223> OTHER INFORMATION: A synthetic construct.
<220> FEATURE:
<221> NAME/KEY: misc_feature
<222> LOCATION: 4, 6, 7
<223> OTHER INFORMATION: n = A,T,C or G

<400> SEQUENCE: 52 mttncnnma                                                           9

<210> SEQ ID NO 53
<211> LENGTH: 5
<212> TYPE: DNA
<213> ORGANISM: Artificial Sequence
<220> FEATURE:
<223> OTHER INFORMATION: A synthetic construct.

<400> SEQUENCE: 53 tratg                                                               5

<210> SEQ ID NO 54
<211> LENGTH: 38
<212> TYPE: DNA
<213> ORGANISM: Artificial Sequence
<220> FEATURE:
<223> OTHER INFORMATION: A synthetic construct.

<400> SEQUENCE: 54
gtactgagac gacgccagcc caagcttagg cctgagtg                          38

<210> SEQ ID NO 55
<211> LENGTH: 38
<212> TYPE: DNA
<213> ORGANISM: Artificial Sequence
<220> FEATURE:
<223> OTHER INFORMATION: A synthetic construct.

<400> SEQUENCE: 55
ggcatgagcg tgaactgact gaactagcgg ccgccgag                          38

<210> SEQ ID NO 56
<211> LENGTH: 24
<212> TYPE: DNA
<213> ORGANISM: Artificial Sequence
<220> FEATURE:
<223> OTHER INFORMATION: A synthetic construct.

<400> SEQUENCE: 56
ggatcccatg gtgaagcgtg agaa                                         24

<210> SEQ ID NO 57
<211> LENGTH: 21
<212> TYPE: DNA
<213> ORGANISM: Artificial Sequence
<220> FEATURE:
<223> OTHER INFORMATION: A synthetic construct.

<400> SEQUENCE: 57
ggatcccatg gtgaaacgcg a                                            21

<210> SEQ ID NO 58
```

<211> LENGTH: 31
<212> TYPE: DNA
<213> ORGANISM: Artificial Sequence
<220> FEATURE:
<223> OTHER INFORMATION: A synthetic construct.

<400> SEQUENCE: 58
ctagcttttt tttctagata atcatgaaga c                          31

<210> SEQ ID NO 59
<211> LENGTH: 32
<212> TYPE: DNA
<213> ORGANISM: Artificial Sequence
<220> FEATURE:
<223> OTHER INFORMATION: A synthetic construct.

<400> SEQUENCE: 59
gcgtagccat ggtaaagcgt gagaaaatg tc                          32

<210> SEQ ID NO 60
<211> LENGTH: 33
<212> TYPE: DNA
<213> ORGANISM: Artificial Sequence
<220> FEATURE:
<223> OTHER INFORMATION: A synthetic construct.

<400> SEQUENCE: 60
ccgactctag attactaacc gccggccttc acc                        33

<210> SEQ ID NO 61
<211> LENGTH: 54
<212> TYPE: DNA
<213> ORGANISM: Artificial Sequence
<220> FEATURE:
<223> OTHER INFORMATION: A synthetic construct.

<400> SEQUENCE: 61
caaaaagctt ggcattccgg tactgttggt aaagccacca tggtgaagcg agag  54

<210> SEQ ID NO 62
<211> LENGTH: 26
<212> TYPE: DNA
<213> ORGANISM: Artificial Sequence
<220> FEATURE:
<223> OTHER INFORMATION: A synthetic construct.

<400> SEQUENCE: 62
caattgttgt tgttaacttg tttatt                                26

<210> SEQ ID NO 63

<400> SEQUENCE: 63

000

<210> SEQ ID NO 64

<400> SEQUENCE: 64

000

<210> SEQ ID NO 65
<211> LENGTH: 10
<212> TYPE: DNA
<213> ORGANISM: Artificial Sequence
<220> FEATURE:
<223> OTHER INFORMATION: A synthetic construct.

<400> SEQUENCE: 65
caccatggct                                                            10

<210> SEQ ID NO 66
<211> LENGTH: 40
<212> TYPE: DNA
<213> ORGANISM: Artificial Sequence
<220> FEATURE:
<223> OTHER INFORMATION: A synthetic construct.

<400> SEQUENCE: 66
aaccatggct tccaaggtgt acgaccccga gcaacgcaaa                            40

<210> SEQ ID NO 67
<211> LENGTH: 40
<212> TYPE: DNA
<213> ORGANISM: Artificial Sequence
<220> FEATURE:
<223> OTHER INFORMATION: A synthetic construct.

<400> SEQUENCE: 67
gctctagaat tactgctcgt tcttcagcac gcgctccacg                            40

<210> SEQ ID NO 68
<211> LENGTH: 31
<212> TYPE: DNA
<213> ORGANISM: Artificial Sequence
<220> FEATURE:
<223> OTHER INFORMATION: A synthetic construct.

<400> SEQUENCE: 68
cgctagccat ggcttcgaaa gtttatgatc c                                    31

<210> SEQ ID NO 69
<211> LENGTH: 25
<212> TYPE: DNA
<213> ORGANISM: Artificial Sequence
<220> FEATURE:
<223> OTHER INFORMATION: A synthetic construct.

<400> SEQUENCE: 69
ggccagtaac tctagaatta ttgtt                                           25

<210> SEQ ID NO 70
<211> LENGTH: 1092
<212> TYPE: DNA
<213> ORGANISM: Artificial Sequence
<220> FEATURE:
<223> OTHER INFORMATION: A synthetic construct.

<400> SEQUENCE: 70
aagcttgcta gcgccaccat gaagaagccc gagctcaccg ctaccagcgt tgaaaaattt     60
ctcatcgaga agttcgacag tgtgagcgac ctgatgcagt gtcggagggg cgaagagagc    120
cgagccttca gcttcgatgt cggcggacgc ggctatgtac tgcgggtgaa tagctgcgct    180
gatggcttct acaaagaccg ctacgtgtac cgccacttcg ccagcgctgc actacccatc    240
cccgaagtgt tggacatcgg cgagttcagc gagagcctga catactgcat cagtagacgc    300
gcccaaggcg ttactctcca agacctcccc gaaacagagc tgcctgctgt gttacagcct    360
gtcgccgaag ctatggatgc tattgccgcc gccgacctca gtcaaaccag cggcttcggc    420
ccattcgggc ccaaggcat cggccagtac acaacctggc gggatttcat ttgcgccatt    480
gctgatcccc atgtctacca ctggcagacc gtgatggacg acaccgtgtc cgccagcgta    540

```
gctcaagccc tggacgaact gatgctgtgg gccgaagact gtcccgaggt gcgccacctc      600
gtccatgccg acttcggcag caacaacgtc ctgaccgaca acggccgcat caccgccgta      660
atcgactggt ccgaagctat gttcggggac agtcagtacg aggtggccaa catcttcttc      720
tggcggccct ggctggcttg catggagcag cagactcgct acttcgagcg ccggcatccc      780
gagctggccg gcagccctcg tctgcgagcc tacatgctgc gcatcggcct ggatcagctc      840
taccagagcc tcgtggacgg caacttcgac gatgctgcct gggctcaagg ccgctgcgat      900
gccatcgtcc gcagcggggc cggcaccgtc ggtcgcacac aaatcgctcg ccggagcgcc      960
gccgtatgga ccgacggctg cgtcgaggtg ctggccgaca gcggcaaccg ccggcccagt     1020
acacgaccgc gcgctaagga gggtggcgga gggagcggtg gcggaggttc ctacgtatag     1080
tctagactcg ag                                                         1092
```

<210> SEQ ID NO 71
<211> LENGTH: 1093
<212> TYPE: DNA
<213> ORGANISM: Artificial Sequence
<220> FEATURE:
<223> OTHER INFORMATION: A synthetic construct.

<400> SEQUENCE: 71

```
aagcttgcta gcgccaccat gaagaagccc gagctcaccg ctaccagcgt tgaaaaattt       60
ctcatcgaga agttcgacag tgtgagcgac ctgatgcagt gtcggaggg cgaagagagc       120 cgagccttca gcttcgatgt cggcggacgc ggctatgtac tgcgggtgaa tagctgcgct      180
gatggcttct acaaagaccg ctacgtgtac cgccacttcg ccagcgctgc actacccatc      240
cccgaagtgt tggacatcgg cgagttcagc gagagcctga catactgcat cagtagacgc      300
gcccaaggcg ttactctcca agacctcccc gaaacagagc tgcctgctgt gttacagcct      360
gtcgccgaag ctatggatgc tattgccgcc gccgacctca gtcaaaccag cggcttcggc      420
ccattcgggc cccaaggcat cggccagtac acaacctggc gggatttcat ttgcgccatt      480
gctgatcccc atgtctacca ctggcagacc gtgatggacg acaccgtgtc cgccagcgta      540
gctcaagccc tggacgaact gatgctgtgg gccgaagact gtcccgaggt gcgccacctc      600
gtccatgccg acttcggcag caacaacgtc ctgaccgaca acggccgcat caccgccgta      660
atcgactggt ccgaagctat gttcggggac agtcagtacg aggtggccaa catcttcttc      720
tggcggccct ggctggcttg catggagcag cagactcgct acttcgagcg ccggcatccc      780
gagctggccg gcagccctcg tctgcgagcc tacatgctgc gcatcggcct ggatcagctc      840
taccagagcc tcgtggacgg caacttcgac gatgctgcct gggctcaagg ccgctgcgat      900
gccatcgtcc gcagcggggc cggcaccgtc ggtcgcacac aaatcgctcg ccggagcgca      960
gccgtatgga ccgacggctg cgtcgaggtg ctggccgaca gcggcaaccg ccggcccagt     1020
acacgaccgc gcgctaagga aggcggtgga ggtagtggtg gcggaggtag ctacgtataa     1080
ctctagactc gag                                                       1093
```

<210> SEQ ID NO 72
<211> LENGTH: 813
<212> TYPE: DNA
<213> ORGANISM: Artificial Sequence
<220> FEATURE:
<223> OTHER INFORMATION: A synthetic construct.

<400> SEQUENCE: 72

```
gctagcgcca ccatgatcga acaagacggc ctccatgctg gcagtcccgc agcttgggtc       60
```

```
gaacgcttgt tcgggtacga ctgggcccag cagaccatcg gatgtagcga tgcggccgtg    120
ttccgtctaa gcgctcaagg ccggcccgtg ctgttcgtga agaccgacct gagcggcgcc    180
ctgaacgagc ttcaagacga ggctgcccgc ctgagctggc tggccaccac cggtgtaccc    240
tgcgccgctg tgttggatgt tgtgaccgaa gccggccggg actggctgct gctgggcgag    300
gtccctggcc aggatctgct gagcagccac cttgcccccg ctgagaaggt ttccatcatg    360
gccgatgcaa tgcggcgcct gcacaccctg gaccccgcta catgccccct cgaccaccag    420
gctaagcatc ggatcgagcg tgctcggacc cgcatggagg ccggcctggt ggaccaggac    480
gacctggacg aggagcatca gggcctggcc ccgctgaac tgttcgcccg cctgaaagcc    540
cgcatgccgg acggtgagga cctggttgtg acacatggtg atgcctgcct ccctaacatc    600
atggtcgaga atggccgctt ctccggcttc atcgactgcg gtcgcctagg agttgccgac    660
cgctaccagg acatcgccct ggccacccgc gacatcgctg aggagcttgg cggcgagtgg    720
gccgaccgct tcttagtctt gtacggcatc gcagctcccg acagccagcg catcgccttc    780
taccgcctgc tcgacgagtt cttttaatct aga                                  813

<210> SEQ ID NO 73
<211> LENGTH: 816
<212> TYPE: DNA
<213> ORGANISM: Artificial Sequence
<220> FEATURE:
<223> OTHER INFORMATION: A synthetic construct.

<400> SEQUENCE: 73
gctagcgcca ccatgatcga acaagacggc ctccatgctg gcagtcccgc agcttgggtc     60
gaacgcttgt tcgggtacga ctgggcccag cagaccatcg gatgtagcga tgcggccgtg    120
ttccgtctaa gcgctcaagg ccggcccgtg ctgttcgtga agaccgacct gagcggcgcc    180
ctgaacgagc ttcaagacga ggctgcccgc ctgagctggc tggccaccac cggcgtaccc    240
tgcgccgctg tgttggatgt tgtgaccgaa gccggccggg actggctgct gctgggcgag    300
gtccctggcc aggatctgct gagcagccac cttgcccccg ctgagaaggt ttctatcatg    360
gccgatgcaa tgcggcgcct gcacaccctg gaccccgcta cctgccccctt cgaccaccag    420 gctaagcatc ggatcgagcg tgctcggacc cgcatggagg ccggcctggt ggaccaggac    480
gacctggacg aggagcatca gggcctggcc ccgctgaac tgttcgcccg actgaaagcc    540
cgcatgccgg acggtgagga cctggttgtc acacacggag atgcctgcct ccctaacatc    600
atggtcgaga atggccgctt ctccggcttc atcgactgcg gtcgcctagg agttgccgac    660
cgctaccagg acatcgccct ggccacccgc gacatcgctg aggagcttgg cggcgagtgg    720
gccgaccgct tcttagtctt gtacggcatc gcagctcccg acagccagcg catcgccttc    780
taccgcttgc tcgacgagtt cttttaatga tctaga                               816

<210> SEQ ID NO 74
<211> LENGTH: 1252
<212> TYPE: DNA
<213> ORGANISM: Artificial Sequence
<220> FEATURE:
<223> OTHER INFORMATION: A synthetic construct.

<400> SEQUENCE: 74
gcggccgcaa atgctaaacc actgcagtgg ttaccagtgc ttgatcagtg aggcaccgat     60
ctcagcgatc tgcctatttc gttcgtccat agtggcctga ctcccgtcg tgtagatcac    120 tacgattcgt gagggcttac catcaggccc cagcgcagca atgatgccgc gagagccgcg    180
```

```
ttcaccggcc cccgatttgt cagcaatgaa ccagccagca gggagggccg agcgaagaag    240
tggtcctgct actttgtccg cctccatcca gtctatgagc tgctgtcgtg atgctagagt    300
aagaagttcg ccagtgagta gtttccgaag agttgtggcc attgctactg gcatcgtggt    360
atcacgctcg tcgttcggta tggcttcgtt caactctggt tcccagcggt caagccgggt    420
cacatgatca cccatattat gaagaaatgc agtcagctcc ttagggcctc cgatcgttgt    480
cagaagtaag ttggccgcgg tgttgtcgct catggtaatg gcagcactac acaattctct    540
taccgtcatg ccatccgtaa gatgcttttc cgtgaccggc gagtactcaa ccaagtcgtt    600
ttgtgagtag tgtatacggc gaccaagctg ctcttgcccg gcgtctatac gggacaacac    660
cgcgccacat agcagtactt tgaaagtgct catcatcggg aatcgttctt cggggcggaa    720
agactcaagg atcttgccgc tattgagatc cagttcgata tagcccactc ttgcacccag    780
ttgatcttca gcatctttta ctttcaccag cgtttcgggg tgtgcaaaaa caggcaagca    840
aaatgccgca aagaagggaa tgagtgcgac acgaaaatgt tggatgctca tactcgtcct    900
ttttcaatat tattgaagca tttatcaggg ttactagtac gtctctcaag gataagtaag    960
taatattaag gtacgggagg tattggacag gccgcaataa aatatcttta ttttcattac   1020
atctgtgtgt tggttttttg tgtgaatcga tagtactaac atacgctctc catcaaaaca   1080
aaacgaaaca aaacaaacta gcaaataggc tgtccccag tgcaagtgca ggtgccagaa    1140
catttctctg gcctaactgg ccggtacctg agctcgctag cctcgaggat atcaagatct   1200
ggcctcggcg ccaagcttg gcaatccggt actgttggta aagccaccat gg            1252
```

```
<210> SEQ ID NO 75

<400> SEQUENCE: 75

000

<210> SEQ ID NO 76
<211> LENGTH: 228
<212> TYPE: DNA
<213> ORGANISM: Artificial Sequence
<220> FEATURE:
<223> OTHER INFORMATION: A synthetic construct.

<400> SEQUENCE: 76
actagtcgtc tctcttgaga gaccgcgatc gccaccatga taagtaagta atattaaata     60
agtaaggcct gagtggccct cgagccagcc ttgagttggt tgagtccaag tcacgtctgg    120
agatctggta cctacgcgtg agctctacgt agctagcggc ctcggcggcc gaattcttgc    180
gatctaagta agcttggcat tccggtactg ttggtaaagc caccatgg                 228

<210> SEQ ID NO 77
<211> LENGTH: 228
<212> TYPE: DNA
<213> ORGANISM: Artificial Sequence
<220> FEATURE:
<223> OTHER INFORMATION: A synthetic construct.

<400> SEQUENCE: 77
actagtacgt ctctcttgag agaccgcgat cgccaccatg ataagtaagt aatattaaat     60
aagtaaggcc tgagtggccc tcgagtccag ccttgagttg gttgagtcca agtcacgtct    120
ggagatctgg tacttacgc gtagagctct acgtagctag cggcctcggc ggccgaattc    180
ttgcgatcta agcttggcaa tccggtactg ttggtaaagc caccatgg                 228
```

```
<210> SEQ ID NO 78
<211> LENGTH: 230
<212> TYPE: DNA
<213> ORGANISM: Artificial Sequence
<220> FEATURE:
<223> OTHER INFORMATION: A synthetic construct.

<400> SEQUENCE: 78
actagtacgt ctctcttgag agaccgcgat cgcatgccta ggtaggtagt attagagcat     60
aggtagaggc ctaagtggcc ctcgagtcca gccttgagtt ggttgagtcc aagtcacgtc    120
tggagatctg gtaccttacg cgtatgagct ctacgtagct agcggcctcg gcggccgaat    180
tcttgcgatc taagcttggc aatccggtac tgttggtaaa gccaccatgg              230

<210> SEQ ID NO 79
<211> LENGTH: 234
<212> TYPE: DNA
<213> ORGANISM: Artificial Sequence
<220> FEATURE:
<223> OTHER INFORMATION: A synthetic construct.

<400> SEQUENCE: 79
actagtacgt ctctcttgag agaccgcgat cgccaccatg tctaggtagg tagtaaacga     60
aagggcttaa aggcctaagt ggccctcgag tccagccttg agttggttga gtccaagtca    120
cgtttggaga tctggtacct tacgcgtatg agctctacgt agctagcggc ctcggcggcc    180
gaattcttgc gatctaagct tggcaatccg gtactgttgg taaagccacc atgg          234

<210> SEQ ID NO 80
<211> LENGTH: 938
<212> TYPE: DNA
<213> ORGANISM: Artificial Sequence
<220> FEATURE:
<223> OTHER INFORMATION: A synthetic construct.

<400> SEQUENCE: 80
actagtaacc ctgataaatg cttcaataat attgaaaaag gaagagtatg agtattcaac     60
atttccgtgt cgcccttatt ccctttttg cggcatttg ccttcctgtt tttgctcacc     120
cagaaacgct ggtgaaagta aaagatgctg aagatcagtt gggtgcacga gtgggttaca    180
tcgaactgga tctcaacagc ggtaagatcc ttgagagttt cgccccgaa gaacgttttc    240 caatgatgag cacttttaaa gttctgctat gtggcgcggt attatcccgt attgacgccg    300
ggcaagagca actcggtcgc cgcatacact attctcagaa tgacttggtt gagtactcac    360
cagtcacaga aaagcatctt acggatggca tgacagtaag agaattatgc agtgctgcca    420
taaccatgag tgataacacc gcggccaact tacttctgac aacgatcgga ggaccgaagg    480
agctaaccgc tttttgcac aacatggggg atcatgtaac tcgccttgat cgttgggaac    540
cggagctgaa tgaagccata ccaaacgacg agcgtgacac cacgatgcct gtagcaatgg    600
caacaacgtt gcgcaaacta ttaactggcg aactacttac tctagcttcc cggcaacaat    660
taatagactg gatggaggcg gataaagttg caggaccact tctgcgctcg gcccttccgg    720
ctggctggtt tattgctgat aaatctggag ccggtgagcg tggctctcgc ggtatcattg    780
cagcactggg gccagatggt aagccctccc gtatcgtagt tatctacacg acggggagtc    840
aggcaactat ggatgaacga aatagacaga tcgctgagat aggtgcctca ctgattaagc    900
attggtaacc actgcagtgg ttttcctttt gcggccgc                             938

<210> SEQ ID NO 81
<211> LENGTH: 938
```

| | |
|---|---|
| <212> TYPE: DNA | |
| <213> ORGANISM: Artificial Sequence | |
| <220> FEATURE: | |
| <223> OTHER INFORMATION: A synthetic construct. | |

<400> SEQUENCE: 81

| | |
|---|---|
| actagtaacc ctgataaatg ctgcaaacat attgaaaaag gaagagtatg agtattcaac | 60 |
| atttccgtgt cgcactcatt cccttctttg cggcattttg cttgcctgtt tttgcacacc | 120 |
| ccgaaacgct ggtgaaagta aaagatgctg aagatcaact gggtgcacga gtgggctata | 180 |
| tcgaactgga tctcaatagc ggtaagatcc ttgagagttt tcgccccgaa gaacgttttc | 240 |
| caatgatgag cacttttaaa gttctgctat gtggcgcggt attatcccgt attgacgccg | 300 |
| ggcaagagca gctcggtcgc cgcatacact actcacagaa cgacttggtt gagtactcgc | 360 |
| cggtcacgga aaagcatctt acggatggca tgacagtaag agaattgtgt agtgctgcca | 420 |
| taaccatgag tgataacacc gcggccaact tacttctgac aacgatcgga ggccctaagg | 480 |
| agctgaccgc atttttgcac aacatggggg atcatgtaac ccggcttgat cgttgggaac | 540 |
| cggagctgaa cgaagccata ccgaacgacg agcgtgacac cacgatgcct gtagcaatgg | 600 |
| caacaacgtt gcgcaaacta ctcactggcg aacttctcac tctagcatca cgacagcaac | 660 |
| tcatagactg gatggaggcg gataaagttg caggaccact tctgcgctcg gcccttccgg | 720 |
| ctggctggtt tatagctgat aaatccggtg ccggtgaacg cggctctcgc gggatcattg | 780 |
| ctgcgctggg gccagatggt aagccctcac gaatcgtagt tatctacacg acggggagtc | 840 |
| aggcaactat ggatgaacga aatagacaga tcgctgagat aggtgcctca ctgatcaagc | 900 |
| actggtagcc actgcagtgg tttagctttt gcggccgc | 938 |

<210> SEQ ID NO 82
<211> LENGTH: 938
<212> TYPE: DNA
<213> ORGANISM: Artificial Sequence
<220> FEATURE:
<223> OTHER INFORMATION: A synthetic construct.

<400> SEQUENCE: 82

| | |
|---|---|
| actagtaacc ctgacaaatg ctgcaaacat attgaaaaag gaagagtatg agcatccaac | 60 |
| attttcgtgt cgcactcatt cccttctttg cggcattttg cttgcctgtt tttgcacacc | 120 |
| ccgaaacgct ggtgaaagta aaagatgctg aagatcaact gggtgcaaga gtgggctata | 180 |
| tcgaactgga tctcaatagc ggcaagatcc ttgagtcttt tcgccccgaa gaacgttttc | 240 |
| cgatgatgag cacttttaaa gttctgctat gtggcgcggt gttgtcccgt atagacgccg | 300 |
| ggcaagagca gcttggtcgc cgtatacact actcacaaaa cgacttggtt gagtactcgc | 360 |
| cggtcacgga aaagcatctt acggatggca tgacggtaag agaattgtgt agtgctgcca | 420 |
| ttaccatgag cgacaatacc gcggccaact tacttctgac aacgatcgga ggccctaagg | 480 |
| agctgaccgc atttttgcac aacatggggg atcatgtaac ccggcttgac cgctgggaac | 540 |
| cggagctgaa cgaagccata ccgaacgacg agcgtgacac cacgatgcct gtagcaatgg | 600 |
| caacaacgtt gcgaaaacta ctcactggcg aacttctcac tctagcatca cgacagcagc | 660 |
| tcatagactg gatggaggcg gacaaagtag caggaccact tcttcgctcg ccctccctg | 720 |
| ctggctggtt cattgctgat aaatccggtg ccggtgaacg cggctctcgc gggatcattg | 780 |
| ctgcgctggg gcctgatggt aagccctcac gaatcgtagt aatctacacg acggggagtc | 840 |
| aggccactat ggacgaacga aatagacaga tcgctgagat cggtgcctca ctgatcaagc | 900 |
| actggtaacc actgcagtgg tttagcattt gcggccgc | 938 |

<210> SEQ ID NO 83
<211> LENGTH: 938
<212> TYPE: DNA
<213> ORGANISM: Artificial Sequence
<220> FEATURE:
<223> OTHER INFORMATION: A synthetic construct.

<400> SEQUENCE: 83

```
actagtaacc ctgacaaatg ctgcaaacat attgaaaaag gaagagtatg agcatccaac      60
attttcgtgt cgcactcatt cccttctttg cggcattttg cttgcctgtt tttgcacacc     120
ccgaaacgct ggtgaaagta aaagatgctg aagatcaact gggtgcaaga gtgggctata     180
tcgaactgga tctcaatagc ggcaagatcc ttgagtcttt ccgccccgaa gaacgttttc     240
cgatgatgag cactttcaaa gtactgctat gtggcgcggt gttgtcccgt atagacgccg     300
ggcaagagca gcttggtcgc cgtatacact actcacaaaa cgacttggtt gagtactcgc     360
cggtcacgga aaagcatctt acggatggca tgacggtaag agaattgtgt agtgctgcca     420
ttaccatgag cgataatacc gcggccaact tacttctgac aacgatcgga ggccctaagg     480
agctgaccgc attttgcac aacatgggtg atcatgtgac ccggcttgac cgctgggaac     540
cggagctgaa cgaagccata ccgaacgacg agcgtgacac cacgatgcct gtagcaatgg     600
caacaactct tcggaaacta ctcactggcg aacttctcac tctagcatca cgacagcagc     660
tcatagactg gatggaggcg gacaaagtag caggaccact tcttcgctcg gccctccctg     720
ctggctggtt cattgctgat aaatctggag ccggtgagcg tggctctcgc ggtatcattg     780
ctgcgctggg gcctgatggt aagcccctca cgaatcgtagt aatctacacg acggggagtc     840
aggccactat ggacgaacga aatagacaga tcgctgagat cggtgcctca ctgatcaagc     900
actggtaacc actgcagtgg tttagcattt gcggccgc                             938
```

<210> SEQ ID NO 84
<211> LENGTH: 938
<212> TYPE: DNA
<213> ORGANISM: Artificial Sequence
<220> FEATURE:
<223> OTHER INFORMATION: A synthetic construct.

<400> SEQUENCE: 84

```
actagtaacc ctgacaaatg ctgcaaacat attgaaaaag gaagagtatg agcatccaac      60
attttcgtgt cgcactcatt cccttctttg cggcattttg cttgcctgtt tttgcacacc     120
ccgaaacgct ggtgaaagta aaagatgctg aagatcaact gggtgcaaga gtgggctata     180
tcgaactgga tctcaatagc ggcaagatcc ttgagtcttt ccgccccgaa gaacgattcc     240
cgatgatgag cactttcaaa gtactgctat gtggcgcggt gttgtcccgt atagacgccg     300
ggcaagagca gcttggtcgc cgtatacact actcacaaaa cgacttggtt gagtactcgc     360
cggtcacgga aaagcatctt acggatggca tgacggtaag agaattgtgt agtgctgcca     420
ttaccatgag cgataatacc gcggccaact tacttctgac aacgatcgga ggccctaagg     480
agctgaccgc attttgcac aacatgggtg atcatgtgac ccggcttgac cgctgggaac     540
cggagctgaa cgaagccata ccgaacgacg agcgtgatac cacgatgcca gtagcaatgg     600
ccacaactct tcggaaacta ctcactggcg aacttctcac tctagcatca cgacagcagc     660
tcatagactg gatggaggcg gacaaagtag caggaccact tcttcgctcg gccctccctg     720
ctggctggtt cattgctgac aaatccggtg ccggtgaacg cggctctcgc ggcatcattg     780
ctgcgctggg gcctgatggt aagcccctca cgaatcgtagt aatctacacg acggggagtc     840
```

| | |
|---|---:|
| aggccactat ggacgaacga aatagacaga tcgctgagat cggtgcctca ctgatcaagc | 900 |
| actggtaacc actgcagtgg tttagcattt gcggccgc | 938 |

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88
<211> LENGTH: 1038
<212> TYPE: DNA
<213> ORGANISM: Artificial Sequence
<220> FEATURE:
<223> OTHER INFORMATION: A synthetic construct.

<400> SEQUENCE: 88

| | |
|---|---:|
| atgaagaagc ccgaactcac cgctaccagc gttgaaaaat ttctcatcga agagttcgac | 60 |
| agtgtgagcg acctgatgca gttgtcggag ggcgaagaga gccgagcctt cagcttcgat | 120 |
| gtcggcggac gcggctatgt actgcgggtg aatagctgcg ctgatggctt ctacaaagac | 180 |
| cgctacgtgt accgccactt cgccagcgct gcactaccca tccccgaagt gttggacatc | 240 |
| ggcgagttca gcgagagcct gacatactgc atcagtagac gcgcccaagg cgttactctc | 300 |
| caagacctcc ccgaaacaga gctgcctgct gtgttacagc ctgtcgccga agctatggat | 360 |
| gctattgccg ccgccgacct cagtcaaacc agcggcttcg gcccattcgg gccccaaggc | 420 |
| atcggccagt acacaacctg gcgggatttc atttgcgcca ttgctgatcc ccatgtctac | 480 |
| cactggcaga ccgtgatgga cgacaccgtg tccgccagcg tagctcaagc cctggacgaa | 540 |
| ctgatgctgt gggccgaaga ctgtcccgag gtgcgccacc tcgtccatgc cgacttcggc | 600 |
| agcaacaacg tcctgaccga caacggccgc atcaccgccg taatcgactg gtccgaagct | 660 |
| atgttcgggg acagtcagta cgaggtggcc aacatcttct tctggcggcc ctggctggct | 720 |
| tgcatggagc agcagactcg ctacttcgag cgccggcatc ccgagctggc cggcagccct | 780 |
| cgtctgcgag cctacatgct gcgcatcggc ctggatcagc tctaccagag cctcgtggac | 840 |
| ggcaacttcg acgatgctgc ctgggctcaa ggccgctgcg atgccatcgt ccgcagcggg | 900 |
| gccggcaccg tcggtcgcac acaaatcgct cgccggagcg cagccgtatg gaccgacggc | 960 |
| tgcgtcgagg tgctggccga cagcggcaac cgccggccca gtacacgacc gcgcgctaag | 1020 |
| gaggtaggtc gagtttaa | 1038 |

<210> SEQ ID NO 89
<211> LENGTH: 4333
<212> TYPE: DNA
<213> ORGANISM: Artificial Sequence
<220> FEATURE:
<223> OTHER INFORMATION: A synthetic construct.

<400> SEQUENCE: 89

```
ggcctaactg gccggtacct gagctcgcta gcctcgagga tatcaagatc tggcctcggc      60
ggccaagctt ggcaatccgg tactgttggt aaagccacca tggaagatgc caaaaacatt     120
aagaagggcc cagcgccatt ctacccactc gaagacggga ccgccggcga gcagctgcac     180
aaagccatga agcgctacgc cctggtgccc ggcaccatcg cctttaccga cgcacatatc     240
gaggtggaca ttacctacgc cgagtacttc gagatgagcg ttcggctggc agaagctatg     300
aagcgctatg ggctgaatac aaaccatcgg atcgtggtgt gcagcgagaa tagcttgcag     360
ttcttcatgc ccgtgttggg tgccctgttc atcggtgtgg ctgtggcccc agctaacgac     420
atctacaacg agcgcgagct gctgaacagc atgggcatca gccagcccac cgtcgtattc     480
gtgagcaaga aagggctgca aaagatcctc aacgtgcaaa agaagctacc gatcatacaa     540
aagatcatca tcatggatag caagaccgac taccagggct tccaaagcat gtacaccttc     600
gtgacttccc atttgccacc cggcttcaac gagtacgact tcgtgcccga gagcttcgac     660
cgggacaaaa ccatcgccct gatcatgaac agtagtggca gtaccggatt gcccaagggc     720
gtagccctac cgcaccgcac cgcttgtgtc cgattcagtc atgcccgcga ccccatcttc     780
ggcaaccaga tcatccccga caccgctatc ctcagcgtgg tgccatttca ccacggcttc     840
ggcatgttca ccacgctggg ctacttgatc tgcggctttc gggtcgtgct catgtaccgc     900
ttcgaggagg agctattctt gcgcagcttg caagactata agattcaatc tgccctgctg     960
gtgcccacac tatttagctt cttcgctaag agcactctca tcgacaagta cgacctaagc    1020
aacttgcacg agatcgccag cggcggggcg ccgctcagca aggaggtagg tgaggccgtg    1080
gccaaacgct tccacctacc aggcatccgc cagggctacg gcctgacaga acaaccagc     1140
gccattctga tcacccccga aggggacgac aagcctggcg cagtaggcaa ggtggtgccc    1200
ttcttcgagg ctaaggtggt ggacttggac accggtaaga cactgggtgt gaaccagcgc    1260
ggcgagctgt gcgtccgtgg ccccatgatc atgagcggct acgttaacaa ccccgaggct    1320
acaaacgctc tcatcgacaa ggacggctgg ctgcacagcg gcgacatcgc ctactgggac    1380
gaggacgagc acttcttcat cgtggaccgg ctgaagagcc tgatcaaata caagggctac    1440
caggtagccc cagccgaact ggagagcatc ctgctgcaac accccaacat cttcgacgcc    1500
ggggtcgccg gcctgcccga cgacgatgcc ggcgagctgc ccgccgcagt cgtcgtgctg    1560
gaacacggta aaaccatgac cgagaaggag atcgtggact atgtggccag ccaggttaca    1620
accgccaaga agctgcgcgg tggtgttgtg ttcgtggacg aggtgcctaa ggactgacc     1680
ggcaagttgg acgccgcaa gatccgcgag attctcatta aggccaagaa gggcggcaag    1740
atcgccgtgt aataattcta gagtcggggc ggccggccgc ttcgagcaga catgataaga    1800
tacattgatg agtttggaca aaccacaact agaatgcagt gaaaaaaatg ctttatttgt    1860
gaaatttgtg atgctattgc tttatttgta accattataa gctgcaataa acaagttaac    1920
aacaacaatt gcattcattt tatgtttcag gttcagggg aggtgtggga ggttttttaa    1980
agcaagtaaa acctctacaa atgtggtaaa atcgataagg atccgtcgac cgatgccctt    2040
gagagccttc aacccagtca gctccttccg gtgggcgcgg ggcatgacta tcgtcgccgc    2100
acttatgact gtcttcttta tcatgcaact cgtaggacag gtgccggcag cgctcttccg    2160
cttcctcgct cactgactcg ctgcgctcgg tcgttcggct gcggcgagcg gtatcagctc    2220
actcaaaggc ggtaatacgg ttatccacag aatcagggga taacgcagga agaacatgt     2280
gagcaaaagg ccagcaaaag gccaggaacc gtaaaaaggc cgcgttgctg gcgttttcc    2340
```

-continued

```
ataggctccg ccccctgac gagcatcaca aaaatcgacg ctcaagtcag aggtggcgaa    2400
acccgacagg actataaaga taccaggcgt ttccccctgg aagctccctc gtgcgctctc    2460
ctgttccgac cctgccgctt accggatacc tgtccgcctt ctcccttcg ggaagcgtgg    2520 cgctttctca tagctcacgc tgtaggtatc tcagttcggt gtaggtcgtt cgctccaagc    2580
tgggctgtgt gcacgaaccc cccgttcagc ccgaccgctg cgccttatcc ggtaactatc    2640
gtcttgagtc caacccggta agacacgact tatcgccact ggcagcagcc actggtaaca    2700
ggattagcag agcgaggtat gtaggcggtg ctacagagtt cttgaagtgg tggcctaact    2760
acggctacac tagaagaaca gtatttggta tctgcgctct gctgaagcca gttaccttcg    2820
gaaaaagagt tggtagctct tgatccggca acaaaccac cgctggtagc ggtggttttt    2880
ttgtttgcaa gcagcagatt acgcgcagaa aaaaggatc tcaagaagat cctttgatct    2940
tttctacggg gtctgacgct cagtggaacg aaaactcacg ttaagggatt ttggtcatga    3000
gattatcaaa aaggatcttc acctagatcc ttttaaatta aaaatgaagt tttaaatcaa    3060
tctaaagtat atatgagtaa acttggtctg acagcggccg caaatgctaa accactgcag    3120
tggttaccag tgcttgatca gtgaggcacc gatctcagcg atctgcctat ttcgttcgtc    3180
catagtggcc tgactccccg tcgtgtagat cactacgatt cgtgagggct taccatcagg    3240
ccccagcgca gcaatgatgc cgcgagagcc gcgttcaccg gccccgatt tgtcagcaat    3300 gaaccagcca gcagggaggg ccgagcgaag aagtggtcct gctactttgt ccgcctccat    3360
ccagtctatg agctgctgtc gtgatgctag agtaagaagt tcgccagtga gtagtttccg    3420
aagagttgtg gccattgcta ctggcatcgt ggtatcacgc tcgtcgttcg gtatggcttc    3480
gttcaactct ggttcccagc ggtcaagccg ggtcacatga tcacccatat tatgaagaaa    3540
tgcagtcagc tccttagggc ctccgatcgt tgtcagaagt aagttggccg cggtgttgtc    3600
gctcatggta atggcagcac tacacaattc tcttaccgtc atgccatccg taagatgctt    3660
ttccgtgacc ggcgagtact caaccaagtc gttttgtgag tagtgtatac ggcgaccaag    3720
ctgctcttgc ccggcgtcta tacgggacaa caccgcgcca catagcagta ctttgaaagt    3780
gctcatcatc gggaatcgtt cttcggggcg aaaagactca aggatcttgc cgctattgag    3840
atccagttcg atatagccca ctcttgcacc cagttgatct tcagcatctt ttactttcac    3900
cagcgtttcg gggtgtgcaa aaacaggcaa gcaaatgcc gcaaagaagg gaatgagtgc    3960
gacacgaaaa tgttggatgc tcatactcgt ccttttcaa tattattgaa gcatttatca    4020
gggttactag tacgtctctc aaggataagt aagtaatatt aaggtacggg aggtattgga    4080
caggccgcaa taaatatct ttattttcat tacatctgtg tgttggtttt tgtgtgaat    4140 cgatagtact aacatacgct ctccatcaaa acaaaacgaa acaaaacaaa ctagcaaaat    4200
aggctgtccc cagtgcaagt gcaggtgcca gaacatttct ctaagtaata ttaaggtacg    4260
ggaggtattg gacaggccgc aataaaatat ctttatttc attacatctg tgtgttggtt    4320
ttttgtgtga atc    4333
```

<210> SEQ ID NO 90
<211> LENGTH: 3522
<212> TYPE: DNA
<213> ORGANISM: Artificial Sequence
<220> FEATURE:
<223> OTHER INFORMATION: A synthetic construct.

<400> SEQUENCE: 90

```
ggcctaactg gccggtacct gagctcgcta gcctcgagga tatcaagatc tggcctcggc    60
```

-continued

```
ggccaagctt ggcaatccgg tactgttggt aaagccacca tggcttccaa ggtgtacgac    120
cccgagcaac gcaaacgcat gatcactggg cctcagtggt gggctcgctg caagcaaatg    180
aacgtgctgg actccttcat caactactat gattccgaga agcacgccga gaacgccgtg    240 attttctgc atggtaacgc tgcctccagc tacctgtgga ggcacgtcgt gcctcacatc     300
gagcccgtgg ctagatgcat catccctgat ctgatcggaa tgggtaagtc cggcaagagc    360
gggaatggct catatcgcct cctggatcac tacaagtacc tcaccgcttg gttcgagctg    420
ctgaaccttc caaagaaaat catctttgtg ggccacgact gggggcttg tctggccttt     480 cactactcct acgagcacca agacaagatc aaggccatcg tccatgctga gagtgtcgtg    540
gacgtgatcg agtcctggga cgagtggcct gacatcgagg aggatatcgc cctgatcaag    600
agcgaagagg gcgagaaaat ggtgcttgag aataacttct tcgtcgagac catgctccca    660
agcaagatca tgcggaaact ggagcctgag gagttcgctg cctacctgga gccattcaag    720
gagaagggcg aggttagacg gcctaccctc tcctggcctc gcgagatccc tctcgttaag    780
ggaggcaagc ccgacgtcgt ccagattgtc cgcaactaca cgcctacct tcgggccagc    840 gacgatctgc ctaagatgtt catcgagtcc gaccctgggt tctttccaa cgctattgtc     900 gagggagcta agaagttccc taacaccgag ttcgtgaagg tgaagggcct ccacttcagc    960
caggaggacg ctccagatga aatgggtaag tacatcaaga gcttcgtgga gcgcgtgctg   1020
aagaacgagc agtaattcta gagtcggggc ggccggccgc ttcgagcaga catgataaga   1080
tacattgatg agtttggaca aaccacaact agaatgcagt gaaaaaaatg ctttatttgt   1140
gaaatttgtg atgctattgc tttatttgta accattataa gctgcaataa acaagttaac   1200
aacaacaatt gcattcattt tatgtttcag gttcaggggg aggtgtggga ggttttttaa   1260
agcaagtaaa acctctacaa atgtggtaaa atcgataagg atccgtcgac cgatgccctt   1320
gagagccttc aacccagtca gctccttccg gtgggcgcgg ggcatgacta tcgtcgccgc   1380
acttatgact gtcttcttta tcatgcaact cgtaggacag gtgccggcag cgctcttccg   1440
cttcctcgct cactgactcg ctgcgctcgg tcgttcggct gcggcgagcg gtatcagctc   1500
actcaaaggc ggtaatacgg ttatccacag aatcagggga taacgcagga agaacatgt    1560 gagcaaaagg ccagcaaaag gccaggaacc gtaaaaaggc cgcgttgctg gcgttttcc    1620 ataggctccg cccccctgac gagcatcaca aaaatcgacg ctcaagtcag aggtggcgaa   1680
acccgacagg actataaaga taccaggcgt ttccccctgg aagctccctc gtgcgctctc   1740
ctgttccgac cctgccgctt accggatacc tgtccgcctt tctcccttcg ggaagcgtgg   1800
cgctttctca tagctcacgc tgtaggtatc tcagttcggt gtaggtcgtt cgctccaagc   1860
tgggctgtgt gcacgaaccc cccgttcagc ccgaccgctg cgccttatcc ggtaactatc   1920
gtcttgagtc aacccggta agacacgact tatcgccact ggcagcagcc actggtaaca    1980
ggattagcag agcgaggtat gtaggcggtg ctacagagtt cttgaagtgg tggcctaact   2040
acggctacac tagaagaaca gtatttggta tctgcgctct gctgaagcca gttaccttcg   2100
gaaaaagagt tggtagctct tgatccggca aacaaaccac cgctggtagc ggtggttttt   2160
ttgtttgcaa gcagcagatt acgcgcagaa aaaaaggatc tcaagaagat cctttgatct   2220
tttctacggg gtctgacgct cagtggaacg aaaactcacg ttaagggatt ttggtcatga   2280
gattatcaaa aaggatcttc acctagatcc ttttaaatta aaaatgaagt tttaaatcaa   2340
tctaaagtat atatgagtaa acttggtctg acagcggccg caaatgctaa accactgcag   2400
tggttaccag tgcttgatca gtgaggcacc gatctcagcg atctgcctat ttcgttcgtc   2460
```

| | |
|---|---|
| catagtggcc tgactcccng tcgtgtagat cactacgatt cgtgagggct taccatcagg | 2520 |
| ccccagcgca gcaatgatgc cgcgagagcc gcgttcaccg gcccccgatt tgtcagcaat | 2580 |
| gaaccagcca gcagggaggg ccgagcgaag aagtggtcct gctactttgt ccgcctccat | 2640 |
| ccagtctatg agctgctgtc gtgatgctag agtaagaagt tcgccagtga gtagtttccg | 2700 |
| aagagttgtg gccattgcta ctggcatcgt ggtatcacgc tcgtcgttcg gtatggcttc | 2760 |
| gttcaactct ggttcccagc ggtcaagccg gtcacatga tcacccatat tatgaagaaa | 2820 |
| tgcagtcagc tccttagggc ctccgatcgt tgtcagaagt aagttggccg cggtgttgtc | 2880 |
| gctcatggta atggcagcac tacacaattc tcttaccgtc atgccatccg taagatgctt | 2940 |
| ttccgtgacc ggcgagtact caaccaagtc gttttgtgag tagtgtatac ggcgaccaag | 3000 |
| ctgctcttgc ccggcgtcta tacgggacaa caccgcgcca catagcagta ctttgaaagt | 3060 |
| gctcatcatc gggaatcgtt cttcggggcg gaaagactca aggatcttgc cgctattgag | 3120 |
| atccagttcg atatagccca ctcttgcacc cagttgatct tcagcatctt ttactttcac | 3180 |
| cagcgtttcg gggtgtgcaa aaacaggcaa gcaaaatgcc gcaagaagg gaatgagtgc | 3240 |
| gacacgaaaa tgttggatgc tcatactcgt ccttttttcaa tattattgaa gcatttatca | 3300 |
| gggttactag tacgtctctc aaggataagt aagtaatatt aaggtacggg aggtattgga | 3360 |
| caggccgcaa taaaatatct ttattttcat tacatctgtg tgttggtttt ttgtgtgaat | 3420 |
| cgatagtact aacatacgct ctccatcaaa acaaaacgaa acaaaacaaa ctagcaaaat | 3480 |
| aggctgtccc cagtgcaagt gcaggtgcca gaacatttct ct | 3522 |

<210> SEQ ID NO 91
<211> LENGTH: 621
<212> TYPE: DNA
<213> ORGANISM: Artificial Sequence
<220> FEATURE:
<223> OTHER INFORMATION: A synthetic construct.

<400> SEQUENCE: 91

| | |
|---|---|
| gctagcgcca ccatgaccga gtacaagccc accgtgcgcc tggccacccg cgacgacgtg | 60 |
| ccccgcgccc tgcgcaccct ggccgccgcc ttcgccgact accccgccac ccgccacacc | 120 |
| gtggaccccg accgccacat cgagcgcgtg accgagctgc aggagctgtt cctgacccgc | 180 |
| gtgggcctgg acatcggcaa ggtgtgggtg gccgacgacg cgccgccgt ggccgtgtgg | 240 |
| accaccccccg agagcgtgga ggccggcgcc gtgttcgccg agatcggccc ccgcatggcc | 300 |
| gagctgagcg gcagccgcct ggccgcccag cagcagatgg agggcctgct ggcccccac | 360 |
| cgccccaagg agcccgcctg gttcctggcc accgtgggcg tgagccccga ccaccagggc | 420 |
| aagggcctgg gcagcgccgt ggtgctgccc ggcgtgagg ccgccgagcg cgccggcgtg | 480 |
| cccgccttcc tggagaccag cgccccccgc aacctgccct tctacgagcg cctgggcttc | 540 |
| accgtgaccg ccgacgtgga ggtgcccgag ggccccgca cctggtgcat gacccgcaag | 600 |
| cccggcgcct aatgatctag a | 621 |

<210> SEQ ID NO 92
<211> LENGTH: 621
<212> TYPE: DNA
<213> ORGANISM: Artificial Sequence
<220> FEATURE:
<223> OTHER INFORMATION: A synthetic construct.

<400> SEQUENCE: 92

| | |
|---|---|
| gctagcgcca ccatgaccga gtacaagcct accgtgcgcc tggccactcg cgatgatgtg | 60 |

```
cccccgcgccg tccgcactct ggccgccgct ttcgccgact accccgctac ccggcacacc      120
gtggaccccg accggcacat cgagcgtgtg acagagttgc aggagctgtt cctgacccgc      180
gtcgggctgg acatcggcaa ggtgtgggta gccgacgacg gcgcggccgt ggccgtgtgg      240 actaccccccg agagcgttga ggccggcgcc gtgttcgccg agatcggccc ccgaatggcc    300
gagctgagcg gcagccgcct ggccgcccag cagcaaatgg agggcctgct tgcccccccat    360 cgtcccaagg agcccgcctg gtttctggcc actgtaggag tgagcccccga ccaccagggc   420 aagggcttgg gcagcgccgt cgtgttgccc ggcgtagagg ccgccgaacg cgccggtgtg   480
cccgcctttc tggagacaag cgctccgcgt aaccttccat tctacgagcg cctgggcttc    540
accgtgaccg ccgatgtcga ggtgcccgag ggaccccgga cctggtgcat gactcgcaag    600
cctggcgcct aatgatctag a                                              621

<210> SEQ ID NO 93
<211> LENGTH: 621
<212> TYPE: DNA
<213> ORGANISM: Artificial Sequence
<220> FEATURE:
<223> OTHER INFORMATION: A synthetic construct.

<400> SEQUENCE: 93
gctagcgcca ccatgaccga gtacaagcct accgtgcgcc tggccactcg cgatgatgtg       60 cccccgcgccg tccgcactct ggccgccgct ttcgccgact accccgctac ccggcacacc     120
gtggaccccg accggcacat cgagcgtgtg acagagttgc aggagctgtt cctgacccgc     180
gtcgggctgg acatcggcaa ggtgtgggta gccgacgacg gcgcggccgt ggccgtgtgg     240 actaccccccg agagcgttga ggccggcgcc gtgttcgccg agatcggccc ccgaatggcc   300
gagctgagcg gcagccgcct ggccgcccag cagcaaatgg agggcctgct tgcccccccat   360 cgtcccaagg agcctgcctg gtttctggcc actgtaggag tgagcccccga ccaccagggc   420 aagggcttgg gcagcgccgt cgtgttgccc ggcgtagagg ccgccgaacg cgccggtgtg    480
cccgcctttc tcgaaacaag cgcaccaaga aaccttccat tctacgagcg cctgggcttc    540
accgtgaccg ccgatgtcga ggtgcccgag ggacctagga cctggtgtat gacacgaaaa   600
cctggcgcct aatgatctag a                                              621

<210> SEQ ID NO 94
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 94
aaagccacca tggaagatgc caaaaacatt aagaaggggc ctgctcccct ctaccctctt       60
gaagatggga ctgctggcga gcaacttcac aaagctatga gcggtatgc tcttgtgcca      120 gggacaattg cgttcacgga tgctcacatt gaagtagaca tcacatacgc tgagtatttt      180
gagatgtcgg tgcggctggc agaagctatg aagcgctatg gctgaatac aaaccataga      240 attgtagtgt gcagtgagaa ctcgttgcag ttctttatgc ccgtgctggg ggctctcttc      300 atcgggggtgg ctgtggctcc tgctaacgac atctacaacg agcgagagct gttgaactcg      360
atggggatct ctcagcctac agtggtgttt gtgagtaaga aagggcttca aaagattctc    420
aatgtgcaaa agaagctgcc tattatacaa aagattatta ttatggactc taagacagac    480 taccagggggt ttcagtccat gtacacattt gtaacctctc atctgcctcc tggcttcaac    540
```

```
gagtacgact tcgtgcccga gtctttcgac agggacaaaa cgattgctct gatcatgaac    600
agctccgggt ctaccgggct gcctaagggt gtagctctgc cccatcgaac agcttgtgtg    660
agattctctc atgccaggga cccgatcttt ggaaaccaga tcatccctga cactgctatt    720
ctgtcggtgg tgccctttca tcatgggttt gggatgttca caacactggg atacctcatt    780
tgcgggttta gagtggtgct catgtatagg tttgaagaag aactattcct acgctctttg    840
caagattata agattcagtc tgctctgctg gtgccaacac tattctcttt ttttgctaag    900
tctacgctca tagacaagta tgacttgtcc aacttgcacg agattgcttc tggcggagca    960
cctctgtcta aggaggtagg tgaggctgtg gctaagcgct tcatctgcc tggtatcaga   1020
caggggtacg ggctaacaga acaacttct gctattctga ttacaccaga gggcgatgac   1080
aaacccgggg ctgtagggaa agtggtgccc tttttgaag ccaaagtagt tgatcttgat   1140
accggtaaga cactaggggt gaaccagcgt ggtgaactgt gtgtgcgggg ccctatgatt   1200
atgtcgggt acgttaacaa ccccgaagct acaaatgctc tcatagacaa ggacgggtgg   1260
cttcatagcg gcgacattgc ctactgggac gaggatgagc atttcttcat cgtggacaga   1320
ctgaagtcgt tgatcaaata caaggggtat caagtagctc ctgccgagct tgagtccatt   1380
ctgcttcaac accccaatat cttcgatgct ggggtggctg ggctgcctga tgatgatgct   1440
ggagagctgc ctgctgctgt agtagtgctt gagcatggta agacaatgac agagaaggag   1500
atcgtggatt atgtggcttc acaagtgaca acagctaaga aactccgagg tggcgttgtg   1560
tttgtggatg aggtgcctaa agggctcact ggcaagctgg atgccagaaa aattcgagag   1620
attctcatta aggctaagaa gggtggaaag attgctgtgt aatagttcta ga          1672
```

<210> SEQ ID NO 95
<211> LENGTH: 1166
<212> TYPE: DNA
<213> ORGANISM: Artificial Sequence
<220> FEATURE:
<223> OTHER INFORMATION: A synthetic construct.

<400> SEQUENCE: 95

```
gcggccgcaa atgctaaacc actgcagtgg ttaccagtgc ttgatcagtg aggcaccgat     60
ctcagcgatc tgtctatttc gttcgtccat agtggcctga ctccccgtcg tgtagattac    120
tacgattcgt gagggcttac catcaggccc cagcgcagca atgatgccgc gagagccgcg    180
ttcaccggca ccggatttgt cagcaatgaa ccagccagca gggagggccg agcgaagaag    240
tggtcctgct actttgtccg cctccatcca gtctatgagc tgctgtcgtg atgctagagt    300
gagaagttcg ccagtgagta gtttccgaag agttgtggcc attgctactg gcatcgtggt    360
atcacgctcg tcgttcggta tggcttcgtt cagctccggt tcccagcggt caagccgggt    420
cacatgatca cccatgttgt gcaaaaatgc ggtcagctcc ttagggcctc cgatcgttgt    480
cagaagtaag ttggccgcgg tattatcgct catggtaatg gcagcactac acaattctct    540
taccgtcatg ccatccgtaa gatgcttttc cgtgaccggc gagtactcaa ccaagtcgtt    600
ttgtgagtag tgtatacggc gaccaagctg ctcttgcccg cgtctatac gggacaacac    660
cgcgccacat agcagtactt tgaaagtgct catcatcggg aatcgttctt cggggcggaa    720
agactcaagg atcttgccgc tattgagatc cagttcgata tagcccactc ttgcacccag    780
ttgatcttca gcatctttta ctttcaccag cgtttcgggg tgtgcaaaaa caggcaagca    840
aaatgccgca agaagggaa tgagtgcgac acgaaaatgt tggatgctca tactcttcct    900
tttttcaatat gtttgcagca tttgtcaggg ttactagtac gtctctcttg agagaccgcg    960
```

```
atcgccacca tgtctaggta ggtagtaaac gaaagggctt aaaggcctaa gtggccctcg   1020
agtccagcct tgagttggtt gagtccaagt cacgtttgga gatctggtac cttacgcgta   1080
tgagctctac gtagctagcg gcctcggcgg ccgaattctt gcgatctaag cttggcaatc   1140
cggtactgtt ggtaaagcca ccatgg                                        1166

<210> SEQ ID NO 96
<211> LENGTH: 1166
<212> TYPE: DNA
<213> ORGANISM: Artificial Sequence
<220> FEATURE:
<223> OTHER INFORMATION: A synthetic construct.

<400> SEQUENCE: 96
gcggccgcaa atgctaaacc actgcagtgg ttaccagtgc ttgatcagtg aggcaccgat     60
ctcagcgatc tgtctatttc gttcgtccat agtggcctga ctcccgtcg tgtagattac    120 tacgattcgt gagggcttac catcaggccc cagcgcagca atgatgccgc gagagccgcg    180
ttcaccggcc cccgatttgt cagcaatgaa ccagccagca gggagggccg agcgaagaag    240
tggtcctgct actttgtccg cctccatcca gtctatgagc tgctgtcgtg atgctagagt    300
aagaagttcg ccagtgagta gtttccgaag agttgtggcc attgctactg gcatcgtggt    360
atcacgctcg tcgttcggta tggcttcgtt caactccggt tcccagcggt caagccgggt    420
cacatgatca cccatgttgt gcaaaaatgc ggtcagctcc ttagggcctc cgatcgttgt    480
cagaagtaag ttggccgcgg tgttgtcgct catggtaatg gcagcactac acaattctct    540
taccgtcatg ccatccgtaa gatgcttttc cgtgaccggc gagtactcaa ccaagtcgtt    600
ttgtgagtag tgtatacggc gaccaagctg ctcttgcccg gcgtctatac gggacaacac    660
cgcgccacat agcagtactt tgaaagtgct catcatcggg aatcgttctt cggggcggaa    720
agactcaagg atcttgccgc tattgagatc cagttcgata tagccactc ttgcacccag    780 ttgatcttca gcatctttta ctttcaccag cgtttcgggg tgtgcaaaaa caggcaagca    840
aaatgccgca aagaagggaa tgagtgcgac acgaaaatgt tggatgctca tactcttcct    900
ttttcaatat gtttgcagca tttgtcaggg ttactagtac gtctctcttg agagaccgcg    960
atcgccacca tgtctaggta ggtagtaaac gaaagggctt aaaggcctaa gtggccctcg   1020
agtccagcct tgagttggtt gagtccaagt cacgtttgga gatctggtac cttacgcgta   1080
tgagctctac gtagctagcg gcctcggcgg ccgaattctt gcgttcgaag cttggcaatc   1140
cggtactgtt ggtaaagcca ccatgg                                        1166

<210> SEQ ID NO 97
<211> LENGTH: 1166
<212> TYPE: DNA
<213> ORGANISM: Artificial Sequence
<220> FEATURE:
<223> OTHER INFORMATION: A synthetic construct.

<400> SEQUENCE: 97
gcggccgcaa atgctaaacc actgcagtgg ttaccagtgc ttgatcagtg aggcaccgat     60
ctcagcgatc tgcctatttc gttcgtccat agtggcctga ctcccgtcg tgtagatcac    120 tacgattcgt gagggcttac catcaggccc cagcgcagca atgatgccgc gagagccgcg    180
ttcaccggcc cccgatttgt cagcaatgaa ccagccagca gggagggccg agcgaagaag    240
tggtcctgct actttgtccg cctccatcca gtctatgagc tgctgtcgtg atgctagagt    300
aagaagttcg ccagtgagta gtttccgaag agttgtggcc attgctactg gcatcgtggt    360
```

```
atcacgctcg tcgttcggta tggcttcgtt caactctggt tcccagcggt caagccgggt      420
cacatgatca cccatgttgt gcaaaaatgc ggtcagctcc ttagggcctc cgatcgttgt      480
cagaagtaag ttggccgcgg tgttgtcgct catggtaatg gcagcactac acaattctct      540
taccgtcatg ccatccgtaa gatgcttttc cgtgaccggc gagtactcaa ccaagtcgtt      600
ttgtgagtag tgtatacggc gaccaagctg ctcttgcccg gcgtctatac gggacaacac      660
cgcgccacat agcagtactt tgaaagtgct catcatcggg aatcgttctt cggggcggaa      720
agactcaagg atcttgccgc tattgagatc cagttcgata tagcccactc ttgcacccag      780
ttgatcttca gcatctttta ctttcaccag cgtttcgggg tgtgcaaaaa caggcaagca      840
aaatgccgca aagaagggaa tgagtgcgac acgaaaatgt tggatgctca tactcttcct      900
ttttcaatat gtttgcagca tttgtcaggg ttactagtac gtctctcttg agagaccgcg      960
atcgccacca tgtctaggta ggtagtaaac gaaagggctt aaaggcctaa gtggccctcg     1020
agtccagcct tgagttggtt gagtccaagt cacgtttgga gatctggtac cttacgcgta     1080
tgagctctac gtagctagcg gcctcggcgg ccgaattctt gcgttcgaag cttggcaatc     1140
cggtactgtt ggtaaagcca ccatgg                                          1166
```

SYNTHETIC NUCLEIC ACID MOLECULE COMPOSITIONS AND METHODS OF PREPARATION

CROSS-REFERENCE TO RELATED APPLICATION(S)

This application is a continuation of U.S. patent application Ser. No. 10/943,508, filed Sep. 17, 2004, now U.S. Pat. No. 7,728,118, which is incorporated by reference herein.

BACKGROUND

Transcription, the synthesis of an RNA molecule from a sequence of DNA is the first step in gene expression. Sequences which regulate DNA transcription include promoter sequences, polyadenylation signals, transcription factor binding sites and enhancer elements. A promoter is a DNA sequence capable of specific initiation of transcription and consists of three general regions. The core promoter is the sequence where the RNA polymerase and its cofactors bind to the DNA. Immediately upstream of the core promoter is the proximal promoter which contains several transcription factor binding sites that are responsible for the assembly of an activation complex that in turn recruits the polymerase complex. The distal promoter, located further upstream of the proximal promoter also contains transcription factor binding sites. Transcription termination and polyadenylation, like transcription initiation, are site specific and encoded by defined sequences. Enhancers are regulatory regions, containing multiple transcription factor binding sites, that can significantly increase the level of transcription from a responsive promoter regardless of the enhancer's orientation and distance with respect to the promoter as long as the enhancer and promoter are located within the same DNA molecule. The amount of transcript produced from a gene may also be regulated by a post-transcriptional mechanism, the most important being RNA splicing that removes intervening sequences (introns) from a primary transcript between splice donor and splice acceptor sequences.

Natural selection is the hypothesis that genotype-environment interactions occurring at the phenotypic level lead to differential reproductive success of individuals and therefore to modification of the gene pool of a population. Some properties of nucleic acid molecules that are acted upon by natural selection include codon usage frequency, RNA secondary structure, the efficiency of intron splicing, and interactions with transcription factors or other nucleic acid binding proteins. Because of the degenerate nature of the genetic code, these properties can be optimized by natural selection without altering the corresponding amino acid sequence.

Under some conditions, it is useful to synthetically alter the natural nucleotide sequence encoding a polypeptide to better adapt the polypeptide for alternative applications. A common example is to alter the codon usage frequency of a gene when it is expressed in a foreign host cell. Although redundancy in the genetic code allows amino acids to be encoded by multiple codons, different organisms favor some codons over others. It has been found that the efficiency of protein translation in a non-native host cell can be substantially increased by adjusting the codon usage frequency but maintaining the same gene product (U.S. Pat. Nos. 5,096,825, 5,670,356, and 5,874,304).

However, altering codon usage may, in turn, result in the unintentional introduction into a synthetic nucleic acid molecule of inappropriate transcription regulatory sequences. This may adversely effect transcription, resulting in anomalous expression of the synthetic DNA. Anomalous expression is defined as departure from normal or expected levels of expression. For example, transcription factor binding sites located downstream from a promoter have been demonstrated to effect promoter activity (Michael et al., 1990; Lamb et al., 1998; Johnson et al., 1998; Jones et al., 1997). Additionally, it is not uncommon for an enhancer element to exert activity and result in elevated levels of DNA transcription in the absence of a promoter sequence or for the presence of transcription regulatory sequences to increase the basal levels of gene expression in the absence of a promoter sequence.

Thus, what is needed is a method for making synthetic nucleic acid molecules with altered codon usage without also introducing inappropriate or unintended transcription regulatory sequences for expression in a particular host cell.

SUMMARY OF THE INVENTION

The invention provides an isolated nucleic acid molecule (a polynucleotide) comprising a synthetic nucleotide sequence having reduced, for instance, 90% or less, e.g., 80%, 78%, 75%, or 70% or less, nucleic acid sequence identity relative to a parent nucleic acid sequence, e.g., a wild-type nucleic acid sequence, and having fewer regulatory sequences such as transcription regulatory sequences. In one embodiment, the synthetic nucleotide sequence has fewer regulatory sequences than would result if the sequence differences between the synthetic nucleotide sequence and the parent nucleic acid sequence, e.g., optionally the result of differing codons, were randomly selected. In one embodiment, the synthetic nucleotide sequence encodes a polypeptide that has an amino acid sequence that is at least 85%, 90%, 95%, or 99%, or 100%, identical to the amino acid sequence of a naturally-occurring (native or wild-type) corresponding polypeptide (protein). Thus, it is recognized that some specific amino acid changes may also be desirable to alter a particular phenotypic characteristic of a polypeptide encoded by the synthetic nucleotide sequence. Preferably, the amino acid sequence identity is over at least 100 contiguous amino acid residues. In one embodiment of the invention, the codons in the synthetic nucleotide sequence that differ preferably encode the same amino acids as the corresponding codons in the parent nucleic acid sequence.

Hence, in one embodiment, the invention provides an isolated nucleic acid molecule comprising a synthetic nucleotide sequence having a coding region for a selectable or screenable polypeptide, wherein the synthetic nucleotide sequence has 90%, e.g., 80%, or less nucleic acid sequence identity to a parent nucleic acid sequence encoding a corresponding selectable or screenable polypeptide, and wherein the synthetic nucleotide sequence encodes a selectable or screenable polypeptide with at least 85% amino acid sequence identity to the corresponding selectable or screenable polypeptide encoded by the parent nucleic acid sequence. The decreased nucleotide sequence identity may be a result of different codons in the synthetic nucleotide sequence relative to the codons in the parent nucleic acid sequence. The synthetic nucleotide sequence of the invention has a reduced number of regulatory sequences relative to the parent nucleic acid sequence, for example, relative to the average number of regulatory sequences resulting from random selections of codons or nucleotides at the sequences which differ between the synthetic nucleotide sequence and the parent nucleic acid sequence. In one embodiment, a nucleic acid molecule may include a synthetic nucleotide sequence which together with other sequences encodes a selectable or screenable polypeptide. For instance, a synthetic nucleotide sequence which forms part of an open reading frame for a selectable or screenable polypeptide may include at least 100, 150, 200, 250, 300 or more nucleotides of the open reading, which nucleotides have reduced nucleic acid sequence identity relative to corresponding sequences in a parent nucleic acid sequence. In one embodiment, the parent nucleic acid sequence is SEQ ID NO:1, SEQ ID NO:6, SEQ ID NO:15 or SEQ ID NO:41, the complement thereof, or a sequence that has 90%, 95% or 99% nucleic acid sequence identity thereto.

In one embodiment, the nucleic acid molecule of the invention comprises sequences which have been optimized for expression in mammalian cells, and more preferably, in human cells (see, e.g., WO 02/16944 which discloses methods to optimize sequences for expression in a cell of interest). For instance, nucleic acid molecules may be optimized for expression in eukaryotic cells by introducing a Kozak sequence and/or one or more introns or decreasing the number of other regulatory sequences, and/or altering codon usage to codons employed more frequently in one or more eukaryotic organisms, e.g., codons employed more frequently in an eukaryotic host cell to be transformed with the nucleic acid molecule.

In one embodiment, the synthetic nucleotide sequence is present in a vector, e.g., a plasmid, and such a vector may include other optimized sequences. In one embodiment, the synthetic nucleotide sequence encodes a polypeptide comprising a selectable polypeptide, which synthetic nucleotide sequence has at least 90% or more nucleic acid sequence identity to an open reading frame in a sequence comprising, for example, SEQ ID NO:5, SEQ ID NO:9, SEQ ID NO:10, SEQ ID NO:11, SEQ ID NO:30, SEQ ID NO:38, SEQ ID NO:39, SEQ ID NO:42, SEQ ID NO:44, SEQ ID NO:70, SEQ ID NO:71, SEQ ID NO:72, SEQ ID NO:73, SEQ ID NO:74, SEQ ID NO:80, SEQ ID NO:81, SEQ ID NO:82, SEQ ID NO:83, SEQ ID NO:84, the complement thereof, or a fragment thereof that encodes a polypeptide with substantially the same activity as the corresponding full-length and optionally wild-type (functional) polypeptide, e.g., a polypeptide encoded by SEQ ID NO:1, SEQ ID NO:6, SEQ ID NO:15 or SEQ ID NO:41, or a portion thereof which together with other parent or wild-type sequences encodes a polypeptide with substantially the same activity as the corresponding full-length and optionally wild-type polypeptide. As used herein, "substantially the same activity" is at least about 70%, e.g., 80%, 90% or more, the activity of a corresponding full-length and optionally wild-type (functional) polypeptide. In one embodiment, an isolated nucleic acid molecule encodes a fusion polypeptide comprising a selectable polypeptide.

Also provided is an isolated nucleic acid molecule comprising a synthetic nucleotide sequence having a coding region for a firefly luciferase, wherein the nucleic acid sequence identity of the synthetic nucleic acid molecule is 90% or less, e.g., 80%, 78%, 75% or less, compared to a parent nucleic acid sequence encoding a firefly luciferase, e.g., a parent nucleic acid sequence having SEQ ID NO:14 or SEQ ID NO:43, which synthetic nucleotide sequence has fewer regulatory sequences including transcription regulatory sequences than would result if the sequence differences, e.g., differing codons, were randomly selected. Preferably, the synthetic nucleotide sequence encodes a polypeptide that has an amino acid sequence that is at least 85%, preferably 90%, and most preferably 95% or 99% identical to the amino acid sequence of a naturally-occurring or parent polypeptide. Thus, it is recognized that some specific amino acid changes may be desirable to alter a particular phenotypic characteristic of the luciferase encoded by the synthetic nucleotide sequence. Preferably, the amino acid sequence identity is over at least 100 contiguous amino acid residues. In one embodiment, the synthetic nucleotide sequence encodes a polypeptide comprising a firefly luciferase, which synthetic nucleotide sequence has at least 90% or more nucleic acid sequence identity to an open reading frame in a sequence comprising, for example, SEQ ID NO:21, SEQ ID NO:22, SEQ ID NO:23, the complement thereof, or a fragment thereof that encodes a polypeptide with substantially the same activity as the corresponding full-length and optionally wild-type (functional) polypeptide, e.g., a polypeptide encoded by SEQ ID NO:14 or SEQ ID NO:43, or a portion thereof which together with other sequences encodes a firefly luciferase. For instance, a synthetic nucleotide sequence which forms part of an open reading frame for a firefly luciferase may include at least 100, 150, 200, 250, 300 or more nucleotides of the open reading, which nucleotides have reduced nucleic acid sequence identity relative to corresponding sequences in a parent nucleic acid sequence.

In another embodiment, the invention provides an isolated nucleic acid molecule comprising a synthetic nucleotide sequence which does not include an open reading frame encoding a peptide or polypeptide of interest, e.g., the synthetic nucleotide sequence may have an open reading frame but it does not include sequences that encode a functional or desirable peptide or polypeptide, but may include one or more stop codons in one or more reading frames, one or more poly(A) adenylation sites, and/or a contiguous sequence for two or more restriction endonucleases (restriction enzymes), i.e., a multiple cloning region (also referred to as a multiple cloning site, "MCS"), and which is generally at least 20, e.g., at least 30, nucleotides in length and up to 1000 or more nucleotides, e.g., up to 10,000 nucleotides, which synthetic nucleotide sequence has fewer regulatory sequences such as transcription regulatory sequences relative to a corresponding parent nucleic acid sequence. In one embodiment, the synthetic nucleotide sequence which does not encode a peptide or polypeptide has 90% or less, e.g., 80%, or less nucleic acid sequence identity to a parent nucleic acid sequence, wherein the decreased sequence identity is a result of a reduced number of regulatory sequences in the synthetic nucleotide sequence relative to the parent nucleic acid sequence.

The regulatory sequences which are reduced in the synthetic nucleotide sequence include, but are not limited to, any combination of transcription factor binding sequences, intron splice sites, poly(A) adenylation sites (poly(A) sequences or poly(A) sites hereinafter), enhancer sequences, promoter modules, and/or promoter sequences, e.g., prokaryotic promoter sequences. Generally, a synthetic nucleic acid molecule lacks at least 10%, 20%, 50% or more of the regulatory sequences, for instance lacks substantially all of the regulatory sequences, e.g., 80%, 90% or more, for instance, 95% or more, of the regulatory sequences, present in a corresponding parent or wild-type nucleotide sequence. Regulatory sequences, e.g., transcription regulatory sequences, are well known in the art. The synthetic nucleotide sequence may also have a reduced number of restriction enzyme recognition sites, and may be modified to include selected sequences, e.g., sequences at or near the 5' and/or 3' ends of the synthetic nucleotide sequence such as Kozak sequences and/or desirable restriction enzyme recognition sites, for instance, restriction enzyme recognition sites useful to introduce a synthetic nucleotide sequence to a specified location, e.g., in a multiple cloning region 5' and/or 3' to a nucleic acid sequence of interest.

In one embodiment, the synthetic nucleotide sequence of the invention has a codon composition that differs from that of the parent or wild-type nucleic acid sequence. Preferred codons for use in the invention are those which are employed more frequently than at least one other codon for the same amino acid in a particular organism and/or those that are not low-usage codons in that organism and/or those that are not low-usage codons in the organism used to clone or screen for the expression of the synthetic nucleotide sequence (for example, E. coli). Moreover, codons for certain amino acids (i.e., those amino acids that have three or more codons), may include two or more codons that are employed more frequently than the other (non-preferred) codon(s). The presence of codons in a synthetic nucleotide sequence that are employed more frequently in one organism than in another organism results in a synthetic nucleotide sequence which, when introduced into the cells of the organism that employs those codons more frequently, has a reduced risk of aberrant expression and/or is expressed in those cells at a level that may be greater than the expression of the wild type (unmodified) nucleic acid sequence in those cells under some conditions. For example, a synthetic nucleic acid molecule of the invention which encodes a selectable or screenable polypeptide may be expressed at a level that is greater, e.g., at least about 2, 3, 4, 5, 10-fold or more relative to that of the parent or wild-type (unmodified) nucleic acid sequence in a cell or cell extract under identical conditions (such as cell culture conditions, vector backbone, and the like). In one embodiment, the synthetic nucleotide sequence of the invention has a codon composition that differs from that of the parent or wild-type nucleic acid sequence at more than 10%, 20% or more, e.g., 30%, 35%, 40% or more than 45%, e.g., 50%, 55%, 60% or more of the codons.

In one embodiment of the invention, the codons that are different are those employed more frequently in a mammal, while in another embodiment the codons that are different are those employed more frequently in a plant. A particular type of mammal, e.g., human, may have a different set of preferred codons than another type of mammal. Likewise, a particular type of plant may have a different set of preferred codons than another type of plant. In one embodiment of the invention, the majority of the codons which differ are ones that are preferred codons in a desired host cell and/or are not low usage codons in a particular host cell. Preferred codons for mammals (e.g., humans) and plants are known to the art (e.g., Wada et al., 1990). For example, preferred human codons include, but are not limited to, CGC (Arg), CTG (Leu), AGC (Ser), ACC (Thr), CCC (Pro), GCC (Ala), GGC (Gly), GTG (Val), ACT (Ile), AAG (Lys), AAC (Asn), CAG (Gln), CAC (His), GAG (Glu), GAC (Asp), TAC (Tyr), TGC (Cys) and TTC (Phe) (Wada et al., 1990). Thus, synthetic nucleotide sequences of the invention have a codon composition which differs from a wild type nucleic acid sequence by having an increased number of preferred human codons, e.g. CGC, CTG, TCT, AGC, ACC, CCC, GCC, GGC, GTG, ACT, AAG, AAC, CAG, CAC, GAG, GAC, TAC, TGC, TTC, or any combination thereof. For example, the synthetic nucleotide sequence of the invention may have an increased number of AGC serine-encoding codons, CCC proline-encoding codons, and/or ACC threonine-encoding codons, or any combination thereof, relative to the parent or wild-type nucleic acid sequence. Similarly, synthetic nucleotide sequences having an increased number of codons that are employed more frequently in plants, have a codon composition which differs from a wild-type nucleic acid sequence by having an increased number of the plant codons including, but not limited to, CGC (Arg), CTT (Leu), TCT (Ser), TCC (Ser), ACC (Thr), CCA (Pro), CCT (Pro), GCT (Ser), GGA (Gly), GTG (Val), ATC (Ile), ATT (Ile), AAG (Lys), AAC (Asn), CAA (Gln), CAC (His), GAG (Glu), GAC (Asp), TAC (Tyr), TGC (Cys), TTC (Phe), or any combination thereof (Murray et al., 1989). Preferred codons may differ for different types of plants (Wada et al., 1990).

The nucleotide substitutions in the synthetic nucleic acid sequence may be influenced by many factors such as, for example, the desire to have an increased number of nucleotide substitutions such as those resulting in a silent nucleotide substitution (encodes the same amino acid) and/or decreased number of regulatory sequences. Under some circumstances (e.g., to permit removal of a transcription factor binding site) it may be desirable to replace a non-preferred codon with a codon other than a preferred codon or a codon other than the preferred codon in order to decrease the number of regulatory sequences.

The invention also provides an expression cassette or vector. The expression cassette or vector of the invention comprises a synthetic nucleotide sequence of the invention operatively linked to a promoter that is functional in a cell or comprises a synthetic nucleotide sequence, respectively. Preferred promoters are those functional in mammalian cells and those functional in plant cells. Optionally, the expression cassette may include other sequences, e.g., one or more restriction enzyme recognition sequences 5' and/or 3' to an open reading frame for a selectable polypeptide or luciferase and/or a Kozak sequence, and be a part of a larger polynucleotide molecule such as a plasmid, cosmid, artificial chromosome or vector, e.g., a viral vector, which may include a multiple cloning region for other sequences, e.g., promoters, enhancers, other open reading frames and/or poly(A) sites. In one embodiment, a vector of the invention includes SEQ ID NO:88, SEQ ID NO:89, SEQ ID NO:90, the complement thereof, or a sequence which has at least 80% nucleic acid sequence identity thereto and encodes a selectable and/or screenable polypeptide.

In one embodiment, the synthetic nucleotide sequence encoding a selectable or screenable polypeptide is introduced into a vector backbone, e.g., one which optionally has a poly(A) site 3' to the synthetic nucleotide sequence, a gene useful for selecting transformed prokaryotic cells which optionally is a synthetic sequence, a gene useful for selecting transformed eukaryotic cells which optionally is a synthetic sequence, a noncoding region for decreasing transcription and/or translation into adjacent linked desirable open reading frames, and/or a multiple cloning region 5' and/or 3' to the synthetic nucleotide sequence encoding a selectable or screenable polypeptide which optionally includes one or more protein destabilization sequences (see U.S. application Ser. No. 10/664,341, filed Sep. 16, 2003, the disclosure of which is incorporated by reference herein). In one embodiment, the vector having a synthetic nucleotide sequence encoding a selectable or screenable polypeptide may lack a promoter and/or enhancer which is operably linked to that synthetic sequence. In another embodiment, the invention provides a vector comprising a promoter, e.g., a prokaryotic or eukaryotic promoter, operably linked to a synthetic nucleotide sequence encoding a selectable or screenable polypeptide. Such vectors optionally include one or more multiple cloning regions, such as ones that are useful to introduce an additional open reading frame and/or a promoter for expression of the open reading frame which promoter optionally is different than the promoter for the selectable or screenable polypeptide, and/or a prokaryotic origin of replication. A "vector backbone" as used herein may include sequences (open reading frames) useful to identify cells with those sequences, e.g., in prokaryotic cells, their promoters, an origin of replication for vector maintenance, e.g., in prokaryotic cells, and optionally one or more other sequences including multiple cloning regions e.g., for insertion of a promoter and/or open reading frame of interest, and sequences which inhibit transcription and/or translation.

Also provided is a host cell comprising the synthetic nucleotide sequence of the invention, an isolated polypeptide (e.g., a fusion polypeptide encoded by the synthetic nucleotide sequence of the invention), and compositions and kits comprising the synthetic nucleotide sequence of the invention, a polypeptide encoded thereby, or an expression cassette or vector comprising the synthetic nucleotide sequence in suitable container means and, optionally, instruction means. The host cell may be an eukaryotic cell such as a plant or vertebrate cell, e.g., a mammalian cell, including but not limited to a human, non-human primate, canine, feline, bovine, equine, ovine or rodent (e.g., rabbit, rat, ferret, hamster, or mouse) cell or a prokaryotic cell.

The invention also provides a method to prepare a synthetic nucleotide sequence of the invention by genetically altering a parent, e.g., a wild-type or synthetic, nucleic acid sequence. The method comprises altering (e.g., decreasing or eliminating) a plurality of regulatory sequences in a parent nucleic acid sequence, e.g., one which encodes a selectable or screenable polypeptide or one which does not encode a peptide or polypeptide, to yield a synthetic nucleotide sequence which has a decreased number of regulatory sequences and, if the synthetic nucleotide sequence encodes a polypeptide, it preferably encodes the same amino acids as the parent nucleic acid molecule. The transcription regulatory sequences which are reduced include but are not limited to any of transcription factor binding sequences, intron splice sites, poly(A) sites, enhancer sequences, promoter modules, and/or promoter sequences. Preferably, the alteration of sequences in the synthetic nucleotide sequence does not result in an increase in regulatory sequences. In one embodiment, the synthetic nucleotide sequence encodes a polypeptide that has at least 85%, 90%, 95% or 99%, or 100%, contiguous amino acid sequence identity to the amino acid sequence of the polypeptide encoded by the parent nucleic acid sequence.

Thus, in one embodiment, a method to prepare a synthetic nucleic acid molecule comprising an open reading frame is provided. The method includes altering the codons and/or regulatory sequences in a parent nucleic acid sequence which encodes a reporter protein such, as a firefly luciferase or a selectable polypeptide such as one encoding resistance to ampicillin, puromycin, hygromycin or neomycin, to yield a synthetic nucleotide sequence which encodes a corresponding reporter polypeptide and which has for instance at least 10% or more, e.g., 20%, 30%, 40%, 50% or more, fewer regulatory sequences relative to the parent nucleic acid sequence. The synthetic nucleotide sequence has 90%, e.g., 85%, 80%, or 78%, or less nucleic acid sequence identity to the parent nucleic acid sequence and encodes a polypeptide with at least 85% amino acid sequence identity to the polypeptide encoded by the parent nucleic acid sequence. The regulatory sequences which are altered include transcription factor binding sequences, intron splice sites, poly(A) sites, promoter modules, and/or promoter sequences. In one embodiment, the synthetic nucleic acid sequence hybridizes under medium stringency hybridization but not stringent conditions to the parent nucleic acid sequence or the complement thereof. In one embodiment, the codons which differ encode the same amino acids as the corresponding codons in the parent nucleic acid sequence.

Also provided is a synthetic (including a further synthetic) nucleotide sequence prepared by the methods of the invention, e.g., a further synthetic nucleotide sequence in which introduced regulatory sequences or restriction endonuclease recognition sequences are optionally removed. Thus, the method of the invention may be employed to alter the codon usage frequency and/or decrease the number of regulatory sequences in any open reading frame or to decrease the number of regulatory sequences in any nucleic acid sequence, e.g., a noncoding sequence. Preferably, the codon usage frequency in a synthetic nucleotide sequence which encodes a selectable or screenable polypeptide is altered to reflect that of the host organism desired for expression of that nucleotide sequence while also decreasing the number of potential regulatory sequences relative to the parent nucleic acid molecule.

Also provided is a method to prepare a synthetic nucleic acid molecule which does not code for a peptide or polypeptide. The method includes altering the nucleotides in a parent nucleic acid sequence having at least 20 nucleotides which optionally does not code for a functional or desirable peptide or polypeptide and which optionally may include sequences which inhibit transcription and/or translation, to yield a synthetic nucleotide sequence which does not include an open reading frame encoding a peptide or polypeptide of interest, e.g., the synthetic nucleotide sequence may have an open reading frame but it does not include sequences that encode a functional or desirable peptide or polypeptide, but may include one or more stop codons in one or more reading frames, one or more poly(A) adenylation sites, and/or a contiguous sequence for two or more restriction endonucleases, i.e., a multiple cloning region. The synthetic nucleotide sequence is generally at least 20, e.g., at least 30, nucleotides in length and up to 1000 or more nucleotides, e.g., up to 10,000 nucleotides, and has fewer regulatory sequences such as transcription regulatory sequences relative to a corresponding parent nucleic acid sequence which does not code for a peptide or polypeptide, e.g., a parent nucleic acid sequence which optionally includes sequences which inhibit transcription and/or translation. The nucleotides are altered to reduce one or more regulatory sequences, e.g., transcription factor binding sequences, intron splice sites, poly(A) sites, enhancer sequences, promoter modules, and/or promoter sequences, in the parent nucleic acid sequence.

The invention also provides a method to prepare an expression vector. The method includes providing a linearized plasmid having a nucleic molecule including a synthetic nucleotide sequence of the invention which encodes a selectable or screenable polypeptide which is flanked at the 5' and/or 3' end by a multiple cloning region. The plasmid is linearized by contacting the plasmid with at least one restriction endonuclease which cleaves in the multiple cloning region. The linearized plasmid and an expression cassette having ends compatible with the ends in the linearized plasmid are annealed, yielding an expression vector. In one embodiment, the plasmid is linearized by cleavage by at least two restriction endonucleases, only one of which cleaves in the multiple cloning region.

Also provided is a method to clone a promoter or open reading frame. The method includes comprising providing a linearized plasmid having a multiple cloning region and a synthetic sequence of the invention which encodes a selectable or screenable polypeptide and/or a synthetic sequence of the invention which does not encode a peptide or polypeptide, which is plasmid is linearized by contacting the plasmid with at least two restriction endonucleases at least one of which cleaves in the multiple cloning region; and annealing the linearized plasmid with DNA having a promoter or an open reading frame with ends compatible with the ends of the linearized plasmid.

Exemplary methods to prepare synthetic sequences for firefly luciferase and a number of selectable polypeptide nucleic acid sequences, as well as non-coding regions present in a vector backbone, are described hereinbelow. For instance, the methods may produce synthetic selectable polypeptide nucleic acid molecules which exhibit similar or significantly enhanced levels of mammalian expression without negatively effecting other desirable physical or biochemical properties and which were also largely devoid of regulatory elements.

Clearly, the present invention has applications with many genes and across many fields of science including, but not limited to, life science research, agrigenetics, genetic therapy, developmental science and pharmaceutical development.

BRIEF DESCRIPTION OF THE FIGURES

FIG. 1. Codons and their corresponding amino acids.

DETAILED DESCRIPTION OF THE INVENTION

Definitions

Figure 2:
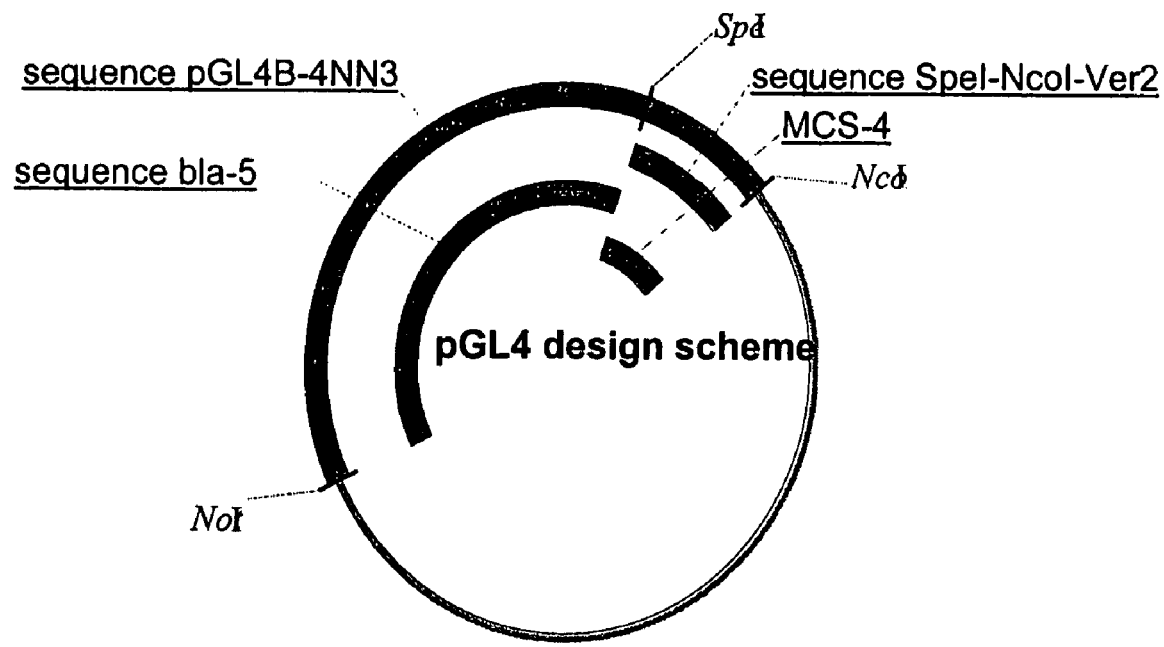
FIG. 2. Design scheme for the pGL4 vector.

The term "nucleic acid molecule" or "nucleic acid sequence" as used herein, refers to nucleic acid, DNA or RNA, that comprises noncoding or coding sequences. Coding sequences are necessary for the production of a polypeptide or protein precursor. The polypeptide can be encoded by a full-length coding sequence or by any portion of the coding sequence, as long as the desired protein activity is retained. Noncoding sequences refer to nucleic acids which do not code for a polypeptide or protein precursor, and may include regulatory elements such as transcription factor binding sites, poly(A) sites, restriction endonuclease sites, stop codons and/or promoter sequences.

A "synthetic" nucleic acid sequence is one which is not found in nature, i.e., it has been derived using molecular biological, chemical and/or informatic techniques.

A "nucleic acid", as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence, i.e., a linear order of nucleotides. A "polynucleotide", as used herein, is a nucleic acid containing a sequence that is greater than about 100 nucleotides in length. An "oligonucleotide" or "primer", as used herein, is a short polynucleotide or a portion of a polynucleotide. An oligonucleotide typically contains a sequence of about two to about one hundred bases. The word "oligo" is sometimes used in place of the word "oligonucleotide".

Nucleic acid molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring.

As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. Typically, promoter and enhancer elements that direct transcription of a linked gene (e.g., open reading frame or coding region) are generally located 5' or upstream of the coding region. However, enhancer elements can exert their effect even when located 3' of the promoter element and the coding region. Transcription termination and polyadenylation signals are located 3' or downstream of the coding region.

The term "codon" as used herein, is a basic genetic coding unit, consisting of a sequence of three nucleotides that specify a particular amino acid to be incorporation into a polypeptide chain, or a start or stop signal. The term "coding region" when used in reference to structural genes refers to the nucleotide sequences that encode the amino acids found in the nascent polypeptide as a result of translation of a mRNA molecule. Typically, the coding region is bounded on the 5' side by the nucleotide triplet "ATG" which encodes the initiator methionine and on the 3' side by a stop codon (e.g., TAA, TAG, TGA). In some cases the coding region is also known to initiate by a nucleotide triplet "TTG".

By "protein", "polypeptide" or "peptide" is meant any chain of amino acids, regardless of length or post-translational modification (e.g., glycosylation or phosphorylation). The nucleic acid molecules of the invention may also encode a variant of a naturally-occurring protein or a fragment thereof. Preferably, such a variant protein has an amino acid sequence that is at least 85%, preferably 90%, and most preferably 95% or 99% identical to the amino acid sequence of the naturally-occurring (native or wild-type) protein from which it is derived.

Polypeptide molecules are said to have an "amino terminus" (N-terminus) and a "carboxy terminus" (C-terminus) because peptide linkages occur between the backbone amino group of a first amino acid residue and the backbone carboxyl group of a second amino acid residue. The terms "N-terminal" and "C-terminal" in reference to polypeptide sequences refer to regions of polypeptides including portions of the N-terminal and C-terminal regions of the polypeptide, respectively. A sequence that includes a portion of the N-terminal region of a polypeptide includes amino acids predominantly from the N-terminal half of the polypeptide chain, but is not limited to such sequences. For example, an N-terminal sequence may include an interior portion of the polypeptide sequence including bases from both the N-terminal and C-terminal halves of the polypeptide. The same applies to C-terminal regions. N-terminal and C-terminal regions may, but need not, include the amino acid defining the ultimate N-terminus and C-terminus of the polypeptide, respectively.

The term "wild-type" as used herein, refers to a gene or gene product that has the characteristics of that gene or gene product isolated from a naturally occurring source. A wild-type gene is that which is most frequently observed in a population and is thus arbitrarily designated the "wild-type" form of the gene. In contrast, the term "mutant" refers to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

The term "fusion polypeptide" refers to a chimeric protein containing a protein of interest (e.g., luciferase) joined to a heterologous sequence (e.g., a non-luciferase amino acid or protein).

The terms "cell," "cell line," "host cell," as used herein, are used interchangeably, and all such designations include progeny or potential progeny of these designations. By "transformed cell" is meant a cell into which (or into an ancestor of which) has been introduced a nucleic acid molecule of the invention, e.g., via transient transfection. Optionally, a nucleic acid molecule synthetic gene of the invention may be introduced into a suitable cell line so as to create a stably-transfected cell line capable of producing the protein or polypeptide encoded by the synthetic gene. Vectors, cells, and methods for constructing such cell lines are well known in the art. The words "transformants" or "transformed cells" include the primary transformed cells derived from the originally transformed cell without regard to the number of transfers. All progeny may not be precisely identical in DNA content, due to deliberate or inadvertent mutations. Nonetheless, mutant progeny that have the same functionality as screened for in the originally transformed cell are included in the definition of transformants.

Nucleic acids are known to contain different types of mutations. A "point" mutation refers to an alteration in the sequence of a nucleotide at a single base position from the wild type sequence. Mutations may also refer to insertion or deletion of one or more bases, so that the nucleic acid sequence differs from the wild-type sequence.

The term "homology" refers to a degree of complementarity between two or more sequences. There may be partial homology or complete homology (i.e., identity). Homology is often measured using sequence analysis software (e.g., EMBOSS, the European Molecular Biology Open Software Suite available at http://www.hgmp.mrc.ac.uk/Software/EMBOSS/overview/html). Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

The term "isolated" when used in relation to a nucleic acid, as in "isolated oligonucleotide" or "isolated polynucleotide" refers to a nucleic acid sequence that is identified and separated from at least one contaminant with which it is ordinarily associated in its source. Thus, an isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide contains at a minimum, the sense or coding strand (i.e., the oligonucleotide may be single-stranded), but may contain both the sense and anti-sense strands (i.e., the oligonucleotide may be double-stranded).

The term "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide is present in a form or setting that is different from that in which it is found in nature. In contrast, non-isolated polypeptides (e.g., proteins and enzymes) are found in the state they exist in nature.

The term "purified" or "to purify" means the result of any process that removes some of a contaminant from the component of interest, such as a protein or nucleic acid. The percent of a purified component is thereby increased in the sample.

The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional (e.g., enzymatically active, capable of binding to a binding partner, capable of inhibiting, etc.) protein or polypeptide is produced.

The term "recombinant DNA molecule" means a hybrid DNA sequence comprising at least two nucleotide sequences not normally found together in nature.

The term "vector" is used in reference to nucleic acid molecules into which fragments of DNA may be inserted or cloned and can be used to transfer DNA segment(s) into a cell and capable of replication in a cell. Vectors may be derived from plasmids, bacteriophages, viruses, cosmids, and the like.

The terms "recombinant vector" and "expression vector" as used herein refer to DNA or RNA sequences containing a desired coding sequence and appropriate DNA or RNA sequences necessary for the expression of the operably linked coding sequence in a particular host organism. Prokaryotic expression vectors include a promoter, a ribosome binding site, an origin of replication for autonomous replication in a host cell and possibly other sequences, e.g. an optional operator sequence, optional restriction enzyme sites. A promoter is defined as a DNA sequence that directs RNA polymerase to bind to DNA and to initiate RNA synthesis. Eukaryotic expression vectors include a promoter, optionally a polyadenylation signal and optionally an enhancer sequence.

A polynucleotide having a nucleotide sequence encoding a protein or polypeptide means a nucleic acid sequence comprising the coding region of a gene, or in other words the nucleic acid sequence encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. In further embodiments, the coding region may contain a combination of both endogenous and exogenous control elements.

The term "regulatory element" or "regulatory sequence" refers to a genetic element or sequence that controls some aspect of the expression of nucleic acid sequence(s). For example, a promoter is a regulatory element that facilitates the initiation of transcription of an operably linked coding region. Other regulatory elements include, but are not limited to, transcription factor binding sites, splicing signals, polyadenylation signals, termination signals and enhancer elements.

Transcriptional control signals in eukaryotes comprise "promoter" and "enhancer" elements. Promoters and enhancers consist of short arrays of DNA sequences that interact specifically with cellular proteins involved in transcription. Promoter and enhancer elements have been isolated from a variety of eukaryotic sources including genes in yeast, insect and mammalian cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types. For example, the SV40 early gene enhancer is very active in a wide variety of cell types from many mammalian species and has been widely used for the expression of proteins in mammalian cells. Two other examples of promoter/enhancer elements active in a broad range of mammalian cell types are those from the human elongation factor 1 gene (Uetsuki et al., 1989; Kim et al., 1990; and Mizushima and Nagata, 1990) and the long terminal repeats of the Rous sarcoma virus (Gorman et al., 1982); and the human cytomegalovirus (Boshart et al., 1985).

The term "promoter/enhancer" denotes a segment of DNA containing sequences capable of providing both promoter and enhancer functions (i.e., the functions provided by a promoter element and an enhancer element as described above). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques) such that transcription of the gene is directed by the linked enhancer/promoter.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook et al., 1989). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamH I/Bcl I restriction fragment and directs both termination and polyadenylation (Sambrook et al., 1989).

Eukaryotic expression vectors may also contain "viral replicons" or "viral origins of replication." Viral replicons are viral DNA sequences which allow for the extrachromosomal replication of a vector in a host cell expressing the appropriate replication factors. Vectors containing either the SV40 or polyoma virus origin of replication replicate to high copy number (up to $10^4$ copies/cell) in cells that express the appropriate viral T antigen. In contrast, vectors containing the replicons from bovine papillomavirus or Epstein-Barr virus replicate extrachromosomally at low copy number (about 100 copies/cell).

The term "in vitro" refers to an artificial environment and to processes or reactions that occur within an artificial environment. In vitro environments include, but are not limited to, test tubes and cell lysates. The term "in vivo" refers to the natural environment (e.g., an animal or a cell) and to processes or reactions that occur within a natural environment.

The term "expression system" refers to any assay or system for determining (e.g., detecting) the expression of a gene of interest. Those skilled in the field of molecular biology will understand that any of a wide variety of expression systems may be used. A wide range of suitable mammalian cells are available from a wide range of sources (e.g., the American Type Culture Collection, Rockland, Md.). The method of transformation or transfection and the choice of expression vehicle will depend on the host system selected. Transformation and transfection methods are described, e.g., in Ausubel et al., 1992. Expression systems include in vitro gene expression assays where a gene of interest (e.g., a reporter gene) is linked to a regulatory sequence and the expression of the gene is monitored following treatment with an agent that inhibits or induces expression of the gene. Detection of gene expression can be through any suitable means including, but not limited to, detection of expressed mRNA or protein (e.g., a detectable product of a reporter gene) or through a detectable change in the phenotype of a cell expressing the gene of interest. Expression systems may also comprise assays where a cleavage event or other nucleic acid or cellular change is detected.

All amino acid residues identified herein are in the natural L-configuration. In keeping with standard polypeptide nomenclature, abbreviations for amino acid residues are as shown in the following Table of Correspondence.

| TABLE OF CORRESPONDENCE | | |
|---|---|---|
| 1-Letter | 3-Letter | AMINO ACID |
| Y | Tyr | L-tyrosine |
| G | Gly | L-glycine |
| F | Phe | L-phenylalanine |

-continued

TABLE OF CORRESPONDENCE

| 1-Letter | 3-Letter | AMINO ACID |
|---|---|---|
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

The terms "complementary" or "complementarity" are used in reference to a sequence of nucleotides related by the base-pairing rules. For example, for the sequence 5' "A-G-T" 3', is complementary to the sequence 3' "T-C-A" 5'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon hybridization of nucleic acids.

When used in reference to a double-stranded nucleic acid sequence such as a cDNA or a genomic clone, the term "substantially homologous" refers to any probe which can hybridize to either or both strands of the double-stranded nucleic acid sequence under conditions of low stringency as described herein.

"Probe" refers to an oligonucleotide designed to be sufficiently complementary to a sequence in a denatured nucleic acid to be probed (in relation to its length) and is bound under selected stringency conditions.

"Hybridization" and "binding" in the context of probes and denatured nucleic acids are used interchangeably. Probes that are hybridized or bound to denatured nucleic acids are base paired to complementary sequences in the polynucleotide. Whether or not a particular probe remains base paired with the polynucleotide depends on the degree of complementarity, the length of the probe, and the stringency of the binding conditions. The higher the stringency, the higher must be the degree of complementarity and/or the longer the probe.

The term "hybridization" is used in reference to the pairing of complementary nucleic acid strands. Hybridization and the strength of hybridization (i.e., the strength of the association between nucleic acid strands) is impacted by many factors well known in the art including the degree of complementarity between the nucleic acids, stringency of the conditions involved such as the concentration of salts, the Tm (melting temperature) of the formed hybrid, the presence of other components (e.g., the presence or absence of polyethylene glycol), the molarity of the hybridizing strands and the G:C content of the nucleic acid strands.

The term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often required when it is desired that nucleic acids that are not completely complementary to one another be hybridized or annealed together. The art knows well that numerous equivalent conditions can be employed to comprise medium or low stringency conditions. The choice of hybridization conditions is generally evident to one skilled in the art and is usually guided by the purpose of the hybridization, the type of hybridization (DNA-DNA or DNA-RNA), and the level of desired relatedness between the sequences (e.g., Sambrook et al., 1989; Nucleic Acid Hybridization, A Practical Approach, IRL Press, Washington D.C., 1985, for a general discussion of the methods).

The stability of nucleic acid duplexes is known to decrease with increasing numbers of mismatched bases, and further to be decreased to a greater or lesser degree depending on the relative positions of mismatches in the hybrid duplexes. Thus, the stringency of hybridization can be used to maximize or minimize stability of such duplexes. Hybridization stringency can be altered by: adjusting the temperature of hybridization; adjusting the percentage of helix destabilizing agents, such as formamide, in the hybridization mix; and adjusting the temperature and/or salt concentration of the wash solutions. For filter hybridizations, the final stringency of hybridizations often is determined by the salt concentration and/or temperature used for the post-hybridization washes.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 g/ml denatured salmon sperm DNA followed by washing in a solution comprising 5×SSPE, 0.1% SDS at 42° C. when a probe of about 500 nucleotides in length is employed.

The term "$T_m$" is used in reference to the "melting temperature". The melting temperature is the temperature at which 50% of a population of double-stranded nucleic acid molecules becomes dissociated into single strands. The equation for calculating the $T_m$ of nucleic acids is well-known in the art. The Tm of a hybrid nucleic acid is often estimated using a formula adopted from hybridization assays in 1 M salt, and commonly used for calculating Tm for PCR primers: [(number of A+T)×2° C.+(number of G+C)×4° C.]. (C. R.

Newton et al., *PCR,* 2nd Ed., Springer-Verlag (New York, 1997), p. 24). This formula was found to be inaccurate for primers longer than 20 nucleotides. (Id.) Another simple estimate of the $T_m$ value may be calculated by the equation: $T_m=81.5+0.41$ (% G+C), when a nucleic acid is in aqueous solution at 1 M NaCl. (e.g., Anderson and Young, Quantitative Filter Hybridization, in *Nucleic Acid Hybridization,* 1985). Other more sophisticated computations exist in the art which take structural as well as sequence characteristics into account for the calculation of $T_m$. A calculated $T_m$ is merely an estimate; the optimum temperature is commonly determined empirically.

The term "promoter/enhancer" denotes a segment of DNA containing sequences capable of providing both promoter and enhancer functions (i.e., the functions provided by a promoter element and an enhancer element as described above). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques) such that transcription of the gene is directed by the linked enhancer/promoter.

The term "sequence homology" means the proportion of base matches between two nucleic acid sequences or the proportion of amino acid matches between two amino acid sequences. When sequence homology is expressed as a percentage, e.g., 50%, the percentage denotes the proportion of matches over the length of sequence from one sequence that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and more preferably not less than 19 matches out of 20 possible base pair matches (95%).

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 100 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, 1972, volume 5, National Biomedical Research Foundation, pp. 101-110, and Supplement 2 to this volume, pp. 1-10. The two sequences or parts thereof are more preferably homologous if their amino acids are greater than or equal to 85% identical when optimally aligned using the ALIGN program.

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 or 100 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller (1988); the local homology algorithm of Smith and Waterman (1981); the homology alignment algorithm of Needleman and Wunsch (1970); the search-for-similarity-method of Pearson and Lipman (1988); the algorithm of Karlin and Altschul (1990), modified as in Karlin and Altschul (1993).

Computer implementations of these mathematical algorithms can be utilized for comparison of sequences to determine sequence identity. Such implementations include, but are not limited to: ClustalW (available, e.g., at http://www.e-bi.ac.uk/clustalw/); the ALIGN program (Version 2.0) and GAP, BESTFIT, BLAST, FASTA, and TFASTA in the Wisconsin Genetics Software Package, Version 8. Alignments using these programs can be performed using the default parameters. The CLUSTAL program is well described by Higgins et al. (1988); Higgins et al. (1989); Corpet et al. (1988); Huang et al. (1992); and Pearson et al. (1994). The ALIGN program is based on the algorithm of Myers and Miller, supra. The BLAST programs of Altschul et al. (1990), are based on the algorithm of Karlin and Altschul supra. To obtain gapped alignments for comparison purposes, Gapped BLAST (in BLAST 2.0) can be utilized as described in Altschul et al. (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. See http://www.ncbi.nlm.nih.gov. Alignment may also be performed manually by inspection The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) for the stated proportion of nucleotides over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 60%, preferably at least 65%, more preferably at least 70%, up to about 85%, and even more preferably at least 90 to 95%, more usually at least 99%, sequence identity as compared to a reference sequence over a comparison window of at least 20 nucleotide positions, frequently over a window of at least 20-50 nucleotides, and preferably at least 300 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

As applied to polypeptides, the term "substantial identity" means that two peptide sequences, when optimally aligned, such as by the programs GAP or BESTFIT using default gap weights, share at least about 85% sequence identity, preferably at least about 90% sequence identity, more preferably at least about 95% sequence identity, and most preferably at least about 99% sequence identity.

Synthetic Nucleotide Sequences and Methods of the Invention

The invention provides compositions comprising synthetic nucleotide sequences, as well as methods for preparing those sequences which yield synthetic nucleotide sequences that are efficiently expressed as a polypeptide or protein with desirable characteristics including reduced inappropriate or unintended transcription characteristics, or do not result in inappropriate or unintended transcription characteristics, when present in a particular cell type.

Natural selection is the hypothesis that genotype-environment interactions occurring at the phenotypic level lead to differential reproductive success of individuals and hence to modification of the gene pool of a population. It is generally accepted that the amino acid sequence of a protein found in nature has undergone optimization by natural selection. However, amino acids exist within the sequence of a protein that do not contribute significantly to the activity of the protein and these amino acids can be changed to other amino acids with little or no consequence. Furthermore, a protein may be useful outside its natural environment or for purposes that differ from the conditions of its natural selection. In these circumstances, the amino acid sequence can be synthetically altered to better adapt the protein for its utility in various applications.

Likewise, the nucleic acid sequence that encodes a protein is also optimized by natural selection. The relationship between coding DNA and its transcribed RNA is such that any change to the DNA affects the resulting RNA. Thus, natural selection works on both molecules simultaneously. However, this relationship does not exist between nucleic acids and proteins. Because multiple codons encode the same amino acid, many different nucleotide sequences can encode an identical protein. A specific protein composed of 500 amino acids can theoretically be encoded by more than $10^{150}$ different nucleic acid sequences.

Natural selection acts on nucleic acids to achieve proper encoding of the corresponding protein. Presumably, other properties of nucleic acid molecules are also acted upon by natural selection. These properties include codon usage frequency, RNA secondary structure, the efficiency of intron splicing, and interactions with transcription factors or other nucleic acid binding proteins. These other properties may alter the efficiency of protein translation and the resulting phenotype. Because of the redundant nature of the genetic code, these other attributes can be optimized by natural selection without altering the corresponding amino acid sequence.

Under some conditions, it is useful to synthetically alter the natural nucleotide sequence encoding a protein to better adapt the protein for alternative applications. A common example is to alter the codon usage frequency of a gene when it is expressed in a foreign host. Although redundancy in the genetic code allows amino acids to be encoded by multiple codons, different organisms favor some codons over others. The codon usage frequencies tend to differ most for organisms with widely separated evolutionary histories. It has been found that when transferring genes between evolutionarily distant organisms, the efficiency of protein translation can be substantially increased by adjusting the codon usage frequency (see U.S. Pat. Nos. 5,096,825, 5,670,356 and 5,874,304).

In one embodiment, the sequence of a reporter gene is modified as the codon usage of reporter genes often does not correspond to the optimal codon usage of the experimental cells. In another embodiment, the sequence of a reporter gene is modified to remove regulatory sequences such as those which may alter expression of the reporter gene or a linked gene. Examples include β-galactosidase (β-gal) and chloramphenicol acetyltransferase (cat) reporter genes that are derived from *E. coli* and are commonly used in mammalian cells; the β-glucuronidase (gus) reporter gene that is derived from *E. coli* and commonly used in plant cells; the firefly luciferase (luc) reporter gene that is derived from an insect and commonly used in plant and mammalian cells; and the *Renilla* luciferase, and green fluorescent protein (up) reporter genes which are derived from coelenterates and are commonly used in plant and mammalian cells. To achieve sensitive quantitation of reporter gene expression, the activity of the gene product must not be endogenous to the experimental host cells. Thus, reporter genes are usually selected from organisms having unique and distinctive phenotypes. Consequently, these organisms often have widely separated evolutionary histories from the experimental host cells.

Previously, to create genes having a more optimal codon usage frequency but still encoding the same gene product, a synthetic nucleic acid sequence was made by replacing existing codons with codons that were generally more favorable to the experimental host cell (see U.S. Pat. Nos. 5,096,825, 5,670,356 and 5,874,304.) The result was a net improvement in codon usage frequency of the synthetic gene. However, the optimization of other attributes was not considered and so these synthetic genes likely did not reflect genes optimized by natural selection.

In particular, improvements in codon usage frequency are intended only for optimization of a RNA sequence based on its role in translation into a protein. Thus, previously described methods did not address how the sequence of a synthetic gene affects the role of DNA in transcription into RNA. Most notably, consideration had not been given as to how transcription factors may interact with the synthetic DNA and consequently modulate or otherwise influence gene transcription. For genes found in nature, the DNA would be optimally transcribed by the native host cell and would yield an RNA that encodes a properly folded gene product. In contrast, synthetic genes have previously not been optimized for transcriptional characteristics. Rather, this property has been ignored or left to chance.

This concern is important for all genes, but particularly important for reporter genes, which are most commonly used to quantitate transcriptional behavior in the experimental host cells, and vector backbone sequences for genes. Hundreds of transcription factors have been identified in different cell types under different physiological conditions, and likely more exist but have not yet been identified. All of these transcription factors can influence the transcription of an introduced gene or sequences linked thereto. A useful synthetic reporter gene or vector backbone of the invention has a minimal risk of influencing or perturbing intrinsic transcriptional characteristics of the host cell because the structure of that gene or vector backbone has been altered. A particularly useful synthetic reporter gene or vector backbone will have desirable characteristics under a new set and/or a wide variety of experimental conditions. To best achieve these characteristics, the structure of the synthetic gene or synthetic vector backbone should have minimal potential for interacting with transcription factors within a broad range of host cells and physiological conditions. Minimizing potential interactions between a reporter gene or vector backbone and a host cell's endogenous transcription factors increases the value of a reporter gene or vector backbone by reducing the risk of inappropriate transcriptional characteristics of the gene or vector backbone within a particular experiment, increasing applicability of the gene or vector backbone in various environments, and increasing the acceptance of the resulting experimental data.

In contrast, a reporter gene comprising a native nucleotide sequence, based on a genomic or cDNA clone from the original host organism, or a vector backbone comprising native sequences found in one or a variety of different organisms, may interact with transcription factors when present in an exogenous host. This risk stems from two circumstances. First, the native nucleotide sequence contains sequences that were optimized through natural selection to influence gene transcription within the native host organism. However, these sequences might also influence transcription when the sequences are present in exogenous hosts, i.e., out of context, thus interfering with its performance as a reporter gene or vector backbone. Second, the nucleotide sequence may inadvertently interact with transcription factors that were not present in the native host organism, and thus did not participate in its natural selection. The probability of such inadvertent interactions increases with greater evolutionary separation between the experimental cells and the native organism of the reporter gene or vector backbone.

These potential interactions with transcription factors would likely be disrupted when using a synthetic reporter gene having alterations in codon usage frequency. However, a synthetic reporter gene sequence, designed by choosing codons based only on codon usage frequency, or randomly replacing sequences or randomly juxtaposing sequences in a vector backbone, is likely to contain other unintended transcription factor binding sites since the resulting sequence has not been subjected to the benefit of natural selection to correct inappropriate transcriptional activities. Inadvertent interactions with transcription factors could also occur whenever an encoded amino acid sequence is artificially altered, e.g., to introduce amino acid substitutions. Similarly, these changes have not been subjected to natural selection, and thus may exhibit undesired characteristics.

Thus, the invention provides a method for preparing synthetic nucleotide sequences that reduce the risk of undesirable interactions of the nucleotide sequence with transcription factors and other trans-acting factors when expressed in a particular host cell, thereby reducing inappropriate or unintended characteristics. Preferably, the method yields synthetic genes containing improved codon usage frequencies for a particular host cell and with a reduced occurrence of regulatory sequences such as transcription factor binding sites and/or vector backbone sequences with a reduced occurrence of regulatory sequences. The invention also provides a method of preparing synthetic genes containing improved codon usage frequencies with a reduced occurrence of transcription factor binding sites and additional beneficial structural attributes. Such additional attributes include the absence of inappropriate RNA splicing junctions, poly(A) addition signals, undesirable restriction enzyme recognition sites, ribosomal binding sites, and/or secondary structural motifs such as hairpin loops.

In one embodiment, a parent nucleic acid sequence encoding a polypeptide is optimized for expression in a particular cell. For example, the nucleic acid sequence is optimized by replacing codons in the wild-type sequence with codons which are preferentially employed in a particular (selected) cell, which codon replacement also reduces the number of regulatory sequences. Preferred codons have a relatively high codon usage frequency in a selected cell, and preferably their introduction results in the introduction of relatively few regulatory sequences such as transcription factor binding sites, and relatively few other undesirable structural attributes. Thus, the optimized nucleotide sequence may have an improved level of expression due to improved codon usage frequency, and a reduced risk of inappropriate transcriptional behavior due to a reduced number of undesirable transcription regulatory sequences. In another embodiment, a parent vector backbone sequence is altered to remove regulatory sequences and optionally restriction endonuclease sites, and optionally retain or add other desirable characteristics, e.g., the presence of one or more stop codons in one or more reading frames, one or more poly(A) sites, and/or restriction endonuclease sites.

The invention may be employed with any nucleic acid sequence, e.g., a native sequence such as a cDNA or one that has been manipulated in vitro. Exemplary genes include, but are not limited to, those encoding lactamase (β-gal), neomycin resistance (Neo), hygromycin resistance (Hyg), puromycin resistance (Puro), ampicillin resistance (Amp), CAT, GUS, galactopyranoside, GFP, xylosidase, thymidine kinase, arabinosidase, luciferase and the like. As used herein, a "reporter gene" is a gene that imparts a distinct phenotype to cells expressing the gene and thus permits cells having the gene to be distinguished from cells that do not have the gene. Such genes may encode either a selectable or screenable polypeptide, depending on whether the marker confers a trait which one can 'select' for by chemical means, i.e., through the use of a selective agent (e.g., a herbicide, antibiotic, or the like), or whether it is simply a "reporter" trait that one can identify through observation or testing, i.e., by 'screening'. Included within the terms selectable or screenable marker genes are also genes which encode a "secretable marker" whose secretion can be detected as a means of identifying or selecting for transformed cells. Examples include markers that encode a secretable antigen that can be identified by antibody interaction, or even secretable enzymes which can be detected by their catalytic activity. Secretable proteins fall into a number of classes, including small, diffusible proteins detectable, e.g., by ELISA, and proteins that are inserted or trapped in the cell membrane.

Elements of the present disclosure are exemplified in detail through the use of particular genes and vector backbone sequences. Of course, many examples of suitable genes and vector backbones are known to the art and can be employed in the practice of the invention. Therefore, it will be understood that the following discussion is exemplary rather than exhaustive. In light of the techniques disclosed herein and the general recombinant techniques that are known in the art, the present invention renders possible the alteration of any gene or vector backbone sequence.

Exemplary genes include, but are not limited to, a neo gene, a puro gene, an amp gene, a β-gal gene, a gus gene, a cat gene, a gpt gene, a hyg gene, a hisD gene, a ble gene, a mprt gene, a bar gene, a nitrilase gene, a mutant acetolactate synthase gene (ALS) or acetoacid synthase gene (AAS), a methotrexate-resistant dhfr gene, a dalapon dehalogenase gene, a mutated anthranilate synthase gene that confers resistance to 5-methyl tryptophan (WO 97/26366), an R-locus gene, a β-lactamase gene, a xylE gene, an α-amylase gene, a tyrosinase gene, a luciferase (luc) gene (e.g., a *Renilla reniformis* luciferase gene, a firefly luciferase gene, or a click beetle luciferase (*Pyrophorus plagiophthalamus* gene), an aequorin gene, or a fluorescent protein gene.

The method of the invention can be performed by, although it is not limited to, a recursive process. The process includes assigning preferred codons to each amino acid in a target molecule, e.g., a native nucleotide sequence, based on codon usage in a particular species, identifying potential transcription regulatory sequences such as transcription factor binding sites in the nucleic acid sequence having preferred codons, e.g., using a database of such binding sites, optionally identifying other undesirable sequences, and substituting an alternative codon (i.e., encoding the same amino acid) at positions where undesirable transcription factor binding sites or other sequences occur. For codon distinct versions, alternative preferred codons are substituted in each version. If necessary, the identification and elimination of potential transcription factor or other undesirable sequences can be repeated until a nucleotide sequence is achieved containing a maximum number of preferred codons and a minimum number of undesired sequences including transcription regulatory sequences or other undesirable sequences. Also, optionally, desired sequences, e.g., restriction enzyme recognition sites, can be introduced. After a synthetic nucleotide sequence is designed and constructed, its properties relative to the parent nucleic acid sequence can be determined by methods well known to the art. For example, the expression of the synthetic and target nucleic acids in a series of vectors in a particular cell can be compared.

Thus, generally, the method of the invention comprises identifying a target nucleic acid sequence, and a host cell of interest, for example, a plant (dicot or monocot), fungus, yeast or mammalian cell. Preferred host cells are mammalian host cells such as CHO, COS, 293, Hela, CV-1 and NIH3T3 cells. Based on preferred codon usage in the host cell(s) and, optionally, low codon usage in the host cell(s), e.g., high usage mammalian codons and low usage *E. coli* and mammalian codons, codons to be replaced are determined. Concurrent, subsequent or prior to selecting codons to be replaced, desired and undesired sequences, such as undesired transcriptional regulatory sequences, in the target sequence are identified. These sequences, including transcriptional regulatory sequences and restriction endonuclease sites, can be identified using databases and software such as TRANSFAC® (Transcription Factor Database, http://www.gene-regulation.com/), Match™ (http://www.gene-regulation.com/), MatInspector (Genomatix, http://www.genomatix.de), EPD (Eukaryotic Promoter Database, http://www.epd.isb-sib.ch/), REBASE® (Restriction Enzyme Database, NEB, http://rebase.neb.com), TESS (Transcription Element Search System, http://www.cbil.upenn.edu/tess/), MAR-Wiz (Futuresoft, http://www.futuresoft.org), Lasergene® (DNASTAR, http://www.dnastar.com), Vector NTI™ (Invitrogen, http://www.invitrogen.com), and Sequence Manipulation Suite (http://www.bioinformatics.org/SMS/index.html). Links to other databases and sequence analysis software are listed at http://www.expasy.org/alinks.html. After one or more sequences are identified, the modification(s) may be introduced. Once a desired synthetic nucleotide sequence is obtained, it can be prepared by methods well known to the art (such as nucleic acid amplification reactions with overlapping primers), and its structural and functional properties compared to the target nucleic acid sequence, including, but not limited to, percent homology, presence or absence of certain sequences, for example, restriction sites, percent of codons changed (such as an increased or decreased usage of certain codons) and/or expression rates.

As described below, the method was used to create synthetic reporter genes encoding firefly luciferases and selectable polypeptides, and synthetic sequences for vector backbones. Synthetic sequences may support greater levels of expression and/or reduced aberrant expression than the corresponding native or parent sequences for the protein. The native and parent sequences may demonstrate anomalous transcription characteristics when expressed in mammalian cells, which are likely not evident in the synthetic sequences.

Exemplary Uses of the Synthetic Nucleotide Sequences

The synthetic genes of the invention preferably encode the same proteins as their native counterpart (or nearly so), but have improved codon usage while being largely devoid of regulatory elements in the coding (it is recognized that a small number of amino acid changes may be desired to enhance a property of the native counterpart protein, e.g. to enhance luminescence of a luciferase) and noncoding regions. This increases the level of expression of the protein the synthetic gene encodes and reduces the risk of anomalous expression of the protein. For example, studies of many important events of gene regulation, which may be mediated by weak promoters, are limited by insufficient reporter signals from inadequate expression of the reporter proteins. Also, the use of some selectable markers may be limited by the expression of that marker in an exogenous cell. Thus, synthetic selectable marker genes which have improved codon usage for that cell, and have a decrease in other undesirable sequences, (e.g., transcription factor binding sites), can permit the use of those markers in cells that otherwise were undesirable as hosts for those markers.

Promoter crosstalk is another concern when a co-reporter gene is used to normalize transfection efficiencies. With the enhanced expression of synthetic genes, the amount of DNA containing strong promoters can be reduced, or DNA containing weaker promoters can be employed, to drive the expression of the co-reporter. In addition, there may be a reduction in the background expression from the synthetic reporter genes of the invention. This characteristic makes synthetic reporter genes more desirable by minimizing the sporadic expression from the genes and reducing the interference resulting from other regulatory pathways.

The use of reporter genes in imaging systems, which can be used for in vivo biological studies or drug screening, is another use for the synthetic genes of the invention. Due to their increased level of expression, the protein encoded by a synthetic gene is more readily detectable by an imaging system. In fact, using a synthetic *Renilla* luciferase gene, luminescence in transfected CHO cells was detected visually without the aid of instrumentation.

In addition, the synthetic genes may be used to express fusion proteins, for example fusions with secretion leader sequences or cellular localization sequences, to study transcription in difficult-to-transfect cells such as primary cells, and/or to improve the analysis of regulatory pathways and genetic elements. Other uses include, but are not limited to, the detection of rare events that require extreme sensitivity (e.g., studying RNA recoding), use with IRES, to improve the efficiency of in vitro translation or in vitro transcription-translation coupled systems such as TnT (Promega Corp., Madison, Wis.), study of reporters optimized to different host organisms (e.g., plants, fungus, and the like), use of multiple genes as co-reporters to monitor drug toxicity, as reporter molecules in multiwell assays, and as reporter molecules in drug screening with the advantage of minimizing possible interference of reporter signal by different signal transduction pathways and other regulatory mechanisms.

Additionally, uses for the synthetic nucleotide sequences of the invention include fluorescence activated cell sorting (FACS), fluorescent microscopy, to detect and/or measure the level of gene expression in vitro and in vivo, (e.g., to determine promoter strength), subcellular localization or targeting (fusion protein), as a marker, in calibration, in a kit (e.g., for dual assays), for in vivo imaging, to analyze regulatory pathways and genetic elements, and in multi-well formats.

Further, although reporter genes are widely used to measure transcription events, their utility can be limited by the fidelity and efficiency of reporter expression. For example, in U.S. Pat. No. 5,670,356, a firefly luciferase gene (referred to as luc+) was modified to improve the level of luciferase expression. While a higher level of expression was observed, it was not determined that higher expression had improved regulatory control.

The invention will be further described by the following nonlimiting examples. In particular, the synthetic nucleic acid molecules of the invention may be derived by other methods as well as by variations on the methods described herein.

EXAMPLE 1

Synthetic Click Beetle (RD and GR) Luciferase Nucleic Acid Molecules

LucPplYG is a wild-type click beetle luciferase that emits yellow-green luminescence (Wood, 1989). A mutant of LucPplYG named YG#81-6G01 was envisioned. YG#81-6G01 lacks a peroxisome targeting signal, has a lower $K_M$ for luciferin and ATP, has increased signal stability and increased temperature stability when compared to the wild type (PCT/WO9914336). YG #81-6G01 was mutated to emit green luminescence by changing Ala at position 224 to Val (A224V is a green-shifting mutation), or to emit red luminescence by simultaneously introducing the amino acid substitutions A224H, S247H, N346I, and H348Q (red-shifting mutation set) (PCT/WO9518853)

Using YG #81-6G01 as a parent gene, two synthetic gene sequences were designed. One codes for a luciferase emitting green luminescence (GR) and one for a luciferase emitting red luminescence (RD). Both genes were designed to 1) have optimized codon usage for expression in mammalian cells, 2) have a reduced number of transcriptional regulatory sites including mammalian transcription factor binding sites, splice sites, poly(A) sites and promoters, as well as prokaryotic (E. coli) regulatory sites, 3) be devoid of unwanted restriction sites, e.g., those which are likely to interfere with standard cloning procedures, and 4) have a low DNA sequence identity compared to each other in order to minimize genetic rearrangements when both are present inside the same cell. In addition, desired sequences, e.g., a Kozak sequence or restriction enzyme recognition sites, may be identified and introduced.

Not all design criteria could be met equally well at the same time. The following priority was established for reduction of transcriptional regulatory sites: elimination of transcription factor (TF) binding sites received the highest priority, followed by elimination of splice sites and poly(A) sites, and finally prokaryotic regulatory sites. When removing regulatory sites, the strategy was to work from the lesser important to the most important to ensure that the most important changes were made last. Then the sequence was rechecked for the appearance of new lower priority sites and additional changes made as needed. Thus, the process for designing the synthetic GR and RD gene sequences, using computer programs described herein, involved 5 optionally iterative steps that are detailed below 1. Optimized codon usage and changed A224V to create GRver1, separately changed A224H, S247H, H348Q and N346I to create RDver1. These particular amino acid changes were maintained throughout all subsequent manipulations to the sequence.

2. Removed undesired restriction sites, prokaryotic regulatory sites, splice sites, poly(A) sites thereby creating GRver2 and RDver2.

3. Removed transcription factor binding sites (first pass) and removed any newly created undesired sites as listed in step 2 above thereby creating GRver3 and RDver3.

4. Removed transcription factor binding sites created by step 3 above (second pass) and removed any newly created undesired sites as listed in step 2 above thereby creating GRver4 and RDver4.

5. Removed transcription factor binding sites created by step 4 above (third Pass) and confirmed absence of sites listed in step 2 above thereby creating GRver5 and RDver5.

6. Constructed the actual genes by PCR using synthetic oligonucleotides corresponding to fragments of GRver5 and RDver5 designed sequences thereby creating GR6 and RD7. GR6, upon sequencing was found to have the serine residue at amino acid position 49 mutated to an asparagine and the proline at amino acid position 230 mutated to a serine (S49N, P230S). RD7, upon sequencing was found to have the histidine at amino acid position 36 mutated to a tyrosine (H36Y). These changes occurred during the PCR process.

4. The mutations described in step 6 above (S49N, P230S for GR6 and H36Y for RD7) were reversed to create GRver5.1 and RDver5.1.

5. RDver5.1 was further modified by changing the arginine codon at position 351 to a glycine codon (R351G) thereby creating RDver5.2 with improved spectral properties compared to RDver5.1.

6. RDver5.2 was further mutated to increase luminescence intensity thereby creating RD156-1H9 which encodes four additional amino acid changes (M2I, S349T, K488T, E538V) and three silent single base changes (see U.S. application Ser. No. 09/645,706, filed Aug. 24, 2000, the disclosure of which is incorporated by reference herein).

1. Optimize Codon Usage and Introduce Mutations Determining Luminescence Color

The starting gene sequence for this design step was YG #81-6G01.

a) Optimize Codon Usage:

The strategy was to adapt the codon usage for optimal expression in human cells and at the same time to avoid *E. coli* low-usage codons. Based on these requirements, the best two codons for expression in human cells for all amino acids with more than two codons were selected (see Wada et al., 1990). In the selection of codon pairs for amino acids with six codons, the selection was biased towards pairs that have the largest number of mismatched bases to allow design of GR and RD genes with minimum sequence identity (codon distinction):

```
Arg: CGC/CGT    Leu: CTG/TTG    Ser: TCT/AGC
Thr: ACC/ACT    Pro: CCA/CCT    Ala: GCC/GCT
Gly: GGC/GGT    Val: GTC/GTG    Ile: ATC/ATT
```

Based on this selection of codons, two gene sequences encoding the YG#81-6G01 luciferase protein sequence were computer generated. The two genes were designed to have minimum DNA sequence identity and at the same time closely similar codon usage. To achieve this, each codon in the two genes was replaced by a codon from the limited list described above in an alternating fashion (e.g., Arg(n) is CGC in gene 1 and CGT in gene 2, $Arg_{(n+1)}$ is CGT in gene 1 and CGC in gene 2).

For subsequent steps in the design process it was anticipated that changes had to be made to this limited optimal codon selection in order to meet other design criteria, however, the following low-usage codons in mammalian cells were not used unless needed to meet criteria of higher priority:

```
Arg: CGA    Leu: CTA    Ser: TCG
Pro: CCG    Val: GTA    Ile: ATA
```

Also, the following low-usage codons in *E. coli* were avoided when reasonable (note that 3 of these match the low-usage list for mammalian cells):

```
Arg: CGA/CGG/AGA/AGG
Leu: CTA          Pro: CCC          Ile: ATA
``` b) Introduce Mutations Determining Luminescence Color:

Into one of the two codon-optimized gene sequences was introduced the single green-shifting mutation and into the other were introduced the 4 red-shifting mutations as described above.

The two output sequences from this first design step were named GRver1 (version 1 GR) and RDver1 (version 1 RD). Their DNA sequences are 63% identical (594 mismatches), while the proteins they encode differ only by the 4 amino acids that determine luminescence color (see FIGS. 2 and 3 for an alignment of the DNA and protein sequences).

Tables 1 and 2 show, as an example, the codon usage for valine and leucine in human genes, the parent gene YG#81-6G01, the codon-optimized synthetic genes GRver1 and RDver1, as well as the final versions of the synthetic genes after completion of step 5 in the design process (GRver5 and RDver5).

TABLE 1

Valine

| Codon | Human | Parent | GR ver1 | RD ver1 | GR ver5 | RD ver5 |
|---|---|---|---|---|---|---|
| GTA | 4 | 13 | 0 | 0 | 1 | 1 |
| GTC | 13 | 4 | 25 | 24 | 21 | 26 |
| GTG | 24 | 12 | 25 | 25 | 25 | 17 |
| GTT | 9 | 20 | 0 | 0 | 3 | 5 |

TABLE 2

Leucine

| Codon | Human | Parent | GR ver1 | RD ver1 | GR ver5 | RD ver5 |
|---|---|---|---|---|---|---|
| CTA | 3 | 5 | 0 | 0 | 0 | 0 |
| CTC | 12 | 4 | 0 | 1 | 12 | 11 |
| CTG | 24 | 4 | 28 | 27 | 19 | 18 |
| CTT | 6 | 12 | 0 | 0 | 1 | 1 |
| TTA | 3 | 17 | 0 | 0 | 0 | 0 |
| TTG | 6 | 13 | 27 | 27 | 23 | 25 |

2. Remove Undesired Restriction Sites, Prokaryotic Regulatory Sites, Splice Sites and Poly(A) Sites The starting gene sequences for this design step were GRver1 and RDver1.

a) Remove Undesired Restriction Sites:

To check for the presence and location of undesired restriction sites, the sequences of both synthetic genes were compared against a database of restriction enzyme recognition sequences (REBASE ver.712, http://www.neb.com/rebase) using standard sequence analysis software (GenePro ver 6.10, Riverside Scientific Ent.).

Specifically, the following restriction enzymes were classified as undesired:

BamH I, Xho I, Sfi I, Kpn I, Sac I, Mlu I, Nhe I, Sma I, Xho I, Bgl II, Hind III, Nco I, Nar I, Xba I, Hpa I, Sal I, other cloning sites commonly used: EcoR I, EcoR V, Cla I, eight-base cutters (commonly used for complex constructs), BstE II (to allow N-terminal fusions), Xcm I (can generate A/T overhang used for T-vector cloning).

To eliminate undesired restriction sites when found in a synthetic gene, one or more codons of the synthetic gene sequence were altered in accordance with the codon optimization guidelines described in 1a above.

b) Remove Prokaryotic (*E. coli*) Regulatory Sequences:

To check for the presence and location of prokaryotic regulatory sequences, the sequences of both synthetic genes were searched for the presence of the following consensus sequences using standard sequence analysis software (GenePro):

TATAAT (−10 Pribnow box of promoter)

AGGA or GGAG (ribosome binding site; only considered if paired with a methionine codon 12 or fewer bases downstream).

To eliminate such regulatory sequences when found in a synthetic gene, one or more codons of the synthetic gene at sequence were altered in accordance with the codon optimization guidelines described in 1a above.

c) Remove Splice Sites:

To check for the presence and location of splice sites, the DNA strand corresponding to the primary RNA transcript of each synthetic gene was searched for the presence of the following consensus sequences (see Watson et al., 1983) using standard sequence analysis software (GenePro):

splice donor site: AG|GTRAGT (exon|intron), the search was performed for AGGTRAG and the lower stringency GGTRAGT;

splice acceptor site: (Y)$_n$NCAG|G (intron|exon), the search was performed with n=1.

To eliminate splice sites found in a synthetic gene, one or more codons of the synthetic gene sequence were altered in accordance with the codon optimization guidelines described in 1a above. Splice acceptor sites were generally difficult to eliminate in one gene without introducing them into the other gene because they tended to contain one of the two only Gln codons (CAG); they were removed by placing the Gln codon CAA in both genes at the expense of a slightly increased sequence identity between the two genes.

d) Remove Poly(A) Sites:

To check for the presence and location of poly(A) sites, the sequences of both synthetic genes were searched for the presence of the following consensus sequence using standard sequence analysis software (GenePro):

AATAAA.

To eliminate each poly(A) addition site found in a synthetic gene, one or more codons of the synthetic gene sequence were altered in accordance with the codon optimization guidelines described in 1a above. The two output sequences from this second design step were named GRver2 and RDver2. Their DNA sequences are 63% identical (590 mismatches).

3. Remove Transcription Factor (TF) Binding Sites then Repeat Steps 2 a-d

The starting gene sequences for this design step were GRver2 and RDver2.

To check for the presence, location and identity of potential TF binding sites, the sequences of both synthetic genes were used as query sequences to search a database of transcription factor binding sites (TRANSFAC v3.2). The TRANSFAC database (http://transfac.gbf.de/TRANSFAC/index:html) holds information on gene regulatory DNA sequences (TF binding sites) and proteins (TFs) that bind to and act through them. The SITE table of TRANSFAC Release 3.2 contains 4,401 entries of individual (putative) TF binding sites (including TF binding sites in eukaryotic genes, in artificial sequences resulting from mutagenesis studies and in vitro selection procedures based on random oligonucleotide mixtures or specific theoretical considerations, and consensus binding sequences (from Faisst and Meyer, 1992).

The software tool used to locate and display these TF binding sites in the synthetic gene sequences was TESS (Transcription Element Search Software, http://agave.humgen.upenn.edu/tess/index.html). The filtered string-based search option was used with the following user-defined search parameters:

Factor Selection Attribute: Organism Classification
Search Pattern: Mammalia
Max. Allowable Mismatch %: 0
Min. element length: 5
Min. log-likelihood: 10

This parameter selection specifies that only mammalian TF binding sites (approximately 1,400 of the 4,401 entries in the database) that are at least 5 bases long will be included in the search. It further specifies that only TF binding sites that have a perfect match in the query sequence and a minimum log likelihood (LLH) score of 10 will be reported. The LLH scoring method assigns 2 to an unambiguous match, 1 to a partially ambiguous match (e.g., A or T match W) and 0 to a match against 'N'. For example, a search with parameters specified above would result in a "hit" (positive result or match) for TATAA (SEQ ID NO:50) (LLH=10), STRATG (SEQ ID NO:51) (LLH=10), and MTTNCNNMA (SEQ ID NO:52) (LLH=10) but not for TRATG (SEQ ID NO: 53) (LLH=9) if these four TF binding sites were present in the query sequence. A lower stringency test was performed at the end of the design process to re-evaluate the search parameters.

When TESS was tested with a mock query sequence containing known TF binding sites it was found that the program was unable to report matches to sites ending with the 3' end of the query sequence. Thus, an extra nucleotide was added to the 3' end of all query sequences to eliminate this problem.

The first search for TF binding sites using the parameters described above found about 100 transcription factor binding sites (hits) for each of the two synthetic genes (GRver2 and RDver2). All sites were eliminated by changing one or more codons of the synthetic gene sequences in accordance with the codon optimization guidelines described in 1a above. However, it was expected that some these changes created new TF binding sites, other regulatory sites, and new restriction sites. Thus, steps 2 a-d were repeated as described, and 4 new restriction sites and 2 new splice sites were removed. The two output sequences from this third design step were named GRver3 and RDver3. Their DNA sequences are 66% identical (541 mismatches).

4. Remove New Transcription Factor (TF) Binding Sites, then Repeat Steps 2 a-d

The starting gene sequences for this design step were GRver3 and RDver3.

This fourth step is an iteration of the process described in step 3. The search for newly introduced TF binding sites yielded about 50 hits for each of the two synthetic genes. All sites were eliminated by changing one or more codons of the synthetic gene sequences in general accordance with the codon optimization guidelines described in 1a above. However, more high to medium usage codons were used to allow elimination of all TF binding sites. The lowest priority was placed on maintaining low sequence identity between the GR and RD genes. Then steps 2 a-d were repeated as described. The two output sequences from this fourth design step were named GRver4 and RDver4. Their DNA sequences are 68% identical (506 mismatches).

5. Remove New Transcription Factor (TF) Binding Sites then Repeat Steps 2 a-d

The starting gene sequences for this design step were GRver4 and RDver4.

This fifth step is another iteration of the process described in step 3 above. The search for new TF binding sites introduced in step 4 yielded about 20 hits for each of the two synthetic genes. All sites were eliminated by changing one or more codons of the synthetic gene sequences in general accordance with the codon optimization guidelines described in 1a above. However, more high to medium usage codons were used (these are all considered "preferred") to allow elimination of all TF binding sites. The lowest priority was placed on maintaining low sequence identity between the GR and RD genes. Then steps 2 a-d were repeated as described. Only one acceptor splice site could not be eliminated. As a final step the absence of all TF binding sites in both genes as specified in step 3 was confirmed. The two output sequences from this fifth and last design step were named GRver5 and RDver5. Their DNA sequences are 69% identical (504 mismatches).

Additional Evaluation of GRver5 and RDver5
a) Use Lower Stringency Parameters for TESS:

The search for TF binding sites was repeated as described in step 3 above, but with even less stringent user-defined parameters:

setting LLH to 9 instead of 10 did not result in new hits;
setting LLH to 0 through 8 (incl.) resulted in hits for two additional sites, MAMAG (22 hits) and CTKTK (24 hits);
setting LLH to 8 and the minimum element length to 4, the search yielded (in addition to the two sites above) different 4-base sites for AP-1, NF-1, and c-Myb that are shortened versions of their longer respective consensus sites which were eliminated in steps 3-5 above.

It was not realistic to attempt complete elimination of these sites without introduction of new sites, so no further changes were made.

B) Search Different Database:

The Eukaryotic Promoter Database (release 45) contains information about reliably mapped transcription start sites (1253 sequences) of eukaryotic genes. This database was searched using BLASTN 1.4.11 with default parameters (optimized to find nearly identical sequences rapidly; see Altschul et al, 1990) at the National Center for Biotechnology Information site (http://www.ncbi.nlm.nih.gov/cgi-bin/BLAST). To test this approach, a portion of pGL3-Control vector sequence containing the SV40 promoter and enhancer was used as a query sequence, yielding the expected hits to SV40 sequences. No hits were found when using the two synthetic genes as query sequences.

Summary of GRver5 and RDver5 Synthetic Gene Properties

Both genes, which at this stage were still only "virtual" sequences in the computer, have a codon usage that strongly favors mammalian high-usage codons and minimizes mammalian and *E. coli* low-usage codons.

Both genes are also completely devoid of eukaryotic TF binding sites consisting of more than four unambiguous bases, donor and acceptor splice sites (one exception: GRver5 contains one splice acceptor site), poly(A) sites, specific prokaryotic (*E. coli*) regulatory sequences, and undesired restriction sites.

The gene sequence identity between GRver5 and RDver5 is only 69% (504 base mismatches) while their encoded proteins are 99% identical (4 amino acid mismatches). Their identity with the parent sequence YG#81-6G1 is 74% (GRver5) and 73% (RDver5). Their base composition is 49.9% GC (GRver5) and 49.5% GC (RDver5), compared to 40.2% GC for the parent YG#81-6G01.

Construction of Synthetic Genes

The two synthetic genes were constructed by assembly from synthetic oligonucleotides in a thermocycler followed by PCR amplification of the full-length genes (similar to Stemmer et al. (1995) *Gene.* 164, pp. 49-53). Unintended mutations that interfered with the design goals of the synthetic genes were corrected.

a) Design of Synthetic Oligonucleotides:

The synthetic oligonucleotides were mostly 40mers that collectively code for both complete strands of each designed gene (1,626 bp) plus flanking regions needed for cloning (1,950 bp total for each gene). The 5' and 3' boundaries of all oligonucleotides specifying one strand were generally placed in a manner to give an average offset/overlap of 20 bases relative to the boundaries of the oligonucleotides specifying the opposite strand.

The ends of the flanking regions of both genes matched the ends of the amplification primers (pRAMtailup: 5'-gtact-gagacgacgccagcccaagcttaggcctgagtg SEQ ID NO:54, and pRAMtaildn: 5'-ggcatgagcgtgaactgactgaactagcggccgccgag SEQ ID NO:55) to allow cloning of the genes into our *E. coli* expression vector pRAM (WO99/14336).

A total of 183 oligonucleotides were designed: fifteen oligonucleotides that collectively encode the upstream and downstream flanking sequences and 168 oligonucleotides (4×42) that encode both strands of the two genes.

All 183 oligonucleotides were run through the hairpin analysis of the OLIGO software (OLIGO 4.0 Primer Analysis Software© 1989-1991 by Wojciech Rychlik) to identify potentially detrimental intra-molecular loop formation. The guidelines for evaluating the analysis results were set according to recommendations of Dr. Sims (Sigma-Genosys Custom Gene Synthesis Department): oligos forming hairpins with $\Delta G < -10$ have to be avoided, those forming hairpins with $\Delta G \leq -7$ involving the 3' end of the oligonucleotide should also be avoided, while those with an overall $\Delta G \leq -5$ should not pose a problem for this application. The analysis identified 23 oligonucleotides able to form hairpins with a $\Delta G$ between $-7.1$ and $-4.9$. Of these, 5 had blocked or nearly blocked 3' ends (0-3 free bases) and were re-designed by removing 1-4 bases at their 3' end and adding it to the adjacent oligonucleotide.

The 40mer oligonucleotide covering the sequence complementary to the poly(A) tail had a very low complexity 3' end (13 consecutive T bases). An additional 40mer was designed with a high complexity 3' end but a consequently reduced overlap with one of its complementary oligonucleotides (11 instead of 20 bases) on the opposite strand.

Even though the oligonucleotides were designed for use in a thermocycler-based assembly reaction, they could also be used in a ligation-based protocol for gene construction. In this approach, the oligonucleotides are annealed in a pairwise fashion and the resulting short double-stranded fragments are ligated using the sticky overhangs. However, this would require that all oligonucleotides be phosphorylated.

b) Gene Assembly and Amplification

In a first step, each of the two synthetic genes was assembled in a separate reaction from 98 oligonucleotides. The total volume for each reaction was 50 μl:

0.5 μM oligonucleotides (=0.25 pmoles of each oligo)
1.0 U Taq DNA polymerase
0.02 U Pfu DNA polymerase
2 mM $MgCl_2$
0.2 mM dNTPs (each)
0.1% gelatin
Cycling conditions: (94° C. for 30 seconds, 52° C. for 30 seconds, and 72° C. for 30 seconds) × 55 cycles.

In a second step, each assembled synthetic gene was amplified in a separate reaction. The total volume for each reaction was 50 μl:

2.5 l assembly reaction
5.0 U Taq DNA polymerase
0.1 U Pfu DNA polymerase
1 M each primer (pRAMtailup, pRAMtaildn)
2 mM $MgCl_2$
0.2 mM dNTPs (each)
Cycling conditions: (94° C. for 20 seconds, 65° C. for 60 seconds, 72° C. for 3 minutes) × 30 cycles.

The assembled and amplified genes were subcloned into the pRAM vector and expressed in *E. coli*, yielding 1-2% luminescent GR or RD clones. Five GR and five RD clones were isolated and analyzed further. Of the five GR clones, three had the correct insert size, of which one was weakly luminescent and one had an altered restriction pattern. Of the five RD clones, two had the correct size insert with an altered restriction pattern and one of those was weakly luminescent. Overall, the analysis indicated the presence of a large number of mutations in the genes, most likely the result of errors introduced in the assembly and amplification reactions.

c) Corrective Assembly and Amplification

To remove the large number of mutations present in the full-length synthetic genes we performed an additional assembly and amplification reaction for each gene using the proof-reading DNA polymerase Tli. The assembly reaction contained, in addition to the 98 GR or RD oligonucleotides, a small amount of DNA from the corresponding full-length clones with mutations described above. This allows the oligos to correct mutations present in the templates.

The following assembly reaction was performed for each of the synthetic genes. The total volume for each reaction was 50 µl:

---
0.5 µM oligonucleotides (=0.25 pmoles of each oligo)
0.016 pmol plasmid (mix of clones with correct insert size)
2.5 U Tli DNA polymerase
2 mM MgCl$_2$
0.2 mM dNTPs (each)
0.1% gelatin
Cycling conditions: 94° C. for 30 seconds, then (94° C. for 30 seconds, 52° C. for 30 seconds, 72° C. for 30 seconds) for 55 cycles, then 72° C. for 5 minutes.

---

The following amplification reaction was performed on each of the assembly reactions. The total volume for each amplification reaction was 50 µl:

---
1-5 µl of assembly reaction
40 pmol each primer (pRAMtailup, pRAMtaildn)
2.5 U Tli DNA polymerase
2 mM MgCl$_2$
0.2 mM dNTPs (each)
Cycling conditions: 94° C. for 30 seconds, then (94° C. for 20 seconds, 65° C. for 60 seconds and 72° C. for 3 minutes) for 30 cycles, then 72° C. for 5 minutes.

---

The genes obtained from the corrective assembly and amplification step were subcloned into the pRAM vector and expressed in *E. coli*, yielding 75% luminescent GR or RD clones. Forty-four GR and 44 RD clones were analyzed with the screening robot described in WO99/14336. The six best GR and RD clones were manually analyzed and one best GR and RD clone was selected (GR6 and RD7). Sequence analysis of GR6 revealed two point mutations in the coding region, both of which resulted in an amino acid substitution (S49N and P230S). Sequence analysis of RD7 revealed three point mutations in the coding region, one of which resulted in an amino acid substitution (H36Y). It was confirmed that none of the silent point mutations introduced any regulatory or restriction sites conflicting with the overall design criteria for the synthetic genes.

d) Reversal of Unintended Amino Acid Substitutions

The unintended amino acid substitutions present in the GR6 and RD7 synthetic genes were reversed by site-directed mutagenesis to match the GRver5 and RDver5 designed sequences, thereby creating GRver5.1 and RDver5.1. The DNA sequences of the mutated regions were confirmed by sequence analysis.

E) Improve Spectral Properties

The RDver5.1 gene was further modified to improve its spectral properties by introducing an amino change (R351G), thereby creating RDver5.2 pGL3 Vectors with RD and GR Genes

The parent click beetle luciferase YG#81-6G1 ("YG"), and the synthetic click beetle luciferase genes GRver5.1 ("GR"), RDver5.2 ("RD"), and RD156-1H9 were cloned into the four pGL3 reporter vectors (Promega Corp.):
  pGL3-Basic=no promoter, no enhancer
  pGL3-Control=SV40 promoter, SV40 enhancer
  pGL3-Enhancer=SV40 enhancer (3' to luciferase coding sequences)
  pGL3-Promoter=SV40 promoter.

The primers employed in the assembly of GR and RD synthetic genes facilitated the cloning of those genes into pRAM vectors. To introduce the genes into pGL3 vectors (Promega Corp., Madison, Wis.) for analysis in mammalian cells, each gene in a pRAM vector (pRAM RDver5.1, pRAM GRver5.1, and pRAM RD156-1H9) was amplified to introduce an Nco I site at the 5' end and an Xba I site at the 3' end of the gene. The primers for pRAM RDver5.1 and pRAM GRver5.1 were:

```
                                     (SEQ ID NO: 56)
GR→5' GGA TCC CAT GGT GAA GCG TGA GAA 3'
or
                                     (SEQ ID NO: 57)
RD→5' GGA TCC CAT GGT GAA ACG CGA 3'
and
                                     (SEQ ID NO: 58)
5' CTA GCT TTT TTT TCT AGA TAA TCA TGA AGA C 3'
```

The primers for pRAM RD156-1H9 were:

```
                                     (SEQ ID NO: 59)
5' GCG TAG CCA TGG TAA AGC GTG AGA AAA ATG TC 3'
and
                                     (SEQ ID NO: 60)
5' CCG ACT CTA GAT TAC TAA CCG CCG GCC TTC ACC 3'
```

The PCR included:

---
100 ng DNA plasmid
1 µM primer upstream
1 µM primer downstream
0.2 mM dNTPs
1X buffer (Promega Corp.)
5 units Pfu DNA polymerase (Promega Corp.)
Sterile nanopure H$_2$O to 50 µl

---

The cycling parameters were: 94° C. for 5 minutes; (94° C. for 30 seconds; 55° C. for 1 minute; and 72° C. for 3 minutes)×15 cycles. The purified PCR product was digested with Nco I and Xba I, ligated with pGL3-control that was also digested with Nco I and Xba I, and the ligated products introduced to *E. coli*. To insert the luciferase genes into the other pGL3 reporter vectors (basic, promoter and enhancer), the pGL3-control vectors containing each of the luciferase genes was digested with Nco I and Xba I, ligated with other pGL3 vectors that also were digested with Nco I and Xba I, and the ligated products introduced to *E. coli*. Note that the polypeptide encoded by GRver5.1 and RDver5.1 (and RD156-1H9, see below) nucleic acid sequences in pGL3 vectors has an amino acid substitution at position 2 to valine as a result of the Nco I site at the initiation codon in the oligonucleotide.

Because of internal Nco I and Xba I sites, the native gene in YG #81-6G01 was amplified from a Hind III site upstream to a Hpa I site downstream of the coding region and which included flanking sequences found in the GR and RD clones. The upstream primer (5'-CAA AAA GCT TGG CAT TCC GGT ACT GTT GGT AAA GCC ACC ATG GTG AAG CGA GAG-3'; SEQ ID NO:61) and a downstream primer (5'-CAA TTG TTG TTG TTA ACT TGT TTA TT-3'; SEQ ID NO:62) were mixed with YG#81-6G01 and amplified using the PCR conditions above. The purified PCR product was digested with Nco I and Xba I, ligated with pGL3-control that was also digested with Hind III and Hpa I, and the ligated products introduced into E. coli. To insert YG#81-6G01 into the other pGL3 reporter vectors (basic, promoter and enhancer), the pGL3-control vectors containing YG#81-6G01 were digested with Nco I and Xba I, ligated with the other pGL3 vectors that also were digested with Nco I and Xba I, and the ligated products introduced to E. coli. Note that the clone of YG#81-6G01 in the pGL3 vectors has a C instead of an A at base 786, which yields a change in the amino acid sequence at residue 262 from Phe to Leu. To determine whether the altered amino acid at position 262 affected the enzyme biochemistry, the clone of YG#81-6G01 was mutated to resemble the original sequence. Both clones were then tested for expression in E. coli, physical stability, substrate binding, and luminescence output kinetics. No significant differences were found.

Partially purified enzymes expressed from the synthetic genes and the parent gene were employed to determine Km for luciferin and ATP (see Table 3).

TABLE 3

| Enzyme | $K_M(LH_2)$ | $K_M(ATP)$ |
|---|---|---|
| YG parent | 2 µM | 17 µM |
| GR | 1.3 µM | 25 µM |
| RD | 24.5 µM | 46 µM |

In vitro eukaryotic transcription/translation reactions were also conducted using Promega's TNT T7 Quick system according to manufacturer's instructions. Luminescence levels were 1 to 37-fold and 1 to 77-fold higher (depending on the reaction time) for the synthetic GR and RD genes, respectively, compared to the parent gene (corrected for luminometer spectral sensitivity).

To test whether the synthetic click beetle luciferase genes and the wild type click beetle gene have improved expression in mammalian cells, each of the synthetic genes and the parent gene was cloned into a series of pGL3 vectors and introduced into CHO cells (Table 8). In all cases, the synthetic click beetle genes exhibited a higher expression than the native gene. Specifically, expression of the synthetic GR and RD genes was 1900-fold and 40-fold higher, respectively, than that of the parent (transfection efficiency normalized by comparison to native Renilla luciferase gene). Moreover, the data (basic versus control vector) show that the synthetic genes have reduced basal level transcription.

Further, in experiments with the enhancer vector where the percentage of activity in reference to the control is compared between the native and synthetic gene, the data showed that the synthetic genes have reduced risk of anomalous transcription characteristics. In particular, the parent gene appeared to contain one or more internal transcriptional regulatory sequences that are activated by the enhancer in the vector, and thus is not suitable as a reporter gene while the synthetic GR and RD genes showed a clean reporter response (transfection efficiency normalized by comparison to native Renilla luciferase gene). See Table 8.

EXAMPLE 2

Synthetic Renilla Luciferase Nucleic Acid Molecule

The synthetic Renilla luciferase genes prepared include 1) an introduced Kozak sequence, 2) codon usage optimized for mammalian (human) expression, 3) a reduction or elimination of unwanted restriction sites, 4) removal of prokaryotic regulatory sites (ribosome binding site and TATA box), 5) removal of splice sites and poly(A) sites, and 6) a reduction or elimination of mammalian transcriptional factor binding sequences.

The process of computer-assisted design of synthetic Renilla luciferase genes by iterative rounds of codon optimization and removal of transcription factor binding sites and other regulatory sites as well as restriction sites can be described in three steps:

1. Using the wild type Renilla luciferase gene as the parent gene, codon usage was optimized, one amino acid was changed (TEA) to generate a Kozak consensus sequence, and undesired restriction sites were eliminated thereby creating synthetic gene Rlucver1.
2. Remove prokaryotic regulatory sites, splice sites, poly(A) sites and transcription factor (TF) binding sites (first pass). Then remove newly created TF binding sites. Then remove newly created undesired restriction enzyme sites, prokaryotic regulatory sites, splice sites, and poly(A) sites without introducing new TF binding sites. This thereby created Rlucver2.
3. Change 3 bases of Rlucver2 thereby creating Rluc-final.
4. The actual gene was then constructed from synthetic oligonucleotides corresponding to the Rluc-final designed sequence. All mutations resulting from the assembly or PCR process were corrected. This gene is Rluc-final.

Codon Selection

Starting with the Renilla reniformis luciferase sequence in Genbank (Accession No. M63501), codons were selected based on codon usage for optimal expression in human cells and to avoid E. coli low-usage codons. The best codon for expression in human cells (or the best two codons if found at a similar frequency) was chosen for all amino acids with more than one codon (Wada et al., 1990):

```
Arg: CGC          Lys: AAG
Leu: CTG          Asn: AAC
Ser: TCT/AGC      Gln: CAG
Thr: ACC          His: CAC
Pro: CCA/CCT      Glu: GAG
Ala: GCC          Asp: GAC
Gly: GGC          Tyr: TAC
Val: GTG          Cys: TGC
Ile: ATC/ATT      Phe: TTC
```

In cases where two codons were selected for one amino acid, they were used in an alternating fashion. To meet other criteria for the synthetic gene, the initial optimal codon selection was modified to some extent later. For example, introduction of a Kozak sequence required the use of GCT for Ala at amino acid position 2 (see below).

The following low-usage codons in mammalian cells were not used unless needed: Arg: CGA, CGU; Leu: CTA, UUA; Ser: TCG; Pro: CCG; Val: GTA; and Ile: ATA. The following low-usage codons in E. coli were also avoided when reasonable (note that 3 of these match the low-usage list for mammalian cells): Arg: CGA/CGG/AGA/AGG, Leu: CTA; Pro: CCC; Ile: ATA.

Introduction of Kozak Sequences

The Kozak sequence: 5' aaccATGGCT 3' (SEQ ID NO: 63) (the Nco I site is underlined, the coding region is shown in capital letters) was introduced to the synthetic *Renilla* luciferase gene. The introduction of the Kozak sequence changes the second amino acid from Thr to Ala (GCT).

Removal of Undesired Restriction Sites

REBASE ver. 808 (updated Aug. 1, 1998; Restriction Enzyme Database; www.neb.com/rebase) was employed to identify undesirable restriction sites as described in Example 1. The following undesired restriction sites (in addition to those described in Example 1) were removed according to the process described in Example 1: EcoICR I, NdeI, NsiI, SphI, SpeI, XmaI, PstI.

The version of *Renilla* luciferase (Rluc) which incorporates all these changes is Rlucver1.

Removal of Prokaryotic (*E. coli*) Regulatory Sequences Splice Sites, and Poly(A) Sites The priority and process for eliminating transcription regulation sites was as described in Example 1.

Removal of TF Binding Sites

The same process, tools, and criteria were used as described in Example 1, however, the newer version 3.3 of the TRANSFAC database was employed.

After removing prokaryotic regulatory sequences, splice sites and poly(A) sites from Rlucver1, the first search for TF binding sites identified about 60 hits. All sites were eliminated with the exception of three that could not be removed without altering the amino acid sequence of the synthetic *Renilla* gene:

1. site at position 63 composed of two codons for W (T GGTGG), for CAC-binding protein T00076;
2. site at position 522 composed of codons for KMV (A ANATGGTN), for myc-DF1 T00517;
3. site at position 885 composed of codons for EMG (G ARATGGGN), for myc-DF1 T00517.

The subsequent second search for (newly introduced) TF binding sites yielded about 20 hits. All new sites were eliminated, leaving only the three sites described above. Finally, any newly introduced restriction sites, prokaryotic regulatory sequences, splice sites and poly(A) sites were removed without introducing new TF binding sites if possible.

Rlucver2 was obtained.

As in Example 1, lower stringency search parameters were specified for the TESS filtered string search to further evaluate the synthetic *Renilla* gene.

With the LLH reduced from 10 to 9 and the minimum element length reduced from 5 to 4, the TESS filtered string search did not show any new hits. When, in addition to the parameter changes listed above, the organism classification was expanded from "mammalia" to "chordata", the search yielded only four more TF binding sites. When the Min LLH was further reduced to between 8 and 0, the search showed two additional 5-base sites (MAMAG and CTKTK) which combined had four matches in Rlucver2, as well as several 4-base sites. Also as in Example 1, Rlucver2 was checked for hits to entries in the EPD (Eukaryotic Promoter Database, Release 45). Three hits were determined one to *Mus musculus* promoter H-2L^d (*Cell*, 44, 261 (1986)), one to Herpes Simplex Virus type 1 promoter b'g'2.7 kb, and one to *Homo sapiens* DHFR promoter (*J. Mol. Biol.*, 176, 169 (1984)). However, no further changes were made to Rlucver2.

Summary of Properties for Rlucver2

All 30 low usage codons were eliminated. The introduction of a Kozak sequence changed the second amino acid from Thr to Ala;

base composition: 55.7% GC (Renilla wild-type parent gene: 36.5%);

one undesired restriction site could not be eliminated: EcoR V at position 488;

the synthetic gene had no prokaryotic promoter sequence but one potentially functional ribosome binding site (RBS) at positions 867-73 (about 13 bases upstream of a Met codon) could not be eliminated;

all poly(A) sites were eliminated;

splice sites: 2 donor splice sites could not be eliminated (both share the amino acid sequence MGK);

TF sites: all sites with a consensus of >4 unambiguous bases were eliminated (about 280 TF binding sites were removed) with 3 exceptions due to the preference to avoid changes to the amino acid sequence.

When introduced into pGL3, Rluc-final has a Kozak sequence (CACCATGGCT; SEQ ID NO:65). The changes in Rluc-final relative to Rlucver2 were introduced during gene assembly. One change was at position 619, a C to an A, which eliminated a eukaryotic promoter sequence and reduced the stability of a hairpin structure in the corresponding oligonucleotide employed to assemble the gene. Other changes included a change from CGC to AGA at positions 218-220 (resulted in a better oligonucleotide for PCR).

Gene Assembly Strategy

The gene assembly protocol employed for the synthetic *Renilla* luciferase was similar to that described in Example 1.

Sense Strand Primer:

```
                                              (SEQ ID NO: 66)
5' AACCATGGCTTCCAAGGTGTACGACCCCGAGCAACGCAAA 3'
```

Anti-sense Strand Primer:

```
                                              (SEQ ID NO: 67)
5' GCTCTAGAATTACTGCTCGTTCTTCAGCACGCGCTCCACG 3'
```

The resulting synthetic gene fragment was cloned into a pRAM vector using Nco I and Xba I. Two clones having the correct size insert were sequenced. Four to six mutations were found in the synthetic gene from each clone. These mutations were fixed by site-directed mutagenesis (Gene Editor from Promega Corp., Madison, Wis.) and swapping the correct regions between these two genes. The corrected gene was confirmed by sequencing.

Other Vectors

To prepare an expression vector for the synthetic *Renilla* luciferase gene in a pGL-3 control vector backbone, 5 μg of pGL3-control was digested with Nco I and Xba I in 50 μl final volume with 2 μl of each enzyme and 5 μl 10× buffer B (nanopure water was used to fill the volume to 50 μl). The digestion reaction was incubated at 37° C. for 2 hours, and the whole mixture was run on a 1% agarose gel in 1×TAE. The desired vector backbone fragment was purified using Qiagen's QIAquick gel extraction kit.

The native *Renilla* luciferase gene fragment was cloned into pGL3-control vector using two oligonucleotides, Nco I-RL-F and Xba I-RL-R, to PCR amplify native *Renilla* luciferase gene using pRL-CMV as the template. The sequence for Nco I-RL-F is 5'-CGCTAGCCATGGCTTC-GAAAGTTTATGATCC-3' (SEQ ID NO:68); the sequence for Xba I-RL-R is 5' GGCCAGTAACTCTAGAATTAT-TGTT-3' (SEQ ID NO:69). The PCR reaction was carried out as follows:

Reaction Mixture (for 100 μl):

| | |
|---|---|
| DNA template (Plasmid) | 1.0 μl (1.0 ng/μl final) |
| 10X Rec. Buffer | 10.0 μl (Stratagene Corp.) |
| dNTPs (25 mM each) | 1.0 μl (final 250 μM) |
| Primer 1 (10 μM) | 2.0 μl (0.2 μM final) |
| Primer 2 (10 μM) | 2.0 μl (0.2 μM final) |
| Pfu DNA Polymerase | 2.0 μl (2.5 U/μl, Stratagene Corp.) |
| | 82.0 μl double distilled water |

PCR Reaction: heat 94° C. for 2 minutes; (94° C. for 20 seconds; 65° C. for 1 minute; 72° C. for 2 minutes; then 72° C. for 5 minutes)×25 cycles, then incubate on ice. The PCR amplified fragment was cut from a gel, and the DNA purified and stored at −20° C.

To introduce native *Renilla* luciferase gene fragment into pGL3-control vector, 5 μg of the PCR product of the native *Renilla* luciferase gene (RAM-RL-synthetic) was digested with Nco I and Xba I. The desired *Renilla* luciferase gene fragment was purified and stored at −20° C.

Then 100 ng of insert and 100 ng of pGL3-control vector backbone were digested with restriction enzymes Nco I and Xba I and ligated together. Then 2 μl of the ligation mixture was transformed into JM109 competent cells. Eight ampicillin resistance clones were picked and their DNA isolated. DNA from each positive clone of pGL3-control-native and pGL3-control-synthetic was purified. The correct sequences for the native gene and the synthetic gene in the vectors were confirmed by DNA sequencing.

To determine whether the synthetic *Renilla* luciferase gene has improved expression in mammalian cells, the gene was cloned into the mammalian expression vector pGL3-control vector under the control of SV40 promoter and SV40 early enhancer. The native *Renilla* luciferase gene was also cloned into the pGL-3 control vector so that the expression from synthetic gene and the native gene could be compared. The expression vectors were then transfected into four common mammalian cell lines (CHO, NIH3T3, Hela and CV-1; Table 9), and the expression levels compared between the vectors with the synthetic gene versus the native gene. The amount of DNA used was at two different levels to ascertain that expression from the synthetic gene is consistently increased at different expression levels. The results show a 70-600 fold increase of expression for the synthetic *Renilla* luciferase gene in these cells (Table 4).

TABLE 4

| Cell Type | Amount Vector | Fold Expression Increase |
|---|---|---|
| CHO | 0.2 μg | 142 |
| | 2.8 μg | 145 |
| NIH3T3 | 0.2 μg | 326 |
| | 2.0 μg | 593 |
| HeLa | 0.2 μg | 185 |
| | 1.0 μg | 103 |

TABLE 4-continued

| Cell Type | Amount Vector | Fold Expression Increase |
|---|---|---|
| CV-1 | 0.2 μg | 68 |
| | 2.0 μg | 72 |

One important advantage of luciferase reporter is its short protein half-life. The enhanced expression could also result from extended protein half-life and, if so, this gives an undesired disadvantage of the new gene. This possibility is ruled out by a cycloheximide chase ("CHX Chase") experiment, which demonstrated that there was no increase of protein half-life resulted from the humanized *Renilla* luciferase gene.

To ensure that the increase in expression is not limited to one expression vector backbone, is promoter specific and/or cell specific, a synthetic *Renilla* gene (Rluc-final) as well as native *Renilla* gene were cloned into different vector backbones and under different promoters. The synthetic gene always exhibited increased expression compared to its wild-type counterpart (Table 5).

TABLE 5

| Vector | NIH-3T3 | HeLa | CHO |
|---|---|---|---|
| pRL-tk, native | 3,834.6 | 922.4 | 7,671.9 |
| pRL-tk, synthetic | 13,252.5 | 9,040.2 | 41,743.5 |
| pRL-CMV, native | 168,062.2 | 842,482.5 | 153,539.5 |
| pRL-CMV, synthetic | 2,168,129 | 8,440,306 | 2,532,576 |
| pRL-SV40, native | 224,224.4 | 346,787.6 | 85,323.6 |
| pRL-SV40, synthetic | 1,469,588 | 2,632,510 | 1,422,830 |
| pRL-null, native | 2,853.8 | 431.7 | 2,434 |
| pRL-null, synthetic | 9,151.17 | 2,439 | 28,317.1 |
| pRGL3b, native | 12 | 21.8 | 17 |
| pRGL3b, synthetic | 130.5 | 212.4 | 1,094.5 |
| pRGL3-tk, native | 27.9 | 155.5 | 186.4 |
| pRGL3-tk, synthetic | 6,778.2 | 8,782.5 | 9,685.9 |
| pRL-tk no intron, native | 31.8 | 165 | 93.4 |
| pRL-tk no intron, synthetic | 6,665.5 | 6,379 | 21,433.1 |

TABLE 6

| | Percent of control vector | | |
|---|---|---|---|
| Vector | CHO cells | NIH3T3 cells | HeLa cells |
| pRL-control native | 100 | 100 | 100 |
| pRL-control synthetic | 100 | 100 | 100 |
| pRL-basic native | 4.1 | 5.6 | 0.2 |
| pRL-basic synthetic | 0.4 | 0.1 | 0.0 |
| pRL-promoter native | 5.9 | 7.8 | 0.6 |
| pRL-promoter synthetic | 15.0 | 9.9 | 1.1 |
| pRL-enhancer native | 42.1 | 123.9 | 52.7 |
| pRL-enhancer synthetic | 2.6 | 1.5 | 5.4 |

With reduced spurious expression the synthetic gene should exhibit less basal level transcription in a promoterless vector. The synthetic and native *Renilla* luciferase genes were cloned into the pGL3-basic vector to compare the basal level of transcription. Because the synthetic gene itself has increased expression efficiency, the activity from the promoterless vector cannot be compared directly to judge the difference in basal transcription, rather, this is taken into consideration by comparing the percentage of activity from the promoterless vector in reference to the control vector (expression from the basic vector divided by the expression in the fully functional expression vector with both promoter and enhancer elements). The data demonstrate that the synthetic *Renilla* luciferase has a lower level of basal transcription than the native gene in mammalian cells (Table 6).

It is well known to those skilled in the art that an enhancer can substantially stimulate promoter activity. To test whether the synthetic gene has reduced risk of inappropriate transcriptional characteristics, the native and synthetic gene were introduced into a vector with an enhancer element (pGL3-enhancer vector). Because the synthetic gene has higher expression efficiency, the activity of both cannot be compared directly to compare the level of transcription in the presence of the enhancer, however, this is taken into account by using the percentage of activity from enhancer vector in reference to the control vector (expression in the presence of enhancer divided by the expression in the fully functional expression vector with both promoter and enhancer elements). Such results show that when native gene is present, the enhancer alone is able to stimulate transcription from 42-124% of the control, however, when the native gene is replaced by the synthetic gene in the same vector, the activity only constitutes 1-5% of the value when the same enhancer and a strong SV40 promoter are employed. This clearly demonstrates that synthetic gene has reduced risk of spurious expression (Table 6).

The synthetic *Renilla* gene (Rluc-final) was used in in vitro systems to compare translation efficiency with the native gene. In a T7 quick coupled transcription/translation system (Promega Corp., Madison, Wis.), pRL-null native plasmid (having the native *Renilla* luciferase gene under the control of the T7 promoter) or the same amount of pRL-null-synthetic plasmid (having the synthetic *Renilla* luciferase gene under the control of the T7 promoter) was added to the TNT reaction mixture and luciferase activity measured every 5 minutes up to 60 minutes. Dual Luciferase assay kit (Promega Corp.) was used to measure *Renilla* luciferase activity. The data showed that improved expression was obtained from the synthetic gene. To further evidence the increased translation efficiency of the synthetic gene, RNA was prepared by an in vitro transcription system, then purified. pRL-null (native or synthetic) vectors were linearized with BamHI. The DNA was purified by multiple phenol-chloroform extraction followed by ethanol precipitation. An in vitro T7 transcription system was employed by prepare RNAs. The DNA template was removed by using RNase-free DNase, and RNA was purified by phenol-chloroform extraction followed by multiple isopropanol precipitations. The same amount of purified RNA, either for the synthetic gene or the native gene, was then added to a rabbit reticulocyte lysate or wheat germ lysate. Again, the synthetic *Renilla* luciferase gene RNA produced more luciferase than the native one. These data suggest that the translation efficiency is improved by the synthetic sequence. To determine why the synthetic gene was highly expressed in wheat germ, plant codon usage was determined. The lowest usage codons in higher plants coincided with those in mammals.

Reporter gene assays are widely used to study transcriptional regulation events. This is often carried out in co-transfection experiments, in which, along with the primary reporter construct containing the testing promoter, a second control reporter under a constitutive promoter is transfected into cells as an internal control to normalize experimental variations including transfection efficiencies between the samples. Control reporter signal, potential promoter cross talk between the control reporter and primary reporter, as well as potential regulation of the control reporter by experimental conditions, are important aspects to consider for selecting a reliable co-reporter vector.

As described above, vector constructs were made by cloning synthetic *Renilla* luciferase gene into different vector backbones under different promoters. All the constructs showed higher expression in the three mammalian cell lines tested (Table 5). Thus, with better expression efficiency, the synthetic *Renilla* luciferase gives out higher signal when transfected into mammalian cells.

Because a higher signal is obtained, less promoter activity is required to achieve the same reporter signal, this reduced risk of promoter interference. CHO cells were transfected with 50 ng pGL3-control (firefly luc+) plus one of 5 different amounts of native pRL-TK plasmid (50, 100, 500, 1000, or 2000 ng) or synthetic pRL-TK (5, 10, 50, 100, or 200 ng). To each transfection, pUC19 carrier DNA was added to a total of 3 µg DNA. 10 fold less pRL-TK DNA gave similar or more signal as the native gene, with reduced risk of inhibiting expression from the primary reporter pGL3-control.

Experimental treatment sometimes may activate cryptic sites within the gene and cause induction or suppression of the co-reporter expression, which would compromise its function as co-reporter for normalization of transfection efficiencies. One example is that TPA induces expression of co-reporter vectors harboring the wild-type gene when transfecting MCF-7 cells. 500 ng pRL-TK (native), 5 µg native and synthetic pRG-B, 2.5 µg native and synthetic pRG-TK were transfected per well of MCF-7 cells. 100 ng/well pGL3-control (firefly luc+) was co-transfected with all RL plasmids. Carrier DNA, pUC19, was used to bring the total DNA transfected to 5.1 µg/well. 15.3 µl TransFast Transfection Reagent (Promega Corp., Madison, Wis.) was added per well. Sixteen hours later, cells were trypsinized, pooled and split into six wells of a 6-well dish and allowed to attach to the well for 8 hours. Three wells were then treated with the 0.2 nM of the tumor promoter, TPA (phorbol-12-myristate-13-acetate, Calbiochem #524400-S), and three wells were mock treated with 20 µl DMSO. Cells were harvested with 0.4 ml Passive Lysis Buffer 24 hours post TPA addition. The results showed that by using the synthetic gene, undesirable change of co-reporter expression by experimental stimuli can be avoided (Table 7). This demonstrates that using synthetic gene can reduce the risk of anomalous expression.

TABLE 7

| Vector | Rlu | Fold Induction |
| --- | --- | --- |
| pRL-tk untreated (native) | 184 | |
| pRL-tk TPA treated (native) | 812 | 4.4 |
| pRG-B untreated (native) | 1 | |
| pRG-B TPA treated (native) | 8 | 8.0 |
| pRG-B untreated (final) | 132 | |
| pRG-B TPA treated (final) | 195 | 1.47 |
| pRG-tk untreated (native) | 44 | |
| pRG-tk TPA treated (native) | 192 | 4.36 |
| pRG-tk untreated (final) | 12,816 | |
| pRG-tk TPA treated (final) | 11,347 | 0.88 |

EXAMPLE 3

Synthetic Firefly Luciferase Genes

The luc+gene (U.S. Pat. No. 5,670,356) was optimized using two approaches. In the first approach (Strategy A), regulatory sequences such as codons were optimized and consensus transcription factor binding sites (TFBS) were removed (see Example 4, although different versions of programs and databases were used). The sequences obtained for the first approach include hluc+ver2AF1 through hluc+ver2AF8 (designations with an "F" indicate the construct included flanking sequences). hluc+ver2AF1 is codon-optimized, hluc+ver2AF2 is a sequence obtained after a first round of removal of identified undesired sequences including transcription factor binding sites, hluc+ver2AF3 was obtained after a second round of removal of identified undesired sequences including transcription factor binding sites, hluc+ver2AF4 was obtained after a third round of removal of identified undesired sequences including transcription factor binding sites, hluc+ver2AF5 was obtained after a fourth round of removal of identified undesired sequences including transcription factor binding sites, hluc+ver2AF6 was obtained after removal of promoter modules and RBS, hluc+ver2AF7 was obtained after further removal of identified undesired sequences including transcription factor binding sites, and hluc+ver2AF8 was obtained after modifying a restriction enzyme recognition site. Pairwise DNA identity of different *P. pyralis* luciferase gene versions:

TABLE 8

|  | luc | luc+ | hluc+ | hluc + ver2A1 | hluc + ver2B1 | hluc + ver2A6 | hluc + ver2B6 |
|---|---|---|---|---|---|---|---|
| Luc | 100 | 95 | 76 | 73 | 77 | 74 | 75 |
| luc+ |  | 100 | 78 | 76 | 78 | 75 | 77 |
| hluc+ |  |  | 100 | 91 | 81 | 87 | 81 |
| hluc + ver2A1 |  |  |  | 100 | 74 | 91 | 78 |
| hluc + ver2B1 |  |  |  |  | 100 | 74 | 85 |
| hluc + ver2A6 |  |  |  |  |  | 100 | 80 |
| hluc + ver2B6 |  |  |  |  |  |  | 100 | luc+ has the following sequence:

(SEQ ID NO: 43)
atggaagacgccaaaaacataaagaaaggcccggcgccattctatccgct ggaagatggaaccgctggagagcaactgcataaggctatgaagagatacg ccctggttcctggaacaattgcttttacagatgcacatatcgaggtggac atcacttacgctgagtacttcgaaatgtccgttcggttggcagaagctat gaaacgatatgggctgaatacaaatcacagaatcgtcgtatgcagtgaaa actctcttcaattctttatgccggtgttgggcgcgttatttatcggagtt gcagttgcgcccgcgaacgacatttataatgaacgtgaattgctcaacag tatgggcatttcgcagcctaccgtggtgttcgtttccaaaaaggggttgc aaaaaattttgaacgtgcaaaaaaagctcccaatcatccaaaaaattatt atcatggattctaaaacggattaccagggatttcagtcgatgtacacgtt cgtcacatctcatctacctcccggttttaatgaatacgattttgtgccag agtccttcgatagggacaagacaattgcactgatcatgaactcctctgga tctactggtctgcctaaaggtgtcgctctgcctcatagaactgcctgcgt gagattctcgcatgccagagatcctatttttggcaatcaaatcattccgg atactgcgattttaagtgttgttccattccatcacggttttggaatgttt actacactcggatatttgatatgtggatttcgagtcgtcttaatgtatag atttgaagaagagctgtttctgaggagccttcaggattacaagattcaaa gtgcgctgctggtgccaaccctattctccttcttcgccaaaagcactctg attgacaaatacgatttatctaatttacacgaaattgcttctggtggcgc tcccctctctaaggaagtcggggaagcggttgccaagaggttccatctgc caggtatcaggcaaggatatgggctcactgagactacatcagctattctg attacacccgagggggatgataaaccgggcgcggtcggtaaagttgttcc attttttgaagcgaaggttgtggatctggataccgggaaaacgctgggcg ttaatcaaagaggcgaactgtgtgtgagaggtcctatgattatgtccggt tatgtaaacaatccggaagcgaccaacgccttgattgacaaggatggatg gctacattctggagacatagcttactgggacgaagacgaacacttcttca tcgttgaccgcctgaagtctctgattaagtacaaaggctatcaggtggct cccgctgaattggaatccatcttgctccaacaccccaacatcttcgacgc aggtgtcgcaggtcttcccgacgatgacgccggtgaacttcccgccgccg ttgttgttttggagcacggaaagacgatgacggaaaaagagatcgtggat tacgtcgccagtcaagtaacaaccgcgaaaaagttgcgcggaggagttgt gtttgtggacgaagtaccgaaaggtcttaccggaaaactcgacgcaagaa aaatcagagagatcctcataaaggccaagaagggcggaaagatcgccgtg taa and hluc+ has the following sequence:

(SEQ ID NO: 14)
atggccgatgctaagaacattaagaagggccctgctcccttctaccctct ggaggatggcaccgctggcgagcagctgcacaaggccatgaagaggtatg ccctggtgcctggcaccattgccttcaccgatgcccacattgaggtggac atcacctatgccgagtacttcgagatgtctgtgcgcctggccgaggccat gaagaggtacggcctgaacaccaaccaccgcatcgtggtgtgctctgaga actctctgcagttcttcatgccagtgctgggcgccctgttcatcggagtg gccgtggcccctgctaacgacatttacaacgagcgcgagctgctgaacag catgggcatttctcagcctaccgtggtgttcgtgtctaagaagggcctgc agaagatcctgaacgtgcagaagaagctgcctatcatccagaagatcatc atcatggactctaagaccgactaccagggcttccagagcatgtacacatt cgtgacatctcatctgcctcctggcttcaacgagtacgacttcgtgccag agtctttcgacagggacaaaaccattgccctgatcatgaacagctctggg tctaccggcctgcctaagggcgtggccctgcctcatcgcaccgcctgtgt gcgcttctctcacgcccgcgaccctatttttggcaaccagatcatccccg acaccgctattctgagcgtggtgccattccaccacggcttcggcatgttc accaccctgggctacctgatttgcggctttcgggtggtgctgatgtaccg cttcgaggaggagctgttcctgcgcagcctgcaagactacaaaattcagt ctgccctgctggtgccaaccctgttcagcttcttcgctaagagcaccctg -continued

```
atcgacaagtacgacctgtctaacctgcacgagattgcctctggcggcgc
cccactgtctaaggaggtgggcgaagccgtggccaagcgctttcatctgc
caggcatccgccagggctacggcctgaccgagacaaccagcgccattctg
attaccccagagggcgacgacaagcctggcgccgtgggcaaggtggtgcc
attcttcgaggccaaggtggtggacctggacaccggcaagaccctgggag
tgaaccagcgcggcgagctgtgtgtgcgcggccctatgattatgtccggc
tacgtgaataaccctgaggccacaaacgccctgatcgacaaggacggctg
gctgcactctggcgacattgcctactgggacgaggacgagcacttcttca
tcgtggaccgcctgaagtctctgatcaagtacaagggctaccaggtggcc
ccagccgagctggagtctatcctgctgcagcaccctaacattttcgacgc
cggagtggccggcctgcccgacgacgatgccggcgagctgcctgccgccg
tcgtcgtgctggaacacggcaagaccatgaccgagaaggagatcgtggac
tatgtggccagccaggtgacaaccgccaagaagctgcgcggcggagtggt
gttcgtggacgaggtgcccaagggcctgaccggcaagctggacgcccgca
agatccgcgagatcctgatcaaggctaagaaaggcggcaagatcgccgtg
taa.
```

TABLE 9

Percent Identity

| | | hluc + ver2A8 | hluc + ver2B10 | luc+ | hluc+ |
|---|---|---|---|---|---|
| Diver-gence | hluc + ver2A8 | | 79.6 | 74 | 86.6 |
| | hluc + ver2B10 | 22.9 | | 75.9 | 80.1 |
| | luc+ | 30.4 | 27.8 | | 77.4 |
| | hluc+ | 14.7 | 22.5 | 25.7 | |

TABLE 10

Composition statistics of different *P. pyralis* luciferase gene versions

| | GC content | CG di-nucleotides |
|---|---|---|
| *H. sapiens* | 53% | — |
| luc | 45% | 99 |
| luc+ | 47% | 97 |
| hluc+ | 60% | 111 |
| hluc + ver2A1 | 66% | 151 |
| hluc + ver2B1 | 46% | 1 |
| hluc + ver2A6 | 58% | 133 |
| hluc + ver2B6 | 49% | 53 | hluc+ver2A1-hluc+ver2A5 have the following sequences (SEQ ID Nos. 16-20):

```
hluc + ver2A1
AAAGCCACCATGGAGGACGCCAAGAACATCAAGAAGGGCCCCGCCCCCTT
CTACCCCCTGGAGGACGGCACCGCCGGCGAGCAGCTGCACAAGGCCATGA
AGCGCTACGCCCTGGTGCCCGGCACCATCGCCTTCACCGACGCCCACATC
GAGGTGGACATCACCTACGCCGAGTACTTCGAGATGAGCGTGCGCCTGGC
CGAGGCCATGAAGCGCTACGGCCTGAACACCAACCACCGCATCGTGGTGT
GCAGCGAGAACAGCCTGCAGTTCTTCATGCCCGTGCTGGGCGCCCTGTTC
ATCGGCGTGGCCGTGGCCCCCGCCAACGACATCTACAACGAGCGCGAGCT
GCTGAACAGCATGGGCATCAGCCAGCCCACCGTGGTGTTCGTGAGCAAGA
AGGGCCTGCAGAAGATCCTGAACGTGCAGAAGAAGCTGCCCATCATCCAG
AAGATCATCATCATGGACAGCAAGACCGACTACCAGGGCTTCCAGAGCAT
GTACACCTTCGTGACCAGCCACCTGCCCCCCGGCTTCAACGAGTACGACT
TCGTGCCCGAGAGCTTCGACCGCGACAAGACCATCGCCCTGATCATGAAC
AGCAGCGGCAGCACCGGCCTGCCCAAGGGCGTGGCCCTGCCCCACCGCAC
CGCCTGCGTGCGCTTCAGCCACGCCCGCGACCCCATCTTCGGCAACCAGA
TCATCCCCGACACCGCCATCCTGAGCGTGGTGCCCTTCCACCACGGCTTC
GGCATGTTCACCACCCTGGGCTACCTGATCTGCGGCTTCCGCGTGGTGCT
GATGTACCGCTTCGAGGAGGAGCTGTTCCTGCGCAGCCTGCAGGACTACA
AGATCCAGAGCGCCCTGCTGGTGCCCACCCTGTTCAGCTTCTTCGCCAAG
AGCACCCTGATCGACAAGTACGACCTGAGCAACCTGCACGAGATCGCCAG
CGGCGGCGCCCCCCTGAGCAAGGAGGTGGGCGAGGCCGTGGCCAAGCGCT
TCCACCTGCCCGGCATCCGCCAGGGCTACGGCCTGACCGAGACCACCAGC
GCCATCCTGATCACCCCCGAGGGCGACGACAAGCCCGGCGCCGTGGGCAA
GGTGGTGCCCTTCTTCGAGGCCAAGGTGGTGGACCTGGACACCGGCAAGA
CCCTGGGCGTGAACCAGCGCGGCGAGCTGTGCGTGCGCGGCCCCATGATC
ATGAGCGGCTACGTGAACAACCCCGAGGCCACCAAGGCCCTGATCGACAA
GGACGGCTGGCTGCACAGCGGCGACATCGCCTACTGGGACGAGGACGAGC
ACTTCTTCATCGTGGACCGCCTGAAGAGCCTGATCAAGTACAAGGGCTAC
CAGGTGGCCCCCGCCGAGCTGGAGAGCATCCTGCTGCAGCACCCCAACAT
CTTCGACGCCGGCGTGGCCGGCCTGCCCGACGACGACGCCGGCGAGCTGC
CCGCCGCCGTGGTGGTGCTGGAGCACGGCAAGACCATGACCGAGAAGGAG
ATCGTGGACTACGTGGCCAGCCAGGTGACCACCGCCAAGAAGCTGCGCGG
CGGCGTGGTGTTCGTGGACGAGGTGCCCAAGGGCCTGACCGGCAAGCTGG
ACGCCCGCAAGATCCGCGAGATCCTGATCAAGGCCAAGAAGGGCGGCAAG
ATCGCCGTGTAATAATTCTAGA hluc + ver2A2
AAAGCCACCATGGAGGACGCCAAGAACATCAAGAAGGGCCCCAGCGCCATT
CTACCCCCTGGAGGACGGCACCGCCGGCGAGCAGCTGCACAAGGCCATGA
AGCGCTACGCCCTGGTGCCCGGCACCATCGCCTTCACCGACGCACATATC
GAGGTGGACATCACCTACGCCGAGTACTTCGAGATGAGCGTTCGGCTGGC
AGAGGCTATGAAGCGCTATGGGCTGAACACCAACCATCGCATCGTGGTGT
GCAGCGAGAACAGCTTGCAGTTCTTCATGCCCGTGTTGGGTGCCCTGTTC
ATCGGCGTGGCTGTGGCCCCAGCTAACGACATCTACAACGAGCGCGAGCT
GCTGAACAGCATGGGCATCAGCCAGCCCACCGTCGTATTCGTGAGCAAGA
AAGGGCTGCAAAAGATCCTGAACGTGCAAAAGAAGCTGCCCATCATCCAA
AAGATCATCATCATGGACAGCAAGACCGACTACCAGGGCTTCCAAAGCAT
GTACACCTTCGTGACCAGCCATTTGCCGCCCGGCTTCAACGAGTACGACT
TCGTGCCCGAGAGCTTCGACCGCGACAAGACCATCGCCCTGATCATGAAC
```

```
AGTAGTGGCAGTACCGGCTTACCTAAGGGCGTGGCCCTACCGCACCGCAC
CGCCTGTGTCCGATTCAGTCATGCCCGCGACCCCATCTTCGGCAACCAGA
TCATCCCCGACACCGCTATCCTGAGCGTGGTGCCATTTCACCACGGCTTC
GGCATGTTCACCACCCTGGGCTACTTGATCTGCGGCTTCCGGGTCGTGCT
GATGTACCGCTTCGAGGAGGAGCTATTCTTGCGCAGCTTGCAAGACTACA
AGATTCAAAGCGCCCTGCTGGTGCCCACCCTGTTCAGTTTCTTCGCCAAG
AGCACCCTGATCGACAAGTACGACCTGAGCAACCTGCACGAGATCGCCAG
CGGCGGCGCCCCGCTCAGCAAGGAGGTGGGCGAGGCCGTGGCCAAGCGCT
TCCACCTGCCAGGCATCCGCCAGGGCTACGGCCTGACCGAGACAACCAGC
GCCATTCTGATCACCCCCGAGGGGACGACAAGCCTGGCGCAGTAGGCAA
GGTGGTGCCCTTCTTCGAGGCTAAGGTGGTGGACCTGGACACCGGTAAAA
CCCTGGGTGTGAACCAGCGCGGCGAGCTGTGCGTCCGTGGCCCCATGATC
ATGAGCGGCTACGTTAACAACCCCGAGGCTACAAACGCCCTGATCGACAA
GGACGGCTGGCTGCACAGCGGCGACATCGCCTACTGGGACGAGGACGAGC
ACTTCTTCATCGTGGACCGGCTGAAGAGCCTGATCAAATACAAGGGCTAC
CAGGTAGCCCCAGCCGAACTGGAGAGCATCCTGCTGCAGCACCCCAACAT
CTTCGACGCCGGGGTCGCCGGCCTGCCCGACGACGATGCCGGCGAGCTGC
CCGCCGCAGTCGTGGTGCTGGAGCACGGTAAAACCATGACCGAGAAGGAG
ATCGTGGACTATGTGGCCAGCCAGGTTACAACCGCCAAGAAGCTGCGCGG
CGGCGTGGTGTTCGTGGACGAGGTGCCTAAAGGCCTGACGGGCAAGTTGG
ACGCCCGCAAGATCCGCGAGATTCTGATCAAGGCCAAGAAGGGCGGCAAG
ATCGCCGTGTAATAATTCTAGA
hluc + ver2A3
AAAGCCACCATGGAAGATGCCAAAAACATTAAGAAGGGCCCAGCGCCATT
CTACCCACTGGAGGACGGCACCGCCGGCGAGCAGCTGCACAAAGCCATGA
AGCGCTACGCCCTGGTGCCCGGCACCATCGCCTTTACCGACGCACATATC
GAGGTGGACATCACCTACGCCGAGTACTTCGAGATGAGCGTTCGGCTGGC
AGAGGCTATGAAGCGCTATGGGCTGAATACCAACCATCGCATCGTGGTGT
GCAGCGAGAATAGCTTGCAGTTCTTCATGCCCGTGTTGGGTGCCCTGTTC
ATCGGTGTGGCTGTGGCCCCAGCTAACGACATCTACAACGAGCGCGAGCT
GCTGAACAGCATGGGCATCAGCCAGCCCACCGTCGTATTCGTGAGCAAGA
AAGGGCTGCAAAAGATCCTCAACGTGCAAAAGAAGCTACCGATCATACAA
AAGATCATCATCATGGATAGCAAGACCGACTACCAGGGCTTCCAAAGCAT
GTACACCTTCGTGACCAGCCATTTGCCACCCGGCTTCAACGAGTACGACT
TCGTGCCCGAGAGCTTCGACCGGGACAAAACCATCGCCCTGATCATGAAC
AGTAGTGGCAGTACCGGATTGCCCAAGGGCGTAGCCCTACCGCACCGCAC
CGCCTTGTGTCCGATTCAGTCATGCCCGCGACCCCATCTTCGGCAACCAGA
TCATCCCCGACACCGCTATCCTCAGCGTGGTGCCATTTCACCACGGCTTC
GGCATGTTCACCACGCTGGGCTACTTGATCTGCGGCTTTCGGGTCGTGCT
CATGTACCGCTTCGAGGAGGAGCTATTCTTGCGCAGCTTGCAAGACTATA
AGATTCAAAGCGCCCTGCTGGTGCCCACACTGTTCAGTTTCTTCGCCAAG
``` hluc + ver2A4
```
AAAGCCACCATGGAAGATGCCAAAAACATTAAGAAGGGCCCAGCGCCATT
CTACCCACTCGAAGACGGCACCGCCGGCGAGCAGCTGCACAAAGCCATGA
AGCGCTACGCCCTGGTGCCCGGCACCATCGCCTTTACCGACGCACATATC
GAGGTGGACATTACCTACGCCGAGTACTTCGAGATGAGCGTTCGGCTGGC
AGAAGCTATGAAGCGCTATGGGCTGAACACCAACCATCGCATCGTGGTGT
GCAGCGAGAATAGCTTGCAGTTCTTCATGCCCGTGTTGGGTGCCCTGTTC
ATCGGTGTGGCTGTGGCCCCAGCTAACGACATCTACAACGAGCGCGAGCT
GCTGAACAGCATGGGCATCAGCCAGCCCACCGTCGTATTCGTGAGCAAGA
AAGGGCTGCAAAAGATCCTCAACGTGCAAAAGAAGCTACCGATCATACAA
AAGATCATCATCATGGATAGCAAGACCGACTACCAGGGCTTCCAAAGCAT
GTACACCTTCGTGACTTCCCATTTGCCACCCGGCTTCAACGAGTACGACT
TCGTGCCCGAGAGCTTCGACCGGGACAAAACCATCGCCCTGATCATGAAC
AGTAGTGGCAGTACCGGATTGCCCAAGGGCGTAGCCCTACCGCACCGCAC
CGCTTGTGTCCGATTCAGTCATGCCCGCGACCCCATCTTCGGCAACCAGA
TCATCCCCGACACCGCTATCCTCAGCGTGGTGCCATTTCACCACGGCTTC
GGCATGTTCACCACGCTGGGCTACTTGATCTGCGGCTTTCGGGTCGTGCT
CATGTACCGCTTCGAGGAGGAGCTATTCTTGCGCAGCTTGCAAGACTATA
AGATTCAAAGCGCCCTGCTGGTGCCCACACTGTTCAGTTTCTTCGCCAAG
AGCACTCTCATCGACAAGTACGACCTAAGCAACTTGCACGAGATCGCCAG
CGGCGGGGCGCCGCTCAGCAAGGAGGTGGGCGAGGCCGTGGCCAAACGCT
TCCACCTACCAGGCATCCGCCAGGGCTACGGCCTGACAGAAACAACCAGC
GCCATTCTGATCACCCCCGAAGGGGACGACAAGCCTGGCGCAGTAGGCAA
GGTGGTGCCCTTCTTCGAGGCTAAGGTGGTGGACTTGGACACCGGTAAGA
CACTGGGTGTGAACCAGCGCGGCGAGCTGTGCGTCCGTGGCCCCATGATC
```

ATGAGCGGCTACGTTAACAACCCCGAGGCTACAAACGCTCTCATCGACAA
GGACGGCTGGCTGCACAGCGGCGACATCGCCTACTGGGACGAGGACGAGC
ACTTCTTCATCGTGGACCGGCTGAAGAGCCTGATCAAATACAAGGGCTAC
CAGGTAGCCCCAGCCGAACTGGAGAGCATCCTGCTGCAACACCCCAACAT
CTTCGACGCCGGGGTCGCCGGCCTGCCCGACGACGATGCCGGCGAGCTGC
CCGCCGCAGTCGTCGTGCTGGAACACGGTAAAACCATGACCGAGAAGGAG
ATCGTGGACTATGTGGCCAGCCAGGTTACAACCGCCAAGAAGCTGCGCGG
TGGTGTTGTGTTCGTGGACGAGGTGCCTAAAGGCCTGACGGGCAAGTTGG
ACGCCCGCAAGATCCGCGAGATTCTCATTAAGGCCAAGAAGGGCGGCAAG
ATCGCCGTGTAATAATTCTAGA hluc+ver2A6 has the following sequence (SEQ ID NO: 21)
AAAGCCACCATGGAaGAtGCCAAaAACATtAAGAAGGGCCCaGCgCCaTT
CTACCCaCTcGAaGACGGCACCGCCGGCGAGCAGCTGCACAAaGCCATGA
AGCGCTACGCCCTGGTGCCCGGCACCATCGCGTTtACCGACGCaCAtATC
GAGGTGGACATtACCTACGCCGAGTACTTCGAGATGAGCGTtCGgCTGGC
aGAaGCtATGAAGCGCTAtGGgCTGAAtACaAACCAtCGgATCGTGGTGT
GCAGCGAGAAtAGCtTGCAGTTCTTCATGCCCGTGtTGGGtGCCCTGTTC
ATCGGtGTGGCtGTGGCCCCaGCtAACGACATCTACAACGAGCGCGAGCT
GCTGAACAGCATGGGCATCAGCCAGCCCACCGTcGTaTTCGTGAGCAAGA
AaGGgCTGCAaAAGATCCTcAACGTGCAaAAGAAGCTaCCgATCATaCAa
AAGATCATCATCATGGAtAGCAAGACCGACTACCAGGGCTTCCAaAGCAT
GTACACCTTCGTGACttcCCAttTGCCaCCCGGCTTCAACGAGTACGACT
TCGTGCCCGAGAGCTTCGACCGgGACAAaACCATCGCCCTGATCATGAAC
AGtAGtGGCAGtACCGGatTgCCcAAGGGCGTaGCCCTaCCgCACCGCAC
CGCtTGtGTcCGaTTCAGtCAtGCCCGCGACCCCATCTTCGGCAACCAGA
TCATCCCCGACACCGCtATCCTcAGCGTGGTGCCaTTtCACCACGGCTTC
GGCATGTTCACCACgCTGGGCTACtTGATCTGCGGCTTtCGgGTcGTGCT
cATGTACCGCTTCGAGGAGGAGCTaTTCtTGCGCAGCtTGCAaGACTAtA
AGATTcAaAGCGCCCTGCTGGTGCCCACaCTGTTCAGtTTCTTCGCtAAG
AGCACtCTcATCGACAAGTACGACCTaAGCAACtTGCACGAGATCGCCAG
CGGCGGgGCgCCgCTcAGCAAGGAGGTaGGtGAGGCCGTGGCCAAaCGCT
TCCACCTaCCaGGGCATCCGCCAGGGCTACGGCCTGACaGAaACaACCAGC
GCCATtCTGATCACCCCCGAaGGgGACGACAAGCCtGGCGCaGTaGGCAA
GGTGGTGCCCTTCTTCGAGGCtAAGGTGGTGGACtTGGACACCGGtAAgA
CaCTGGGtGTGAACCAGCGCGGCGAGCTGTGCGTcCGtGGCCCCATGATC
ATGAGCGGCTACGTtAACAACCCCGAGGCtACaAACGCtCTcATCGACAA
GGACGGCTGGCTGCACAGCGGCGACATCGCCTACTGGGACGAGGACGAGC
ACTTCTTCATCGTGGACCGgCTGAAGAGCCTGATCAAaTACAAGGGCTAC
CAGGTaGCCCCaGCCGAaCTGGAGAGCATCCTGCTGCAaCACCCCAACAT
CTTCGACGCCGGgGTcGCCGGCCTGCCCGACGACGAtGCCGGCGAGCTGC
CCGCCGCaGTcGTcGTGCTGGAaCACGGtAAaACCATGACCGAGAAGGAG
ATCGTGGACTAtGTGGCCAGCCAGGTtACaACCGCCAAGAAGCTGCGCGG
tGGtGTtGTGTTCGTGGACGAGGTGCCtAAaGGCCTGACgGGCAAGtTGG
ACGCCCGCAAGATCCGCGAGATtCTcATtAAGGCCAAGAAGGGCGGCAAG
ATCGCCGTGTAATAATTCTAGA.

hluc + ver2A5
AAAGCCACCATGGAAGATGCCAAAAACATTAAGAAGGGCCCAGCGCCATT
CTACCCACTCGAAGACGGCACCGCCGGCGAGCAGCTGCACAAAGCCATGA
AGCGCTACGCCCTGGTGCCCGGCACCATCGCCTTTACCGACGCACATATC
GAGGTGGACATTACCTACGCCGAGTACTTCGAGATGAGCGTTCGGCTGGC
AGAAGCTATGAAGCGCTATGGGCTGAACACCAACCATCGGATCGTGGTGT
GCAGCGAGAATAGCTTGCAGTTCTTCATGCCCGTGTTGGGTGCCCTGTTC
ATCGGTGTGGCTGTGGCCCCAGCTAACGACATCTACAACGAGCGCGAGCT
GCTGAACAGCATGGGCATCAGCCAGCCCACCGTCGTATTCGTGAGCAAGA
AAGGGCTGCAAAAGATCCTCAACGTGCAAAAGAAGCTACCGATCATACAA
AAGATCATCATCATGGATAGCAAGACCGACTACCAGGGCTTCCAAAGCAT
GTACACCTTCGTGACTTCCCATTTGCCACCCGGCTTCAACGAGTACGACT
TCGTGCCCGAGAGCTTCGACCGGGACAAAACCATCGCCCTGATCATGAAC
AGTAGTGGCAGTACCGGATTGCCCAAGGGCGTAGCCCTACCGCACCGCAC
CGCTTGTGTCCGATTCAGTCATGCCCGCGACCCCATCTTCGGCAACCAGA
TCATCCCCGACACCGCTATCCTCAGCGTGGTGCCATTTCACCACGGCTTC
GGCATGTTCACCACGCTGGGCTACTTGATCTGCGGCTTTCGGGTCGTGCT
CATGTACCGCTTCGAGGAGGAGCTATTCTTGCGCAGCTTGCAAGACTATA
AGATTCAAAGCGCCCTGCTGGTGCCCACACTGTTCAGTTTCTTCGCTAAG
AGCACTCTCATCGACAAGTACGACCTAAGCAACTTGCACGAGATCGCCAG
CGGCGGGGCGCCGCTCAGCAAGGAGGTGGGCGAGGCCGTGGCCAAACGCT
TCCACCTACCAGGCATCCGCCAGGGCTACGGCCTGACAGAAACAACCAGC
GCCATTCTGATCACCCCCGAAGGGACGACAAGCCTGGCGCAGTAGGCAA
GGTGGTGCCCTTCTTCGAGGCTAAGGTGGTGGACTTGGACACCGGTAAGA
CACTGGGTGTGAACCAGCGCGGCGAGCTGTGCGTCCGTGGCCCCATGATC
ATGAGCGGCTACGTTAACAACCCCGAGGCTACAAACGCTCTCATCGACAA
GGACGGCTGGCTGCACAGCGGCGACATCGCCTACTGGGACGAGGACGAGC
ACTTCTTCATCGTGGACCGGCTGAAGAGCCTGATCAAATACAAGGGCTAC
CAGGTAGCCCCAGCCGAACTGGAGAGCATCCTGCTGCAACACCCCAACAT
CTTCGACGCCGGGGTCGCCGGCCTGCCCGACGACGATGCCGGCGAGCTGC
CCGCCGCAGTCGTCGTGCTGGAACACGGTAAAACCATGACCGAGAAGGAG The hluc+ver2A6 sequence was modified yielding hluc+ver2A7:

(SEQ ID NO: 22)
```
AAAGCCACCATGGAaGAtGCCAAaAACATtAAGAAGGGCCCaGCgCCaTT
CTACCCaCTcGAaGACGGgACCGCCGGCGAGCAGCTGCACAAaGCCATGA
AGCGCTACGCCCTGGTGCCCGGCACCATCGCCTTtACCGACGCaCAtATC
GAGGTGGACATtACCTACGCCGAGTACTTCGAGATGAGCGTtCGgCTGGC
aGAaGCtATGAAGCGCTAtGGgCTGAAtACaAACCAtCGgATCGTGGTGT
GCAGCGAGAAtAGCtTGCAGTTCTTCATGCCCGTGtTGGGtGCCCTGTTC
ATCGGtGTGGCtGTGGCCCCaGCtAACGACATCTACAACGAGCGCGAGCT
GCTGAACAGCATGGGCATCAGCCAGCCCACCGTcGTaTTCGTGAGCAAGA
AaGGgCTGCAaAAGATCCTcAACGTGCAaAAGAAGCTaCCgATCATaCAa
AAGATCATCATCATGGAtAGCAAGACCGACTACCAGGGCTTCCAaAGCAT
GTACACCTTCGTGACttcCCAttTGCCaCCCGGCTTCAACGAGTACGACT
TCGTGCCCGAGAGCTTCGACCGgGACAAaACCATCGCCCTGATCATGAAC
AGtAGtGGCAGtACCGGatTgCCcAAGGGCGTaGCCCTaCCgCACCGCAC
CGCtTGtGTcCGaTTCAGtCAtGCCCGCGACCCCATCTTCGGCAACCAGA
TCATCCCCGACACCGCtATCCTcAGCGTGGTGCCaTTtCACCACGGCTTC
GGCATGTTCACCACgCTGGGCTACtTGATCTGCGGCTTtCGgGTcGTGCT
cATGTACCGCTTCGAGGAGGAGCTaTTCtTGCGCAGCtTGCAaGACTAtA
AGATTcAatctGCCCTGCTGGTGCCCACaCTaTTtAGcTTCTTCGCtAAG
AGCACtCTcATCGACAAGTACGACCTaAGCAACtTGCACGAGATCGCCAG
CGGCGGgGCgCCgCTcAGCAAGGAGGTaGGtGAGGCCGTGGCCAAaCGCT
TCCACCTaCCaGGCATCCGCCAGGGCTACGGCCTGACaGAaACaACCAGC
GCCATtCTGATCACCCCCGAaGGgGACGACAAGCCtGGCGCaGTaGGCAA
GGTGGTGCCCTTCTTCGAGGCtAAGGTGGTGGACtTGGACACCGGtAAgA
CaCTGGGtGTGAACCAGCGCGGCGAGCTGTGCGTcCGtGGCCCCATGATC
ATGAGCGGCTACGTtAACAACCCCGAGGCtACaAACGCtCTcATCGACAA
GGACGGCTGGCTGCACAGCGGCGACATCGCCTACTGGGACGAGGACGAGC
ACTTCTTCATCGTGGACCGgCTGAAGAGCCTGATCAAaTACAAGGGCTAC
CAGGTaGCCCCaGCCGAaCTGGAGAGCATCCTGCTGCAaCACCCCAACAT
CTTCGACGCCGGgGTcGCCGGCCTGCCCGACGACGAtGCCGGCGAGCTGC
CCGCCGCaGTcGTcGTGCTGGAaCACGGtAAaACCATGACCGAGAAGGAG
ATCGTGGACTAtGTGGCCAGCCAGGTtACaACCGCCAAGAAGCTGCGCGG
tGGtGTtGTGTTCGTGGACGAGGTGCCtAAaGGCCTGACgGGCAAGtTGG
ACGCCCGCAAGATCCGCGAGATtCTcATtAAGGCCAAGAAGGGCGGCAAG
ATCGCCGTGTAATAATTCTAGA.
```

For vectors with a BglI site in the multiple cloning region, the BglI site present in the firefly sequence can be removed. The luciferase gene from hluc+ver2AF8, which lacks a BglI site, displays an average of a 7.2-fold increase in expression when assayed in four mammalian cell lines, i.e., NIH3T3, CHO, HeLa and HEK293 cells.

hluc+ver2A8 has the following sequence:

(SEQ ID NO: 23)
```
AAAGCCACCATGGAaGAtGCCAAaAACATtAAGAAGGGCCCaGCgCCaTT
CTACCCaCTcGAaGACGGgACCGCCGGCGAGCAGCTGCACAAaGCCATGA
AGCGCTACGCCCTGGTGCCCGGCACCATCGCCTTtACCGACGCaCAtATC
GAGGTGGACATtACCTACGCCGAGTACTTCGAGATGAGCGTtCGgCTGGC
aGAaGCtATGAAGCGCTAtGGgCTGAAtACaAACCAtCGgATCGTGGTGT
GCAGCGAGAAtAGCtTGCAGTTCTTCATGCCCGTGtTGGGtGCCCTGTTC
ATCGGtGTGGCtGTGGCCCCaGCtAACGACATCTACAACGAGCGCGAGCT
GCTGAACAGCATGGGCATCAGCCAGCCCACCGTcGTaTTCGTGAGCAAGA
AaGGgCTGCAaAAGATCCTcAACGTGCAaAAGAAGCTaCCgATCATaCAa
AAGATCATCATCATGGAtAGCAAGACCGACTACCAGGGCTTCCAaAGCAT
GTACACCTTCGTGACttcCCAttTGCCaCCCGGCTTCAACGAGTACGACT
TCGTGCCCGAGAGCTTCGACCGgGACAAaACCATCGCCCTGATCATGAAC
AGtAGtGGCAGtACCGGatTgCCcAAGGGCGTaGCCCTaCCgCACCGCAC
CGCtTGtGTcCGaTTCAGtCAtGCCCGCGACCCCATCTTCGGCAACCAGA
TCATCCCCGACACCGCtATCCTcAGCGTGGTGCCaTTtCACCACGGCTTC
GGCATGTTCACCACgCTGGGCTACtTGATCTGCGGCTTtCGgGTcGTGCT
cATGTACCGCTTCGAGGAGGAGCTaTTCtTGCGCAGCtTGCAaGACTAtA
AGATTcAatctGCCCTGCTGGTGCCCACaCTaTTtAGcTTCTTCGCtAAG
AGCACtCTcATCGACAAGTACGACCTaAGCAACtTGCACGAGATCGCCAG
CGGCGGgGCgCCgCTcAGCAAGGAGGTaGGtGAGGCCGTGGCCAAaCGCT
TCCACCTaCCaGGCATCCGCCAGGGCTACGGCCTGACaGAaACaACCAGC
GCCATtCTGATCACCCCCGAaGGgGACGACAAGCCtGGCGCaGTaGGCAA
GGTGGTGCCCTTCTTCGAGGCtAAGGTGGTGGACtTGGACACCGGtAAgA
CaCTGGGtGTGAACCAGCGCGGCGAGCTGTGCGTcCGtGGCCCCATGATC
ATGAGCGGCTACGTtAACAACCCCGAGGCtACaAACGCtCTcATCGACAA
GGACGGCTGGCTGCACAGCGGCGACATCGCCTACTGGGACGAGGACGAGC
ACTTCTTCATCGTGGACCGgCTGAAGAGCCTGATCAAaTACAAGGGCTAC
CAGGTaGCCCCaGCCGAaCTGGAGAGCATCCTGCTGCAaCACCCCAACAT
CTTCGACGCCGGgGTcGCCGGCCTGCCCGACGACGAtGCCGGCGAGCTGC
CCGCCGCaGTcGTcGTGCTGGAaCACGGtAAaACCATGACCGAGAAGGAG
ATCGTGGACTAtGTGGCCAGCCAGGTtACaACCGCCAAGAAGCTGCGCGG
tGGtGTtGTGTTCGTGGACGAGGTGCCtAAaGGaCTGACcGGCAAGtTGG
ACGCCCGCAAGATCCGCGAGATtCTcATtAAGGCCAAGAAGGGCGGCAAG
ATCGCCGTGTAATAATTCTAGA.
```

For the second approach, firefly luciferase luc+codons were optimized for mammalian expression, and the number of consensus transcription factor binding site, and CG dinucleotides (CG islands, potential methylation sites) was reduced. The second approach yielded: versions hluc+ver2BF1 through hluc+ver2BF5. hluc+ver2BF1 is codon-optimized, hluc+ver2BF2 is a sequence obtained after a first round of removal of identified undesired sequences including transcription factor binding sites, hluc+ver2BF3 was obtained after a second round of removal of identified undesired sequences including transcription factor binding sites, hluc+ver2BF4 was obtained after a third round of removal of identified undesired sequences including transcription factor binding sites, hluc+ver2BF5 was obtained after a fourth round of removal of identified undesired sequences including transcription factor binding sites, hluc+ver2BF6 was obtained after removal of promoter modules and RBS, hluc+ver2BF7 was obtained after further removal of identified undesired sequences including transcription factor binding sites, and hluc+ver2BF8 was obtained after modifying a restriction enzyme recognition site.

hluc+ver2B1-B5 have the following sequences (SEQ ID Nos. 24-28):

```
hluc + ver2B1
AAAGCCACCATGGAGGATGCTAAGAATATTAAGAAGGGGCCTGCTCCTTT
TTATCCTCTGGAGGATGGGACAGCTGGGGAGCAGCTGCATAAGGCTATGA
AGAGATATGCTCTGGTGCCTGGGACAATTGCTTTTACAGATGCTCATATT
GAGGTGGATATTACATATGCTGAGTATTTTGAGATGTCTGTGAGACTGGC
TGAGGCTATGAAGAGATATGGGCTGAATACAAATCATAGAATTGTGGTGT
GTTCTGAGAATTCTCTGCAGTTTTTTATGCCTGTGCTGGGGGCTCTGTTT
ATTGGGGTGGCTGTGGCTCCTGCTAATGATATTTATAATGAGAGAGAGCT
GCTGAATTCTATGGGGATTTCTCAGCCTACAGTGGTGTTTGTGTCTAAGA
AGGGGCTGCAGAAGATTCTGAATGTGCAGAAGAAGCTGCCTATTATTCAG
AAGATTATTATTATGGATTCTAAGACAGATTATCAGGGGTTTCAGTCTAT
GTATACATTTGTGACATCTCATCTGCCTCCTGGGTTTAATGAGTATGATT
TTGTGCCTGAGTCTTTTGATAGAGATAAGACAATTGCTCTGATTATGAAT
TCTTCTGGGTCTACAGGGCTGCCTAAGGGGGTGGCTCTGCCTCATAGAAC
AGCTTGTGTGAGATTTTCTCATGCTAGAGATCCTATTTTTGGGAATCAGA
TTATTCCTGATACAGCTATTCTGTCTGTGGTGCCTTTTCATCATGGGTTT
GGGATGTTTACAACACTGGGGTATCTGATTTGTGGGTTTAGAGTGGTGCT
GATGTATAGATTTGAGGAGGAGCTGTTTCTGAGATCTCTGCAGGATTATA
AGATTCAGTCTGCTCTGCTGGTGCCTACACTGTTTTCTTTTTTTGCTAAG
TCTACACTGATTGATAAGTATGATCTGTCTAATCTGCATGAGATTGCTTC
TGGGGGGGCTCCTCTGTCTAAGGAGGTGGGGGAGGCTGTGGCTAAGAGAT
TCATCTGCCTGGGATTAGACAGGGGTATGGGCTGACAGAGACAACATCT
GCTATTCTGATTACACCTGAGGGGATGATAAGCCTGGGGCTGTGGGAA
GGTGGTGCCTTTTTTTGAGGCTAAGGTGGTGGATCTGGATACAGGGAAGA
CACTGGGGGTGAATCAGAGAGGGAGCTGTGTGTGAGAGGGCCTATGATT
ATGTCTGGGTATGTGAATAATCCTGAGGCTACAAATGCTCTGATTGATAA
GGATGGGTGGCTGCATTCTGGGGATATTGCTTATTGGGATGAGGATGAGC
ATTTTTTTATTGTGGATAGACTGAAGTCTCTGATTAAGTATAAGGGGTAT
CAGGTGGCTCCTGCTGAGCTGGAGTCTATTCTGCTGCAGCATCCTAATAT
TTTTGATGCTGGGGTGGCTGGGCTGCCTGATGATGATGCTGGGGAGCTGC
CTGCTGCTGTGGTGGTGCTGGAGCATGGGAAGACAATGACAGAGAAGGAG
ATTGTGGATTATGTGGCTTCTCAGGTGACAACAGCTAAGAAGCTGAGAGG
GGGGGTGGTGTTTGTGGATGAGGTGCCTAAGGGGCTGACAGGGAAGCTGG
ATGCTAGAAAGATTAGAGAGATTCTGATTAAGGCTAAGAAGGGGGGGAAG
ATTGCTGTGTAATAATTCTAGA hluc + ver2B2
AAAGCCACCATGGAAGATGCTAAAAACATTAAGAAGGGGCCTGCTCCTTT
CTACCCTCTGGAGGATGGGACTGCCGGGGAGCAGCTGCATAAAGCTATGA
AGCGGTATGCTCTGGTGCCAGGCACAATTGCGTTCACGGATGCTCACATT
GAGGTGGACATTACATACGCTGAGTATTTTGAGATGTCGGTGCGGCTGGC
TGAGGCTATGAAGCGATATGGGCTGAATACAAACCATAGAATTGTAGTGT
GCTCTGAGAACTCGTTGCAGTTTTTTATGCCTGTGCTGGGGGCTCTCTTC
ATCGGGGTGGCTGTGGCTCCTGCTAACGACATTTACAATGAGAGAGAGCT
TTTGAACTCGATGGGGATTTCTCAGCCTACAGTGGTGTTTGTGAGTAAGA
AAGGGCTTCAAAAGATTCTCAATGTGCAAAAGAAGCTGCCTATTATTCAA
AAGATTATTATTATGGACTCTAAGACAGACTACCAGGGGTTTCAGTCTAT
GTATACATTTGTGACATCTCATCTGCCTCCTGGGTTCAACGAGTATGACT
TTGTGCCCGAGTCTTTTCGACAGAGATAAGACAATTGCTCTGATTATGAAT
TCATCTGGGTCTACCGGGCTGCCTAAGGGTGTAGCTCTGCCACATAGAAC
AGCTTGTGTGAGATTTTCTCATGCTAGGGACCCTATTTTTGGGAATCAGA
TTATTCCTGATACTGCTATTCTGTCGGTTGTGCCCTTTCATCATGGGTTT
GGGATGTTTACAACACTGGGCTACCTGATATGTGGGTTTAGAGTGGTGCT
CATGTATAGGTTTGAGGAGGAGCTTTTTTTGCGCTCTCTGCAAGATTATA
AGATTCAGTCTGCTCTGCTGGTGCCTACACTGTTTTCTTTTTTTGCTAAG
TCTACCCTGATCGATAAGTATGATCTGTCCAACCTGCACGAGATTGCTTC
TGGGGGGGCTCCTCTGTCTAAGGAGGTAGGTGAGGCTGTGGCTAAGCGCT
TCATCTGCCTGGAATCAGACAGGGGTATGGGCTAACAGAAACAACATCT
GCTATTCTGATTACACCAGAGGGGATGATAAGCCCGGGGCTGTAGGGAA
AGTGGTGCCCTTTTTTGAAGCTAAAGTAGTTGATCTTGATACCGGTAAGA
CACTGGGGGTGAATCAGCGAGGGAACTGTGTGTGAGAGGGCCTATGATT
ATGTCGGGGTATGTGAACAACCCTGAGGCTACAAATGCTCTGATTGATAA
GGATGGGTGGCTGCATTCGGGCGATATTGCTTACTGGGATGAGGATGAGC
ATTTCTTCATCGTGGACAGACTGAAGTCGTTGATCAAATATAAGGGGTAT
CAAGTAGCTCCTGCTGAGCTGGAGTCCATTCTGCTTCAACATCCTAACAT
TTTCGATGCTGGGGTGGCTGGGCTGCCTGATGATGATGCTGGGGAGCTGC
CTGCTGCTGTAGTGGTGCTGGAGCACGGTAAGACAATGACAGAGAAGGAG
ATTGTGGATTATGTGGCTTCACAAGTGACAACAGCTAAGAAACTGAGAGG
TGGCGTTGTGTTTGTGGATGAGGTGCCTAAAGGGCTGACAGGCAAGCTGG
ATGCTAGAAAAATTCGAGAGATTCTGATTAAGGCTAAGAAGGGTGGAAAG
ATTGCTGTGTAATAGTTCTAGA hluc + ver2B3
AAAGCCACCATGGAAGATGCTAAAAACATTAAGAAGGGGCCTGCTCCTTT
CTACCCTCTTGAAGATGGGACTGCTGGCGAGCAACTTCACAAAGCTATGA
```

AGCGGTATGCTCTTGTGCCAGGCACAATTGCGTTCACGGATGCTCACATT
GAGGTGGACATCACATACGCTGAGTATTTTGAGATGTCGGTGCGGCTGGC
AGAAGCTATGAAGCGCTATGGGCTGAATACAAACCATAGAATTGTAGTGT
GCAGTGAGAACTCGTTGCAGTTCTTTATGCCCGTGCTGGGGGCTCTCTTC
ATCGGGGTGGCTGTGGCTCCTGCTAACGACATCTACAACGAGCGAGAGCT
GTTGAACTCGATGGGGATTTCTCAGCCTACAGTGGTGTTTGTGAGTAAGA
AAGGGCTTCAAAAGATTCTCAATGTGCAAAAGAAGCTGCCTATTATTCAA
AAGATTATTATTATGGACTCTAAGACCGACTACCAGGGGTTTCAGTCTAT
GTATACATTTGTGACATCTCATCTGCCTCCTGGCTTCAACGAGTACGACT
TCGTGCCCGAGTCTTTCGACAGAGATAAGACAATTGCTCTGATCATGAAT
TCATCCGGGTCTACCGGGCTGCCTAAGGGTGTAGCTCTGCCCCATAGAAC
AGCTTGTGTGAGATTTTCTCATGCTAGGGACCTATTTTTGGGAATCAGAT
TATTCCTGACACTGCTATTCTGTCGGTGGTGCCCTTTCATCATGGGTTTG
GGATGTTTACAACACTGGGCTACCTAATATGTGGGTTTAGAGTGGTGCTC
ATGTATAGGTTTGAAGAAGAGCTGTTCTTACGCTCTTTGCAAGATTATAA
GATTCAGTCTGCTCTGCTGGTGCCAACACTATTCTCTTTTTTTGCTAAGT
CTACGCTCATAGACAAGTATGACTTGTCCAACTTGCACGAGATTGCTTCT
GGCGGAGCACCTCTGTCTAAGGAGGTAGGTGAGGCTGTGGCTAAGCGCTT
TCATCTGCCTGGTATCAGACAGGGGTATGGGCTAACAGAAACAACATCTG
CTATTCTGATTACACCAGAGGGGATGATAAGCCCGGGGCTGTAGGGAAA
GTGGTGCCCTTTTTTGAAGCCAAAGTAGTTGATCTTGATACCGGTAAGAC
ACTAGGGGTGAACCAGCGTGGTGAACTGTGTGTGAGAGGGCCTATGATTA
TGTCGGGGTACGTTAACAACCCCGAAGCTACAAATGCTCTGATTGATAAG
GATGGCTGGCTGCATTCGGGCGACATTGCTTACTGGGATGAGGATGAGCA
TTTCTTCATCGTGGACAGACTGAAGTCGTTGATCAAATACAAGGGGTATC
AAGTAGCTCCTGCTGAGCTGGAATCCATTCTGCTTCAACATCCCAACATT
TTCGATGCTGGGGTGGCTGGGCTGCCTGATGATGATGCTGGGGAGTTGCC
TGCTGCTGTAGTGGTGCTTGAGCACGGTAAGACAATGACAGAGAAGGAGA
TCGTGGATTATGTGGCTTCACAAGTGACAACAGCTAAGAAACTGAGAGGT
GGCGTTGTGTTTGTGGATGAGGTGCCTAAAGGGCTCACTGGCAAGCTGGA
TGCTAGAAAAATTCGAGAGATTCTGATTAAGGCTAAGAAGGGTGGAAAGA
TTGCTGTGTAATAGTTCTAGA hluc + ver2B4
AAAGCCACCATGGAAGATGCTAAAAACATTAAGAAGGGGCCTGCTCCCTT
CTACCCTCTTGAAGATGGGACTGCTGGCGAGCAACTTCACAAAGCTATGA
AGCGGTATGCTCTTGTGCCAGGCACAATTGCGTTCACGGATGCTCACATT
GAGGTGGACATCACATACGCTGAGTATTTTGAGATGTCGGTGCGGCTGGC
AGAAGCTATGAAGCGCTATGGGCTGAATACAAACCATAGAATTGTAGTGT
GCAGTGAGAACTCGTTGCAGTTCTTTATGCCCGTGCTGGGGGCTCTCTTC
ATCGGGGTGGCTGTGGCTCCTGCTAACGACATCTACAACGAGCGAGAGCT
GTTGAACTCGATGGGGATCTCTCAGCCTACAGTGGTGTTTGTGAGTAAGA
AAGGGCTTCAAAAGATTCTCAATGTGCAAAAGAAGCTGCCTATTATTCAA
AAGATTATTATTATGGACTCTAAGACAGACTACCAGGGGTTTCAGTCCAT
GTATACATTTGTGACATCTCATCTGCCTCCTGGCTTCAACGAGTACGACT
TCGTGCCCGAGTCTTTCGACAGAGATAAGACAATTGCTCTGATCATGAAT
TCATCCGGGTCTACCGGGCTGCCTAAGGGTGTAGCTCTGCCCCATCGAAC
AGCTTGTGTGAGATTCTCTCATGCCAGGGACCCGATCTTTGGGAATCAGA
TTATTCCTGACACTGCTATTCTGTCGGTGGTGCCCTTTCATCATGGGTTT
GGGATGTTTACAACACTGGGATACCTAATATGTGGGTTTAGAGTGGTGCT
CATGTATAGGTTTGAAGAAGAACTGTTCTTACGCTCTTTGCAAGATTATA
AGATTCAGTCTGCTCTGCTGGTGCCAACACTATTCTCTTTTTTTGCTAAG
TCTACGCTCATAGACAAGTATGACTTGTCCAACTTGCACGAGATTGCTTC
TGGCGGAGCACCTCTGTCTAAGGAGGTAGGTGAGGCTGTGGCTAAGCGCT
TTCATCTGCCTGGTATCAGACAGGGGTACGGGCTAACAGAAACAACTTCT
GCTATTCTGATTACACCAGAGGGCGATGACAAGCCCGGGGCTGTAGGGAA
AGTGGTGCCCTTTTTTGAAGCCAAAGTAGTTGATCTTGATACCGGTAAGA
CACTAGGGGTGAACCAGCGTGGTGAACTGTGTGTGCGGGGCCCTATGATT
ATGTCGGGGTACGTTAACAACCCCGAAGCTACAAATGCTCTTATTGATAA
GGATGGCTGGTTGCATTCGGGCGACATTGCCTACTGGGATGAGGATGAGC
ATTTCTTCATCGTGGACAGACTGAAGTCGTTGATCAAATACAAGGGGTAT
CAAGTAGCTCCTGCTGAGCTGGAATCCATTCTGCTTCAACATCCAAACAT
TTTCGATGCTGGGTGGCTGGGCTGCCTGATGATGATGCTGGAGAGTTGC
CTGCTGCTGTAGTAGTGCTTGAGCACGGTAAGACAATGACAGAGAAGGAG
ATCGTGGATTATGTGGCTTCACAAGTGACAACAGCTAAGAAACTGAGAGG
TGGCGTTGTGTTTGTGGATGAGGTGCCTAAAGGGCTCACTGGCAAGCTGG
ATGCCAGAAAAATTCGAGAGATTCTCATTAAGGCTAAGAAGGGTGGAAAG
ATTGCTGTGTAATAGTTCTAGA hluc + ver2B5
AAAGCCACCATGGAAGATGCTAAAAACATTAAGAAGGGGCCTGCTCCCTT
CTACCCTCTTGAAGATGGGACTGCTGGCGAGCAACTTCACAAAGCTATGA
AGCGGTATGCTCTTGTGCCAGGCACAATTGCGTTCACGGATGCTCACATT
GAGGTGGACATCACATACGCTGAGTATTTTGAGATGTCGGTGCGGCTGGC
AGAAGCTATGAAGCGCTATGGGCTGAATACAAACCATAGAATTGTAGTGT
GCAGTGAGAACTCGTTGCAGTTCTTTATGCCCGTGCTGGGGGCTCTCTTC
ATCGGGGTGGCTGTGGCTCCTGCTAACGACATCTACAACGAGCGAGAGCT
GTTGAACTCGATGGGGATCTCTCAGCCTACAGTGGTGTTTGTGAGTAAGA
AAGGGCTTCAAAAGATTCTCAATGTGCAAAAGAAGCTGCCTATTATACAA
AAGATTATTATTATGGACTCTAAGACCGACTACCAGGGGTTTCAGTCCAT
GTACACATTTGTAACCTCTCATCTGCCTCCTGGCTTCAACGAGTACGACT
TCGTGCCCGAGTCTTTCGACAGGGACAAAACGATTGCTCTGATCATGAAT
TCATCCGGGTCTACCGGGCTGCCTAAGGGTGTAGCTCTGCCCCATCGAAC
AGCTTGTGTGAGATTCTCTCATGCCAGGGACCCGATCTTTGGGAATCAGA

TTATTCCTGACACTGCTATTCTGTCGGTGGTGCCCTTTCATCATGGGTTT

GGGATGTTCACAACACTGGGATACCTCATTTGCGGGTTTAGAGTGGTGCT

CATGTATAGGTTTGAAGAAGAACTATTCCTACGCTCTTTGCAAGATTATA

AGATTCAGTCTGCTCTGCTGGTGCCAACACTATTCTCTTTTTTTGCTAAG

TCTACGCTCATAGACAAGTATGACTTGTCCAACTTGCACGAGATTGCTTC

TGGCGGAGCACCTCTGTCTAAGGAGGTAGGTGAGGCTGTGGCTAAGCGCT

TTCATCTGCCTGGTATCAGACAGGGGTACGGGCTAACAGAAACAACTTCT

GCTATTCTGATTACACCAGAGGGCGATGACAAACCCGGGGCTGTAGGGAA

AGTGGTGCCCTTTTTTGAAGCCAAAGTAGTTGATCTTGATACCGGTAAGA

CACTAGGGGTGAACCAGCGTGGTGAACTGTGTGTGCGGGGCCCTATGATT

ATGTCGGGGTACGTTAACAACCCCGAAGCTACAAATGCTCTTATTGATAA

GGATGGCTGGTTGCATTCGGGCGACATTGCCTACTGGGATGAGGATGAGC

ATTTCTTCATCGTGGACAGACTGAAGTCGTTGATCAAATACAAGGGGTAT

CAAGTAGCTCCTGCTGAGCTGGAATCCATTCTGCTTCAACATCCTAACAT

TTTCGATGCTGGGGTGGCTGGGCTGCCTGATGATGATGCTGGAGAGTTGC

CTGCTGCTGTAGTAGTGCTTGAGCACGGTAAGACAATGACAGAGAAGGAG

ATCGTGGATTATGTGGCTTCACAAGTGACAACAGCTAAGAAACTGAGAGG

TGGCGTTGTGTTTGTGGATGAGGTGCCTAAAGGGCTCACTGGCAAGCTGG

ATGCCAGAAAAATTCGAGAGATTCTCATTAAGGCTAAGAAGGGTGGAAAG

ATTGCTGTGTAATAGTTCTAGA hluc+ver2B6 has the following sequence:

(SEQ ID NO: 29)
AAAGCCACCATGGAaGATGCcAAaAAcATTAAGAAGGGGCCTGCTCCcTT cTAcCCTCTtGAaGATGGGACtGCtGGcGAGCAaCTtCAcAAaGCTATGA

AGcGgTATGCTCTtGTGCCaGGcACAATTGCgTTcACgGATGCTCAcATT

GAaGTaGAcATcACATAcGCTGAGTATTTTGAGATGTCgGTGCgGcTGGC aGAaGCTATGAAGcGcTATGGGCTGAATACAAAcCATAGAATTGTaGTGT

GcagTGAGAAcTCgtTGCAGTTcTTTATGCCcGTGCTGGGGGCTCTcTTc

ATcGGGGTGGCTGTGGCTCCTGCTAAcGAcATcTAcAAcGAGcGAGAGCT gtTGAAcTCgATGGGGATcTCTCAGCCTACAGTGGTGTTTGTGagTAAGA

AaGGGCTtCAaAAGATTCTcAATGTGCAaAAGAAGCTGCCTATTATaCAa

AAGATTATTATTATGGAcTCtAAGACcGAcTAcCAGGGGTTTCAGTCCAT

GTAcACATTTGTaACcTCTCATCTGCCTCCTGGcTTcAAcGAGTAcGAcT

TcGTGCCcGAGTCTTTcGAcAGgGAcAAaACgATTGCTCTGATcATGAAc agcTCcGGGTCTACcGGGCTGCCTAAGGGtGTaGCTCTGCCcCATCGAAC AGCTTGTGTGAGATTcTCTCATGCcAGgGAcCCgATcTTtGGaAAcCAGA TcATcCCTGAcACtGCTATTCTGTCgGtGgTGCCcTTTCATCATGGGTTT GGGATGTTcACAACACTGGGaTAccTcATtTGcGGGTTTAGAGTGGTGCT cATGTATAGgTTTGAaGAaGAaCTaTTccTacGcTCTtGCAaGATTATA AGATTCAGTCTGCTCTGCTGGTGCCaACACTaTTcTCTTTTTTTGCTAAG TCTACgCTcATaGAcAAGTATGActTGTCcAActTGCAcGAGATTGCTTC TGGcGGaGCaCCTCTGTCTAAGGAGGTaGGtGAGGCTGTGGCTAAGcGcT TTCATCTGCCTGGtATcAGACAGGGGTAcGGGCTaACAGAaACAACtTCT GCTATTCTGATTACACCaGAGGGcGATGAcAAaCCcGGGGCTGTaGGGAA aGTGGTGCCcTTTTTTGAaGCcAAaGTaGTtGATCTtGATACcGGtAAGA CACTaGGGGTGAAcCAGcGtGGtGAaCTGTGTGTGCgGgGCcCTATGATT ATGTCgGGGTAcGTtAAcAAcCCcGAaGCTACAAATGCTCTcATaGAcAA GGAcGGgTGGcTtCATAgcGGcGAcATTGCcTAcTGGGAcGAGGATGAGC ATTTcTTcATcGTGGAcAGACTGAAGTCgtTGATcAAaTAcAAGGGGTAT CAaGTaGCTCCTGCTGAGCTGGAaTCcATTCTGCTTcAaCAcCCcAAtAT cTTcGATGCTGGGGTGGCTGGGCTGCCTGATGATGATGCTGGaGAGcTGC CTGCTGCTGTaGTaGTGCTtGAGCAcGGtAAGACAATGACAGAGAAGGAG ATcGTGGATTATGTGGCTTCaCAaGTGACAACAGCTAAGAAaCTGAGAGG tGGcGTtGTGTTTGTGGATGAGGTGCCTAAaGGGCTcACtGGcAAGCTGG ATGCcAGAAAaATTcGAGAGATTCTcATTAAGGCTAAGAAGGGtGGaAAG ATTGCTGTGTAATAgTTCTAGA.

hluc+ver2BF8 was created by removing a Ptx1 consensus transcription factor binding site from hluc+ver2BF7. hluc+ver2B7 has the following sequence:

(SEQ ID NO: 94)
AAAGCCACCATGGAAGATGCCAAAAACATTAAGAAGGGGCCTGCTCCCTT

CTACCCTCTTGAAGATGGGACTGCTGGCGAGCAACTTCACAAAGCTATGA

AGCGGTATGCTCTTGTGCCAGGGACAATTGCGTTCACGGATGCTCACATT

GAAGTAGACATCACATACGCTGAGTATTTTGAGATGTCGGTGCGGCTGGC

AGAAGCTATGAAGCGCTATGGGCTGAATACAAACCATAGAATTGTAGTGT

GCAGTGAGAACTCGTTGCAGTTCTTTATGCCCGTGCTGGGGGCTCTCTTC

ATCGGGGTGGCTGTGGCTCCTGCTAACGACATCTACAACGAGCGAGAGCT

GTTGAACTCGATGGGGATCTCTCAGCCTACAGTGGTGTTTGTGAGTAAGA

AAGGGCTTCAAAAGATTCTCAATGTGCAAAAGAAGCTGCCTATTATACAA

AAGATTATTATTATGGACTCTAAGACAGACTACCAGGGGTTTCAGTCCAT

GTACACATTTGTAACCTCTCATCTGCCTCCTGGCTTCAACGAGTACGACT

TCGTGCCCGAGTCTTTCGACAGGGACAAAACGATTGCTCTGATCATGAAC

AGCTCCGGGTCTACCGGGCTGCCTAAGGGTGTAGCTCTGCCCCATCGAAC

AGCTTGTGTGAGATTCTCTCATGCCAGGGACCCGATCTTTGGAAACCAGA

TCATCCCTGACACTGCTATTCTGTCGGTGGTGCCCTTTCATCATGGGTTT

GGGATGTTCACAACACTGGGATACCTCATTTGCGGGTTTAGAGTGGTGCT

CATGTATAGGTTTGAAGAAGAACTATTCCTACGCTCTTTGCAAGATTATA

AGATTCAGTCTGCTCTGCTGGTGCCAACACTATTCTCTTTTTTTGCTAAG

TCTACGCTCATAGACAAGTATGACTTGTCCAACTTGCACGAGATTGCTTC

TGGCGGAGCACCTCTGTCTAAGGAGGTAGGTGAGGCTGTGGCTAAGCGCT

TTCATCTGCCTGGTATCAGACAGGGGTACGGGCTAACAGAAACAACTTCT

GCTATTCTGATTACACCAGAGGGCGATGACAAACCCGGGGCTGTAGGGAA
AGTGGTGCCCTTTTTTGAAGCCAAAGTAGTTGATCTTGATACCGGTAAGA
CACTAGGGGTGAACCAGCGTGGTGAACTGTGTGTGCGGGGCCCTATGATT
ATGTCGGGGTACGTTAACAACCCCGAAGCTACAAATGCTCTCATAGACAA
GGACGGGTGGCTTCATAGCGGCGACATTGCCTACTGGGACGAGGATGAGC
ATTTCTTCATCGTGGACAGACTGAAGTCGTTGATCAAATACAAGGGGTAT
CAAGTAGCTCCTGCCGAGCTTGAGTCCATTCTGCTTCAACACCCCAATAT
CTTCGATGCTGGGGTGGCTGGGCTGCCTGATGATGATGCTGGAGAGCTGC
CTGCTGCTGTAGTAGTGCTTGAGCATGGTAAGACAATGACAGAGAAGGAG
ATCGTGGATTATGTGGCTTCACAAGTGACAACAGCTAAGAAACTCCGAGG
TGGCGTTGTGTTTGTGGATGAGGTGCCTAAAGGGCTCACTGGCAAGCTGG
ATGCCAGAAAAATTCGAGAGATTCTCATTAAGGCTAAGAAGGGTGGAAAG
ATTGCTGTGTAATAGTTCTAGA hluc+ver2B8 has the following sequence (SEQ ID NO: 31)
AAAGCCACCATGGAaGATGCcAAaAAcATTAAGAAGGGGCCTGCTCCcTT
cTAcCCTCTtGAaGATGGGACtGCtGGcGAGCAaCTtCAcAAaGCTATGA
AGcGgTATGCTCTtGTGCCaGGgACAATTGCgTTcACgGATGCTCAcATT
GAaGTaGAcATcACATAcGCTGAGTATTTTGAGATGTCgGTGcGgCTGGC
aGAaGCTATGAAGcGcTATGGGCTGAATACAAAcCATAGAATTGTaGTGT
GcagTGAGAAcTCgtTGCAGTTcTTTATGCCcGTGCTGGGGGCTCTcTTc
ATcGGGGTGGCTGTGGCTCCTGCTAAcGAcATcTAcAAcGAGcGAGAGCT
gtTGAAcTCgATGGGGATcTCTCAGCCTACAGTGGTGTTTGTGagTAAGA
AaGGGCTtCAaAAGATTCTcAATGTGCAaAAGAAGCTaCCgATcATaCAa
AAGATcATcATcATGGAtagcAAGACcGAcTAcCAGGGGTTTCAGTCcAT
GTAcACATTTGTaACcTCTCATCTGCCTCCTGGcTTcAAtGAGTAtGAcT
TcGTGCCcGAGTCTTTcGAcAGgGAcAAaACgATTGCTCTGATcATGAAc
agcTCcGGGTCTACcGGGCTGCCTAAGGGtGTaGCTCTGCCcCATcGAAC
AGCTTGTGTGAGATTcTCTCATGCcAGgGAcCCgATcTTtGGaAAcCAGA
TcATcCCTGAcACtGCTATTCTGTCgGTgGTGCCcTTTCATCATGGGTTT
GGGATGTTcACAACACTGGGaTAccTcATtTGcGGGTTTAGAGTGGTGCT
cATGTATAGgTTTGAaGAaGAaCTaTTccTacGcTCTtTGCAaGATTATA
AGATTCAGTCTGCTCTGCTGGTGCCaACACTaTTcTCTTTTTTTGCTAAG
TCTACgCTcATaGAcAAGTATGActTGTCcAActTGCAcGAGATTGCTTC
TGGcGGaGCaCCTCTGTCTAAGGAGGTaGGtGAGGCTGTGGCTAAGcGcT
TTCATCTGCCTGGtATcAGACAGGGGTAcGGGCTaACAGAaACAACtTCT
GCTATTCTGATTACACCaGAGGGcGATGAcAAaCCtGGGGCTGTaGGGAA
aGTGGTGCCcTTTTTTGAaGCcAAaGTaGTtGATCTtGATACcGGtAAGA
CACTaGGGGTGAAcCAGcGtGGtGAaCTGTGTGTGCgGGgCCTATGATT
ATGTCgGGGTAcGTtAAcAAcCCcGAaGCTACAAATGCTCTcATaGACAA hluc+ver2BF8 was modified to yield hluc+ver2BF9.
hluc+ver2B9 has the following sequence (SEQ ID NO: 32)
AAAGCCACCATGGAaGATGCcAAaAAcATTAAGAAGGGGCCTGCTCCcTT
cTAcCCTCTtGAaGATGGGACtGCtGGcGAGCAaCTtCAcAAaGCTATGA
AGcGgTATGCTCTtGTGCCaGGgACAATTGCgTTcACgGATGCTCAcATT
GAaGTaGAcATcACATAcGCTGAGTATTTTGAGATGTCgGTGcGgCTGGC
aGAaGCTATGAAGcGcTATGGGCTGAATACAAAcCATAGAATTGTaGTGT
GcagTGAGAAcTCgtTGCAGTTcTTTATGCCcGTGCTGGGGGCTCTcTTc
ATtGGGGTGGCTGTGGCTCCTGCTAAtGAcATcTAcAAcGAGcGAGAGCT
gtTGAAcagtATGGGGATcTCTCAGCCTACAGTGGTGTTTGTGagTAAGA
AaGGGCTtCAaAAGATTCTcAATGTGCAaAAGAAGCTaCCgATcATaCAa
AAGATcATcATcATGGAtagcAAGACcGAcTAcCAGGGGTTTCAGTCcAT
GTAcACATTTGTaACcTCTCATCTGCCTCCTGGcTTcAAtGAGTAtGAcT
TcGTGCCcGAGTCTTTcGAcAGgGAcAAaACgATTGCTCTGATcATGAAc
agcagtGGGTCTACcGGGCTGCCTAAGGGtGTaGCTCTGCCcCATcGAAC
AGCTTGTGTGAGATTcTCTCATGCcAGgGAcCCgATcTTtGGaAAcCAGA
TcATcCCTGAcACtGCTATTCTGTCgGTgGTGCCcTTTCATCATGGGTTT
GGGATGTTcACAACACTGGGaTAccTcATtTGcGGGTTTAGAGTGGTGCT
cATGTATAGgTTTGAaGAaGAaCTaTTccTacGcTCTtTGCAaGATTATA
AGATTCAGTCTGCTCTGCTGGTGCCaACACTaTTcTCTTTTTTTGCTAAG
TCTACgCTcATaGAcAAGTATGActTGTCcAActTGCAcGAGATTGCTTC
TGGcGGaGCaCCTCTGTCTAAGGAGGTaGGtGAGGCTGTGGCTAAGcGcT
TTCATCTGCCTGGtATcAGACAGGGGTAcGGGCTaACAGAaACAACtTCT
GCTATTCTGATTACACCaGAGGGcGATGAcAAaCCtGGGGCTGTaGGGAA
aGTGGTGCCcTTTTTTGAaGCcAAaGTaGTtGATCTtGATACcGGtAAGA
CACTaGGGGTGAAcCAGaGaGGtGAatTGTGTGTGaGgGGcCCTATGATT
ATGTCgGGGTAcGTtAAcAAcCCcGAaGCTACAAATGCTCTcATaGACAA
GGAcGGgTGGcTtCATAgtGGaGAtATTGCcTAcTGGGAtGAaGATGAGC
ATTTcTTcATcGTGGAcAGACTGAAGTCgtTGATcAAaTAcAAGGGGTAT
CAaGTaGCTCCTGCcGAGCTtGAgTCcATTCTGCTtCAaCAcCCcAATAT
cTTcGATGCTGGGGTGGCTGGGCTGCCTGATGATGATGCTGGaGAGcTGC CTGCTGCTGTaGTaGTGCTtGAGcCAtGGtAAGACAATGACAGAGAAGGAG ATcGTGGATTATGTGGCTTCaCAaGTGACAACAGCTAAGAAaCTccGAGG tGGcGTtGTGTTTGTGGATGAGGTGCCTAAaGGGCTcACtGGcAAGCTGG ATGCcAGAAAaATTcGAGAGATTCTcATTAAGGCTAAGAAGGGtGGaAAG ATTGCTGTGTAATAgTTCTAGA.

The BglI sequence in hluc+ver2BF9 was removed resulting in hluc+ver2BF10. hluc+ver2BF10 demonstrated poor expression.
hluc+ver2B10 has the following sequence (SEQ ID NO: 33)
AAAGCCACCATGGAaGATGCcAAaAAcATTAAGAAGGGGCCTGCTCCcTT cTAcCCTCTtGAaGATGGGACtGCtGGcGAGCAAaCTtCAcAAaGCTATG AAGcGgTATGCTCTtGTGCCaGGgACAATTGCgTTcACgGATGCTCAcAT TGAaGTaGAcATcACATAcGCTGAGTATTTTGAGATGTCgGTGcGgCTGG CaGAaGCTATGAAGcGcTATGGGCTGAATACAAAcCATAGAATTGTaGTG TGcagTGAGAAcTCgtTGCAGTTcTTTATGCCcGTGCTGGGGGCTCTcTT cATtGGGGTGGCTGTGGCTCCTGCTAAtGAcATcTAcAAcGAGcGAGAGC TgtTGAAcagtATGGGGATcTCTCAGCCTACAGTGGTGTTTGTGagTAAG AAaGGGCTtCAaAAGATTCTcAATGTGCAaAAGAAGCTaCCgATcATaCA aAAGATcATcATcATGGAtagcAAGACcGAcTAcCAGGGGTTTCAGTCcA TGTAcACATTTGTaACcTCTCATCTGCCTCCTGGcTTcAAtGAGTAtGAc TTcGTGCCcGAGTCTTTcGAcAGgGAcAAaACgATTGCTCTGATcATGAA cagcagtGGGTCTACcGGGCTGCCTAAGGGtGTaGCTCTGCCcCATcGAA CAGCTTGTGTGAGATTcTCTCATGCcAGgGAcCCgATcTTtGGaAAcCAG ATcATcCCTGAcACtGGTATTCTGTCgGTgGTGGCcTTTCATCATGGGTT TGGGATGTTcACAACACTGGGaTAccTcATtTGcGGGTTTAGAGTGGTGC TcATGTATAGgTTTGAaGAaGAaCTaTTccTacGcTCTtTGCAaGATTAT AAGATTCAGTCTGCTCTGCTGGTGCCaACACTaTTcTCTTTTTTTGCTAA GTCTACgCTcATaGAcAAGTATGAcTTGTCcAAcTGCAcGAGATTGCTT CTGGcGGaGCaCCTCTGTCTAAGGAGGTaGGtGAGGCTGTGGCTAAGcGc TTTCATCTGCCTGGtATcAGACAGGGGTAcGGGCTaACAGAaACAACtTC TGCTATTCTGATTACACCaGAGGGcGATGAcAAaCCtGGGGCTGTaGGGA AaGTGGTGCCcTTTTTTGAaGCcAAaGTaGTtGATCTtGATACcGGtAAG ACACTaGGGGTGAAcCAGaGaGGtGAatTGTGTGTGaGgGGcCCTATGAT TATGTCgGGGTAcGTtAAcAAcCCcGAaGCTACAAATGCTCTcATaGAcA AGGAcGGgTGGcTtCATagtGGaGAtATTGCcTAcTGGGAtGAaGATGAG CATTTcTTcATcGTGGAcAGACTGAAGTCgtTGATcAAaTAcAAGGGGTA TCAaGTaGCTCCTGCcGAGCTtGAgTCcATTCTGCTtCAacAcCCcAAtA TcTTcGATGCTGGGGTGGCTGGGCTGCCTGATGATGATGCTGGaGAGcTG CCTGCTGCTGTaGTaGTGCTtGAGcCAtGGtAAGACAATGACAGAGAAGGA GATcGTGGATTATGTGGCTTcACAaGTGACAACAGCTAAGAAaCTccGAG GtGGcGTtGTGTTTGTGGATGAGGTGCCTAAaGGaCTcACtGGcAAGCTG GATGCcAGAAAaATTcGAGAGATTCTcATTAAGGCTAAGAAGGGtGGaAA GATTGCTGTGTAATAgTTCTAGA.

TABLE 11

Summary of Firefly Luciferase Constructs

| Firefly luciferase Gene | Number of consensus transcription factor binding sites | Number of Promoter modules* | CG dinucleotides (possible methylation sites) |
|---|---|---|---|
| Luc+ | 287 | 7 | 97 |
| hluc + ver2AF8 | 3 | 0 | 132 |
| hluc + ver2BF10 | 3 | 0 | 43 |

*Promoter modules are defined as a composite regulatory element, with 2 TFBS separated by a spacer, which has been shown to exhibit synergistic or antagonistic function.

EXAMPLE 4

Synthetic Selectable Polypeptide Genes

Design Process
Define Sequences
    Protein sequence that should be maintained:
    Neo: from neo gene of pCI-neo (Promega) (SEQ ID NO:1)
    Hyg: from hyg gene of pcDNA3.1/Hygro (Invitrogen) (SEQ ID NO:6)
    DNA flanking regions for starting sequence:
    5' end: Kozak sequence from neo gene of pCI-neo (GCCACCATGA; SEQ ID NO:34)), PflMI site (CCANNNNNTGG; SEQ ID NO:35), add Ns at end (to avoid search algorithm errors & keep ORF1):
    neo/hyg: NNNNNCCAnnnnnTGGCCACC-ATG-G (SEQ ID NO:36)
    Change: replace PflMI with SbfI (CCTGCAGG)
    3' end: two stop codons (at least one TAA), PflMI site (not compatible with that at 5' end to allow directional cloning), add Ns at end (to avoid search algorithm errors):
    neo/hyg: TAATAACCAnnnnnTGGNNN (SEQ ID NO:37)
    Change: replace PflMI with AflII (CTTAAG)
Define Codon Usage
Codon Usage was Obtained from the Codon Usage Database (http://www.kazusa.or.jp/codon/):
    Based on: GenBank Release 131.0 [15 Aug. 2002] (Nakamura et al., 2000).
    Codon Usage Tables were Downloaded for:
    HS: *Homo sapiens* [gbpri] 50,031 CDS's (21,930,294 codons)
    MM: *Mus musculus* [gbrod] 23,113 CDS's (10,345,401 codons)
    EC: *Escherichia coli* [gbbct] 11,985 CDS's (3,688,954 codons)
    EC K12: *Escherichia coli* K12 [gbbct] 4,291 CDS's (1,363,716 codons)
    ⇨HS and MM were compared and found to be closely similar, use HS table
    ⇨EC and EC K12 were compared and found to be closely similar, use EC K12 table
Codon Selection Strategy:
    Overall strategy is to adapt codon usage for optimal expression in mammalian cells while avoiding low-usage *E. coli* codons. One "best" codon was selected for each amino acid and used to back-translate the desired protein sequence to yield a starting gene sequence.

Strategy A was chosen for the design of the neo and hyg genes (see Table 12). (Strategy A: Codon bias optimized: emphasis on codons showing the highest usage frequency in HS. Best codons are those with highest usage in HS, unless a codon with slightly lower usage has substantially higher usage in E. coli.).

TABLE 12

| Amino acid | Codon Choices in Examples 1-2 | Codon Choices in Codon Bias Optimized Strategy A |
|---|---|---|
| Gly | GGC/GGT | GGC |
| Glu | GAG | GAG |
| Asp | GAC | GAC |
| Val | GTG/GTC | GTG |
| Ala | GCC/GCT | GCC |
| Arg | CGC/CGT | CGC |
| Ser | TCT/AGC | AGC |
| Lys | AAG | AAG |
| Asn | AAC | AAC |
| Ile | ATC/ATT | ATC |
| Thr | ACC/ACT | ACC |
| Cys | TGC | TGC |
| Tyr | TAC | TAC |
| Leu | CTG/TTG | CTG |
| Phe | TTC | TTC |
| Gln | CAG | CAG |
| His | CAC | CAC |
| Pro | CCA/CCT | CCC |

Generate Starting Gene Sequences
Use Custom Codon Usage Table in Vector NTI 8.0 (Informax) ("Strategy A")
Back-Translate neo and hyg Protein Sequences
Neo (Based on Neomycin Gene from Promega's pCI-neo)

(SEQ ID NO: 2)
MIEQDGLHAGSPAAWVERLFGYDWAQQTIGCSDAAVFRLSAQGRPVLFVK

TDLSGALNELQDEAARLSWLATTGVPCAAVLDVVTEAGRDWLLLGEVPGQ

DLLSSHLAPAEKVSIMADAMRRLHTLDPATCPFDHQAKHRIERARTRMEA

GLVDQDDLDEEHQGLAPAELFARLKARMPDGEDLVVTHGDACLPNIMVEN

GRFSGFIDCGRLGVADRYQDIALATRDIAEELGGEWADRFLVLYGIAAPD

SQRIAFYRLLDEFF
and encoded by (SEQ ID NO: 1)
Atgattgaacaagatggattgcacgcaggttctccggccgcttggtgga gaggctattcggctatgactgggcacaacagacaatcggctgctctgatg ccgccgtgttccggctgtcagcgcagggcgcccggttcttttgtcaag accgacctgtccggtgccctgaatgaactgcaggacgaggcagcgcggct atcgtggctggccacgacgggcgttccttgcgcagctgtgctcgacgttg tcactgaagcgggaagggactggctgctattgggcgaagtgccggggcag gatctcctgtcatctcaccttgctcctgccgagaaagtatccatcatggc tgatgcaatgcggcggctgcatacgcttgatccggctacctgcccattcg accaccaagcgaaacatcgcatcgagcgagcacgtactcggatggaagcc ggtcttgtcgatcaggatgatctggacgaagagcatcaggggctcgcgcc agccgaactgttcgccaggctcaaggcgcgcatgcccgacggcgaggatc tcgtcgtgacccatggcgatgcctgcttgccgaatatcatggtggaaaat ggccgcttttctggattcatcgactgtggccggctgggtgtggcggaccg ctatcaggacatagcgttggctacccgtgatattgctgaagagcttggcg gcgaatgggctgaccgcttcctcgtgctttacggtatcgccgctcccgat tcgcagcgcatcgccttctatcgccttcttgacgagttcttctga Hyg (Based on Hygromycin Gene from Invitrogen's pcDNA3.1/Hygro)

(SEQ ID NO: 7)
MKKPELTATSVEKFLIEKFDSVSDLMQLSEGEESRAFSFDVGGRGYVLRV

NSCADGFYKDRYVYRHFASAALPIPEVLDIGEFSESLTYCISRRAQGVTL

QDLPETELPAVLQPVAEAMDAIAAADLSQTSGFGPFGPQGIGQYTTWRDF

ICAIADPHVYHWQTVMDDTVSASVAQALDELMLWAEDCPEVRHLVHADFG

SNNVLTDNGRITAVIDWSEAMFGDSQYEVANIFFWRPWLACMEQQTRYFE

RRHPELAGSPRLRAYMLRIGLDQLYQSLVDGNFDDAAWAQGRCDAIVRSG

AGTVGRTQIARRSAAVWTDGCVEVLADSGNRRPSTRPRAKE
encoded by (SEQ ID NO: 6)
Atgaaaaagcctgaactcaccgcgacgtctgtcgagaagtttctgatcga aaagttcgacagcgtctccgacctgatgcagctctcggagggcgaagaat ctcgtgctttcagcttcgatgtaggagggcgtggatatgtcctgcgggta aatagctgcgccgatggtttctacaaagatcgttatgtttatcggcactt tgcatcggccgcgctcccgattccggaagtgcttgacattggggaattca gcgagagcctgacctattgcatctcccgccgtgcacagggtcacgttgca agacctgcctgaaaccgaactgcccgctgttctgcagccggtcgcggagg ccatggatgcgatcgctgcggccgatcttagccagacgagcgggttcggc ccattcggaccgcaaggaatcggtcaatacactacatggcgtgatttcat atgcgcgattgctgatccccatgtgtatcactggcaaactgtgatggacg acaccgtcagtgcgtccgtcgcgcaggctctcgatgagctgatgctttgg gccgaggactgccccgaagtccggcacctcgtgcacgcggatttcggctc caacaatgtcctgacggacaatggccgcataacagcggtcattgactgga gcgaggcgatgttcggggattcccaatacgaggtcgccaacatcttcttc tggaggccgtggttggcttgtatggagcagcagacgcgctacttcgagcg -continued gaggcatccggagcttgcaggatcgccgcggctccgggcgtatatgctcc gcattggtcttgaccaactctatcagagcttggttgacggcaatttcgat gatgcagcttgggcgcagggtcgatgcgacgcaatcgtccgatccggagc cgggactgtcgggcgtacacaaatcgcccgcagaagcgcggccgtctgga ccgatggctgtgtagaagtactcgccgatagtggaaaccgacgcccagc actcgtccgagggcaaaggaat.

TABLE 13

Nomenclature of exemplary neo and hyg gene versions

| Gene name | Description |
| --- | --- |
| Neo | from pCI-neo (Promega) |
| Hneo | humanized (codon usage strategy A) ORF |
| hneo-F | humanized ORF with 5' and 3' flanking regions |
| hneo-1F | humanized ORF with 5' and 3' flanking regions after first removal of undesired sequence matches |
| hneo-2F | humanized ORF with 5' and 3' flanking regions after second removal of undesired sequence matches |
| hneo-3F | humanized ORF with 5' and 3' flanking regions after third removal of undesired sequence matches |
| hneo-3FB | Changed 5' and 3' flanking cloning sites |
| Hyg | from pcDNA3.1/Hygro (Invitrogen) |
| Hhyg | humanized (codon usage strategy A) ORF |
| hhyg-F | humanized ORF with 5' and 3' flanking regions |
| hhyg-1F | humanized ORF with 5' and 3' flanking regions after first removal of undesired sequence matches |
| hhyg-2F | humanized ORF with 5' and 3' flanking regions after second removal of undesired sequence matches |
| hhyg-3F | humanized ORF with 5' and 3' flanking regions after third removal of undesired sequence matches |
| hhyg-3FB | Changed 5' and 3' flanking cloning sites |

"h" indicates humanized codons, "F" indicates presence of 5' and 3' flanking sequences.

Create Starting (Codon-Optimized) Gene Sequences:

hneo (Humanized Starting Gene Sequence without Flanking Regions in hneo-F)

(SEQ ID NO: 3)
CCACTCAGTGGCCACCATGATCGAGCAGGACGGCCTGCACGCCGGCAGCC

CCGCCGCCTGGGTGGAGCGCCTGTTCGGCTACGACTGGGCCCAGCAGACC

ATCGGCTGCAGCGACGCCGCCGTGTTCCGCCTGAGCGCCCAGGGCCGCCC

CGTGCTGTTCGTGAAGACCGACCTGAGCGGCGCCCTGAACGAGCTGCAGG

ACGAGGCCGCCCGCCTGAGCTGGCTGGCCACCACCGGCGTGCCCTGCGCC

GCCGTGCTGGACGTGGTGACCGAGGCCGGCCGCGACTGGCTGCTGCTGGG

CGAGGTGCCCGGCCAGGACCTGCTGAGCAGCCACCTGGCCCCCGCCGAGA

AGGTGAGCATCATGGCCGACGCCATGCGCCGCCTGCACACCCTGGACCCC

GCCACCTGCCCCTTCGACCACCAGGCCAAGCACCGCATCGAGCGCGCCCG

CACCCGCATGGAGGCCGGCCTGGTGGACCAGGACGACCTGGACGAGGAGC

ACCAGGGCCTGGCCCCCGCCGAGCTGTTCGCCCGCCTGAAGGCCCGCATG

CCCGACGGCGAGGACCTGGTGGTGACCCACGGCGACGCCTGCCTGCCCAA

CATCATGGTGGAGAACGGCCGCTTCAGCGGCTTCATCGACTGCGGCCGCC

TGGGCGTGGCCGACCGCTACCAGGACATCGCCCTGGCCACCCGCGACATC

GCCGAGGAGCTGGGCGGCGAGTGGGCCGACCGCTTCCTGGTGCTGTACGG

CATCGCCGCCCCCGACAGCCAGCGCATCGCCTTCTACCGCCTGCTGGACG

AGTTCTTCTAATAACCAGTCTCTGG.

hhyg (Humanized Starting Gene Sequence without Flanking Regions)

(SEQ ID NO: 8)
CCACTCAGTGGCCACCATGAAGAAGCCCGAGCTGACCGCCACCAGCGTGG

AGAAGTTCCTGATCGAGAAGTTCGACAGCGTGAGCGACCTGATGCAGCTG

AGCGAGGGCGAGGAGAGCCGCGCCTTCAGCTTCGACGTGGGCGGCCGCGG

CTACGTGCTGCGCGTGAACAGCTGCGCCGACGGCTTCTACAAGGACCGCT

ACGTGTACCGCCACTTCGCCAGCGCCGCCCTGCCCATCCCCGAGGTGCTG

GACATCGGCGAGTTCAGCGAGAGCCTGACCTACTGCATCAGCCGCCGCGC

CCAGGGCGTGACCCTGCAGGACCTGCCCGAGACCGAGCTGCCCGCCGTGC

TGCAGCCCGTGGCCGAGGCCATGGACGCCATCGCCGCCGCCGACCTGAGC

CAGACCAGCGGCTTCGGCCCCTTCGGCCCCCAGGGCATCGGCCAGTACAC

CACCTGGCGCGACTTCATCTGCGCCATCGCCGACCCCCACGTGTACCACT

GGCAGACCGTGATGGACGACACCGTGAGCGCCAGCGTGGCCCAGGCCCTG

GACGAGCTGATGCTGTGGGCCGAGGACTGCCCCGAGGTGCGCCACCTGGT

GCACGCCGACTTCGGCAGCAACAACGTGCTGACCGACAACGGCCGCATCA

CCGCCGTGATCGACTGGAGCGAGGCCATGTTCGGCGACAGCCAGTACGAG

GTGGCCAACATCTTCTTCTGGCGCCCCTGGCTGGCCTGCATGGAGCAGCA

GACCCGCTACTTCGAGCGCCGCCACCCCGAGCTGGCCGGCAGCCCCCGCC

TGCGCGCCTACATGCTGCGCATCGGCCTGGACCAGCTGTACCAGAGCCTG

GTGGACGGCAACTTCGACGACGCCGCCTGGGCCCAGGGCCGCTGCGACGC

CATCGTGCGCAGCGGCGCCGGCACCGTGGGCCGCACCCAGATCGCCCGCC

GCAGCGCCGCCGTGTGGACCGACGGCTGCGTGGAGGTGCTGGCCGACAGC

GGCAACCGCCGCCCCAGCACCCGCCCCCGCGCCAAGGAGTAATAACCAGC

TCTTGG.

Programs and Databases Used for Identification and Removal of Sequence Motifs
All from Genomatix Software GmbH (Munich, Germany, http://www.genomatix.de):

---

GEMS Launcher Release 3.5.2 (June 2003)
MatInspector professional Release 6.2.1 June 2003
Matrix Family Library Ver 3.1.2 June 2003 (incl. 318 vertebrate matrices in 128 families)
ModelInspector professional Release 4.8 October 2002
Model Library Ver 3.1 March 2003 (226 modules)
SequenceShaper tool
User Defined Matrices

---

Sequence Motifs to Remove from Starting Gene Sequences (In Order of Priority)
  Restriction Enzyme Recognition Sequences:
    See user-defined matrix subset neo and hyg. Same as those used for design of hluc+version 2.0
    Generally includes those required for cloning (pGL4) or commonly used for cloning
    Change: also SbfI, AflI, AccIII Transcription Factor Binding Sequences:
Promoter modules (2 TF binding sites with defined orientation) with default score or greater
Vertebrate TF binding sequences with score of at least core=0.75/matrix=optimized
Eukaryotic Transcription Regulatory Sites:
Kozak sequence
Splice donor/acceptor sequences in (+) strand
PolyA addition sequences in (+) strand
Prokaryotic Transcription Regulatory Sequences:
E. coli promoters
E. coli RBS (if less than 20 bp upstream of Met codon)
User-defined Matrix Subset "neo+hyg"
Format: Matrix name (core similarity threshold/matrix similarity threshold)
U$AatII (0.75/1.00)
U$BamHI (0.75/1.00)
U$BglI (0.75/1.00)
U$BglII (0.75/1.00)
U$BsaI (0.75/1.00)
U$BsmAI (0.75/1.00)
U$BsmBI (0.75/1.00)
U$BstEII (0.75/1.00)
U$BstXI (0.75/1.00)
U$Csp45I (0.75/1.00)
U$CspI (0.75/1.00)
U$EC-P-10 (1.00/Optimized)
U$EC-P-35 (1.00/Optimized)
U$EC-Prom (1.00/Optimized)
U$EC-RBS (0.75/1.00)
U$EcoRI (0.75/1.00)
U$HindIII (0.75/1.00)
U$Kozak (0.75/Optimized)
U$KpnI (0.75/1.00)
U$MluI (0.75/1.00)
U$NcoI (0.75/1.00)
U$NdeI (0.75/1.00)
U$NheI (0.75/1.00)
U$NotI (0.75/1.00)
U$NsiI (0.75/1.00)
U$PflMI (0.75/1.00)
U$PmeI (0.75/1.00)
U$PolyAsig (0.75/1.00)
U$PstI (0.75/1.00)
U$SacI (0.75/1.00)
U$SacII (0.75/1.00)
U$SalI (0.75/1.00)
U$SfiI (0.75/1.00)
U$SgfI (0.75/1.00)
U$SmaI (0.75/1.00)
U$SnaBI (0.75/1.00)
U$SpeI (0.75/1.00)
U$Splice-A (0.75/Optimized)
U$Splice-D (0.75/Optimized)
U$XbaI (0.75/1.00)
U$XcmI (0.75/1.00)
U$XhoI (0.75/1.00)
ALL vertebrates.lib (0.75/Optimized)
User-defined Matrix Subset "neo+hyg-EC"
Format: Matrix name (core similarity threshold/matrix similarity threshold)
U$AatII (0.75/1.00)
U$BamHI (0.75/1.00)
U$BglI (0.75/1.00)
U$BglII (0.75/1.00)
U$BsaI (0.75/1.00)
U$BsmAI (0.75/1.00)
U$BsmBI (0.75/1.00)
U$BstEII (0.75/1.00)
U$BstXI (0.75/1.00)
U$Csp45I (0.75/1.00)
U$CspI (0.75/1.00)
U$EcoRI (0.75/1.00)
U$HindIII (0.75/1.00)
U$Kozak (0.75/Optimized)
U$KpnI (0.75/1.00)
U$MluI (0.75/1.00)
U$NcoI (0.75/1.00)
U$NdeI (0.75/1.00)
U$NheI (0.75/1.00)
U$NotI (0.75/1.00)
U$NsiI (0.75/1.00)
U$PflMI (0.75/1.00)
U$PmeI (0.75/1.00)
U$PolyAsig (0.75/1.00)
U$PstI (0.75/1.00)
U$SacI (0.75/1.00)
U$SacII (0.75/1.00)
U$SalI (0.75/1.00)
U$SfiI (0.75/1.00)
U$SgfI (0.75/1.00)
U$SmaI (0.75/1.00)
U$SnaBI (0.75/1.00)
U$SpeI (0.75/1.00)
U$Splice-A (0.75/Optimized)
U$Splice-D (0.75/Optimized)
U$XbaI (0.75/1.00)
U$XcmI (0.75/1.00)
U$XhoI (0.75/1.00)
ALL vertebrates.lib (0.75/Optimized)
User-defined Matrix Subset "pGL4-072503"
Format: Matrix name (core similarity threshold/matrix similarity threshold)
U$AatII (0.75/1.00)
U$AccIII (0.75/1.00)
U$AflII (0.75/1.00)
U$BamHI (0.75/1.00)
U$BglI (0.75/1.00)
U$BglII (0.75/1.00)
U$BsaI (0.75/1.00)
U$BsmAI (0.75/1.00)
U$BsmBI (0.75/1.00)
U$BstEII (0.75/1.00)
U$BstXI (0.75/1.00)
U$Csp45I (0.75/1.00)
U$CspI (0.75/1.00)
U$EC-P-10 (1.00/Optimized)
U$EC-P-35 (1.00/Optimized)
U$EC-Prom (1.00/Optimized)
U$EC-RBS (0.75/1.00)
U$EcoRI (0.75/1.00)
U$HindIII (0.75/1.00)
U$Kozak (0.75/Optimized)
U$KpnI (0.75/1.00)
U$MluI (0.75/1.00)
U$NcoI (0.75/1.00)
U$NdeI (0.75/1.00)
U$NheI (0.75/1.00)
U$NotI (0.75/1.00)
U$NsiI (0.75/1.00)
U$PflMI (0.75/1.00)
U$PmeI (0.75/1.00)
U$PolyAsig (0.75/1.00)
U$PstI (0.75/1.00)

U$SacI (0.75/1.00)
U$SacII (0.75/1.00)
U$SalI (0.75/1.00)
U$SbfI (0.75/1.00)
U$SfiI (0.75/1.00)
U$SgfI (0.75/1.00)
U$SmaI (0.75/1.00)
U$SnaBI (0.75/1.00)
U$SpeI (0.75/1.00)
U$Splice-A (0.75/Optimized)
U$Splice-D (0.75/Optimized)
U$XbaI (0.75/1.00)
U$XcmI (0.75/1.00)
U$XhoI (0.75/1.00)
ALL vertebrates.lib Strategy for Removal of Sequence Motifs The undesired sequence motifs specified above were removed from the starting gene sequence by selecting alternate codons that allowed retention of the specified protein and flanking sequences. Alternate codons were selected in a way to conform to the overall codon selection strategy as much as possible.

General Steps:
  Identify undesired sequence matches with MatInspector using matrix family subset "neo+hyg" or "neo+hyg-EC" and with ModelInspector using default settings.
  Identify possible replacement codons to remove undesired sequence matches with SequenceShaper (keep ORF).
  Incorporate changes into a new version of the synthetic gene sequence and re-analyze with MatInspector and ModelInspector.

Specific Steps:
  First try to remove undesired sequence matches using subset "neo+hyg-EC" and SequenceShaper default remaining thresholds (0.70/Opt-0.20).
  For sequence matches that cannot be removed with this approach use lower SequenceShaper remaining thresholds (e.g. 0.70/Opt-0.05).
  For sequence matches that still cannot be removed, try different combinations of manually chosen replacement codons (especially if more than 3 base changes might be needed). If that introduces new sequence matches, try to remove those using the steps above (a different starting sequence sometimes allows a different removal solution).
  Use subset "neo+hyg" to check whether problematic *E. coli* sequence matches were introduced, and if so try to remove them using an analogous approach to that described above for non *E. coli* sequences.

Use an analogous strategy for the flanking (non-ORF) sequences. Final check with subset "pGL4-072503" after change in flanking cloning sites After codon optimizing neo and hyg, hneo and hhyg were obtained. Regulatory sequences were removed from hneo and hhyg yielding hneo-1F and hhyg-1F (the corresponding sequences without flanking regions are SEQ ID Nos. 38 and 30, respectively). Regulatory sequences were removed from hneo-1F and hhyg-1F yielding hneo-2F and hhyg-2F (the corresponding sequences without flanking regions are SEQ ID Nos. 39 and 42, respectively). Regulatory sequences were removed from hneo-2F and hhyg-2F yielding hneo-3F and hhyg-3F. Hneo-3F and hhyg-3F were further modified by altering 5' and 3' cloning sites yielding hneo-3FB and hhyg-3FB:

hneo-3 (after 3rd round of sequence removal, subset neo+hyg) has the following sequence:

(SEQ ID NO: 4)
CCACTCcGTGGCCACCATGATCGAaCAaGACGGCCTcCAtGCtGGCAGtC

CCGCaGCtTGGGTcGAaCGCtTGTTCGGgTACGACTGGGCCCAGCAGACC

ATCGGaTGtAGCGAtGCgGCCGTGTTCCGtCTaAGCGCtCAaGGCCGgCC

CGTGCTGTTCGTGAAGACCGACCTGAGCGGCGCCCTGAACGAGCTtCAAg

ACGAGGCtGCCCGCCTGAGCTGGCTGGCCACCACCGGtGTaCCCTGCGCC

GCtGTGtTGGAtGTtGTGACCGAaGCCGGCCGgGACTGGCTGCTGCTGGG

CGAGGTcCCtGGCCAGGAtCTGCTGAGCAGCCACCTtGCCCCCGCtGAGA

AGGTtTcCATCATGGCCGAtGCaATGCGgCGCCTGCACACCCTGGACCCC

GCtACaTGCCCCTTCGACCACCAGGCtAAGCAtCGgATCGAGCGtGCtCG gACCCGCATGGAGGCCGGCCTGGTGGACCAGGACGACCTGGACGAGGAGC

AtCAGGGCCTGGCCCCCGCtGAaCTGTTCGCCCGCCTGAAaGCCCGCATG

CCgGACGGtGAGGACCTGGTtGTGACaCAtGGtGAtGCCTGCCTcCCtAA

CATCATGGTcGAGAAtGGcCGCTTCtcCGGCTTCATCGACTGCGGtCGCC

TaGGaGTtGCCGACCGCTACCAGGACATCGCCCTGGCCACCCGCGACATC

GCtGAGGAGCTtGGCGGCGAGTGGGCCGACCGCTTCttTaGTctTGTACGG

CATCGCaGCtCCCGACAGCCAGCGCATCGCCTTCTACCGCCTGCTcGACG

AGTTCTTtTAATGACCAGgCTCTGG;

hneo-3FB (change PflMI sites to SbfI at 5' end and AflII at 3' end) has the following sequence:

(SEQ ID NO: 5)
cctgcaggCCACCATGATCGAACAAGACGGCCTCCATGCTGGCAGTCCCG

CAGCTTGGGTCGAACGCTTGTTCGGGTACGACTGGGCCCAGCAGACCATC

GGATGTAGCGATGCGGCCGTGTTCCGTCTAAGCGCTCAAGGCCGGCCCGT

GCTGTTCGTGAAGACCGACCTGAGCGGCGCCCTGAACGAGCTTCAAGACG

AGGCTGCCCGCCTGAGCTGGCTGGCCACCACCGGTGTACCCTGCGCCGCT

GTGTTGGATGTTGTGACCGAAGCCGGCCGGGACTGGCTGCTGCTGGGCGA

GGTCCCTGGCCAGGATCTGCTGAGCAGCCACCTTGCCCCCGCTGAGAAGG

TTTCCATCATGGCCGATGCAATGCGGCGCCTGCACACCCTGGACCCCGCT

ACATGCCCCTTCGACCACCAGGCTAAGCATCGGATCGAGCGTGCTCGGAC

CCGCATGGAGGCCGGCCTGGTGGACCAGGACGACCTGGACGAGGAGCATC

AGGGCCTGGCCCCCGCTGAACTGTTCGCCCGCCTGAAAGCCCGCATGCCG

GACGGTGAGGACCTGGTTGTGACACATGGTGATGCCTGCCTCCCTAACAT

CATGGTCGAGAATGGCCGCTTCTCCGGCTTCATCGACTGCGGTCGCCTAG

GAGTTGCCGACCGCTACCAGGACATCGCCCTGGCCACCCGCGACATCGCT

GAGGAGCTTGGCGGCGAGTGGGCCGACCGCTTCTTAGTCTTGTACGGCAT

CGCAGCTCCCGACAGCCAGCGCATCGCCTTCTACCGCCTGCTCGACGAGT

TCTTTTAATGAgcttaag;

hhyg-3 (after 3rd round of sequence removal, subset neo+ hyg) has the following sequence:

(SEQ ID NO: 9)
CCACTCcGTGGCCACCATGAAGAAGCCCGAGCTGACCGCtACCAGCGTtG

AaAAaTTtCTcATCGAGAAGTTCGACAGtGTGAGCGACCTGATGCAGtTg tcgGAGGGCGAaGAgAGCCGaGCCTTCAGCTTCGAtGTcGGCGGaCGCGG CTAtGTaCTGCGgGTGAAtAGCTGCGCtGAtGGCTTCTACAAaGACCGCT ACGTGTACCGCCACTTCGCCAGCGCtGCaCTaCCCATCCCCGAaGTGtTG GACATCGGCGAGTTCAGCGAGAGCCTGACaTACTGCATCAGtaGaCGCGC CCAaGGCGTtACtCTcCAaGACCTcCCCGAaACaGAGCTGCCtGCtGTGt TaCAGCCtGTcGCCGAaGCtATGGAtGCtATtGCCGCCGCCGACCTcAGt CAaACCAGCGGCTTCGGCCCaTTCGGgCCCCAaGGCATCGGCCAGTACAC aACCTGGCGgGAtTTCATtTGCGCCATtGCtGAtCCCCAtGTcTACCACT GGCAGACCGTGATGGACGACACCGTGtcCGCCAGCGTaGCtCAaGCCCTG GACGAaCTGATGCTGTGGGCCGAaGACTGtCCCGAGGTGCGCCAccTcGT cCAtGCCGACTTCGGCAGCAACAACGTcCTGACCGACAACGGCCGCATCA CCGCCGTaATCGACTGGtcCGAaGCtATGTTCGGgGACAGtCAGTACGAG GTGGCCAACATCTTCTTCTGGCGgCCCTGGCTGGCtTGCATGGAGCAGCA GACtCGCTACTTCGAGCGCCGgCAtCCCGAGCTGGCCGGCAGCCCtCGtC TGCGaGCCTACATGCTGCGCATCGGCCTGGAtCAGCTcTACCAGAGCCTc GTGGACGGCAACTTCGACGAtGCtGCCTGGGCtCAaGGCCGCTGCGAtGC CATCGTcCGCAGCGGgGCCGGCACCGTcGGtCGCACaCAaATCGCtGGCC GgAGCGCCGCCGTaTGGACCGACGGCTGCGTcGAGGTGCTGGCCGACAGC GGCAACCGCCGgCCCAGtACaCGaCCgCGCGCtAAGGAGTAgTAACCAGg ctcTGG;
and hhyg-3FB (change PflMI sites to SbfI at 5' end and AflII at 3' end) has the following sequence:

(SEQ ID NO: 10)
cctgcaggCCACCATGAAGAAGCCCGAGCTGACCGCTACCAGCGTTGAAA

AATTTCTCATCGAGAAGTTCGACAGTGTGAGCGACCTGATGCAGTTGTCG

GAGGGCGAAGAGAGCCGAGCCTTCAGCTTCGATGTCGGCGGACGCGGCTA

TGTACTGCGGGTGAATAGCTGCGCTGATGGCTTCTACAAAGACCGCTACG

TGTACCGCCACTTCGCCAGCGCTGCACTACCCATCCCCGAAGTGTTGGAC

ATCGGCGAGTTCAGCGAGAGCCTGACATACTGCATCAGTAGACGCGCCCA

AGGCGTTACTCTCCAAGACCTCCCCGAAACAGAGCTGCCTGCTGTGTTAC

AGCCTGTCGCCGAAGCTATGGATGCTATTGCCGCCGCCGACCTCAGTCAA

ACCAGCGGCTTCGGCCCATTCGGGCCCCAAGGCATCGGCCAGTACACAAC

CTGGCGGGATTTCATTTGCGCCATTGCTGATCCCCATGTCTACCACTGGC

AGACCGTGATGGACGACACCGTGTCCGCCAGCGTAGCTCAAGCCCTGGAC

GAACTGATGCTGTGGGCCGAAGACTGTCCCGAGGTGCGCCACCTCGTCCA

TGCCGACTTCGGCAGCAACAACGTCCTGACCGACAACGGGCGCATGACCG

CCGTAATCGACTGGTCCGAAGCTATGTTCGGGGACAGTCAGTACGAGGTG

GCCAACATCTTCTTCTGGCGGCCCTGGCTGGCTTGCATGGAGCAGCAGAC

TCGCTACTTCGAGCGCCGGCATCCCGAGCTGGCCGGCAGCCCTCGTCTGC

GAGCCTACATGCTGCGCATCGGCCTGGATCAGCTCTACCAGAGCCTCGTG

GACGGCAACTTCGACGATGCTGCCTGGGCTCAAGGCCGCTGCGATGCCAT

CGTCCGCAGCGGGGCCGGCACCGTCGGTCGCACACAAATCGCTCGCCGGA

GCGCCGCCGTATGGACCGACGGCTGCGTCGAGGTGCTGGCCGACAGCGGC

AACCGCCGGCCCAGTACACGACCGCGCGCTAAGGAGTAGTAActtaag.

Analysis of hneo-3FB and hhyg-3FB hneo-3FB had no transcription factor binding sequence, including promoter module, matches (GEMS release 3.5.2 June 2003; vertebrate TF binding sequence families (core similarity: 0.75/matrix similarity: opt); and promoter modules (default parameters: optimized threshold or 80% of maximum score)), while hhyg-3FB had 4 transcription factor binding sequence matches remaining but no promoter modules (Table 10). The following transcription factor binding sequences were found in hhyg-3FB:

1) V$MINI
Family: Muscle Initiators (2 members)
Best match: Muscle Initiator Sequence 1
Ref: Laura L. Lopez & James W. Fickett "Muscle-Specific Regulation of Transcription: A Catalog of Regulatory Elements"
http://www.cbil.upenn.edu/MTIR/HomePage.html Position in ORF: −7 to 11

2) V$PAX5
Family: PAX-5/PAX-9 B-cell-specific activating proteins (4 members)
Best match: B-cell-specific activating protein
Ref: MEDLINE 94010299

Position in ORF: 271 to 299

3) V$AREB
Family: Atp1a1 regulatory element binding (4 members)
Best match: AREB6
Ref: MEDLINE 96061934

Position in ORF: 310 to 322

4) V$VMYB
Family: AMV-viral myb oncogene (2 members)
Best match: v-Myb
Ref: MEDLINE 94147510

Position in ORF: 619 to 629

Other sequences remaining in hneo-3F included one E. coli RBS 8 bases upstream of Met (ORF position 334 to 337); hneo-3FB included a splice acceptor site (+) and PstI site as part of a 5' cloning site for SbfI, and one E. coli RBS 8 bases upstream of Met (ORF position 334 to 337); hhyg-3F had no other sequence matches; and hhyg-3FB included a splice acceptor site (+) and PstI site as part of a 5' cloning site for SbfI.

Subsequently, regulatory sequences were removed from hneo-3F and hhyg-3F yielding hneo-4 and hhyg-4. Then regulatory sequences were removed from hneo-4 yielding hneo-5.

TABLE 14

| Gene name | TF binding sequences 5' F/ORF/3' F | Promoter modules 5' F/ORF/3' F |
|---|---|---|
| Neo | —/53/— | —/0/— |
| hneo-F | 1/61/2 | 0/2/0 |
| hneo-3F | 0/0/0 | 0/0/0 |
| hneo-3FB | 0/0/0 | 0/0/0 |
| Hyg | —/74/— | —/3/— |
| hhyg-F | 1/94/1 | 0/4/0 |
| hhyg-3F | 1/3/0 | 0/0/0 |
| hhyg-3FB | 1/3/0 | 0/0/0 |

*Promoter modules are defined as a composite regulatory element, with 2 transcription factor binding sites separated by a spacer, which has been shown to exhibit synergistic or antagonistic function.

Table 15 summarizes the identity of various genes.

TABLE 15

Pairwise identity of different gene versions
Comparisons were of open reading frames (ORFs).

|  | neo | hneo | Hneo-3 | hneo-4 | hneo-5 | Final hNeo |
|---|---|---|---|---|---|---|
| Neo | — | 79 | 78 | 78 | 78 | 77 |
| hneo | | — | 90 | 90 | 90 | 89 |
| hneo-3 | | | — | 100 | 99 | 98 |
| hneo-4 | | | | — | 99 | 98 |
| hneo-5 | | | | | — | 99 |
| Final hNeo | | | | | | — |

|  | hyg | hhyg | hhyg-3 | hHygro | hhyg-4 | Final hHyg |
|---|---|---|---|---|---|---|
| Hyg | — | 79 | 78 | 73 | 76 | 78 |
| hhyg | | — | 88 | 83 | 86 | 88 |
| hhyg-3 | | | — | 94 | 96 | 98 |
| hHygro | | | | — | 96 | 94 |
| hhyg-4 | | | | | — | 97 |
| Final hHyg | | | | | | — |

| Percent Identity | | | | |
|---|---|---|---|---|
| Divergence | 1 | 2 | | |
| 1 | | 82.2 | 1 | Synthetic puro-SEQ ID NO: 11 |
| 2 | 19.6 | | 2 | Starting puro-SEQ ID NO: 15 |
| | 1 | 2 | | |

An expression cassette (hNeo-cassette) with a synthetic neomycin gene flanked by a SV40 promoter and a synthetic poly(A) site is shown below.

```
(SEQ ID NO: 44)
GGATCCGTTTGCGTATTGGGCGCTCTTCCGCTGATCTGCGCAGCACCATG

GCCTGAAATAACCTCTGAAAGAGGAACTTGGTTAGCTACCTTCTGAGGCG

GAAAGAACCAGCTGTGGAATGTGTGTCAGTTAGGGTGTGGAAAGTCCCCA

GGCTCCCCAGCAGGCAGAAGTATGCAAAGCATGCATCTCAATTAGTCAGC

AACCAGGTGTGGAAAGTCCCCAGGCTCCCCAGCAGGCAGAAGTATGCAAA

GCATGCATCTCAATTAGTCAGCAACCATAGTCCCGCCCCTAACTCCGCCC

ATCCCGCCCCTAACTCCGCCCAGTTCCGCCCATTCTCCGCCCCATGGCTG

ACTAATTTTTTTATTTATGCAGAGGCCGAGGCCGCCTCTGCCTCTGAGC

TATTCCAGAAGTAGTGAGGAGGCTTTTTTGGAGGCCTAGGCTTTTGCAAA

AAGCTCGATTCTTCTGACACTAGCGCCACCATGATCGAACAAGACGGCCT

CCATGCTGGCAGTCCCGCAGCTTGGGTCGAACGCTTGTTCGGGTACGACT

GGGCCCAGCAGACCATCGGATGTAGCGATGCGGCCGTGTTCCGTCTAAGC

GCTCAAGGCCGGCCCGTGCTGTTCGTGAAGACCGACCTGAGCGGCGCCCT

GAACGAGCTTCAAGACGAGGCTGCCCGCCTGAGCTGGCTGGCCACCACCG

GCGTACCCTGCGCCGCTGTGTTGGATGTTGTGACCGAAGCCGGCCGGGAC

TGGCTGCTGCTGGGCGAGGTCCCTGGCCAGGATCTGCTGAGCAGCCACCT

TGCCCCCGCTGAGAAGGTTTCTATCATGGCCGATGCAATGCGGCGCCTGC

ACACCCTGGACCCCGCTACCTGCCCCTTCGACCACCAGGCTAAGCATCGG

ATCGAGCGTGCTCGGACCCGCATGGAGGCCGGCCTGGTGGACCAGGACGA

CCTGGACGAGGAGCATCAGGGCCTGGCCCCCGCTGAACTGTTCGCCCGAC

TGAAAGCCCGCATGCCGGACGGTGAGGACCTGGTTGTCACACACGGAGAT

GCCTGCCTCCCTAACATCATGGTCGAGAATGGCCGCTTCTCCGGCTTCAT

CGACTGCGGTCGCCTAGGAGTTGCCGACCGCTACCAGGACATCGCCCTGG

CCACCCGCGACATCGCTGAGGAGCTTGGCGGCGAGTGGGCCGACCGCTTC

TTAGTCTTGTACGGCATCGCAGCTCCCGACAGCCAGCGCATCGCCTTCTA

CCGCTTGCTCGACGAGTTCTTTTAATGATCTAGAACCGGTCATGGCCGCA

ATAAAATATCTTTATTTTCATTACATCTGTGTGTTGGTTTTTTGTGTGTT

CGAACTAGATGCTGTCGAC.
```

An expression cassette (hPuro-cassette) with a synthetic puromycin gene flanked by a SV40 promoter and a synthetic poly(A) site is shown below.

```
(SEQ ID NO: 11)
GGATCCGTTTGCGTATTGGGCGCTCTTCCGCTGATCTGCGCAGCACCATG

GCCTGAAATAACCTCTGAAAGAGGAACTTGGTTAGCTACCTTCTGAGGCG

GAAAGAACCAGCTGTGGAATGTGTGTCAGTTAGGGTGTGGAAAGTCCCCA

GGCTCCCCAGCAGGCAGAAGTATGCAAAGCATGCATCTCAATTAGTCAGC

AACCAGGTGTGGAAAGTCCCCAGGCTCCCCAGCAGGCAGAAGTATGCAAA

GCATGCATCTCAATTAGTCAGCAACCATAGTCCCGCCCCTAACTCCGCCC

ATCCCGCCCCTAACTCCGCCCAGTTCCGCCCATTCTCCGCCCCATGGCTG

ACTAATTTTTTTATTTATGCAGAGGCCGAGGCCGCCTCTGCCTCTGAGC

TATTCCAGAAGTAGTGAGGAGGCTTTTTTGGAGGCCTAGGCTTTTGCAAA

AAGCTCGATTCTTCTGACACTAGCGCCACCATGACCGAGTACAAGCCTAC

CGTGCGCCTGGCCACTCGCGATGATGTGCCCCGCGCCGTCCGCACTCTGG

CCGCCGCTTTCGCCGACTACCCCGCTACCCGGCACACCGTGGACCCCGAC

CGGCACATCGAGCGTGTGACAGAGTTGCAGGAGCTGTTCCTGACCCGCGT

CGGGCTGGACATCGGCAAGGTGTGGGTAGCCGACGACGGCGCGGCCGTGG

CCGTGTGGACTACCCCCGAGAGCGTTGAGGCCGGCGCCGTGTTCGCCGAG

ATCGGCCCCGAATGGCCGAGCTGAGCGGCAGCGCCTGGCCGCCCAGCA

GCAAATGGAGGGCCTGCTTGCCCCCCATCGTCCCAAGGAGCCTGCCTGGT

TTCTGGCCACTGTAGGAGTGAGCCCCGACCACCAGGGCAAGGGCTTGGGC

AGCGCCGTCGTGTTGCCCGGCGTAGAGGCCGCCGAACGCGCCGGTGTGCC

CGCCTTTCTCGAAACAAGCGCACCAAGAAACCTTCCATTCTACGAGCGCC

TGGGCTTCACCGTGACCGCCGATGTCGAGGTGCCCGAGGGACCTAGGACC
```

```
                               -continued
TGGTGTATGACACGAAAACCTGGCGCCTAATGATCTAGAACCGGTCATGG

CCGCAATAAAATATCTTTATTTTCATTACATCTGTGTGTTGGTTTTTTGT

GTGTTCGAACTAGATGCTGTCGAC;

hpuro:
                                                  (SEQ ID NO: 91)
GCTAGCGCCACCATGACCGAGTACAAGCCCACCGTGCGCCTGGCCACCCG

CGACGACGTGCCCCGCGCCGTGCGCACCCTGGCCGCCGCCTTCGCCGACT

ACCCCGCCACCCGCCACACCGTGGACCCCGACCGCCACATCGAGCGCGTG

ACCGAGCTGCAGGAGCTGTTCCTGACCCGCGTGGGCCTGGACATCGGCAA

GGTGTGGGTGGCCGACGACGGCGCCGCCGTGGCCGTGTGGACCACCCCCG

AGAGCGTGGAGGCCGGCGCCGTGTTCGCCGAGATCGGCCCCCGCATGGCC

GAGCTGAGCGGCAGCCGCCTGGCCGCCCAGCAGCAGATGGAGGGCCTGCT

GGCCCCCACCGCCCCAAGGAGCCCGCCTGGTTCCTGGCCACCGTGGGCG

TGAGCCCCGACCACCAGGGCAAGGGCCTGGGCAGCGCCGTGGTGCTGCCC

GGCGTGGAGGCCGCCGAGCGCGCCGGCGTGCCCGCCTTCCTGGAGACCAG

CGCCCCCCGCAACCTGCCCTTCTACGAGCGCCTGGGCTTCACCGTGACCG

CCGACGTGGAGGTGCCCGAGGGCCCCCGCACCTGGTGCATGACCCGCAAG

CCCGGCGCCTAATGATCTAGA;

hpuro-1:
                                                  (SEQ ID NO: 92)
gctagcgccaccatgaccgagtacaagcctaccgtgcgcctggccactcg cgatgatgtgccccgcgccgtccgcactctggccgccgctttcgccgact
```

```
                               -continued
accccgctacccggcacaccgtggaccccgaccggcacatcgagcgtgtg acagagttgcaggagctgttcctgacccgcgtcgggctggacatcggcaa ggtgtgggtagccgacgacggcgcggccgtggccgtgtggactaccccg agagcgttgaggccggcgccgtgttcgccgagatcggcccccgaatggcc gagctgagcggcagccgcctggccgcccagcagcaaatggagggcctgct tgccccccatcgtcccaaggagcctgcctggtttctggccactgtaggag tgagccccgaccaccagggcaagggcttgggcagcgccgtcgtgttgccc ggcgtagaggccgccgaacgcgccggtgtgcccgcctttctggagacaag cgctccgcgtaaccttccattctacgagcgcctgggcttcaccgtgaccg ccgatgtcgaggtgcccgagggaccccggacctggtgcatgactcgaag cctggcgcctaatgatctaga;
``` and

```
hpuro-2
                                                  (SEQ ID NO: 93)
GCTAGCGCCACCATGACCGAGTACAAGCCTACCGTGCGCCTGGCCACTCG

CGATGATGTGCCCCGCGCCGTCCGCACTCTGGCCGCCGCTTTCGCCGACT

ACCCCGCTACCCGGCACACCGTGGACCCCGACCGGCACATCGAGCGTGTG

ACAGAGTTGCAGGAGCTGTTCCTGACCCGCGTCGGGCTGGACATCGGCAA

GGTGTGGGTAGCCGACGACGGCGCGGCCGTGGCCGTGTGGACTACCCCCG

AGAGCGTTGAGGCCGGCGCCGTGTTCGCCGAGATCGGCCCCCGAATGGCC

GAGCTGAGCGGCAGCCGCCTGGCCGCCCAGCAGCAAATGGAGGGCCTGCT

TGCCCCCCATCGTCCCAAGGAGCCTGCCTGGTTTCTGGCCACTGTAGGAG

TGAGCCCCGACCACCAGGGCAAGGGCTTGGGCAGCGCCGTCGTGTTGCCC

GGCGTAGAGGCCGCCGAACGCGCCGGTGTGCCCGCCTTTCTCGAAACAAG

CGCACCAAGAAACCTTCCATTCTACGAGCGCCTGGGCTTCACCGTGACCG

CCGATGTCGAGGTGCCCGAGGGACCTAGGACCTGGTGTATGACACGAAAA

CCTGGCGCCTAATGATCTAGA.
```

The starting puro sequence (from psi STRIKE) has SEQ ID NO:15

```
(atgaccgagt acaagcccac ggtgcgcctc gccacccgcg acgacgtccc ccgggccgta
 cgcaccctcg ccgccgcgtt cgccgactac cccgccacgc gccacaccgt cgacccggac
 cgccacatcg agcgggtcac cgagctgcaa gaactcttcc tcacgcgcgt cgggctcgac
 atcggcaagg tgtgggtcgc ggacgacggc gccgcggtgg cggtctggac cacgccggag
 agcgtcgaag cggggcggt gttcgccgag atcggccccc gcatggccga gttgagcggt
 tcccggctgg ccgcgcagca acagatggaa ggcctcctgg cgccgcaccg gcccaaggag
 cccgcgtggt tcctggccac cgtcggcgtg tcgcccgacc accagggcaa gggtctgggc
 agcgccgtcg tgctccccgg agtggaggcg gccgagcgcg ccggggtgcc cgccttcctg
 gagacctccg cgccccgcaa cctcccctc tacgagcggc tcggcttcac cgtcaccgcc
 gacgtcgagg tgcccgaagg accgcgcacc tggtgcatga cccgcaagcc cggtgcc).
```

Other synthetic hyg and neo genes include

```
hneo-1:
                                                  (SEQ ID NO: 38)
CCACTCAGTGGCCACCATGATCGAGCAGGACGGCCTcCAtGCtGGCAGtC CCGCaGCCTGGGTcGAGCGCtTGTTCGGgTACGACTGGGCCCAGCAGACC ATCGGaTGtAGCGAtGCCGCaGTGTTCCGCCTGAGCGCtCAaGGCCGgCC CGTGCTGTTCGTGAAGACCGACCTGAGCGGCGCCCTGAACGAGCTtCAaG ACGAGGCtGCCCGCCTGAGCTGGCTGGCCACCACCGGtGTaCCCTGCGCC GCtGTGTtGGAtGTtGTGACCGAaGCCGGCCGCGACTGGCTGCTGCTGGG CGAGGTGCCtGGCCAGGACCTGCTGAGCAGCCACCTGGCCCCCGCtGAGA AGGTGAGCATCATGGCCGACGCCATGCGGcGCCCTGCACACCCTGGACCCC GCtACaTGCCCCTTCGACCACCAGGCtAAGCACCGCATCGAGCGgGCTCG gACCCGCATGGAGGCCGGCCTGGTGGACCAGGACGACCTGGACGAGGAGC
```

ACCAGGGCCTGGCCCCCGCtGAaCTGTTCGCCCGCCTGAAaGCCCGCATG

CCgGACGGtGAGGACCTGGTtGTGACaCACGGCGACGCCTGCCTcCCtAA

CATCATGGTcGAGAACGGgCGCTTCtcCGGCTTCATCGACTGCGGCCGCC

TGGGCGTtGCCGACCGCTACCAGGACATCGCCCTGGCCACCCGCGACATC

GCCGAGGAGCTGGGCGGCGAGTGGGCCGACCGCTTCCTGGTctTGTACGG

CATCGCaGCtCCCGACAGCCAGCGCATCGCCTTCTACCGCCTGCTGGACG

AGTTCTTCTAgTAACCAGgCTCTGG;

hneo-2

(SEQ ID NO: 39)

CCACTCcGTGGCCACCATGATCGAaCAaGACGGCCTcCAtGCtGGCAGtC

CCGCaGCtTGGGTcGAaCGCtTGTTCGGgTACGACTGGGCCCAGCAGACC

ATCGGaTGtAGCGAtGCgGCCGTGTTCCGtCTaAGCGCtCAaGGCCGgCC

CGTGCTGTTCGTGAAGACCGACCTGAGCGGCGCCCTGAACGAGCTtCAaG

ACGAGGCtGCCCGCCTGAGCTGGCTGGCCACCACCGGtGTaCCCTGCGCC

GCtGTGtTGGAtGTtGTGACCGAaGCCGGCCGgGACTGGCTGCTGCTGGG

CGAGGTcCCtGGCCAGGAtCTGCTGAGCAGCCACCTtGCCCCCGCtGAGA

AGGTttcCATCATGGCCGAtGCaATGCGgCGCCTGCACACCCTGGACCCC

GCtACaTGCCCCTTCGACCACCAGGCtAAGCAtCGgATCGAGCGtGCtCG gACCCGCATGGAGGCCGGCCTGGTGGACCAGGACGACCTGGACGAGGAGC

AtCAGGGCCTGGCCCCCGCtGAaCTGTTCGCCCGCCTGAAaGCCCGCATG

CCgGACGGtGAGGACCTGGTtGTGACaCAtGGaGAtGCCTGCCTcCCtAA

CATCATGGTcGAGAAtGGcCGCTTCtcCGGCTTCATCGACTGCGGtCGCC

TaGGaGTtGCCGACCGCTACCAGGACATCGCCCTGGCCACCCGCGACATC

GCtGAGGAGCTtGGCGGCGAGTGGGCCGACCGCTTCtTaGTctTGTACGG

CATCGCaGCtCCCGACAGCCAGCGCATCGCCTTCTACCGCCTGCTcGACG

AGTTCTTtTAATGACCAGgCTCTGG;

hhyg-1

(SEQ ID NO: 30)

CCACTCAGTGGCCACCATGAAGAAGCCCGAGCTGACCGCTACCAGCGTTG

AGAAGTTCCTGATCGAGAAGTTCGACAGCGTGAGCGACCTGATGCAGTTA

AGCGAGGGCGAGGAAAGCCGCGCCTTCAGCTTCGATGTCGGCGGACGCGG

CTATGTACTGCGGGTGAATAGCTGCGCTGATGGCTTCTACAAAGACCGCT

ACGTGTACCGCCACTTCGCCAGCGCTGCACTGCCCATCCCCGAGGTGCTG

GACATCGGCGAGTTCAGCGAGAGCCTGACATACTGCATCAGCCGCCGCGC

TCAAGGCGTGACTCTCCAAGACCTGCCCGAGACAGAGCTGCCCGCTGTGC

TACAGCCTGTCGCCGAGGCTATGGACGCTATTGCCGCCGCCGACCTGAGC

CAGACCAGCGGCTTCGGCCCATTCGGGCCCCAAGGCATCGGCCAGTACAC

CACCTGGCGCGACTTCATCTGCGCCATTGCTGATCCCCATGTCTACCACT

GGCAGACCGTGATGGACGACACCGTGAGCGCCAGCGTAGCTCAAGCCCTG

GACGAGCTGATGCTGTGGGCCGAGGACTGCCCCGAGGTGCGCCATCTCGT

CCATGCCGACTTCGGCAGCAACAACGTCCTGACCGACAACGGCCGCATCA

CCGCCGTAATCGACTGGAGCGAGGCCATGTTCGGGGACAGTCAGTACGAG

GTGGCCAACATCTTCTTCTGGCGGCCCTGGCTGGCCTGCATGGAGCAGCA

AACCCGCTACTTCGAGCGCCGCCATCCCGAGCTGGCCGGCAGCCCCGTC

TGCGAGCCTACATGCTGCGCATCGGCCTGGATCAGCTCTACCAGAGCCTC

GTGGACGGCAACTTCGACGATGCTGCCTGGGCTCAAGGCCGCTGCGATGC

CATCGTCCGCAGCGGGGCCGGCACCGTCGGTCGCACACAAATCGCTCGCC

GGAGCGCCGCCGTATGGACCGACGGCTGCGTCGAGGTGCTGGCCGACAGC

GGCAACCGCCGGCCCAGTACACGACCGCGCGCTAAGGAGTAGTAACCAGC

TCTTGG;

hhyg-2:

(SEQ ID NO: 42)

CCACTCCGTGGCCACCATGAAGAAGCCCGAGCTGACCGCTACCAGCGTTG

AAAAATTTCTCATCGAGAAGTTCGACAGTGTGAGCGACCTGATGCAGTTG

TCGGAGGGCGAAGAGAGCCGAGCCTTCAGCTTCGATGTCGGCGGACGCGG

CTATGTACTGCGGGTGAATAGCTGCGCTGATGGCTTCTACAAAGACCGCT

ACGTGTACCGCCACTTCGCCAGCGCTGCACTACCCATCCCCGAAGTGTTG

GACATCGGCGAGTTCAGCGAGAGCCTGACATACTGCATCAGTAGACGCGC

CCAAGGCGTTACTCTCCAAGACCTCCCCGAAACAGAGCTGCCTGCTGTGT

TACAGCCTGTCGCCGAAGCTATGGATGCTATTGCCGCCGCCGACCTCAGT

CAAACCAGCGGCTTCGGCCCATTCGGGCCCCAAGGCATCGGCCAGTACAC

AACCTGGCGGGATTTCATTTGCGCCATTGCTGATCCCCATGTCTACCACT

GGCAGACCGTGATGGACGACACCGTGTCCGCCAGCGTAGCTCAAGCCCTG

GACGAACTGATGCTGTGGGCCGAAGACTGTCCCGAGGTGCGCCACCTCGT

CCATGCCGACTTCGGCAGCAACAACGTCCTGACCGACAACGGCCGCATCA

CCGCCGTAATCGACTGGAGCGAGGCTATGTTCGGGGACAGTCAGTACGAG

GTGGCCAACATCTTCTTCTGGCGGCCCTGGCTGGCTTGCATGGAGCAGCA

GACTCGCTACTTCGAGCGCCGGCATCCCGAGCTGGCCGGCAGCCCTCGTC

TGCGAGCCTACATGCTGCGCATCGGCCTGGATCAGCTCTACCAGAGCCTC

GTGGACGGCAACTTCGACGATGCTGCCTGGGCTCAAGGCCGCTGCGATGC

CATCGTCCGCAGCGGGGCCGGCACCGTCGGTCGCACACAAATCGCTCGCC

GGAGCGCCGCCGTATGGACCGACGGCTGCGTCGAGGTGCTGGCCGACAGC

GGCAACCGCCGGCCCAGTACACGACCGCGCGCTAAGGAGTAGTAACCAGC

TCTTGG;

hHygro (SacI site in ORF near 5' end, insert in-frame linker coding for 12 amino acids at 3' end, and SnaBI site added at 3' end in ORF)

(SEQ ID NO: 70)

aagcttgctagcgccaccatgaagaagcccgagctcaccgctaccagcgt tgaaaaatttctcatcgagaagttcgacagtgtgagcgacctgatgcagt tgtcggagggcgaagagagccgagccttcagcttcgatgtcggcggacgc ggctatgtactgcgggtgaatagctgcgctgatggcttctacaaagaccg ctacgtgtaccgccacttcgccagcgctgcactacccatccccgaagtgtt ggacatcggcgagttcagcgagagcctgacatactgcatcagtagacgcg -continued
```
cccaaggcgttactctccaagacctccccgaaacagagctgcctgctgtg
ttacagcctgtcgccgaagctatggatgctattgccgccgccgacctcag
tcaaaccagcggcttcggcccattcgggccccaaggcatcggccagtaca
caacctggcgggatttcatttgcgccattgctgatcccatgtctaccac
tggcagaccgtgatggacgacaccgtgtccgccagcgtagctcaagccct
ggacgaactgatgctgtgggccgaagactgtcccgaggtgcgccacctcg
tccatgccgacttcggcagcaacaacgtcctgaccgacaacggccgcatc
accgccgtaatcgactggtccgaagctatgttcggggacagtcagtacga
ggtggccaacatcttcttctggcggccctggctggcttgcatggagcagc
agactcgctacttcgagcgccggcatcccgagctggccggcagccctcgt
ctgcgagcctacatgctgcgcatcggcctggatcagctctaccagagcct
cgtggacggcaacttcgacgatgctgcctgggctcaaggccgctgcgatg
ccatcgtccgcagcggggccggcaccgtcggtcgcacacaaatcgctcgc
cggagcgccgccgtatggaccgacggctgcgtcgaggtgctggccgacag
cggcaaccgccggcccagtacacgaccgcgcgctaaggagggtggcggag
ggagcggtggcggaggttcctacgtatagtctagactcgag;
```
hhyg-4
(SEQ ID NO: 71)
```
atgaagaagcccgagctcaccgctaccagcgttgaaaaamctcatcgaga
agttcgacagtgtgagcgacctgatgcagttgtcggagggcgaagagagc
cgagccttcagcttcgatgtcggcggacgcggctatgtactgcgggtgaa
tagctgcgctgatggcttctacaaagaccgctacgtgtaccgccacttcg
ccagcgctgcactacccatccccgaagtgttggacatcggcgagttcagc
gagagcctgacatactgcatcagtagacgcgcccaaggcgttactctcca
agacctccccgaaacagagctgcctgctgtgttacagcctgtcgccgaag
ctatggatgctattgccgccgccgacctcagtcaaaccagcggcttcggc
ccattcgggccccaaggcatcggccagtacacaacctggcgggatttcat
ttgcgccattgctgatcccatgtctaccactggcagaccgtgatggacg
acaccgtgtccgccagcgtagctcaagccctggacgaactgatgctgtgg
gccgaagactgtcccgaggtgcgccacctcgtccatgccgacttcggcag
caacaacgtcctgaccgacaacggccgcatcaccgccgtaatcgactggt
ccgaagctatgttcggggacagtcagtacgaggtggccaacatcttcttc
tggcggccctggctggcttgcatggagcagcagactcgctacttcgagcg
ccggcatcccgagctggccggcagccctcgtctgcgagcctacatgctgc
gcatcggcctggatcagctctaccagagcctcgtggacggcaacttcgac
gatgctgcctgggctcaaggccgctgcgatgccatcgtccgcagcggggc
cggcaccgtcggtcgcacacaaatcgctcgccggagcgccgccgtatgga
ccgacggctgcgtcgaggtgctggccgacagcggcaaccgccggcccagt
acacgaccgcgcgctaaggaaggcggtggaggtagtggtggcggaggtag
ctacgta;
```
hneo-4:
(SEQ ID NO: 72)
```
GCTAGCGCCACCATGATCGAACAAGACGGCCTCCATGCTGGCAGTCCCGC
AGCTTGGGTCGAACGCTTGTTCGGGTACGACTGGGCCCAGCAGACCATCG
GATGTAGCGATGCGGCCGTGTTCCGTCTAAGCGCTCAAGGCCGGCCCGTG
CTGTTCGTGAAGACCGACCTGAGCGGCGCCCTGAACGAGCTTCAAGACGA
GGCTGCCCGCCTGAGCTGGCTGGCCACCACCGGTGTACCCTGCGCCGCTG
TGTTGGATGTTGTGACCGAAGCCGGCCGGGACTGGCTGCTGCTGGGCGAG
GTCCCTGGCCAGGATCTGCTGAGCAGCCACCTTGCCCCCGCTGAGAAGGT
TTCCATCATGGCCGATGCAATGCGGCGCCTGCACACCCTGGACCCCGCTA
CATGCCCTTCGACCACCAGGCTAAGCATCGGATCGAGCGTGCTCGGACC
CGCATGGAGGCCGGCCTGGTGGACCAGGACGACCTGGACGAGGAGCATCA
GGGCCTGGCCCCCGCTGAACTGTTCGCCCGCCTGAAAGCCCGCATGCCGG
ACGGTGAGGACCTGGTTGTGACACATGGTGATGCCTGCCTCCCTAACATC
ATGGTCGAGAATGGCCGCTTCTCCGGCTTCATCGACTGCGGTCGCCTAGG
AGTTGCCGACCGCTACCAGGACATCGCCCTGGCCACCCGCGACATCGCTG
AGGAGCTTGGCGGCGAGTGGGCCGACCGCTTCTTAGTCTTGTACGGCATC
GCAGCTCCCGACAGCCAGCGCATCGCCTTCTACCGCCTGCTCGACGAGTT
CTTTTAATCTAGA;
```
and
hneo-5:
(SEQ ID NO: 73)
```
GCTAGCGCCACCATGATCGAACAAGACGGCCTCCATGCTGGCAGTCCCGC
AGCTTGGGTCGAACGCTTGTTCGGGTACGACTGGGCCCAGCAGACCATCG
GATGTAGCGATGCGGCCGTGTTCCGTCTAAGCGCTCAAGGCCGGCCCGTG
CTGTTCGTGAAGACCGACCTGAGCGGCGCCCTGAACGAGCTTCAAGACGA
GGCTGCCCGCCTGAGCTGGCTGGCCACCACCGGCGTACCCTGCGCCGCTG
TGTTGGATGTTGTGACCGAAGCCGGCCGGGACTGGCTGCTGCTGGGCGAG
GTCCCTGGCCAGGATCTGCTGAGCAGCCACCTTGCCCCCGCTGAGAAGGT
TTCTATCATGGCCGATGCAATGCGGCGCCTGCACACCCTGGACCCCGCTA
CCTGCCCCTTCGACCACCAGGCTAAGCATCGGATCGAGCGTGCTCGGACC
CGCATGGAGGCCGGCCTGGTGGACCAGGACGACCTGGACGAGGAGCATCA
GGGCCTGGCCCCCGCTGAACTGTTCGCCCGACTGAAAGCCCGCATGCCGG
ACGGTGAGGACCTGGTTGTCACACACGGAGATGCCTGCCTCCCTAACATC
ATGGTCGAGAATGGCCGCTTCTCCGGCTTCATCGACTGCGGTCGCCTAGG
AGTTGCCGACCGCTACCAGGACATCGCCCTGGCCACCCGCGACATCGCTG
AGGAGCTTGGCGGCGAGTGGGCCGACCGCTTCTTAGTCTTGTACGGCATC
GCAGCTCCCGACAGCCAGCGCATCGCCTTCTACCGCTTGCTCGACGAGTT
CTTTTAATGATCTAGA.
```

The synthetic nucleotide sequence of the invention may be employed in fusion constructs. For instance, a synthetic sequence for a selectable polypeptide may be fused to a wild-type sequence or to another synthetic sequence which encodes a different polypeptide. For instance, the neo sequence in the following examples of a synthetic *Renilla* luciferase-neo sequence may be replaced with a synthetic neo sequence of the invention:

(hrl-neo fusion; SEQ ID NO: 12)
atggcttccaaggtgtacgaccccgagcaacgcaaacgcatgatcactgg
gcctcagtggtgggctcgctgcaagcaaatgaacgtgctggactccttca
tcaactactatgattccgagaagcacgccgagaacgccgtgattttttgca
tggtaacgctgcctccagctacctgtggaggcacgtcgtgcctcacatcg
agcccgtggctagatgcatcatccctgatctgatcggaatgggtaagtcc
ggcaagagcgggaatggctcatatcgcctcctggatcactacaagtacct
caccgcttggttcgagctgctgaaccttccaaagaaaatcatctttgtgg
gccacgactgggggcttgtctggcctttcactactcctacgagcaccaa
gacaagatcaaggccatcgtccatgctgagagtgtcgtggacgtgatcga
gtcctgggacgagtggcctgacatcgaggaggatatcgccctgatcaaga
gcgaagagggcgagaaaatggtgcttgagaataacttcttcgtcgagacc
atgctcccaagcaagatcatgcggaaactggagcctgaggagttcgctgc
ctacctggagccattcaaggagaagggcgaggttagacggcctaccctct
cctggcctcgcgagatccctctcgttaagggaggcaagcccgacgtcgtc
cagattccgcaactacaacgcctaccttcgggccagcgacgatctgccta
agatgttcatcgagtccgaccctgggttcttttccaacgctattgtcgag
ggagctaagaagttccctaacaccgagttcgtgaaggtgaagggcctcca
cttcagccaggaggacgctccagatgaaatgggtaagtacatcaagagct
tcgtggagcgcgtgctgaagaacgagcagaccggtggtgggagcggagt
ggcggatcaggtggcggaggctccggagggattgaacaagatggattgca
cgcaggttctccggccgcttgggtggagaggctattcggctatgactggg
cacaacagacaatcggctgctctgatgccgccgtgttccggctgtcagcg
caggggcgcccggttcttttttgtcaagaccgacctgtccggtgccctgaa
tgaactgcaggacgaggcagcgcggctatcgtggctggccacgacgggcg
ttccttgcgcagctgtgctcgacgttgtcactgaagcgggaagggactgg
ctgctattgggcgaagtgccggggcaggatctcctgtcatctcaccttgc
tcctgccgagaaagtatccatcatggctgatgcaatgcggcggctgcata
cgcttgatccggctacctgcccattcgaccaccaagcgaaacatcgcatc
gagcgagcacgtactcggatggaagccggtcttgtcgatcaggatgatct
ggacgaagagcatcaggggctcgcgccagccgaactgttcgccaggctca
aggcgcgcatgcccgacggcgaggatctcgtcgtgacccatggcgatgcc
tgcttgccgaatatcatggtggaaaatggccgcttttctggattcatcga
ctgtggccggctgggtgtggcggaccgctatcaggacatagcgttggcta
cccgtgatattgctgaagagcttggcggcgaatgggctgaccgcttcctc
gtgctttacggtatcgccgctcccgattcgcagcgcatcgccttctatcg
ccttcttgacgagttcttctaa and (neo-hrl-fusion; SEQ ID NO: 13)
atgattgaacaagatggattgcacgcaggttctccggccgcttgggtgga
gaggctattcggctatgactgggcacaacagacaatcggctgctctgatg
ccgccgtgttccggctgtcagcgcaggggcgcccggttcttttttgtcaag
accgacctgtccggtgccctgaatgaactgcaggacgaggcagcgcggct
atcgtggctggccacgacgggcgttccttgcgcagctgtgctcgacgttg
tcactgaagcgggaagggactggctgctattgggcgaagtgccggggcag
gatctcctgtcatctcaccttgctcctgccgagaaagtatccatcatggc
tgatgcaatgcggcggctgcatacgcttgatccggctacctgcccattcg
accaccaagcgaaacatcgcatcgagcgagcacgtactcggatggaagcc
ggtcttgtcgatcaggatgatctggacgaagagcatcaggggctcgcgcc
agccgaactgttcgccaggctcaaggcgcgcatgcccgacggcgaggatc
tcgtcgtgacccatggcgatgcctgcttgccgaatatcatggtggaaaat
ggccgcttttctggattcatcgactgtggccggctgggtgtggcggaccg
ctatcaggacatagcgttggctacccgtgatattgctgaagagcttggcg
gcgaatgggctgaccgcttcctcgtgctttacggtatcgccgctcccgat
tcgcagcgcatcgccttctatcgccttcttgacgagttcttcaccggtgg
tgggagcggaggtggcggatcaggtggcggaggctccggagggcttcca
aggtgtacgaccccgagcaacgcaaacgcatgatcactgggcctcagtgg
tgggctcgctgcaagcaaatgaacgtgctggactccttcatcaactacta
tgattccgagaagcacgccgagaacgccgtgattttttctgcatggtaacg
ctgcctccagctacctgtggaggcacgtcgtgcctcacatcgagcccgtg
gctagatgcatcatccctgatctgatcggaatgggtaagtccggcaagag
cgggaatggctcatatcgcctcctggatcactacaagtacctcaccgctt
ggttcgagctgctgaaccttccaaagaaaatcatctttgtgggccacgac
tgggggcttgtctggcctttcactactcctacgagcaccaagacaagat
caaggccatcgtccatgctgagagtgtcgtggacgtgatcgagtcctggg
acgagtggcctgacatcgaggaggatatcgccctgatcaagagcgaagag
ggcgagaaaatggtgcttgagaataacttcttcgtcgagaccatgctccc
aagcaagatcatgcggaaactggagcctgaggagttcgctgcctacctgg
agccattcaaggagaagggcgaggttagacggcctaccctctcctggcct
cgcgagatccctctcgttaagggaggcaagcccgacgtcgtccagattcc
gcaactacaacgcctaccttcgggccagcgacgatctgcctaagatgttc
atcgagtccgaccctgggttcttttccaacgctattgtcgagggagctaa
gaagttccctaacaccgagttcgtgaaggtgaagggcctccacttcagcc
aggaggacgctccagatgaaatgggtaagtacatcaagagcttcgtggag
cgcgtgctgaagaacgagcagtaa.

EXAMPLE 5

Transcription Factor Binding Sites Used to Identify Sites in Selected Synthetic Sequences TF Binding Site Libraries The TF binding site library ("Matrix Family Library") is part of the GEMS Launcher package. Table 16 shows the version of the Matrix Family Library which was used in the design of a particular sequence and Table 17 shows a list of all vertebrate TF binding sites ("matrices") in Matrix Family Library Version 2.4, as well as all changes made to vertebrate matrices in later versions up to 4.1 (section "GENOMATIX MATRIX FAMILY LIBRARY INFORMATION Versions 2.4 to 4.1"). (Genomatix has a copyright to all Matrix Library Family information).

TABLE 16

| Synthetic DNA sequence | Genomatix Matrix Family Library |
|---|---|
| pGL4B-NN3* | Version 2.4 May 2002 |
| luc2A8 and luc2B10 | Version 3.0 November 2002 |
|  | Version 3.1.1 April 2003 |
| hhyg3 | Version 3.1.2 June 2003 |
| hneo3 |  |
| hhyg4 | Version 3.3 August 2003 |
| SpeI-NcoI-Ver2** | Version 4.0 November 2003 |
| hneo5 | Version 4.1 February 2004 |
| hpuro2 |  |

*NotI-NcoI fragment in pGL4 including amp gene (pGL4B-NN3)
**SpeI-NcoI-Ver2 (replacement for SpeI-NcoI fragment in pGL4B-NN3)

TABLE 17

GENOMATIX MATRIX FAMILY LIBRARY INFORMATION
Versions 2.4 to 4.1

A. Matrix Family Library Version 2.4
Matrix Family Library Version 2.4 (May 2002) contains 412 weight matrices in 193 families
(Vertebrates: 275 matrices in 106 families)
Vertebrates

| Family | Family Information | Matrix Name | Information |
|---|---|---|---|
| V$AHRR | AHR-arnt heterodimers and AHR-related factors | V$AHRARNT.01 | aryl hydrocarbon receptor/Arnt heterodimers |
|  |  | V$AHR.01 | aryl hydrocarbon/dioxin receptor |
|  |  | V$AHRARNT.02 | aryl hydrocarbon/Arnt heterodimers, fixed core |
| V$AP1F | AP1 and related factors | V$AP1.01 | AP1 binding site |
|  |  | V$AP1.02 | activator protein 1 |
|  |  | V$AP1.03 | activator protein 1 |
|  |  | V$AP1FJ.01 | activator protein 1 |
|  |  | V$NFE2.01 | NF-E2 p45 |
|  |  | V$VMAF.01 | v-Maf |
|  |  | V$TCF11MAFG.01 | TCF11/MafG heterodimers, binding to subclass of AP1 sites |
|  |  | V$BEL1.01 | Bel-1 similar region |
| V$AP2F | Activator Protein 2 | V$AP2.01 | activator protein 2 |
| V$AP4R | AP4 and Related proteins | V$AP4.01 | activator protein 4 |
|  |  | V$AP4.02 | activator protein 4 |
|  |  | V$TH1E47.01 | Thing1/E47 heterodimer. TH1 bHLH member specific expression in a variety of embryonic tissues |
|  |  | V$TAL1ALPHAE47.01 | Tal-1alpha/E47 heterodimer |
|  |  | V$TAL1BETAE47.01 | Tal-1beta/E47 heterodimer |
|  |  | V$TAL1BETAITF2.01 | Tal-1beta/ITF-2 heterodimer |
|  |  | V$AP4.03 | activator protein 4 |
| V$AREB | Atp1a1 regulatory element binding | V$AREB6.04 | AREB6 (Atp1a1 regulatory element binding factor 6) |
|  |  | V$AREB6.02 | AREB6 (Atp1a1 regulatory element binding factor 6) |
|  |  | V$AREB6.03 | AREB6 (Atp1a1 regulatory element binding factor 6) |
|  |  | V$AREB6.01 | AREB6 (Atp1a1 regulatory element binding factor 6) |
| V$ARP1 | Apolipoprotein aI and cIII gene Repressor Protein | V$ARP1.01 | apolipoprotein AI regulatory protein 1 |

TABLE 17-continued

GENOMATIX MATRIX FAMILY LIBRARY INFORMATION
Versions 2.4 to 4.1

| | | | |
|---|---|---|---|
| V$BARB | BARbiturate-Inducible El. box from Pro + eukaryot. genes | V$BARBIE.01 | barbiturate-inducible element |
| V$BCL6 | POZ domain zinc finger expressed in B-Cells | V$BCL6.01 | POZ/zinc finger protein, transcriptional repressor, translocations observed in diffuse large cell lymphoma |
| | | V$BCL6.02 | POZ/zinc finger protein, transcriptional repressor, translocations observed in diffuse large cell lymphoma |
| V$BRAC | Brachyury gene, mesoderm developmental factor | V$TBX5.01 | T-Box factor 5 site (TBX5), mutations related to Holt-Oram syndrome |
| | | V$BRACH.01 | Brachyury |
| V$BRNF | Brn POU domain factors | V$BRN3.01 | POU transcription factor Brn-3 |
| | | V$BRN2.01 | POU factor Brn-2 (N-Oct 3) |
| V$CABL | C-abl DNA binding sites | V$CABL.01 | Multifunctional c-Abl src type tyrosine kinase |
| V$CART | Cart-1 (cartilage homeoprotein 1) | V$XVENT2.01 | Xenopus homeodomain factor Xvent-2; early BMP signaling response |
| | | V$CART1.01 | Cart-1 (cartilage homeoprotein 1) |
| V$CDXF | Vertebrate caudal related homeodomain protein | V$CDX2.01 | Cdx-2 mammalian caudal related intestinal transcr. factor |
| V$CEBP | Ccaat/Enhancer Binding Protein | V$CEBPB.01 | CCAAT/enhancer binding protein beta |
| | | V$CEBP.02 | C/EBP binding site |
| V$CHOP | CHOP binding protein | V$CHOP.01 | heterodimers of CHOP and C/EBPalpha |
| V$CLOX | CLOX and CLOX homology (CDP) factors | V$CDPCR3HD.01 | cut-like homeodomain protein |
| | | V$CDP.01 | cut-like homeodomain protein |
| | | V$CDP.02 | transcriptional repressor CDP |
| | | V$CDPCR3.01 | cut-like homeodomain protein |
| | | V$CLOX.01 | Clox |
| V$CMYB | C-MYB, cellular transcriptional activator | V$CMYB.01 | c-Myb, important in hematopoesis, cellular equivalent to avian myoblastosis virus oncogene v-myb |
| V$COMP | factors which COoperate with Myogenic Proteins | V$COMP1.01 | COMP1, cooperates with myogenic proteins in multicomponent complex |
| V$COUP | Repr. of RXR-mediated activ. & retinoic acid responses | V$COUP.01 | COUP antagonizes HNF-4 by binding site competition or synergizes by direct protein - protein interaction with HNF-4 |
| V$CP2F | CP2-erythrocyte Factor related to drosophila Elf1 | V$CP2.01 | CP2 |
| V$CREB | Camp-Responsive Element Binding proteins | V$CREBP1.01 | cAMP-responsive element binding protein 1 |
| | | V$CREBP1CJUN.01 | CRE-binding protein 1/c-Jun heterodimer |
| | | V$CREB.01 | cAMP-responsive element binding protein |
| | | V$HLF.01 | hepatic leukemia factor |
| | | V$E4BP4.01 | E4BP4, bZIP domain, transcriptional repressor |
| | | V$CREB.02 | cAMP-response element binding protein |
| | | V$CREB.03 | cAMP-responsive element-binding protein |

TABLE 17-continued

GENOMATIX MATRIX FAMILY LIBRARY INFORMATION
Versions 2.4 to 4.1

| | | | |
|---|---|---|---|
| | | V$CREB.04 | cAMP-response element binding protein |
| | | V$CREBP1.02 | CRE-binding protein 1 |
| | | V$ATF.02 | ATF binding site |
| | | V$ATF.01 | activating transcription factor |
| | | V$TAXCREB.01 | Tax/CREB complex |
| | | V$TAXCREB.02 | Tax/CREB complex |
| | | V$VJUN.01 | v-Jun |
| V$E2FF | E2F-myc activator/cell cycle regulator | V$E2F.02 | E2F, involved in cell cycle regulation, interacts with Rb p107 protein |
| | | V$E2F.03 | E2F, involved in cell cycle regulation, interacts with Rb p107 protein |
| | | V$E2F.01 | E2F, involved in cell cycle regulation, interacts with Rb p107 protein |
| V$E2TF | papillioma virus E2 Transcriptional activator | V$E2.01 | BPV bovine papilloma virus regulator E2 |
| | | V$E2.02 | papilloma virus regulator E2 |
| V$EBOR | E-BOx Related factors | V$DELTAEF1.01 | deltaEF1 |
| | | V$XBP1.01 | X-box-binding protein 1 |
| V$EBOX | E-BOX binding factors | V$USF.02 | upstream stimulating factor |
| | | V$USF.03 | upstream stimulating factor |
| | | V$MYCMAX.03 | MYC-MAX binding sites |
| | | V$SREBP.03 | Sterol regulatory element binding protein |
| | | V$SREBP.02 | Sterol regulatory element binding protein |
| | | V$MYCMAX.02 | c-Myc/Max heterodimer |
| | | V$NMYC.01 | N-Myc |
| | | V$ATF6.01 | Member of b-zip family, induced by ER damage/stress |
| | | V$USF.01 | upstream stimulating factor |
| | | V$MYCMAX.01 | c-Myc/Max heterodimer |
| | | V$MAX.01 | Max |
| | | V$ARNT.01 | AhR nuclear translocator homodimers |
| | | V$SREBP.01 | Sterol regulatory element binding protein 1 and 2 |
| V$ECAT | Enhancer-CcAaT binding factors | V$NFY.02 | nuclear factor Y (Y-box binding factor) |
| | | V$NFY.03 | nuclear factor Y (Y-box binding factor) |
| | | V$NFY.01 | nuclear factor Y (Y-box binding factor) |
| V$EGRF | EGR/nerve growth Factor Induced protein C & rel. fact. | V$EGR1.01 | Egr-1/Krox-24/NGFI-A immediate-early gene product |
| | | V$EGR2.01 | Egr-2/Krox-20 early growth response gene product |
| | | V$EGR3.01 | early growth response gene 3 product |
| | | V$NGFIC.01 | nerve growth factor-induced protein C |
| | | V$WT1.01 | Wilms Tumor Suppressor |
| V$EKLF | Erythroid krueppel like factor | V$EKLF.01 | Erythroid krueppel like factor (EKLF) |
| V$ETSF | Human and murine ETS1 Factors | V$CETS1P54.01 | c-Ets-1(p54) |
| | | V$NRF2.01 | nuclear respiratory factor 2 |
| | | V$GABP.01 | GABP: GA binding protein |
| | | V$ELK1.02 | Elk-1 |
| | | V$FLI.01 | ETS family member FLI |
| | | V$ETS2.01 | c-Ets-2 binding site |
| | | V$ETS1.01 | c-Ets-1 binding site |
| | | V$ELK1.01 | Elk-1 |

TABLE 17-continued

GENOMATIX MATRIX FAMILY LIBRARY INFORMATION
Versions 2.4 to 4.1

| | | | |
|---|---|---|---|
| | | V$PU1.01 | Pu.1 (Pu120) Ets-like transcription factor identified in lymphoid B-cells |
| V$EVI1 | EVI1-myleoid transforming protein | V$EVI1.06 | Ecotropic viral integration site 1 encoded factor |
| | | V$EVI1.02 | Ecotropic viral integration site 1 encoded factor |
| | | V$EVI1.03 | Ecotropic viral integration site 1 encoded factor |
| | | V$EVI1.05 | Ecotropic viral integration site 1 encoded factor |
| | | V$EVI1.04 | Ecotropic viral integration site 1 encoded factor |
| | | V$EVI1.01 | Ecotropic viral integration site 1 encoded factor |
| V$FKHD | Fork Head Domain factors | V$HFH1.01 | HNF-3/Fkh Homolog 1 |
| | | V$HFH2.01 | HNF-3/Fkh Homolog 2 |
| | | V$HFH3.01 | HNF-3/Fkh Homolog 3 (=Freac-6) |
| | | V$HFH8.01 | HNF-3/Fkh Homolog-8 |
| | | V$XFD1.01 | Xenopus fork head domain factor 1 |
| | | V$XFD2.01 | Xenopus fork head domain factor 2 |
| | | V$XFD3.01 | Xenopus fork head domain factor 3 |
| | | V$HNF3B.01 | Hepatocyte Nuclear Factor 3beta |
| | | V$FREAC2.01 | Fork head RElated ACtivator-2 |
| | | V$FREAC3.01 | Fork head RElated ACtivator-3 |
| | | V$FREAC4.01 | Fork head RElated ACtivator-4 |
| | | V$FREAC7.01 | Fork head RElated ACtivator-7 |
| V$GATA | GATA binding factors | V$LMO2COM.02 | complex of Lmo2 bound to Tal-1, E2A proteins, and GATA-1, half-site 2 |
| | | V$GATA1.04 | GATA-binding factor 1 |
| | | V$GATA1.05 | GATA-binding factor 1 |
| | | V$GATA2.01 | GATA-binding factor 2 |
| | | V$GATA2.02 | GATA-binding factor 2 |
| | | V$GATA3.01 | GATA-binding factor 3 |
| | | V$GATA3.02 | GATA-binding factor 3 |
| | | V$GATA.01 | GATA-binding site (consensus) |
| | | V$GATA1.03 | GATA-binding factor 1 |
| | | V$GATA1.01 | GATA-binding factor 1 |
| | | V$GATA1.02 | GATA-binding factor 1 |
| V$GFI1 | Growth Factor Independence-transcriptional repressor | V$GFI1.01 | growth factor independence 1 zinc finger protein acts as transcriptional repressor |
| V$GKLF | Gut-enriched Krueppel Like binding Factor | V$GKLF.01 | gut-enriched Krueppel-like factor |
| V$GREF | Glucocorticoid responsive and related elements | V$GRE.01 | Glucocorticoid receptor, C2C2 zinc finger protein binds glucocorticoid dependent to GREs |
| | | V$ARE.01 | Androgene receptor binding site |
| | | V$PRE.01 | Progesterone receptor binding site |
| V$HAML | Human Acute Myelogenous Leukemia factors | V$AML1.01 | runt-factor AML-1 |
| V$HEAT | HEATshock factors | V$HSF1.01 | heat shock factor 1 |

TABLE 17-continued

GENOMATIX MATRIX FAMILY LIBRARY INFORMATION
Versions 2.4 to 4.1

| | | | |
|---|---|---|---|
| V$HEN1 | E-box binding factor without transcript. activation | V$HEN1.01<br>V$HEN1.02 | HEN1<br>HEN1 |
| V$HMTB | Human muscle-specific Mt binding site | V$MTBF.01 | muscle-specific Mt binding site |
| V$HNF1 | Hepatic Nuclear Factor 1 | V$HNF1.01<br>V$HNF1.02 | hepatic nuclear factor 1<br>Hepatic nuclear factor 1 |
| V$HNF4 | Hepatic Nuclear Factor 4 | V$HNF4.01<br>V$HNF4.02 | Hepatic nuclear factor 4<br>Hepatic nuclear factor 4 |
| V$HOMS | Homeodomain subfamily S8 | V$S8.01 | Binding site for S8 type homeodomains |
| V$HOXF | Factors with moderate activity to homeodomain consensus sequence | V$HOXA9.01<br><br>V$HOX1-3.01 | Member of the vertebrate HOX - cluster of homeobox factors<br>Hox-1.3, vertebrate homeobox protein |
| V$IKRS | Ikaros zinc finger family | V$LYF1.01 | LyF-1 (Ikaros 1), enriched in B and T lymphocytes |
| | | V$IK2.01 | Ikaros 2, potential regulator of lymphocyte differentiation |
| | | V$IK1.01 | Ikaros 1, potential regulator of lymphocyte differentiation |
| | | V$IK3.01 | Ikaros 3, potential regulator of lymphocyte differentiation |
| V$IRFF | Interferon Regulatory Factors | V$IRF1.01 | interferon regulatory factor 1 |
| | | V$IRF2.01 | interferon regulatory factor 2 |
| | | V$ISRE.01 | interferon-stimulated response element |
| V$LEFF | LEF1/TCF | V$LEF1.01 | TCF/LEF-1, involved in the Wnt signal transduction pathway |
| V$LTUP | Lentiviral Tata UPstream element | V$TAACC.01 | Lentiviral TATA upstream element |
| V$MEF2 | MEF2-myocyte-specific enhancer-binding factor | V$MEF2.05<br>V$MEF2.01 | MEF2<br>myogenic enhancer factor 2 |
| | | V$HMEF2.01<br>V$MMEF2.01<br>V$RSRFC4.01 | myocyte enhancer factor<br>myocyte enhancer factor<br>related to serum response factor, C4 |
| | | V$RSRFC4.02 | related to serum response factor, C4 |
| | | V$AMEF2.01<br>V$MEF2.02 | myocyte enhancer factor<br>myogenic MADS factor MEF-2 |
| | | V$MEF2.03 | myogenic MADS factor MEF-2 |
| | | V$MEF2.04 | myogenic MADS factor MEF-2 |
| V$MEF3 | MEF3 BINDING SITES | V$MEF3.01 | MEF3 binding site, present in skeletal muscle-specific transcriptional enhancers |
| V$MEIS | Homeodomain factor aberrantly expressed in myeloid leukemia | V$MEIS1.01 | Homeobox protein MEIS1 binding site |
| V$MINI | Muscle INItiator | V$MUSCLE_INI.01 | Muscle Initiator Sequence |
| | | V$MUSCLE_INI.02 | Muscle Initiator Sequence |
| | | V$MUSCLE_INI.03 | Muscle Initiator Sequence |
| V$MOKF | Mouse Krueppel like factor | V$MOK2.01 | Ribonucleoprotein associated zinc finger protein MOK-2 |
| V$MTF1 | Metal induced transcription factor | V$MTF-1.01 | Metal transcription factor 1, MRE |

TABLE 17-continued

GENOMATIX MATRIX FAMILY LIBRARY INFORMATION
Versions 2.4 to 4.1

| | | | |
|---|---|---|---|
| V$MYOD | MYOblast Determining factor | V$MYOD.02 | myoblast determining factor |
| | | V$MYF5.01 | Myf5 myogenic bHLH protein |
| | | V$MYOD.01 | myoblast determination gene product |
| | | V$LMO2COM.01 | complex of Lmo2 bound to Tal-1, E2A proteins, and GATA-1, half-site 1 |
| | | V$E47.01 | MyoD/E47 and MyoD/E12 dimers |
| | | V$E47.02 | TAL1/E47 dimers |
| V$MYOF | MYOgenic Factors | V$NF1.01 | nuclear factor 1 |
| | | V$MYOGNF1.01 | myogenin/nuclear factor 1 or related factors |
| V$MYT1 | *Xenopus* MYT1 C2HC zinc finger protein | V$MYT1.02 | MyT1 zinc finger transcription factor involved in primary neurogenesis |
| | | V$MYT1.01 | MyT1 zinc finger transcription factor involved in primary neurogenesis |
| V$MZF1 | Myeloid Zinc Finger 1 factors | V$MZF1.01 | MZF1 |
| V$NFAT | Nuclear Factor of Activated T-cells | V$NFAT.01 | Nuclear factor of activated T-cells |
| V$NFKB | Nuclear Factor Kappa B/c-rel | V$CREL.01 | c-Rel |
| | | V$NFKAPPAB.01 | NF-kappaB |
| | | V$NFKAPPAB65.01 | NF-kappaB (p65) |
| | | V$NFKAPPAB50.01 | NF-kappaB (p50) |
| | | V$NFKAPPAB.02 | NF-kappaB |
| | | V$NFKAPPAB.03 | NF-kappaB |
| V$NKXH | NKX - Homeodomain sites | V$NKX25.01 | homeo domain factor Nkx-2.5/Csx, tinman homolog, high affinity sites |
| | | V$NKX25.02 | homeo domain factor Nkx-2.5/Csx, tinman homolog low affinity sites |
| | | V$NKX31.01 | prostate-specific homeodomain protein NKX3.1 |
| V$NOLF | Neuron-specific-OLFactory factor | V$OLF1.01 | olfactory neuron-specific factor |
| V$NRSF | Neuron-Restrictive Silencer Factor | V$NRSF.01 | neuron-restrictive silencer factor |
| | | V$NRSE.01 | neural-restrictive-silencer-element |
| V$OAZF | Olfactory associated zinc finger protein | V$ROAZ.01 | Rat C2H2 Zn finger protein involved in olfactory neuronal differentiation |
| V$OCT1 | OCTamer binding protein | V$OCT1.02 | octamer-binding factor 1 |
| | | V$OCT1.06 | octamer-binding factor 1 |
| | | V$OCT.01 | Octamer binding site (OCT1/OCT2 consensus) |
| | | V$OCT1.05 | octamer-binding factor 1 |
| | | V$OCT1.04 | octamer-binding factor 1 |
| | | V$OCT1.03 | octamer-binding factor 1 |
| | | V$OCT1.01 | octamer-binding factor 1 |
| V$OCTB | OCT6 Binding factors_astrocytes + glioblastoma cells | V$TST1.01 | POU-factor Tst-1/Oct-6 |
| V$OCTP | OCT1 binding factor (POU-specific domain) | V$OCT1P.01 | octamer-binding factor 1, POU-specific domain |
| V$P53F | p53 tumor suppr.-neg. regulat. of the tumor suppr. Rb | V$P53.01 | tumor suppressor p53 |
| V$PAX1 | PAX-1 binding site | V$PAX1.01 | Pax1 paired domain protein, expressed in the developing vertebral column of mouse embryos |
| V$PAX3 | PAX-3 binding sites | V$PAX3.01 | Pax-3 paired domain protein, expressed in |

TABLE 17-continued

GENOMATIX MATRIX FAMILY LIBRARY INFORMATION
Versions 2.4 to 4.1

| | | | |
|---|---|---|---|
| V$PAX4 | Heterogeneous PAX-4 binding sites | V$PAX4.01 | embryogenesis, mutations correlate to Waardenburg Syndrome Pax-4 paired domain protein, together with PAX-6 involved in pancreatic development |
| V$PAX5 | PAX-5/PAX-9 B-cell-specific activating protein | V$PAX9.01 | zebrafish PAX9 binding sites |
| | | V$PAX5.01 | B-cell-specific activating protein |
| | | V$PAX5.02 | B-cell-specific activating protein |
| V$PAX6 | Activ. involved in Iris development in the mouse eye | V$PAX6.01 | Pax-6 paired domain protein |
| V$PAX8 | PAX-2/5/8 binding sites | V$PAX8.01 | PAX 2/5/8 binding site |
| V$PBXF | Homeo domain factor PBX-1 | V$PBX1.01 | homeo domain factor Pbx-1 |
| V$PCAT | Promoter-CcAaT binding factors | V$ACAAT.01 | Avian C-type LTR CCAAT box |
| | | V$CAAT.01 | cellular and viral CCAAT box |
| | | V$CLTR_CAAT.01 | Mammalian C-type LTR CCAAT box |
| V$PDX1 | Pancreatic and intestinal homeodomain transcr. factor | V$PDX1.01 | Pdx1 (IDX1/IPF1) pancreatic and intestinal homeodomain TF |
| | | V$ISL1.01 | Pancreatic and intestinal lim-homeodomain factor |
| V$PERO | PERoxisome proliferator-activated receptor | V$PPARA.01 | PPAR/RXR heterodimers |
| V$PIT1 | GHF-1 pituitary specific pou domain transcription factor | V$PIT1.01 | Pit1, GHF-1 pituitary specific pou domain transcription factor |
| V$RARF | Nuclear receptor for retenoic acid | V$RAR.01 | Retinoic acid receptor, member of nuclear receptors |
| | | V$RTR.01 | Retinoid receptor-related testis-associated receptor (GCNF/RTR) |
| V$RBIT | Regulator of B-Cell IgH transcription | V$BRIGHT.01 | Bright, B cell regulator of IgH transcription |
| V$RBPF | RBPJ-kappa | V$RBPJK.01 | Mammalian transcriptional repressor RBP-Jkappa/CBF1 |
| V$REBV | Epstein-Barr virus transcription factor R | V$EBVR.01 | Epstein-Barr virus transcription factor R |
| V$RORA | Estrogen receptor and rar-Rel. Orphan Receptor Alpha | V$RORA1.01 | RAR-related orphan receptor alpha1 |
| | | V$RORA2.01 | RAR-related orphan receptor alpha2 |
| | | V$ER.01 | estrogen receptor |
| V$RREB | Ras-REsponsive element Binding protein | V$RREB1.01 | Ras-responsive element binding protein 1 |
| V$RXRF | RXR heterodimer binding sites | V$FXRE.01 | Farnesoid X - activated receptor (RXR/FXR dimer) |
| | | V$VDR_RXR.01 | VDR/RXR Vitamin D receptor RXR heterodimer site |
| | | V$VDR_RXR.02 | VDR/RXR Vitamin D receptor RXR heterodimer site |
| | | V$LXRE.01 | Nuclear receptor involved in the regulation lipid homeostasis |
| V$SATB | Special AT-rich sequence binding protein | V$SATB1.01 | Special AT-rich sequence-binding protein 1, predominantly expressed in thymocytes, |

TABLE 17-continued

GENOMATIX MATRIX FAMILY LIBRARY INFORMATION
Versions 2.4 to 4.1

| | | | |
|---|---|---|---|
| | | | binds to matrix attachment regions (MARs) |
| V$SEF1 | SEF1 protein in mouse Retrovirus SL3-3 | V$SEF1.01 | SEF1 binding site |
| V$SF1F | Vertebrate steroidogenic factor | V$SF1.01 | SF1 steroidogenic factor 1 |
| V$SMAD | Vertebrate SMAD family of transcription factors | V$SMAD3.01 | Smad3 transcription factor involved in TGF-beta signaling |
| | | V$SMAD4.01 | Smad4 transcription factor involved in TGF-beta signaling |
| | | V$FAST1.01 | FAST-1 SMAD interacting protein |
| V$SORY | SOx/sRY-sex/testis determinig and related HMG Box factors | V$SOX5.01 | Sox-5 |
| | | V$SRY.01 | sex-determining region Y gene product |
| | | V$HMGIY.01 | HMGI(Y) high-mobility-group protein I (Y), architectural transcription factor organizing the framework of a nuclear protein-DNA transcriptional complex |
| | | V$SOX9.01 | SOX (SRY-related HMG box) |
| V$SP1F | GC-Box factor_SP1/GC | V$SP1-01 | stimulating protein 1 SP1, ubiquitous zinc finger transcription factors |
| | | V$GC.01 | GC box elements |
| V$SRFF | Serum Response element binding factor | V$SRF.02 | serum response factor |
| | | V$SRF.03 | serum responsive factor |
| | | V$SRF.01 | serum response factor |
| V$STAT | Signal Transducer and Activator of Transcript. factors | V$STAT.01 | signal transducers and activators of transcription |
| | | V$STAT5.01 | STAT5: signal transducer and activator of transcription 5 |
| | | V$STAT6.01 | STAT6: signal transducer and activator of transcription 6 |
| | | V$STAT1.01 | signal transducer and activator of transcription 1 |
| | | V$STAT3.01 | signal transducer and activator of transcription 3 |
| V$T3RH | Viral homolog of thyroid hormon recetor alpha1 (AEV vErbA) | V$T3R.01 | vErbA, viral homolog of thyroid hormone receptor alpha1 |
| V$TBPF | Tata-Binding Protein Factor | V$TATA.02 | Mammalian C-type LTR TATA box |
| | | V$ATATA.01 | Avian C-type LTR TATA box |
| | | V$TATA.01 | cellular and viral TATA box elements |
| | | V$MTATA.01 | Muscle TATA box |
| V$TCFF | TCF11 transcription Factor | V$TCF11.01 | TCF11/KCR-F1/Nrf1 homodimers |
| V$TEAF | TEA/ATTS DNA binding domain factors | V$TEF1.01 | TEF-1 related muscle factor |
| V$TTFF | Thyroid transcription factor-1 | V$TTF1.01 | Thyroid transcription factor-1 (TTF1) binding site |
| V$VBPF | chicken Vitellogenin gene Binding Protein factor | V$VBP.01 | PAR-type chicken vitellogenin promoter-binding protein |
| V$VMYB | AMV-viral myb oncogene | V$VMYB.02 | v-Myb |
| | | V$VMYB.01 | v-Myb |
| V$WHZF | Winged Helix and ZF5 binding sites | V$WHN.01 | winged helix protein, involved in hair keratinization and thymus epithelium differentiation |

TABLE 17-continued

GENOMATIX MATRIX FAMILY LIBRARY INFORMATION
Versions 2.4 to 4.1

| Family | Family Information | Matrix Name | Matrix Information |
|---|---|---|---|
| V$XBBF | X-box binding Factor | V$RFX1.01 | X-box binding protein RFX1 |
| | | V$RFX1.02 | X-box binding protein RFX1 |
| | | V$MIF1.01 | MIB-1/RFX1 complex |
| V$XSEC | *Xenopus* SEleno Cystein t-RNA activiating factor | V$STAF.02 | Se-Cys tRNA gene transcription activating factor |
| | | V$STAF.01 | Se-Cys tRNA gene transcription activating factor |
| V$YY1F | activator/repressor binding to transcr. init. site | V$YY1.01 | Yin and Yang 1 |
| V$ZBPF | Zinc binding protein factor | V$ZBP89.01 | Zinc finger transcription factor ZBP-89 |
| V$ZFIA | ZincFinger with InterAction domain factors | V$ZID.01 | zinc finger with interaction domain |

© Genomatix Software GmbH 1998-2002 - All rights reserved.
B. Changes from Family Library Version 2.4 to Version 3.0
Matrix Family Library Version 3.0 (November 2002) contains 452 weight matrices in 216 families
(Vertebrates: 314 matrices in 128 families)
New weight matrices - Vertebrates

| Family | Family Information | Matrix Name | Matrix Information |
|---|---|---|---|
| V$AP1F | AP1 and related factors | V$BACH1.01 | BTB/POZ-bZIP transcription factor BACH1 forms heterodimers with the small Maf protein family |
| V$CIZF | CAS interating zinc finger protei | V$NMP4.01 | NMP4 (nuclear matrix protein 4)/CIZ (Cas-interacting zinc finger protein) |
| V$CREB | Camp-Responsive Element Binding proteins | V$ATF6.02 | Activating transcription factor 6, member of b-zip family, induced by ER stress |
| V$E4FF | Ubiquitous GLI-Krueppel like zinc finger involved in cell cycle regulation | V$E4F.01 | GLI-Krueppel-related transcription factor, regulator of adenovirus E4 promoter |
| V$GFI1 | Growth Factor Independence-transcriptional repressor | V$GfI1B.01 | Growth factor independence 1 zinc finger protein Gfi-1B |
| V$GLIF | GLI zinc finger family | V$GLI1.01 | Zinc finger transcription factor GLI1 |
| V$HAML | Human Acute Myelogenous Leukemia factors | V$AML3.01 | Runt-related transcription factor 2/CBFA1 (core-binding factor, runt domain, alpha subunit 1) |
| V$HESF | Vertebrate homologues of enhancer of split complex | V$HES1.01 | *Drosophila* hairy and enhancer of split homologue 1 (HES-1) |
| V$HIFF | Hypoxia inducible factor, bHLH/PAS protein family | V$HIF1.01 | Hypoxia induced factor-1 (HIF-1) |
| | | V$HIF1.02 | Hypoxia inducible factor, bHLH/PAS protein family |
| V$HNF6 | Onecut Homeodomain factor HNF6 | V$HNF6.01 | Liver enriched Cut - Homeodomain transcription factor HNF6 (ONECUT) |
| V$HOXF | Factors with moderate activity to homeo domain consensus sequence | V$CRX.01 | Cone-rod homeobox-containing transcription factor/otx-like homeobox gene |
| | | V$EN1.01 | Homeobox protein engrailed (en-1) |

TABLE 17-continued

GENOMATIX MATRIX FAMILY LIBRARY INFORMATION
Versions 2.4 to 4.1

| | | | |
|---|---|---|---|
| | | V$PTX1.01 | Pituitary Homeobox 1 (Ptx1) |
| V$IRFF | Interferon Regulatory Factors | V$IRF3.01 | Interferon regulatory factor 3 (IRF-3) |
| | | V$IRF7.01 | Interferon regulatory factor 7 (IRF-7) |
| V$MAZF | Myc associated zinc fingers | V$MAZ.01 | Myc associated zinc finger protein (MAZ) |
| | | V$MAZR.01 | MYC-associated zinc finger protein related transcription factor |
| V$MEIS | Homeodomain factor aberrantly expressed in myeloid leukemia | V$MEIS1.01 | Binding site of monomeric Meis1 homeodomain protein |
| V$MITF | Microphthalmia transcription factor | V$MIT.01 | MIT (microphthalmia transcription factor) and TFE3 |
| V$MOKF | Mouse Krueppel like factor | V$MOK2.02 | Ribonucleoprotein associated zinc finger protein MOK-2 (human) |
| V$NEUR | NeuroD, Beta2, HLH domain | V$NEUROD1.01 | DNA binding site for NEUROD1 (BETA-2/E47 dimer) |
| V$NF1F | Nuclear Factor 1 | V$NF1.02 | Nuclear factor 1 (CTF1) |
| V$NKXH | NKX/DLX - Homeodomain sites | V$DLX1.01 | DLX-1, -2, and -5 binding sites |
| | | V$DLX3.01 | Distal-less 3 homeodomain transcription facto |
| | | V$HMX3.01 | H6 homeodomain HMX3/Nkx5.1 transcription factor |
| | | V$MSX.01 | Homeodomain proteins MSX-1 and MSX-2 |
| | | V$MSX2.01 | Muscle segment homeo box 2, homologue of *Drosophila* (HOX 8) |
| V$NRLF | Neural retina leucine zipper | V$NRL.01 | Neural retinal basic leucine zipper factor (bZIP) |
| V$PARF | PAR/bZIP family | V$DBP.01 | Albumin D-box binding protein |
| V$PBXC | PBX1 - MEIS1 complexes | V$PBX1_MEIS1.01 | Binding site for a Pbx1/Meis1 heterodimer |
| | | V$PBX1_MEIS1.02 | Binding site for a Pbx1/Meis1 heterodimer |
| | | V$PBX1_MEIS1.03 | Binding site for a Pbx1/Meis1 heterodimer |
| V$PLZF | C2H2 zinc finger protein PLZF | V$PLZF.01 | Promyelocytic leukemia zink finger (TF with nine Krueppel-like zink fingers) |
| V$PXRF | Pregnane X receptor | V$PXRCAR.01 | Halfsite of PXR (pregnane X receptor)/RXR resp. CAR (constitutive androstane receptor)/RXR heterodimer binding site |
| V$RORA | v-ERB and rar-related Orphan Receptor Alpha | V$NBRE.01 | Monomers of the nur subfamily of nuclear receptors (nur77, nurr1, nor-1) |
| V$SF1F | Vertebrate steroidogenic factor | V$FTF.01 | Alpha (1)-fetoprotein transcription factor (FTF), liver receptor homologue-1 (LHR-1) |
| V$SIXF | Sine oculis (SIX) homeodomain factors | V$SIX3.01 | SIX3/SIXdomain (SD) and Homeodomain (HD) transcription factor |
| V$TALE | TALE Homeodomain class recognizing TG motives | V$TGIF.01 | TG-interacting factor belonging to TALE class of homeodomain factors |

TABLE 17-continued

GENOMATIX MATRIX FAMILY LIBRARY INFORMATION
Versions 2.4 to 4.1

| | | | |
|---|---|---|---|
| V$ZF5F | ZF5 POZ domain zinc finger | V$ZF5.01 | Zinc finger/POZ domain transcription factor |

Weight matrices renamed
V$MEIS1.01 renamed to V$MEIS1_HOXA9.01
Weight matrices moved to other families
V$BEL1.01 moved from V$AP1F to V$BEL1
V$NF1.01 moved from V$MYOF to V$NF1
V$ER.01 moved from V$RORA to V$EREF
V$T3R.01 moved from V$T3RH to V$RORA
V$CLTR_CAAT.01 moved from V$PCAT to V$RCAT
V$FAST1.01 moved from V$SMAD to V$FAST
Weight matrices removed
V$MUSCLE_INI.03

C. Changes from Family Library Version 3.0 to Version 3.1
Matrix Family Library Version 3.1 contains 456 weight matrices in 216 families
(Vertebrates: 318 matrices in 128 families)
New weight matrices - Vertebrates

| Family | Family Information | Matrix Name | Matrix Information |
|---|---|---|---|
| V$LEFF | LEF1/TCF | V$LEF1.02 | TCF/LEF-1, involved in the Wnt signal transduction pathway |
| V$PAX2 | PAX-2 binding sites | V$PAX2.01 | Zebrafish PAX2 paired domain protein |
| V$PAX5 | PAX-5/PAX-9 B-cell-specific activating protein | V$PAX5.03 | PAX5 paired domain protein |
| V$PAX6 | PAX-4/PAX-6 paired domain binding sites | V$PAX4_PD.01 | PAX4 paired domain binding site |
| | | V$PAX6.02 | PAX6 paired domain and homeodomain are required for binding to this site |
| V$ZBPF | Zinc binding protein factor | V$ZF9.01 | Core promoter-binding protein (CPBP) with 3 Krueppel-type zinc fingers |

Weight matrices modified
V$AML1.01
V$AML3.01
Weight matrices moved to other families
V$ARNT.01 moved from V$EBOX to V$HIFF (ARNT is a synonym for HIF1 B)
Weight matrices removed
V$SEF1.01
V$OCT1.03
Version 3.1.1 (April 2003)
Matrices V$IRF3.01 and V$IRF7.01 corrected.
Version 3.1.2 (June 2003)
Matrix V$Gfl1B.01 corrected.

D. Changes from Family Library Version 3.1 to Version 3.3
Matrix Family Library Version 3.3 (August 2003) contains 485 weight matrices
in 233 families
(Vertebrates: 326 matrices in 130 families)
New weight matrices - Vertebrates

| Family | Family Information | Matrix Name | Matrix Information |
|---|---|---|---|
| V$EREF | Estrogen Response Elements | V$ER.02 | Canonical palindromic estrogen response element (ERE) |
| V$SP1F | GC-Box factors_SP1/GC | V$BTEB3.01 | Basic transcription element (BTE) binding protein, BTEB3, FKLF-2 |
| V$CDEF | Cell cycle regulators: Cell cycle dependent element | V$CDE.01 | Cell cycle-dependent element, CDF-1 binding site (CDE/CHR tandem elements regulate cell cycle dependent repression) |
| V$CHRF | Cell cycle regulators: Cell cycle homology | V$CHR.01 | Cell cycle gene homology region (CDE/CHR tandem |

TABLE 17-continued

GENOMATIX MATRIX FAMILY LIBRARY INFORMATION
Versions 2.4 to 4.1

| | | | |
|---|---|---|---|
| | element | | elements regulate cell cycle dependent repression) |
| V$HIFF | Hypoxia inducible factor, bHLH/ PAS protein family | V$CLOCK_BMAL1.01 | Binding site of Clock/BMAL1 heterodimer, NPAS2/BMAL1 heterodimer |
| V$FKHD | Fork Head Domain factors | V$FKHRL1.01 | Fkh-domain factor FKHRL1 (FOXO) |
| V$P53F | p53 tumor suppr.- neg. regulat. of the tumor suppr. Rb | V$P53.02 | Tumor suppressor p53 (5' half site) |
| | | V$P53.03 | Tumor suppressor p53 (3' half site) |

Weight matrices modified
V$GFI1.01

E. Changes from Family Library Version 3.3 to Version 4.0
Matrix Family Library Version 4.0 (November 2003) contains 535 weight matrices in 253 families
(Vertebrates: 339 matrices in 136 families)
New weight matrices - Vertebrates

| Family | Family Information | Matrix Name | Matrix Information |
|---|---|---|---|
| V$AARF | AARE binding factors | V$AARE.01 | Amino acid response element, ATF4 binding site |
| V$AP1R | MAF and AP1 related factors | V$BACH2.01 | Bach2 bound TRE |
| | | V$NFE2L2.01 | Nuclear factor (erythroid-derived 2)-like 2, NRF2 |
| V$CDXF | Vertebrate caudal related homeodomain protein | V$CDX1.01 | Intestine specific homeodomain factor CDX-1 |
| V$DEAF | Homolog to deformed epidermal autoregulatory factor-1 from D. melanogaster | V$NUDR.01 | NUDR (nuclear DEAF-1 related transcriptional regulator protein |
| V$ETSF | Human and murine ETS1 factors | V$ELF2.01 | Ets - family member ELF-2 (NERF1a) |
| V$GABF | GA-boxes | V$GAGA.01 | GAGA-Box |
| V$HNF1 | Hepatic Nuclear Factor 1 | V$HNF1.03 | Hepatic nuclear factor 1 |
| V$HOXF | Factors with moderate activity to homeo domain consensus sequence | V$GSC.01 | Vertebrate bicoid-type homeodomain protein Goosecoid |
| V$LHXF | Lim homeodomain factors | V$LHX3.01 | Homeodomain binding site in LIM/Homeodomain factor LHX3 |
| V$NKXH | NKX/DLX - homeodomain sites | V$NKX32.01 | Homeodomain protein NKX3.2 (BAPX1, NKX3B, Bagpipe homolog) |
| V$RBPF | RBPJ - kappa | V$RBPJK.02 | Mammalian transcriptional repressor RBP-Jkappa/CBF1 |
| V$RP58 | RP58 (ZFP238) zinc finger protein | V$RP58.01 | Zinc finger protein RP58 (ZNF238), associated preferentially with heterochromatin |

Weight matrices modified
V$GRE.01
V$NFY.03
Weight matrices moved to other families
V$BACH1.01 moved from V$AP1F to V$AP1R
V$NFE2.01 moved from V$AP1F to V$AP1R
V$TCF11MAFG.01 moved from V$AP1F to V$AP1R
V$VMAF.01 moved from V$AP1F to V$AP1R

F. Changes from Family Library Version 4.0 to Version 4.1
Matrix Family Library Version 4.1 (February 2004) contains 564 weight matrices in 262 families
(Vertebrates: 356 matrices in 138 families)
New weight matrices - Vertebrates

| Family | Family Information | Matrix Name | Matrix Information |
|---|---|---|---|
| V$BNCF | Basonuclein rDNA transcription factor (PolI) | V$BNC.01 | Basonuclin, cooperates with USF1 in rDNA PolI transcription) |

TABLE 17-continued

GENOMATIX MATRIX FAMILY LIBRARY INFORMATION
Versions 2.4 to 4.1

| | | | |
|---|---|---|---|
| V$CMYB | C-myb, cellular transcriptional activator | V$CMYB.02 | c-Myb, important in hematopoesis, cellular equivalent to avian myoblastosis virus oncogene v-myb |
| V$CP2F | CP2-erythrocyte Factor related to *drosophila* Elf1 | V$CP2.02 | LBP-1c (leader-binding protein-1c), LSF (late SV40 factor), CP2, SEF (SAA3 enhancer factor) |
| V$EKLF | Basic and erythroid Krueppel like factors | V$BKLF.01 | Basic krueppel-like factor (KLF3) |
| V$HAND | bHLH transcription factor dimer of HAND2 and E12 | V$HAND2_E12.01 | Heterodimers of the bHLH transcription factors HAND2 (Thing2) and E12 |
| V$HIFF | Hypoxia inducible factor, bHLH/PAS protein family | V$DEC1.01 | Basic helix-loop-helix protein known as Dec1, Stra13 or Sharp2 |
| V$HNF6 | Onecut Homeodomain factor HNF6 | V$OC2.01 | CUT-homeodomain transcription factor Onecut-2 |
| V$HOXF | Factors with moderate activity to homeo domain consensus sequence | V$OTX2.01 | Homeodomain transcription factor Otx2 (homolog of *Drosophila* orthodenticle) |
| | | V$GSH1.01 | Homeobox transcription factor Gsh-1 |
| V$IRFF | Interferon Regulatory Factors | V$IRF4.01 | Interferon regulatory factor (IRF)-related protein (NF-EM5, PIP, LSIRF, ICSAT) |
| V$LHXF | Lim homeodomain factors | V$LMX1B.01 | LIM-homeodomain transcription factor |
| V$MYT1 | MYT1 C2HC zinc finger protein | V$MYT1L.01 | Myelin transcription factor 1-like, neuronal C2HC zinc finger factor 1 |
| V$NEUR | NeuroD, Beta2, HLH domain | V$NEUROG.01 | Neurogenin 1 and 3 (ngn1/3) binding sites |
| V$VMYB | AMV-viral myb oncogene | V$VMYB.03 | v-Myb, viral myb variant from transformed BM2 cells |
| | | V$VMYB.04 | v-Myb, AMV v-myb |
| | | V$VMYB.05 | v-Myb, variant of AMV v-myb |
| V$ZBPF | Zinc binding protein factor | V$ZNF202.01 | Transcriptional repressor, binds to elements found predominantly in genes that participate in lipid metabolism |

Weight matrices modified
V$CMYB.01
V$PTX1.01
Copyright © Genomatix Software GmbH 1998-2004 - All rights reserved

EXAMPLE 6

Summary of Design for Particular Selectable Genes

TF binding Sites and Search Parameters

Each TF binding site ("matrix") belongs to a matrix family that groups functionally similar matrices together, eliminating redundant matches by MatInspector professional (the search program). Searches were limited to vertebrate TF binding sites. Searches were performed by matrix family, i.e., the results show only the best match from a family for each site. MatInspector default parameters were used for the core and matrix similarity values (core similarity=0.75, matrix similarity=optimized).

TABLE 18

Gene Designations

| Sequence | Description | Matrix Library |
|---|---|---|
| A. Synthetic hygromycin gene | | |
| hyg | from pcDNA3.1/Hygro | Not applicable |
| hhyg | humanized ORF | Not applicable |
| hhyg-1 | First removal of undesired sequence matches | Ver 3.1.2 June 2003 |
| hhyg-2 | Second removal of undesired sequence matches | Ver 3.1.2 June 2003 |

TABLE 18-continued

Gene Designations

| Sequence | Description | Matrix Library |
|---|---|---|
| hhyg-3 | Third removal of undesired sequence matches | Ver 3.1.2 June 2003 |
| hHygro | Changes to ORF and add linker | Ver 3.3 August 2003 |
| hhyg-4 | Fourth removal of undesired sequence matches | Ver 3.3 August 2003 |

B. Synthetic neomycin gene

| | | |
|---|---|---|
| neo | from pCI-neo or psiSTRIKE neo | Not applicable |
| hneo | humanized ORF | Not applicable |
| hneo-1 | First removal of undesired sequence matches | Ver 3.1.2 June 2003 |
| hneo-2 | Second removal of undesired sequence matches | Ver 3.1.2 June 2003 |
| hneo-3 | Third removal of undesired sequence matches | Ver 3.1.2 June 2003 |
| hneo-4 | Changed 5' and 3' flanking regions/cloning sites | Ver 4.1 February 2004 |
| hneo-5 | Fourth removal of undesired sequence matches | Ver 4.1 February 2004 |

C. Synthetic puromycin gene

| | | |
|---|---|---|
| puro | from psiSTRIKE puromycin | Not applicable |
| hpuro | humanized ORF | Not applicable |
| hpuro-1 | First removal of undesired sequence matches | Ver 4.1 February 2004 |
| hpuro-2 | Second removal of undesired sequence matches | Ver 4.1 February 2004 |

Note:
the above sequence names designate the ORF only (except for Hhygro which includes flanking sequences). Addition of "F" to the sequence name indicates the presence of up- and down-stream flanking sequences. Additional letters (e.g., "B") indicate changes were made only to the flanking regions

TABLE 19

Sequences in Synthetic Hygromycin Genes

| Family/matrix** | Further Information |
|---|---|

TFBS in hhyg
Before removal of TFBS from hhyg (94 matches)

| Family/matrix** | Further Information |
|---|---|
| V$PCAT/CAAT.01 | cellular and viral CCAAT box |
| V$MINI/MUSCLE_INI.02 | Muscle Initiator Sequence |
| V$MINI/MUSCLE_INI.01 | Muscle Initiator Sequence |
| V$ETSF/PU1.01 | Pu.1 (Pu120) Ets-like transcription factor identified in lymphoid B-cells |
| V$AHRR/AHRARNT.02 | Aryl hydrocarbon/Arnt heterodimers, fixed core |
| V$EGRF/EGR3.01 | early growth response gene 3 product |
| V$AP4R/AP4.01 | Activator protein 4 |
| V$EGRF/NGFIC.01 | Nerve growth factor-induced protein C |
| V$MAZF/MAZ.01 | Myc associated zinc finger protein (MAZ) |
| V$ZBPF/ZF9.01 | Core promoter-binding protein (CPBP) with 3 Krueppel-type zinc fingers |
| V$CREB/ATF6.02 | Activating transcription factor 6, member of b-zip family, induced by ER stress |
| V$EGRF/EGR3.01 | early growth response gene 3 product |
| V$ZBPF/ZF9.01 | Core promoter-binding protein (CPBP) with 3 Krueppel-type zinc fingers |
| V$HIFF/HIF1.02 | Hypoxia inducible factor, bHLH/PAS protein family |
| V$E2FF/E2F.01 | E2F, involved in cell cycle regulation, interacts with Rb p107 protein |
| V$AP4R/AP4.01 | Activator protein 4 |
| V$HEN1/HEN1.02 | HEN1 |
| V$MYOD/E47.01 | MyoD/E47 and MyoD/E12 dimers |
| V$EGRF/EGR3.01 | early growth response gene 3 product |
| V$MOKF/MOK2.02 | Ribonucleoprotein associated zinc finger protein MOK-2 (human) |
| V$SP1F/GC.01 | GC box elements |
| V$NRSF/NRSE.01 | Neural-restrictive-silencer-element |
| V$RORA/RORA2.01 | RAR-related orphan receptor alpha2 |
| V$ZBPF/ZF9.01 | Core promoter-binding protein (CPBP) with 3 Krueppel-type zinc fingers |
| V$ZF5F/ZF5.01 | Zinc finger/POZ domain transcription factor |
| V$AHRR/AHRARNT.02 | Aryl hydrocarbon/Arnt heterodimers, fixed core |
| V$AP1F/TCF11MAFG.01 | TCF11/MafG heterodimers, binding to subclass of AP1 sites |
| V$EKLF/EKLF.01 | Erythroid krueppel like factor (EKLF) |
| V$NRSF/NRSF.01 | Neuron-restrictive silencer factor |
| V$NRSF/NRSE.01 | Neural-restrictive-silencer-element |
| V$EBOX/MYCMAX.03 | MYC-MAX binding sites |
| V$RXRF/FXRE.01 | Farnesoid X - activated receptor (RXR/FXR dimer) |
| V$AHRR/AHRARNT.02 | Aryl hydrocarbon/Arnt heterodimers, fixed core |
| V$WHZF/WHN.01 | Winged helix protein, involved in hair keratinization and thymus epithelium differentiation |
| V$EGRF/EGR1.01 | Egr-1/Krox-24/NGFI-A immediate-early gene product |
| V$SMAD/SMAD3.01 | Smad3 transcription factor involved in TGF-beta signaling |
| V$MOKF/MOK2.01 | Ribonucleoprotein associated zinc finger protein MOK-2 (mouse) |
| V$MYOD/MYOD.02 | Myoblast determining factor |
| V$E4FF/E4F.01 | GLI-Krueppel-related transcription factor, regulator of adenovirus E4 promoter |
| V$MOKF/MOK2.01 | Ribonucleoprotein associated zinc finger protein MOK-2 (mouse) |
| V$EGRF/EGR2.01 | Egr-2/Krox-20 early growth response gene product |
| V$EGRF/EGR3.01 | early growth response gene 3 product |
| V$HIFF/HIF1.02 | Hypoxia inducible factor, bHLH/PAS protein family |
| V$EBOX/USF.02 | Upstream stimulating factor |
| V$HIFF/ARNT.01 | AhR nuclear translocator homodimers |
| V$ZF5F/ZF5.01 | Zinc finger/POZ domain transcription factor |
| V$EBOX/ATF6.01 | Member of b-zip family, induced by ER damage/stress, binds to the ERSE in association with NF-Y |
| V$BEL1/BEL1.01 | Bel-1 similar region (defined in Lentivirus LTRs) |
| V$NRSF/NRSE.01 | Neural-restrictive-silencer-element |
| V$MYOD/MYOD.01 | Myoblast determination gene product |
| V$NEUR/NEUROD1.01 | DNA binding site for NEUROD1 (BETA-2/E47 dimer) |
| V$AHRR/AHRARNT.01 | Aryl hydrocarbon receptor/Arnt heterodimers |
| V$HIFF/ARNT.01 | AhR nuclear translocator homodimers |
| V$VMYB/VMYB.02 | v-Myb |
| V$MOKF/MOK2.01 | Ribonucleoprotein associated zinc finger protein MOK-2 (mouse) |
| V$PAX5/PAX5.01 | B-cell-specific activating protein |
| V$PBXC/PBX1_MEIS1.02 | Binding site for a Pbx1/Meis1 heterodimer |
| V$MYOF/MYOGNF1.01 | Myogenin/nuclear factor 1 or related factors |
| V$SRFF/SRF.03 | Serum responsive factor |
| V$CP2F/CP2.01 | CP2 |
| V$OAZF/ROAZ.01 | Rat C2H2 Zn finger protein involved in olfactory neuronal differentiation |
| V$AHRR/AHR.01 | Aryl hydrocarbon/dioxin receptor |
| V$MINI/MUSCLE_INI.01 | Muscle Initiator Sequence |
| V$PAX5/PAX5.02 | B-cell-specific activating protein |
| V$ZBPF/ZF9.01 | Core promoter-binding protein (CPBP) with 3 Krueppel-type zinc fingers |
| V$EBOX/ATF6.01 | Member of b-zip family, induced by ER damage/stress, binds to the ERSE in association with NF-Y |

TABLE 19-continued

Sequences in Synthetic Hygromycin Genes

| Family/matrix** | Further Information |
|---|---|
| V$EGRF/NGFIC.01 | Nerve growth factor-induced protein C |
| V$ZF5F/ZF5.01 | Zinc finger/POZ domain transcription factor |
| V$AP4R/AP4.02 | Activator protein 4 |
| V$XBBF/MIF1.01 | MIBP-1/RFX1 complex |
| V$EGRF/EGR3.01 | early growth response gene 3 product |
| V$WHZF/WHN.01 | Winged helix protein, involved in hair keratinization and thymus epithelium differentiation |
| V$PAX5/PAX5.01 | B-cell-specific activating protein |
| V$WHZF/WHN.01 | Winged helix protein, involved in hair keratinization and thymus epithelium differentiation |
| V$PAX5/PAX5.01 | B-cell-specific activating protein |
| V$PAX5/PAX5.03 | PAX5 paired domain protein |
| V$PAX5/PAX5.03 | PAX5 paired domain protein |
| V$ZBPF/ZF9.01 | Core promoter-binding protein (CPBP) with 3 Krueppel-type zinc fingers |
| V$CP2F/CP2.01 | CP2 |
| V$MINI/MUSCLE_INI.02 | Muscle Initiator Sequence |
| V$AP2F/AP2.01 | Activator protein 2 |
| V$PAX5/PAX5.01 | B-cell-specific activating protein |
| V$AHRR/AHRARNT.02 | Aryl hydrocarbon/Arnt heterodimers, fixed core |
| V$MINI/MUSCLE_INI.02 | Muscle Initiator Sequence |
| V$EGRF/EGR3.01 | early growth response gene 3 product |
| V$SP1F/SP1.01 | stimulating protein 1 SP1, ubiquitous zinc finger transcription factor |
| V$ZBPF/ZF9.01 | Core promoter-binding protein (CPBP) with 3 Krueppel-type zinc fingers |
| V$EGRF/EGR1.01 | Egr-1/Krox-24/NGFI-A immediate-early gene product |
| V$EGRF/WT1.01 | Wilms Tumor Suppressor |
| V$SP1F/SP1.01 | stimulating protein 1 SP1, ubiquitous zinc finger transcription factor |
| V$RCAT/CLTR_CAAT.01 | Mammalian C-type LTR CCAAT box |
| V$ZBPF/ZF9.01 | Core promoter-binding protein (CPBP) with 3 Krueppel-type zinc fingers |
| V$EGRF/WT1.01 | Wilms Tumor Suppressor |
| V$EGRF/WT1.01 | Wilms Tumor Suppressor |
| V$NF1F/NF1.01 | Nuclear factor 1 |
| V$PDX1/PDX1.01 | Pdx1 (IDX1/IPF1) pancreatic and intestinal homeodomain TF |
| TFBS in hhyg3 | |
| After removal of TFBS from hhyg2 (3 matches) | |
| V$MINI/MUSCLE_INI.02 | Muscle Initiator Sequence |
| V$PAX5/PAX5.02 | B-cell-specific activating protein |
| V$VMYB/VMYB.02 | v-Myb |
| TFBS in hHygro | |
| Before removal of TFBS from hHygro (5 matches, excluding linker) | |
| V$MINI/MUSCLE_INI.02 | Muscle Initiator Sequence |
| V$PAX5/PAX5.02 | B-cell-specific activating protein |
| V$AREB/AREB6.04 | AREB6 (Atp1a1 regulatory element binding factor 6) |
| V$VMYB/VMYB.02 | v-Myb |
| V$CDEF/CDE.01 | Cell cycle-dependent element, CDF-1 binding site (CDE/CHR tandem elements regulate cell cycle dependent repression) |
| TFBS in hhyg4 | |
| After removal of TFBS from hHygro (4 matches) | |
| V$MINI/MUSCLE_INI.02 | Muscle Initiator Sequence |
| V$PAX5/PAX5.02 | B-cell-specific activating protein |
| V$AREB/AREB6.04 | AREB6 (Atp1a1 regulatory element binding factor 6) |
| V$VMYB/VMYB.02 | v-Myb |

**matches are listed in order of occurrence in the corresponding sequence

TABLE 20

Sequences in Synthetic Neomycin Genes

| Family/matrix** | Further Information |
|---|---|
| TFBS in hneo | |
| Before removal of TFBS from hneo (69 matches) | |
| V$PCAT/CAAT.01 | cellular and viral CCAAT box |
| V$ZFIA/ZID.01 | Zinc finger with interaction domain |
| V$AP1F/TCF11MAFG.01 | TCF11/MafG heterodimers, binding to subclass of AP1 sites |
| V$MINI/MUSCLE_INI.01 | Muscle Initiator Sequence |
| V$AHRR/AHRARNT.01 | Aryl hydrocarbon receptor/Arnt heterodimers |
| V$HIFF/HIF1.02 | Hypoxia inducible factor, bHLH/PAS protein family |
| V$SP1F/GC.01 | GC box elements |
| V$MINI/MUSCLE_INI.02 | Muscle Initiator Sequence |
| V$CP2F/CP2.01 | CP2 |
| V$WHZF/WHN.01 | Winged helix protein, involved in hair keratinization and thymus epithelium differentiation |
| V$PAX5/PAX5.02 | B-cell-specific activating protein |
| V$ZF5F/ZF5.01 | Zinc finger/POZ domain transcription factor |
| V$ZBPF/ZF9.01 | Core promoter-binding protein (CPBP) with 3 Krueppel-type zinc fingers |
| V$ZBPF/ZF9.01 | Core promoter-binding protein (CPBP) with 3 Krueppel-type zinc fingers |
| V$HIFF/HIF1.02 | Hypoxia inducible factor, bHLH/PAS protein family |
| V$AHRR/AHRARNT.01 | Aryl hydrocarbon receptor/Arnt heterodimers |
| V$NRSF/NRSE.01 | Neural-restrictive-silencer-element |
| V$HIFF/HIF1.02 | Hypoxia inducible factor, bHLH/PAS protein family |
| V$CREB/ATF6.02 | Activating transcription factor 6, member of b-zip family, induced by ER stress |
| V$RXRF/VDR_RXR.01 | VDR/RXR Vitamin D receptor RXR heterodimer site |
| V$PCAT/CAAT.01 | cellular and viral CCAAT box |
| V$NRSF/NRSE.01 | Neural-restrictive-silencer-element |
| V$P53F/P53.01 | Tumor suppressor p53 |
| V$NEUR/NEUROD1.01 | DNA binding site for NEUROD1 (BETA-2/E47 dimer) |
| V$EBOX/USF.03 | Upstream stimulating factor |
| V$MYOD/MYOD.02 | Myoblast determining factor |
| V$NRSF/NRSE.01 | Neural-restrictive-silencer-element |
| V$WHZF/WHN.01 | Winged helix protein, involved in hair keratinization and thymus epithelium differentiation |
| V$EBOX/MYCMAX.03 | MYC-MAX binding sites |
| V$HESF/HES1.01 | *Drosophila* hairy and enhancer of split homologue 1 (HES-1) |
| V$NEUR/NEUROD1.01 | DNA binding site for NEUROD1 (BETA-2/E47 dimer) |
| V$MYOD/MYOD.02 | Myoblast determining factor |
| V$REBV/EBVR.01 | Epstein-Barr virus transcription factor R |
| V$PAX5/PAX5.02 | B-cell-specific activating protein |
| V$ZF5F/ZF5.01 | Zinc finger/POZ domain transcription factor |
| V$ZF5F/ZF5.01 | Zinc finger/POZ domain transcription factor |
| V$EGRF/WT1.01 | Wilms Tumor Suppressor |
| V$EGRF/WT1.01 | Wilms Tumor Suppressor |
| V$ZBPF/ZF9.01 | Core promoter-binding protein (CPBP) with 3 Krueppel-type zinc fingers |
| V$MINI/MUSCLE_INI.01 | Muscle Initiator Sequence |
| V$NRSF/NRSF.01 | Neuron-restrictive silencer element |
| U$PflMI/PflMI | RE II-IP |
| V$NRSF/NRSE.01 | Neural-restrictive-silencer-element |
| V$MOKF/MOK2.02 | Ribonucleoprotein associated zinc finger protein MOK-2 (human) |
| V$AP2F/AP2.01 | Activator protein 2 |
| V$AP1F/AP1FJ.01 | Activator protein 1 |
| V$PAX5/PAX5.03 | PAX5 paired domain protein |
| V$EGRF/EGR3.01 | early growth response gene 3 product |
| V$WHZF/WHN.01 | Winged helix protein, involved in hair keratinization and thymus epithelium differentiation |

TABLE 20-continued

Sequences in Synthetic Neomycin Genes

| Family/matrix** | Further Information |
|---|---|
| V$PAX6/PAX4_PD.01 | PAX4 paired domain binding site |
| V$VMYB/VMYB.02 | v-Myb |
| V$BEL1/BEL1.01 | Bel-1 similar region (defined in Lentivirus LTRs) |
| V$MOKF/MOK2.01 | Ribonucleoprotein associated zinc finger protein MOK-2 (mouse) |
| V$EGRF/EGR1.01 | Egr-1/Krox-24/NGFI-A immediate-early gene product |
| V$EBOX/ATF6.01 | Member of b-zip family, induced by ER damage/stress, binds to the ERSE in association with NF-Y |
| V$EGRF/EGR3.01 | early growth response gene 3 product |
| V$NRSF/NRSE.01 | Neural-restrictive-silencer-element |
| V$ETSF/ETS1.01 | c-Ets-1 binding site |
| V$NRSF/NRSF.01 | Neuron-restrictive silencer factor |
| V$SP1F/SP1.01 | stimulating protein 1 SP1, ubiquitous zinc finger transcription factor |
| V$ZBPF/ZBP89.01 | Zinc finger transcription factor ZBP-89 |
| V$PAX5/PAX5.03 | PAX5 paired domain protein |
| V$GREF/ARE.01 | Androgene receptor binding site |
| V$BCL6/BCL6.02 | POZ/zinc finger protein, transcriptional repressor, translocations observed in diffuse large cell lymphoma |
| V$CLOX/CDP.01 | cut-like homeodomain protein |
| TFBS in hneo3 | |
| After removal of TFBS from hneo2 = before removal of TFBS from hneo3 (0 matches) | |
| TFBS in hneo4 | |
| After removal of TFBS from hneo3 = before removal of TFBS from hneo4 (7 matches) | |
| V$PAX5/PAX9.01 | Zebrafish PAX9 binding sites |
| V$AARF/AARE.01 | Amino acid response element, ATF4 binding site |
| V$P53F/P53.02 | Tumor suppressor p53 (5' half site) |
| V$AP1R/BACH2.01 | Bach2 bound TRE |
| V$NEUR/NEUROG.01 | Neurogenin 1 and 3 (ngn1/3) binding sites |
| V$CMYB/CMYB.01 | c-Myb, important in hematopoesis, cellular equivalent to avian myoblastosis virus oncogene v-myb |
| V$HOXF/CRX.01 | Cone-rod homeobox-containing transcription factor/otx-like homeobox gene |
| TFBS in hneo5 | |
| After removal of TFBS from hneo4 (0 matches) | |

**matches are listed in order of occurrence in the corresponding sequence

TABLE 21

Sequences in Synthetic Puromycin Genes

| Family/matrix** | Further Information |
|---|---|
| TFBS matches in hpuro | |
| Before removal of TFBS from hpuro (68 matches) | |
| V$CDEF/CDE.01 | Cell cycle-dependent element, CDF-1 binding site (CDE/CHR tandem elements regulate cell cycle dependent repression) |
| V$PAX3/PAX3.01 | Pax-3 paired domain protein, expressed in embryogenesis, mutations correlate to Waardenburg Syndrome |
| V$CREB/ATF6.02 | Activating transcription factor 6, member of b-zip family, induced by ER stress |
| V$EBOR/XBP1.01 | X-box-binding protein 1 |
| V$P53F/P53.03 | Tumor suppressor p53 (3' half site) |
| V$HESF/HES1.01 | *Drosophila* hairy and enhancer of split homologue 1 (HES-1) |
| V$MTF1/MTF-1.01 | Metal transcription factor 1, MRE |
| V$EKLF/EKLF.01 | Erythroid krueppel like factor (EKLF) |

TABLE 21-continued

Sequences in Synthetic Puromycin Genes

| Family/matrix** | Further Information |
|---|---|
| V$EGRF/EGR1.01 | Egr-1/Krox-24/NGFI-A immediate-early gene product |
| V$EBOX/ATF6.01 | Member of b-zip family, induced by ER damage/stress, binds to the ERSE in association with NF-Y |
| V$EBOX/ATF6.01 | Member of b-zip family, induced by ER damage/stress, binds to the ERSE in association with NF-Y |
| V$CMYB/CMYB.01 | c-Myb, important in hematopoesis, cellular equivalent to avian myoblastosis virus oncogene v-myb |
| V$AHRR/AHRARNT.01 | Aryl hydrocarbon receptor/Arnt heterodimers |
| V$EBOX/MYCMAX.03 | MYC-MAX binding sites |
| V$RORA/RORA2.01 | RAR-related orphan receptor alpha2 |
| V$EBOX/MYCMAX.03 | MYC-MAX binding sites |
| V$HIFF/HIF1.02 | Hypoxia inducible factor, bHLH/PAS protein family |
| V$EGRF/EGR3.01 | early growth response gene 3 product |
| V$EGRF/WT1.01 | Wilms Tumor Suppressor |
| V$HAML/AML3.01 | Runt-related transcription factor 2/CBFA1 (core-binding factor, runt domain, alpha subunit 1) |
| V$PAX5/PAX5.03 | PAX5 paired domain protein |
| V$EBOX/ATF6.01 | Member of b-zip family, induced by ER damage/stress, binds to the ERSE in association with NF-Y |
| V$HIFF/HIF1.02 | Hypoxia inducible factor, bHLH/PAS protein family |
| V$ZBPF/ZBP89.01 | Zinc finger transcription factor ZBP-89 |
| V$OAZF/ROAZ.01 | Rat C2H2 Zn finger protein involved in olfactory neuronal differentiation |
| V$GABF/GAGA.01 | GAGA-Box |
| V$EBOX/MYCMAX.03 | MYC-MAX binding sites |
| V$MYOD/MYF5.01 | Myf5 myogenic bHLH protein |
| V$AP4R/TAL1BETAE47.01 | Tal-1beta/E47 heterodimer |
| V$NEUR/NEUROG.01 | Neurogenin 1 and 3 (ngn1/3) binding sites |
| V$HAND/HAND2_E12.01 | Heterodimers of the bHLH transcription factors HAND2 (Thing2) and E12 |
| V$MAZF/MAZR.01 | MYC-associated zinc finger protein related transcription factor |
| V$ZBPF/ZNF202.01 | Transcriptional repressor, binds to elements found predominantly in genes that participate in lipid metabolism |
| V$SP1F/SP1.01 | Stimulating protein 1 SP1, ubiquitous zinc finger transcription factor |
| V$AP2F/AP2.01 | Activator protein 2 |
| V$RREB/RREB1.01 | Ras-responsive element binding protein 1 |
| V$XBBF/MIF1.01 | MIBP-1/RFX1 complex |
| V$CREB/TAXCREB.01 | Tax/CREB complex |
| V$EGRF/EGR3.01 | early growth response gene 3 product |
| V$MOKF/MOK2.01 | Ribonucleoprotein associated zinc finger protein MOK-2 (mouse) |
| V$MOKF/MOK2.01 | Ribonucleoprotein associated zinc finger protein MOK-2 (mouse) |
| V$PAX5/PAX5.01 | B-cell-specific activating protein |
| V$NRSF/NRSE.01 | Neural-restrictive-silencer-element |
| V$MINI/MUSCLE_INI.02 | Muscle Initiator Sequence |
| V$EBOX/ATF6.01 | Member of b-zip family, induced by ER damage/stress, binds to the ERSE in association with NF-Y |
| V$DEAF/NUDR.01 | NUDR (nuclear DEAF-1 related transcriptional regulator protein) |
| V$AHRR/AHRARNT.01 | Aryl hydrocarbon receptor/Arnt heterodimers |
| V$ZF5F/ZF5.01 | Zinc finger/POZ domain transcription factor |
| V$EGRF/EGR1.01 | Egr-1/Krox-24/NGFI-A immediate-early gene product |
| V$HIFF/HIF1.02 | Hypoxia inducible factor, bHLH/PAS protein family |

TABLE 21-continued

Sequences in Synthetic Puromycin Genes

| Family/matrix** | Further Information |
|---|---|
| V$ETSF/ETS1.01 | c-Ets-1 binding site |
| V$STAT/STAT1.01 | Signal transducer and activator of transcription 1 |
| V$BCL6/BCL6.01 | POZ/zinc finger protein, transcriptional repressor, translocations observed in diffuse large cell lymphoma |
| V$ZF5F/ZF5.01 | Zinc finger/POZ domain transcription factor |
| V$BCL6/BCL6.02 | POZ/zinc finger protein, transcriptional repressor, translocations observed in diffuse large cell lymphoma |
| V$EGRF/EGR3.01 | early growth response gene 3 product |
| V$CREB/ATF6.02 | Activating transcription factor 6, member of b-zip family, induced by ER stress |
| V$HIFF/HIF1.02 | Hypoxia inducible factor, bHLH/PAS protein family |
| V$EBOR/XBP1.01 | X-box-binding protein 1 |
| V$DEAF/NUDR.01 | NUDR (nuclear DEAF-1 related transcriptional regulator protein) |
| V$RXRF/VDR_RXR.01 | VDR/RXR Vitamin D receptor RXR heterodimer site |
| V$AP2F/AP2.01 | Activator protein 2 |
| V$REBV/EBVR.01 | Epstein-Barr virus transcription factor R |
| V$ZBPF/ZF9.01 | Core promoter-binding protein (CPBP) with 3 Krueppel-type zinc fingers |
| V$MYOD/LMO2COM.01 | Complex of Lmo2 bound to Tal-1, E2A proteins, and GATA-1, half-site 1 |
| V$AREB/AREB6.03 | AREB6 (Atp1a1 regulatory element binding factor 6) |
| V$RXRF/FXRE.01 | Farnesoid X - activated receptor (RXR/FXR dimer) |
| V$AHRR/AHR.01 | Aryl hydrocarbon/dioxin receptor |
| colspan="2" | TFBS matches in hpuro1 After removal of TFBS from hpuro = before removal of TFBS from hpuro1 (4 matches) |
| V$NEUR/NEUROG.01 | Neurogenin 1 and 3 (ngn1/3) binding sites |
| V$PAX5/PAX5.02 | B-cell-specific activating protein |
| V$REBV/EBVR.01 | Epstein-Barr virus transcription factor R |
| V$AHRR/AHR.01 | Aryl hydrocarbon/dioxin receptor |
| colspan="2" | TFBS matches in hpuro2 After removal of TFBS from hpuro1 (2 matches) |
| V$NEUR/NEUROG.01 | Neurogenin 1 and 3 (ngn1/3) binding sites |
| V$BCL6/BCL6.02 | POZ/zinc finger protein, transcriptional repressor, translocations observed in diffuse large cell lymphoma |

**matches are listed in order of occurrence in the corresponding sequence

EXAMPLE 7

Summary of Design of Synthetic Firefly Luciferase Genes

TF Binding Sites and Search Parameters

The TF binding sites are from the TF binding site library ("Matrix Family Library") that is part of the GEMS Launcher package. Each TF binding site ("matrix") belongs to a matrix family that groups functionally similar matrices together, eliminating redundant matches by MatInspector professional (the search program). Searches were limited to vertebrate TF binding sites. Searches were performed by matrix family, i.e. the results show only the best match from a family for each site. MatInspector default parameters were used for the core and matrix similarity values (core similarity=0.75, matrix similarity=optimized).

TABLE 22

Luc Gene Designations
Synthetic luc gene (versions A and B)

| Sequence* | Description | Matrix Library |
|---|---|---|
| Luc | wild-type gene | (not applicable) |
| luc+ | improved gene from Promega's pGL3 vectors | (not applicable) |
| hluc+ | Improved gene form Promega's pGL3(R2.1)-Basic | (not applicable) |
| colspan="3" | Codon optimization strategy A |
| hluc + ver2A1 | codon optimized luc+ (strategy A) | Ver 3.0 November 2002 |
| hluc + ver2A2 | First removal of undesired sequence matches | Ver 3.0 November 2002 |
| hluc + ver2A3 | Second removal of undesired sequence matches | Ver 3.0 November 2002 |
| hluc + ver2A4 | Third removal of undesired sequence matches | Ver 3.0 November 2002 |
| hluc + ver2A5 | Fourth removal of undesired sequence matches | Ver 3.0 November 2002 |
| hluc + ver2A6 | Fifth removal of undesired sequence matches | Ver 3.0 November 2002 |
| hluc + ver2A7 | Sixth removal of undesired sequence matches | Ver 3.1.1 April 2003 |
| hluc + ver2A8 | Removal of BglI (RE) site | Ver 3.1.1 April 2003 |
| colspan="3" | Codon optimization strategy B |
| hluc + ver2B1 | codon optimized luc+ (strategy B) | Ver 3.0 November 2002 |
| hluc + ver2B2 | First removal of undesired sequence matches | Ver 3.0 November 2002 |
| hluc + ver2B3 | Second removal of undesired sequence matches | Ver 3.0 November 2002 |
| hluc + ver2B4 | Third removal of undesired sequence matches | Ver 3.0 November 2002 |

TABLE 22-continued

Luc Gene Designations
Synthetic luc gene (versions A and B)

| Sequence* | Description | Matrix Library |
|---|---|---|
| hluc + ver2B5 | Fourth removal of undesired sequence matches | Ver 3.0 November 2002 |
| hluc + ver2B6 | Fifth removal of undesired sequence matches | Ver 3.0 November 2002 |
| hluc + ver2B7 | Sixth removal of undesired sequence matches | Ver 3.1.1 April 2003 |
| hluc + ver2B8 | Removal of SmaI (RE), Ptx1 (TF) sites | Ver 3.1.1 April 2003 |
| hluc + ver2B9 | Removal of additional CpG sequences | Ver 3.1.1 April 2003 |
| hluc + ver2B10 | Removal of BglI (RE) site | Ver 3.1.1 April 2003 |

*the sequence names designate open reading frames;
RE = restriction enzyme recognition sequence

TABLE 23

Sequences in Synthetic Luc Genes (version A)

TFBS in hluc + ver2A1
Before removal of TFBS from hluc + ver2A1 (110 matches)

| Family/matrix** | Further Information |
|---|---|
| V$MINI/MUSCLE_INI.02 | Muscle Initiator Sequence |
| V$WHZF/WHN.01 | winged helix protein, involved in hair keratinization and thymus epithelium differentiation |
| V$GREF/PRE.01 | Progesterone receptor binding site |
| V$MAZF/MAZR.01 | MYC-associated zinc finger protein related transcription factor |
| V$SP1F/SP1.01 | stimulating protein 1 SP1, ubiquitous zinc finger transcription factor |
| V$ZBPF/ZBP89.01 | Zinc finger transcription factor ZBP-89 |
| V$SF1F/SF1.01 | SF1 steroidogenic factor 1 |
| V$EGRF/NGFIC.01 | Nerve growth factor-induced protein C |
| V$MINI/MUSCLE_INI.01 | Muscle Initiator Sequence |
| V$EGRF/EGR2.01 | Egr-2/Krox-20 early growth response gene product |
| V$ZF5F/ZF5.01 | Zinc finger/POZ domain transcription factor |
| V$HESF/HES1.01 | Drosophila hairy and enhancer of split homologue 1 (HES-1) |
| V$NRSF/NRSE.01 | neural-restrictive-silencer-element |
| V$PAX5/PAX5.02 | B-cell-specific activating protein |
| V$HAML/AML3.01 | Runt-related transcription factor 2/CBFA1 (core-binding factor, runt domain, alpha subunit 1) |
| V$GREF/PRE.01 | Progesterone receptor binding site |
| V$P53F/P53.01 | tumor suppressor p53 |
| V$ZF5F/ZF5.01 | Zinc finger/POZ domain transcription factor |
| V$EBOX/ATF6.01 | Member of b-zip family, induced by ER damage/stress, binds to the ERSE in association with NF-Y |
| V$EGRF/EGR3.01 | early growth response gene 3 product |
| V$NF1F/NF1.01 | Nuclear factor 1 |
| V$EGRF/EGR3.01 | early growth response gene 3 product |
| V$REBV/EBVR.01 | Epstein-Barr virus transcription factor R |
| V$MOKF/MOK2.01 | Ribonucleoprotein associated zinc finger protein MOK-2 (mouse) |
| V$PBXC/PBX1_MEIS1.01 | Binding site for a Pbx1/Meis1 heterodimer |
| V$XSEC/STAF.01 | Se-Cys tRNA gene transcription activating factor |
| V$COMP/COMP1.01 | COMP1, cooperates with myogenic proteins in multicomponent complex |
| V$MYOF/MYOGNF1.01 | Myogenin/nuclear factor 1 or related factors |
| V$NEUR/NEUROD1.01 | DNA binding site for NEUROD1 (BETA-2/E47 dimer) |
| V$MYOD/MYOD.02 | myoblast determining factor |
| V$AP2F/AP2.01 | Activator protein 2 |
| V$EVI1/EVI1.02 | Ecotropic viral integration site 1 encoded factor |
| V$SMAD/SMAD4.01 | Smad4 transcription factor involved in TGF-beta signaling |
| V$MYOD/MYF5.01 | Myf5 myogenic bHLH protein |
| V$HESF/HES1.01 | Drosophila hairy and enhancer of split homologue 1 (HES-1) |
| V$PAX5/PAX5.01 | B-cell-specific activating protein |
| V$EBOX/ATF6.01 | Member of b-zip family, induced by ER damage/stress, binds to the ERSE in association with NF-Y |
| V$SP1F/GC.01 | GC box elements |
| V$MAZF/MAZR.01 | MYC-associated zinc finger protein related transcription factor |
| V$RREB/RREB1.01 | Ras-responsive element binding protein 1 |
| V$AHRR/AHRARNT.01 | Aryl hydrocarbon receptor/Arnt heterodimers |
| V$HIFF/HIF1.02 | Hypoxia inducible factor, bHLH/PAS protein family |
| V$ZF5F/ZF5.01 | Zinc finger/POZ domain transcription factor |
| V$EBOX/ATF6.01 | Member of b-zip family, induced by ER damage/stress, binds to the ERSE in association with NF-Y |
| V$YY1F/YY1.01 | Yin and Yang 1 |
| V$ETSF/GABP.01 | GABP: GA binding protein |
| V$MOKF/MOK2.01 | Ribonucleoprotein associated zinc finger protein MOK-2 (mouse) |
| V$ETSF/ELK1.02 | Elk-1 |
| V$EBOX/MYCMAX.03 | MYC-MAX binding sites |
| V$E4FF/E4F.01 | GLI-Krueppel-related transcription factor, regulator of adenovirus E4 promoter |
| V$XBBF/RFX1.01 | X-box binding protein RFX1 |
| V$EVI1/EVI1.06 | Ecotropic viral integration site 1 encoded factor |
| V$MOKF/MOK2.01 | Ribonucleoprotein associated zinc finger protein MOK-2 (mouse) |
| V$NF1F/NF1.01 | Nuclear factor 1 |
| V$PBXC/PBX1_MEIS1.02 | Binding site for a Pbx1/Meis1 heterodimer |
| V$ZF5F/ZF5.01 | Zinc finger/POZ domain transcription factor |
| V$HESF/HES1.01 | Drosophila hairy and enhancer of split homologue 1 (HES-1) |
| V$PAX5/PAX5.01 | B-cell-specific activating protein |
| V$ETSF/GABP.01 | GABP: GA binding protein |
| V$MYOD/MYOD.02 | myoblast determining factor |
| V$XSEC/STAF.01 | Se-Cys tRNA gene transcription activating factor |
| V$OAZF/ROAZ.01 | Rat C2H2 Zn finger protein involved in olfactory neuronal differentiation |
| V$AP2F/AP2.01 | Activator protein 2 |
| V$PAX3/PAX3.01 | Pax-3 paired domain protein, expressed in embryogenesis, mutations correlate to Waardenburg Syndrome |
| V$AP2F/AP2.01 | Activator protein 2 |
| V$MTF1/MTF-1.01 | Metal transcription factor 1, MRE |
| V$SF1F/FTF.01 | Alpha (1)-fetoprotein transcription factor (FTF), liver receptor homologue-1 (LHR-1) |

TABLE 23-continued

Sequences in Synthetic Luc Genes (version A)

| Family/matrix | Further Information |
|---|---|
| V$SMAD/SMAD4.01 | Smad4 transcription factor involved in TGF-beta signaling |
| V$NFKB/NFKAPPAB.01 | NF-kappaB |
| V$EKLF/EKLF.01 | Erythroid krueppel like factor (EKLF) |
| V$CREB/TAXCREB.01 | Tax/CREB complex |
| V$E2FF/E2F.03 | E2F, involved in cell cycle regulation, interacts with Rb p107 protein |
| V$CP2F/CP2.01 | CP2 |
| V$AHRR/AHRARNT.01 | Aryl hydrocarbon receptor/Arnt heterodimers |
| V$EGRF/EGR2.01 | Egr-2/Krox-20 early growth response gene product |
| V$ZF5F/ZF5.01 | Zinc finger/POZ domain transcription factor |
| V$EBOR/XBP1.01 | X-box-binding protein 1 |
| V$FKHD/XFD3.01 | *Xenopus* fork head domain factor 3 |
| V$AP2F/AP2.01 | Activator protein 2 |
| V$EGRF/NGFIC.01 | Nerve growth factor-induced protein C |
| V$PCAT/ACAAT.01 | Avian C-type LTR CCAAT box |
| V$PBXC/PBX1_MEIS1.02 | Binding site for a Pbx1/Meis1 heterodimer |
| V$AHRR/AHRARNT.02 | Aryl hydrocarbon/Arnt heterodimers, fixed core |
| V$MOKF/MOK2.01 | Ribonucleoprotein associated zinc finger protein MOK-2 (mouse) |
| V$GREF/GRE.01 | Glucocorticoid receptor, C2C2 zinc finger protein binds glucocorticoid dependent to GREs |
| V$NEUR/NEUROD1.01 | DNA binding site for NEUROD1 (BETA-2/E47 dimer) |
| V$NRSF/NRSE.01 | neural-restrictive-silencer-element |
| V$NRSF/NRSE.01 | neural-restrictive-silencer-element |
| V$AHRR/AHRARNT.02 | Aryl hydrocarbon/Arnt heterodimers, fixed core |
| V$EBOX/ATF6.01 | Member of b-zip family, induced by ER damage/stress, binds to the ERSE in association with NF-Y |
| V$HIFF/HIF1.02 | Hypoxia inducible factor, bHLH/PAS protein family |
| V$EGRF/EGR3.01 | early growth response gene 3 product |
| V$EGRF/EGR3.01 | early growth response gene 3 product |
| V$WHZF/WHN.01 | winged helix protein, involved in hair keratinization and thymus epithelium differentiation |
| V$AP2F/AP2.01 | Activator protein 2 |
| V$HIFF/HIF1.02 | Hypoxia inducible factor, bHLH/PAS protein family |
| V$NRSF/NRSE.01 | neural-restrictive-silencer-element |
| V$ZFIA/ZID.01 | zinc finger with interaction domain |
| V$SMAD/SMAD4.01 | Smad4 transcription factor involved in TGF-beta signaling |
| V$AHRR/AHRARNT.02 | Aryl hydrocarbon/Arnt heterodimers, fixed core |
| V$EBOX/MYCMAX.01 | c-Myc/Max heterodimer |
| V$EBOX/USF.03 | upstream stimulating factor |
| V$EGRF/EGR1.01 | Egr-1/Krox-24/NGFI-A immediate-early gene product |
| V$MINI/MUSCLE_INI.01 | Muscle Initiator Sequence |
| V$MOKF/MOK2.01 | Ribonucleoprotein associated zinc finger protein MOK-2 (mouse) |
| V$NRSF/NRSE.01 | neural-restrictive-silencer-element |
| V$NF1F/NF1.01 | Nuclear factor 1 |
| V$SF1F/SF1.01 | SF1 steroidogenic factor 1 |
| TFBS in hluc + ver2A3 After removal of TFBS from hluc + ver2A2 = before removal of TFBS from hluc + ver2A3 (8 matches) | |
| V$EGRF/EGR2.01 | Egr-2/Krox-20 early growth response gene product |
| V$HAML/AML3.01 | Runt-related transcription factor 2/CBFA1 (core-binding factor, runt domain, alpha subunit 1) |
| V$MYOF/MYOGNF1.01 | Myogenin/nuclear factor 1 or related factors |
| V$NF1F/NF1.01 | Nuclear factor 1 |
| V$ETSF/GABP.01 | GABP: GA binding protein |
| V$NFKB/NFKAPPAB.01 | NF-kappaB |
| V$EKLF/EKLF.01 | Erythroid krueppel like factor (EKLF) |
| V$FKHD/XFD3.01 | *Xenopus* fork head domain factor 3 |
| TFBS in hluc + ver2A6 After removal of TFBS from hluc + ver2A5 (2 matches) | |
| V$HAML/AML3.01 | Runt-related transcription factor 2/CBFA1 (core-binding factor, runt domain, alpha subunit 1) |
| V$FKHD/XFD3.01 | *Xenopus* fork head domain factor 3 |
| TFBS in hluc + ver2A6 Before removal of TFBS from hluc + ver2A6 (4 matches) | |
| V$PAX5/PAX5.03 | PAX5 paired domain protein |
| V$LEFF/LEF1.02 | TCF/LEF-1, involved in the Wnt signal transduction pathway |
| V$IRFF/IRF7.01 | Interferon regulatory factor 7 (IRF-7) |
| V$FKHD/XFD3.01 | *Xenopus* fork head domain factor 3 |

| Family/matrix | Further Information |
|---|---|
| TFBS in hluc + ver2A7 After removal of TFBS from hluc + ver2A6 = before removal of TFBS from hluc + ver2A7 (1 match) | |
| V$FKHD/XFD3.01 | *Xenopus* fork head domain factor 3 |
| TFBS in hluc + ver2A8 After removal of TFBS from hluc + ver2A7 (1 match) | |
| V$FKHD/XFD3.01 | *Xenopus* fork head domain factor 3 |

**matches are listed in order of occurrence in the corresponding sequence

TABLE 24

Sequences in Synthetic Luc Genes (version B)

| Family/matrix** | Further Information |
|---|---|
| TFBS in hluc + ver2B1 Before removal of TFBS from hluc + ver2B1 (187 matches) | |
| V$HOXF/PTX1.01 | Pituitary Homeobox 1 (Ptx1) |
| V$OCT1/OCT1.04 | octamer-binding factor 1 |
| V$OCTP/OCT1P.01 | octamer-binding factor 1, POU-specific domain |
| V$NKXH/NKX25.02 | homeo domain factor Nkx-2.5/Csx, tinman homolog low affinity sites |
| V$BARB/BARBIE.01 | barbiturate-inducible element |
| V$TBPF/TATA.01 | cellular and viral TATA box elements |
| V$GATA/GATA.01 | GATA binding site (consensus) |
| V$AP4R/AP4.01 | Activator protein 4 |
| V$HEN1/HEN1.02 | HEN1 |
| V$SRFF/SRF.01 | serum response factor |
| V$PARF/DBP.01 | Albumin D-box binding protein |
| V$MOKF/MOK2.01 | Ribonucleoprotein associated zinc finger protein MOK-2 (mouse) |
| V$EVI1/EVI1.04 | Ecotropic viral integration site 1 encoded factor |
| V$GFI1/Gfi1B.01 | Growth factor independence 1 zinc finger protein Gfi-1B |
| V$RBPF/RBPJK.01 | Mammalian transcriptional repressor RBP-Jkappa/CBF1 |
| V$TBPF/TATA.02 | Mammalian C-type LTR TATA box |
| V$AP4R/TAL1ALPHAE47.01 | Tal-1alpha/E47 heterodimer |
| V$SRFF/SRF.01 | serum response factor |
| V$OCTP/OCT1P.01 | octamer-binding factor 1, POU-specific domain |
| V$BRNF/BRN2.01 | POU factor Brn-2 (N-Oct 3) |
| V$CREB/E4BP4.01 | E4BP4, bZIP domain, transcriptional repressor |
| V$VBPF/VBP.01 | PAR-type chicken vitellogenin promoter-binding protein |
| V$EVI1/EVI1.04 | Ecotropic viral integration site 1 encoded factor |
| V$CLOX/CDPCR3.01 | cut-like homeodomain protein |
| V$GFI1/Gfi1B.01 | Growth factor independence 1 zinc finger protein Gfi-1B |

TABLE 24-continued

Sequences in Synthetic Luc Genes (version B)

| | |
|---|---|
| V$GATA/LMO2COM.02 | complex of Lmo2 bound to Tal-1, E2A proteins, and GATA-1, half-site 2 |
| V$SRFF/SRF.01 | serum response factor |
| V$HOXT/MEIS1_HOXA9.01 | Homeobox protein MEIS1 binding site |
| V$OCT1/OCT1.03 | octamer-binding factor 1 |
| V$GFI1/GFI1.01 | Growth factor independence 1 zinc finger protein acts as transcriptional repressor |
| V$HNF6/HNF6.01 | Liver enriched Cut - Homeodomain transcription factor HNF6 (ONECUT) |
| V$HAML/AML1.01 | runt-factor AML-1 |
| V$GREF/PRE.01 | Progesterone receptor binding site |
| V$STAT/STAT5.01 | STAT5: signal transducer and activator of transcription 5 |
| V$TBPF/TATA.01 | cellular and viral TATA box elements |
| V$CLOX/CDP.01 | cut-like homeodomain protein |
| V$FKHD/HFH8.01 | HNF-3/Fkh Homolog-8 |
| V$FAST/FAST1.01 | FAST-1 SMAD interacting protein |
| V$GFI1/GfI1B.01 | Growth factor independence 1 zinc finger protein Gfi-1B |
| V$CART/CART1.01 | Cart-1 (cartilage homeoprotein 1) |
| V$HMTB/MTBF.01 | muscle-specific Mt binding site |
| V$TBPF/TATA.01 | cellular and viral TATA box elements |
| V$FKHD/XFD2.01 | *Xenopus* fork head domain factor 2 |
| V$BRNF/BRN2.01 | POU factor Brn-2 (N-Oct 3) |
| V$MEF2/AMEF2.01 | myocyte enhancer factor |
| V$BRNF/BRN2.01 | POU factor Brn-2 (N-Oct 3) |
| V$BEL1/BEL1.01 | Bel-1 similar region (defined in Lentivirus LTRs) |
| V$NOLF/OLF.01 | olfactory neuron-specific factor |
| V$OCT1/OCT1.06 | octamer-binding factor 1 |
| V$NFKB/NFKAPPAB.02 | NF-kappaB |
| V$BCL6/BCL6.02 | POZ/zinc finger protein, transcriptional repressor, translocations observed in diffuse large cell lymphoma |
| V$MOKF/MOK2.01 | Ribonucleoprotein associated zinc finger protein MOK-2 (mouse) |
| V$HEAT/HSF.01 | heat shock factor 1 |
| V$OCTP/OCT1P.01 | octamer-binding factor 1, POU-specific domain |
| V$PIT1/PIT1.01 | Pit1, GHF-1 pituitary specific pou domain transcription factor |
| V$HOXF/CRX.01 | Cone-rod homeobox-containing transcription factor/otx-like homeobox gene |
| V$HNF6/HNF6.01 | Liver enriched Cut - Homeodomain transcription factor HNF6 (ONECUT) |
| V$CLOX/CLOX.01 | Clox |
| V$BCL6/BCL6.02 | POZ/zinc finger protein, transcriptional repressor, translocations observed in diffuse large cell lymphoma |
| V$HOXF/PTX1.01 | Pituitary Homeobox 1 (Ptx1) |
| V$GATA/GATA1.02 | GATA-binding factor 1 |
| V$FKHD/FREAC4.01 | Fork head RElated ACtivator-4 |
| V$E4FF/E4F.01 | GLI-Krueppel-related transcription factor, regulator of adenovirus E4 promoter |
| V$PDX1/ISL1.01 | Pancreatic and intestinal lim-homeodomain factor |
| V$CART/CART1.01 | Cart-1 (cartilage homeoprotein 1) |
| V$GFI1/GFI1.01 | Growth factor independence 1 zinc finger protein acts as transcriptional repressor |
| V$IRFF/IRF3.01 | Interferon regulatory factor 3 (IRF-3) |
| V$BARB/BARBIE.01 | barbiturate-inducible element |
| V$PBXF/PBX1.01 | homeo domain factor Pbx-1 |
| V$EVI1/EVI1.02 | Ecotropic viral integration site 1 encoded factor |
| V$GATA/GATA2.01 | GATA-binding factor 2 |
| V$BRNF/BRN2.01 | POU factor Brn-2 (N-Oct 3) |
| V$PARF/DBP.01 | Albumin D-box binding protein |
| V$BRNF/BRN3.01 | POU transcription factor Brn-3 |
| V$ZBPF/ZBP89.01 | Zinc finger transcription factor ZBP-89 |
| V$CREB/TAXCREB.02 | Tax/CREB complex |
| V$GREF/PRE.01 | Progesterone receptor binding site |
| V$RBPF/RBPJK.01 | Mammalian transcriptional repressor RBP-Jkappa/CBF1 |
| V$GATA/GATA3.02 | GATA-binding factor 3 |
| V$STAT/STAT.01 | signal transducers and activators of transcription |
| V$IKRS/IK2.01 | Ikaros 2, potential regulator of lymphocyte differentiation |
| V$SRFF/SRF.01 | serum response factor |
| V$SEF1/SEF1.01 | SEF1 binding site |
| V$HAML/AML1.01 | runt-factor AML-1 |
| V$MOKF/MOK2.02 | Ribonucleoprotein associated zinc finger protein MOK-2 (human) |
| V$FKHD/FREAC2.01 | Fork head RElated ACtivator-2 |
| V$HMTB/MTBF.01 | muscle-specific Mt binding site |
| V$GFI1/GFI1.01 | Growth factor independence 1 zinc finger protein acts as transcriptional repressor |
| V$ECAT/NFY.03 | nuclear factor Y (Y-box binding factor) |
| V$HOXT/MEIS1_HOXA9.01 | Homeobox protein MEIS1 binding site |
| V$PCAT/ACAAT.01 | Avian C-type LTR CCAAT box |
| V$HNF6/HNF6.01 | Liver enriched Cut - Homeodomain transcription factor HNF6 (ONECUT) |
| V$CLOX/CLOX.01 | Clox |
| V$GATA/GATA3.02 | GATA-binding factor 3 |
| V$AREB/AREB6.04 | AREB6 (Atp1a1 regulatory element binding factor 6) |
| V$GATA/GATA3.02 | GATA-binding factor 3 |
| V$FKHD/HNF3B.01 | Hepatocyte Nuclear Factor 3beta |
| V$IRFF/IRF1.01 | interferon regulatory factor 1 |
| V$NKXH/NKX31.01 | prostate-specific homeodomain protein NKX3.1 |
| V$PBXF/PBX1.01 | homeo domain factor Pbx-1 |
| V$ECAT/NFY.03 | nuclear factor Y (Y-box binding factor) |
| V$PBXC/PBX1_MEIS1.02 | Binding site for a Pbx1/Meis1 heterodimer |
| V$CLOX/CDP.02 | transcriptional repressor CDP |
| V$HOXT/MEIS1_HOXA9.01 | Homeobox protein MEIS1 binding site |
| V$HOXF/HOXA9.01 | Member of the vertebrate HOX - cluster of homeobox factors |
| V$GATA/GATA.01 | GATA binding site (consensus) |
| V$NKXH/NKX31.01 | prostate-specific homeodomain protein NKX3.1 |
| V$GATA/GATA3.02 | GATA-binding factor 3 |
| V$HOXF/CRX.01 | Cone-rod homeobox-containing transcription factor/otx-like homeobox gene |
| V$CART/CART1.01 | Cart-1 (cartilage homeoprotein 1) |
| V$OCT1/OCT1.02 | octamer-binding factor 1 |
| V$MAZF/MAZR.01 | MYC-associated zinc finger protein related transcription factor |
| V$ZBPF/ZBP89.01 | Zinc finger transcription factor ZBP-89 |
| V$GATA/GATA3.02 | GATA-binding factor 3 |
| V$HOXF/CRX.01 | Cone-rod homeobox-containing transcription factor/otx-like homeobox gene |
| V$CLOX/CDPCR3.01 | cut-like homeodomain protein |
| V$AP1F/VMAF.01 | v-Maf |
| V$AP4R/TAL1ALPHAE47.01 | Tal-1alpha/E47 heterodimer |
| V$PAX8/PAX8.01 | PAX 2/5/8 binding site |
| V$BRAC/BRACH.01 | Brachyury |
| V$GATA/GATA1.02 | GATA-binding factor 1 |
| V$RREB/RREB1.01 | Ras-responsive element binding protein 1 |
| V$MZF1/MZF1.01 | MZF1 |
| V$MOKF/MOK2.02 | Ribonucleoprotein associated zinc finger protein MOK-2 (human) |
| V$HOXF/PTX1.01 | Pituitary Homeobox 1 (Ptx1) |
| V$LTUP/TAACC.01 | Lentiviral TATA upstream element |
| V$AP4R/TH1E47.01 | Thing1/E47 heterodimer, TH1 bHLH member specific expression in a variety of embryonic tissues |
| V$XSEC/STAF.01 | Se-Cys tRNA gene transcription activating factor |
| V$IKRS/IK3.01 | Ikaros 3, potential regulator of lymphocyte differentiation |
| V$AP1F/AP1.01 | AP1 binding site |
| V$MAZF/MAZ.01 | Myc associated zinc finger protein (MAZ) |
| V$MZF1/MZF1.01 | MZF1 |
| V$CLOX/CDPCR3.01 | cut-like homeodomain protein |
| V$P53F/P53.01 | tumor suppressor p53 |
| V$SMAD/SMAD3.01 | Smad3 transcription factor involved in TGF-beta signaling |
| V$HMTB/MTBF.01 | muscle-specific Mt binding site |
| V$OCT1/OCT1.03 | octamer-binding factor 1 |

TABLE 24-continued

Sequences in Synthetic Luc Genes (version B)

| | |
|---|---|
| V$FKHD/XFD3.01 | *Xenopus* fork head domain factor 3 |
| V$PIT1/PIT1.01 | Pit1, GHF-1 pituitary specific pou domain transcription factor |
| V$OCTP/OCT1P.01 | octamer-binding factor 1, POU-specific domain |
| V$HOXF/HOX1-3.01 | Hox-1.3, vertebrate homeobox protein |
| V$PBXF/PBX1.01 | homeo domain factor Pbx-1 |
| V$ECAT/NFY.03 | nuclear factor Y (Y-box binding factor) |
| V$PBXC/PBX1_MEIS1.02 | Binding site for a Pbx1/Meis1 heterodimer |
| V$CLOX/CDP.02 | transcriptional repressor CDP |
| V$HOXT/MEIS1_HOXA9.01 | Homeobox protein MEIS1 binding site |
| V$HOXF/HOXA9.01 | Member of the vertebrate HOX - cluster of homeobox factors |
| V$GATA/GATA1.02 | GATA-binding factor 1 |
| V$PCAT/ACAAT.01 | Avian C-type LTR CCAAT box |
| V$XSEC/STAF.01 | Se-Cys tRNA gene transcription activating factor |
| V$OCTP/OCT1P.01 | octamer-binding factor 1, POU-specific domain |
| V$CLOX/CDP.01 | cut-like homeodomain protein |
| V$FAST/FAST1.01 | FAST-1 SMAD interacting protein |
| V$ECAT/NFY.01 | nuclear factor Y (Y-box binding factor) |
| V$MEF2/MMEF2.01 | myocyte enhancer factor |
| V$TBPF/TATA.02 | Mammalian C-type LTR TATA box |
| V$FAST/FAST1.01 | FAST-1 SMAD interacting protein |
| V$LTUP/TAACC.01 | Lentiviral TATA upstream element |
| V$MOKF/MOK2.01 | Ribonucleoprotein associated zinc finger protein MOK-2 (mouse) |
| V$BRNF/BRN2.01 | POU factor Brn-2 (N-Oct 3) |
| V$HOXF/CRX.01 | Cone-rod homeobox-containing transcription factor/otx-like homeobox gene |
| V$NKXH/NKX31.01 | prostate-specific homeodomain protein NKX3.1 |
| V$HEN1/HEN1.01 | HEN1 |
| V$BEL1/BEL1.01 | Bel-1 similar region (defined in Lentivirus LTRs) |
| V$HOXF/PTX1.01 | Pituitary Homeobox 1 (Ptx1) |
| V$BRNF/BRN2.01 | POU factor Brn-2 (N-Oct 3) |
| V$NFKB/NFKAPPAB.01 | NF-kappaB |
| V$HAML/AML1.01 | runt-factor AML-1 |
| V$ZFIA/ZID.01 | zinc finger with interaction domain |
| V$XSEC/STAF.02 | Se-Cys tRNA gene transcription activating factor |
| V$IKRS/IK1.01 | Ikaros 1, potential regulator of lymphocyte differentiation |
| V$FAST/FAST1.01 | FAST-1 SMAD interacting protein |
| V$MOKF/MOK2.01 | Ribonucleoprotein associated zinc finger protein MOK-2 (mouse) |
| V$BEL1/BEL1.01 | Bel-1 similar region (defined in Lentivirus LTRs) |
| V$EGRF/WT1.01 | Wilms Tumor Suppressor |
| V$MAZF/MAZR.01 | MYC-associated zinc finger protein related transcription factor |
| V$ZBPF/ZBP89.01 | Zinc finger transcription factor ZBP-89 |
| V$ZBPF/ZBP89.01 | Zinc finger transcription factor ZBP-89 |
| V$SP1F/GC.01 | GC box elements |
| V$RREB/RREB1.01 | Ras-responsive element binding protein 1 |
| V$MOKF/MOK2.01 | Ribonucleoprotein associated zinc finger protein MOK-2 (mouse) |
| V$MEIS/MEIS1.01 | Binding site for monomeric Meis1 homeodomain protein |
| V$BCL6/BCL6.02 | POZ/zinc finger protein, transcriptional repressor, translocations observed in diffuse large cell lymphoma |
| V$GATA/GATA3.02 | GATA-binding factor 3 |
| V$HOXF/CRX.01 | Cone-rod homeobox-containing transcription factor/otx-like homeobox gene |
| V$HOXF/CRX.01 | Cone-rod homeobox-containing transcriptionf actor/otx-like homeobox gene |
| V$MAZF/MAZR.01 | MYC-associated zinc finger protein related transcription factor |
| V$MZF1/MZF1.01 | MZF1 |
| V$PDX1/PDX1.01 | Pdx1 (IDX1/IPF1) pancreatic and intestinal homeodomain TF |

TFBS in hluc + ver2B3
After removal of TFBS from hluc + ver2B2 = before removal of TFBS from hluc + ver2B3 (35 matches)

| | |
|---|---|
| V$OCT1/OCT1.04 | octamer-binding factor 1 |
| V$BARB/BARBIE.01 | barbiturate-inducible element |
| V$NFKB/NFKAPPAB.02 | NF-kappaB |
| V$OCTP/OCT1P.01 | octamer-binding factor 1, POU-specific domain |
| V$PIT1/PIT1.01 | Pit1, GHF-1 pituitary specific pou domain transcription factor |
| V$HOXF/PTX1.01 | Pituitary Homeobox 1 (Ptx1) |
| V$FKHD/FREAC4.01 | Fork head RElated ACtivator-4 |
| V$E4FF/E4F.01 | GLI-Krueppel-related transcription factor, regulator of adenovirus E4 promoter |
| V$EVI1/EVI1.02 | Ecotropic viral integration site 1 encoded factor |
| V$GATA/GATA2.01 | GATA-binding factor 2 |
| V$GREF/PRE.01 | Progesterone receptor binding site |
| V$RBPF/RBPJK.01 | Mammalian transcriptional repressor RBP-Jkappa/CBF1 |
| V$STAT/STAT.01 | signal transducers and activators of transcription |
| V$IKRS/IK2.01 | Ikaros 2, potential regulator of lymphocyte differentiation |
| V$FKHD/FREAC2.01 | Fork head RElated ACtivator-2 |
| V$SRFF/SRF.01 | serum response factor |
| V$GREF/PRE.01 | Progesterone receptor binding site |
| V$CLOX/CDPCR3.01 | cut-like homeodomain protein |
| V$AP4R/TAL1ALPHAE47.01 | Tal-1alpha/E47 heterodimer |
| V$GATA/GATA1.02 | GATA-binding factor 1 |
| V$FKHD/XFD3.01 | *Xenopus* fork head domain factor 3 |
| V$PBXF/PBX1.01 | homeo domain factor Pbx-1 |
| V$ECAT/NFY.03 | nuclear factor Y (Y-box binding factor) |
| V$PBXC/PBX1_MEIS1.02 | Binding site for a Pbx1/Meis1 heterodimer |
| V$CLOX/CDP.02 | transcriptional repressor CDP |
| V$HOXT/MEIS1_HOXA9.01 | Homeobox protein MEIS1 binding site |
| V$HOXF/HOXA9.01 | Member of the vertebrate HOX - cluster of homeobox factors |
| V$GATA/GATA1.02 | GATA-binding factor 1 |
| V$MINI/MUSCLE_INI.01 | Muscle Initiator Sequence |
| V$CLOX/CDP.01 | cut-like homeodomain protein |
| V$BRNF/BRN2.01 | POU factor Brn-2 (N-Oct 3) |
| V$NFKB/NFKAPPAB.01 | NF-kappaB |
| V$ZFIA/ZID.01 | zinc finger with interaction domain |
| V$BCL6/BCL6.02 | POZ/zinc finger protein, transcriptional repressor, translocations observed in diffuse large cell lymphoma |
| V$HOXF/CRX.01 | Cone-rod homeobox-containing transcription factor/otx-like homeobox gene |

TFBS in hluc + ver2B6
After removal of TFBS from hluc + ver2B5 (2 matches)

| | |
|---|---|
| V$HOXF/PTX1.01 | Pituitary Homeobox 1 (Ptx1) |
| V$FKHD/XFD3.01 | *Xenopus* fork head domain factor 3 |

TFBS in hluc + ver2B6
Before removal of TFBS from hluc + ver2B6 (6 matches)

| | |
|---|---|
| V$PAX6/PAX4_PD.01 | PAX4 paired domain binding site |
| V$HOXF/PTX1.01 | Pituitary Homeobox 1 (Ptx1) |
| V$FKHD/XFD3.01 | *Xenopus* fork head domain factor 3 |
| V$PAX6/PAX6.02 | PAX6 paired domain and homeodomain are required for binding to this site |
| V$PAX5/PAX5.03 | PAX5 paired domain protein |
| V$IRFF/IRF3.01 | Interferon regulatory factor 3 (IRF-3) |

TFBS in hluc + ver2B7
After removal of TFBS from hluc + ver2B6 = before removal of TFBS from hluc + ver2B7 (2 matches)

| | |
|---|---|
| V$HOXF/PTX1.01 | Pituitary Homeobox 1 (Ptx1) |
| V$FKHD/XFD3.01 | *Xenopus* fork head domain factor 3 |

TABLE 24-continued

Sequences in Synthetic Luc Genes (version B)

| Family/matrix | Further Information |
|---|---|
| | TFBS in hluc + ver2B8 |
| | After removal of TFBS from hluc + ver2B7 = before removal of TFBS from hluc + ver2B8 (1 match) |
| V$FKHD/XFD3.01 | *Xenopus* fork head domain factor 3 |
| | TFBS in hluc + ver2B9 |
| | After removal of TFBS from hluc + ver2B8 = before removal of TFBS from hluc + ver2B9 (1 match) |
| V$FKHD/XFD3.01 | *Xenopus* fork head domain factor 3 |
| | TFBS in hluc + ver2B10 |
| | After removal of TFBS from hluc + ver2B9 (1 match) |
| V$FKHD/XFD3.01 | *Xenopus* fork head domain factor 3 |

**matches are listed in order of occurrence in the corresponding sequence

EXAMPLE 8

Summary of Design for pGL4 Sequences

FIG. 2 depicts the design scheme for the pGL4 vector. A portion of the vector backbone in pGL3 which includes an bla gene and a sequence between bla and a multiple cloning region, but not a second open reading frame, was modified to yield pGL4. pGL4 includes an ampicillin resistance gene between a NotI and a SpeI site, the sequence of which was modified to remove regulatory sequences but not to optimize codons for mammalian expression (bla-1-bla-5), and a SpeI-NcoI fragment that includes a multiple cloning region and a translation trap. The translation trap includes about 60 nucleotides having at least two stop codons in each reading frame. The SpeI-NcoI fragment from a parent vector, pGL4-basics-5F2G-2, was modified to decrease undesired regulatory sequences (MCS-1 to MCS-4; SEQ ID Nos. 76-79). One of the resulting sequences, MCS-4, was combined with a modified ampicillin resistance gene, bla-5 (SEQ ID NO:84), to yield pGL4B-4NN (SEQ ID NO:95). pGLAB-4NN was further modified (pGLA-NN1-3; SEQ ID Nos. 96-98). To determine if additional polyA sequences in the SpeI-NcoI fragment further reduced expression from the vector backbone, various polyA sequences were inserted therein. For instance, pGL4NN-Blue Heron included a c-mos polyA sequence in the SpeI-NcoI fragment. However, removal of regulatory sequences in polyA sequences may alter the secondary structure and thus the function of those sequences.

In one vector, the SpeI-NcoI fragment from pGL3 (SpeI-NcoI start ver 2; SEQ ID NO:48) was modified to remove one transcription factor binding site and one restriction enzyme recognition site, and alter the multiple cloning region, yielding SpeI-NcoI ver2 (SEQ ID NO:49).

TF Binding Sites and Search Parameters

Each TF binding site ("matrix") belongs to a matrix family that groups functionally similar matrices together, eliminating redundant matches by MatInspector professional (the search program). Searches were limited to vertebrate TF binding sites. Searches were performed by matrix family, i.e., the results show only the best match from a family for each site. MatInspector default parameters were used for the core and matrix similarity values (core similarity=0.75, matrix similarity=optimized), except for sequence MCS-1 (core similarity=1.00, matrix similarity=optimized).

TABLE 25

Description of Designed Sequences pGL4 sequences

| Sequence | Description | Matrix Library |
|---|---|---|
| | SpeI-NcoI fragment with MCS, translation trap | |
| MCS-1 | SpeI-NcoI from pGL4-basics-5F2G-2 | Ver 2.2 September 2001 |
| MCS-2 | First removal of undesired sequence matches | Ver 2.2 September 2001 |
| MCS-3 | Second removal of undesired sequence matches | Ver 2.2 September 2001 |
| MCS-4 | Third removal of undesired sequence matches | Ver 2.3 February 2001 |
| | NotI-SpeI fragment with bla gene | |
| Bla | Beta-lactamase gene from pGL3 vectors | |
| bla-1* | SacII (RE) added, BsmAI (RE) site removed(*) | Ver 2.2 September 2001 |
| bla-2* | First removal of undesired sequence matches | Ver 2.3 February 2001 |
| bla-3* | Second removal of undesired sequence matches | Ver 2.3 February 2001 |
| bla-4* | Third removal of undesired sequence matches | Ver 2.3 February 2001 |
| bla-5* | Fourth removal of undesired sequence matches | Ver 2.3 February 2001 |
| | NotI-NcoI fragment with bla, translation trap, MCS | |
| pGL4B-4NN | Combination of bla-5 and MCS-4 sections | Ver 2.4 May 2002 |
| pGL4B-4NN1 | First removal of undesired sequence matches | Ver 2.4 May 2002 |
| pGL4B-4NN2 | Second removal of undesired sequence matches | Ver 2.4 May 2002 |
| pGL4B-4NN3 | Third version after removal of CEBP (TF) site | Ver 2.4 May 2002 |
| | SpeI-NcoI fragment with translation trap, polyA, MCS | |
| SpeI-NcoI-Ver2-start | Existing MCS replaced with new MCS | Ver 4.0 November 2003 |
| SpeI-NcoI-Ver2 | First removal of undesired sequence matches | Ver 4.0 November 2003 |

(*)Bla codon usage was not optimized for expression in mammalian cells. Low usage *E. coli* codons were avoided when changes were introduced to remove undesired sequence elements.

TABLE 26

Sequences in Synthetic SpeI-NcoI fragment of pGL4

| Name of family/matrix** | Further Information |
|---|---|
| | TFBS in MCS-1 |
| | Before removal of TFBS from MCS-1 (14 matches) |
| V$PAX3/PAX3.01 | Pax-3 paired domain protein, expressed in embryogenesis, mutations correlate to Waardenburg Syndrome |
| V$GATA/GATA.01 | GATA binding site (consensus) |
| V$NKXH/NKX31.01 | prostate-specific homeodomain protein NKX3.1 |
| V$CREB/E4BP4.01 | E4BP4, bZIP domain, transcriptional repressor |
| V$BRN2/BRN2.01 | POU factor Brn-2 (N-Oct 3) |
| V$CREB/E4BP4.01 | E4BP4, bZIP domain, transcriptional repressor |
| V$NKXH/NKX31.01 | prostate-specific homeodomain protein NKX3.1 |
| V$ZFIA/ZID.01 | zinc finger with interaction domain |
| V$CP2F/CP2.01 | CP2 |

TABLE 26-continued

Sequences in Synthetic SpeI-NcoI fragment of pGL4

| Name of family/matrix** | Further Information |
|---|---|
| V$BRAC/BRACH.01 | Brachyury |
| V$PAX6/PAX6.01 | Pax-6 paired domain protein |
| V$NKXH/NKX31.01 | prostate-specific homeodomain protein NKX3.1 |
| V$TEAF/TEF1.01 | TEF-1 related muscle factor |
| V$ETSF/ELK1.02 | Elk-1 |

TFBS in MCS-2
After removal of TFBS from MCS-1 = before removal of TFBS from MCS-2 (12 matches)

| | |
|---|---|
| V$GATA/GATA.01 | GATA binding site (consensus) |
| V$NKXH/NKX31.01 | prostate-specific homeodomain protein NKX3.1 |
| V$TBPF/ATATA.01 | Avian C-type LTR TATA box |
| V$CART/CART1.01 | Cart-1 (cartilage homeoprotein 1) |
| V$CREB/E4BP4.01 | E4BP4, bZIP domain, transcriptional repressor |
| V$BRN2/BRN2.01 | POU factor Brn-2 (N-Oct 3) |
| V$CREB/E4BP4.01 | E4BP4, bZIP domain, transcriptional repressor |
| V$TBPF/ATATA.01 | Avian C-type LTR TATA box |
| V$NKXH/NKX31.01 | prostate-specific homeodomain protein NKX3.1 |
| V$PAX6/PAX6.01 | Pax-6 paired domain protein |
| V$PAX8/PAX8.01 | PAX 2/5/8 binding site |
| V$PAX1/PAX1.01 | Pax1 paired domain protein, expressed in the developing vertebral column of mouse embryos |

TFBS in MCS-3
After removal of TFBS from MCS-2 = before removal of TFBS from MCS-4 (0 matches)
TFBS in MCS-4
After removal of TFBS from MCS-3 (0 matches)

**matches are listed in order of occurrence in the corresponding sequence

TABLE 27

Sequences in Synthetic NotI-SpeI Fragment of pGL4

| Name of family/matrix** | Further Information |
|---|---|

TFBS in bla-1
Before removal of TFBS from bla-1 (94 matches)

| | |
|---|---|
| V$GATA/GATA1.02 | GATA-binding factor 1 |
| V$HOXF/HOX1-3.01 | Hox-1.3, vertebrate homeobox protein |
| V$TBPF/ATATA.01 | Avian C-type LTR TATA box |
| V$ETSF/NRF2.01 | nuclear respiratory factor 2 |
| V$OCTP/OCT1P.01 | octamer-binding factor 1, POU-specific domain |
| V$ETSF/ELK1.02 | Elk-1 |
| V$GKLF/GKLF.01 | gut-enriched Krueppel-like factor |
| V$E2FF/E2F.02 | E2F, involved in cell cycle regulation, interacts with Rb p107 protein |
| V$ETSF/NRF2.01 | nuclear respiratory factor 2 |
| V$AP1F/VMAF.01 | v-Maf |
| V$XBBF/RFX1.01 | X-box binding protein RFX1 |
| V$AREB/AREB6.04 | AREB6 (Atp1a1 regulatory element binding factor 6) |
| V$CMYB/CMYB.01 | c-Myb, important in hematopoesis, cellular equivalent to avian myoblastosis virus oncogene v-myb |
| V$VMYB/VMYB.02 | v-Myb |
| V$EBOX/NMYC.01 | N-Myc |
| V$VBPF/VBP.01 | PAR-type chicken vitellogenin promoter-binding protein |
| V$CMYB/CMYB.01 | c-Myb, important in hematopoesis, cellular equivalent to avian myoblastosis virus oncogene v-myb |
| V$GATA/GATA3.02 | GATA-binding factor 3 |
| V$PAX8/PAX8.01 | PAX 2/5/8 binding site |
| V$HNF4/HNF4.02 | Hepatic nuclear factor 4 |

TABLE 27-continued

Sequences in Synthetic NotI-SpeI Fragment of pGL4

| Name of family/matrix** | Further Information |
|---|---|
| V$E2FF/E2F.01 | E2F, involved in cell cycle regulation, interacts with Rb p107 protein |
| V$NFAT/NFAT.01 | Nuclear factor of activated T-cells |
| V$ECAT/NFY.02 | nuclear factor Y (Y-box binding factor) |
| V$TBPF/TATA.02 | Mammalian C-type LTR TATA box |
| V$MYT1/MYT1.02 | MyT1 zinc finger transcription factor involved in primary neurogenesis |
| V$GATA/GATA3.01 | GATA-binding factor 3 |
| V$CREB/CREB.02 | cAMP-responsive element binding protein |
| V$WHZF/WHN.01 | winged helix protein, involved in hair keratinization and thymus epithelium differentiation |
| V$IRFF/ISRE.01 | interferon-stimulated response element |
| V$NRSF/NRSE.01 | neural-restrictive-silencer-element |
| V$TCFF/TCF11.01 | TCF11/KCR-F1/Nrf1 homodimers |
| V$STAT/STAT.01 | signal transducers and activators of transcription |
| V$ECAT/NFY.03 | nuclear factor Y (Y-box binding factor) |
| V$OCT1/OCT1.05 | octamer-binding factor 1 |
| V$OCTP/OCT1P.01 | octamer-binding factor 1, POU-specific domain |
| V$NKXH/NKX25.02 | homeo domain factor Nkx-2.5/Csx, tinman homolog low affinity sites |
| V$PIT1/PIT1.01 | Pit1, GHF-1 pituitary specific pou domain transcription factor |
| V$CLOX/CDPCR3.01 | cut-like homeodomain protein |
| V$GREF/ARE.01 | Androgene receptor binding site |
| V$GATA/GATA1.04 | GATA-binding factor 1 |
| V$E2TF/E2.02 | papilloma virus regulator E2 |
| V$RPOA/POLYA.01 | Mammalian C-type LTR Poly A signal |
| V$VMYB/VMYB.02 | v-Myb |
| V$CEBP/CEBPB.01 | CCAAT/enhancer binding protein beta |
| V$VBPF/VBP.01 | PAR-type chicken vitellogenin promoter-binding protein |
| V$CREB/HLF.01 | hepatic leukemia factor |
| V$SF1F/SF1.01 | SF1 steroidogenic factor 1 |
| V$XBBF/MIF1.01 | MIBP-1/RFX1 complex |
| V$IKRS/IK2.01 | Ikaros 2, potential regulator of lymphocyte differentiation |
| V$MINI/MUSCLE_INI.02 | Muscle Initiator Sequence |
| V$PCAT/CLTR_CAAT.01 | Mammalian C-type LTR CCAAT box |
| V$PAX5/PAX5.01 | B-cell-specific activating protein |
| V$RPAD/PADS.01 | Mammalian C-type LTR Poly A downstream element |
| V$XBBF/RFX1.02 | X-box binding protein RFX1 |
| V$CEBP/CEBPB.01 | CCAAT/enhancer binding protein beta |
| V$CREB/HLF.01 | hepatic leukemia factor |
| V$HNF1/HNF1.01 | hepatic nuclear factor 1 |
| V$VMYB/VMYB.01 | v-Myb |
| V$NKXH/NKX31.01 | prostate-specific homeodomain protein NKX3.1 |
| V$XBBF/RFX1.01 | X-box binding protein RFX1 |
| V$STAT/STAT.01 | signal transducers and activators of transcription |
| V$HNF1/HNF1.01 | hepatic nuclear factor 1 |
| V$HMYO/S8.01 | S8 |
| V$SORY/SOX5.01 | Sox-5 |
| V$RBIT/BRIGHT.01 | Bright, B cell regulator of IgH transcription |
| V$NKXH/NKX25.02 | homeo domain factor Nkx-2.5/Csx, tinman homolog low affinity sites |
| V$GATA/GATA1.02 | GATA-binding factor 1 |
| V$BARB/BARBIE.01 | barbiturate-inducible element |
| V$MTF1/MTF-1.01 | Metal transcription factor 1, MRE |
| V$NFKB/CREL.01 | c-Rel |
| V$ETSF/ELK1.02 | Elk-1 |
| V$CLOX/CDP.01 | cut-like homeodomain protein |
| V$RPOA/LPOLYA.01 | Lentiviral Poly A signal |
| V$GATA/GATA1.03 | GATA-binding factor 1 |
| V$ZFIA/ZID.01 | zinc finger with interaction domain |
| V$WHZF/WHN.01 | winged helix protein, involved in hair keratinization and thymus epithelium differentiation |

TABLE 27-continued

Sequences in Synthetic NotI-SpeI Fragment of pGL4

| Name of family/matrix** | Further Information |
|---|---|
| V$PAX1/PAX1.01 | Pax1 paired domain protein, expressed in the developing vertebral column of mouse embryos |
| V$GATA/LMO2COM.02 | complex of Lmo2 bound to Tal-1, E2A proteins, and GATA-1, half-site 2 |
| V$NRSF/NRSF.01 | neuron-restrictive silencer factor |
| V$AP4R/TAL1BETAE47.01 | Tal-1beta/E47 heterodimer |
| V$GATA/LMO2COM.02 | complex of Lmo2 bound to Tal-1, E2A proteins, and GATA-1, half-site 2 |
| V$GATA/GATA1.02 | GATA-binding factor 1 |
| V$XBBF/RFX1.01 | X-box binding protein RFX1 |
| V$AHRR/AHRARNT.02 | aryl hydrocarbon/Arnt heterodimers, fixed core |
| V$PAX5/PAX9.01 | zebrafish PAX9 binding sites |
| V$CLOX/CDP.02 | transcriptional repressor CDP |
| V$GATA/GATA1.01 | GATA-binding factor 1 |
| V$AP1F/TCF11MAFG.01 | TCF11/MafG heterodimers, binding to subclass of AP1 sites |
| V$BRN2/BRN2.01 | POU factor Brn-2 (N-Oct 3) |
| V$NKXH/NKX25.02 | homeo domain factor Nkx-2.5/Csx, tinman homolog low affinity sites |
| V$ECAT/NFY.02 | nuclear factor Y (Y-box binding factor) |
| V$FKHD/FREAC4.01 | Fork head RElated ACtivator-4 |
| V$NFAT/NFAT.01 | Nuclear factor of activated T-cells |
| V$IRFF/IRF1.01 | interferon regulatory factor 1 |
| V$E2FF/E2F.02 | E2F, involved in cell cycle regulation, interacts with Rb p107 protein TFBS in bla-2 |
| After removal of TFBS from bla-1 = before removal of TFBS from bla-2 = (51 matches) | |
| V$GATA/GATA1.02 | GATA-binding factor 1 |
| V$ETSF/NRF2.01 | nuclear respiratory factor 2 |
| V$OCTP/OCT1P.01 | octamer-binding factor 1, POU-specific domain |
| V$ETSF/ELK1.02 | Elk-1 |
| V$EBOX/NMYC.01 | N-Myc |
| V$GATA/GATA3.02 | GATA-binding factor 3 |
| V$PAX8/PAX8.01 | PAX 2/5/8 binding site |
| V$HNF4/HNF4.02 | Hepatic nuclear factor 4 |
| V$E2FF/E2F.01 | E2F, involved in cell cycle regulation, interacts with Rb p107 protein |
| V$NFAT/NFAT.01 | Nuclear factor of activated T-cells |
| V$ECAT/NFY.02 | nuclear factor Y (Y-box binding factor) |
| V$TBPF/TATA.02 | Mammalian C-type LTR TATA box |
| V$MYT1/MYT1.02 | MyT1 zinc finger transcription factor involved in primary neurogenesis |
| V$GATA/GATA3.01 | GATA-binding factor 3 |
| V$CREB/CREB.02 | cAMP-responsive element binding protein |
| V$WHZF/WHN.01 | winged helix protein, involved in hair keratinization and thymus epithelium differentiation |
| V$NRSF/NRSE.01 | neural-restrictive-silencer-element |
| V$OCT1/OCT1.05 | octamer-binding factor 1 |
| V$CLOX/CDPCR3.01 | cut-like homeodomain protein |
| V$GREF/ARE.01 | Androgene receptor binding site |
| V$GATA/GATA1.04 | GATA-binding factor 1 |
| V$CEBP/CEBPB.01 | CCAAT/enhancer binding protein beta |
| V$CREB/HLF.01 | hepatic leukemia factor |
| V$VBPF/VBP.01 | PAR-type chicken vitellogenin promoter-binding protein |
| V$XBBF/MIF1.01 | MIBP-1/RFX1 complex |
| V$IKRS/IK2.01 | Ikaros 2, potential regulator of lymphocyte differentiation |
| V$PAX5/PAX5.01 | B-cell-specific activating protein |
| V$XBBF/RFX1.02 | X-box binding protein RFX1 |
| V$CEBP/CEBPB.01 | CCAAT/enhancer binding protein beta |
| V$CREB/HLF.01 | hepatic leukemia factor |
| V$XBBF/RFX1.02 | X-box binding protein RFX1 |
| V$GATA/GATA1.02 | GATA-binding factor 1 |
| V$BARB/BARBIE.01 | barbiturate-inducible element |
| V$MTF1/MTF-1.01 | Metal transcription factor 1, MRE |
| V$NFKB/CREL.01 | c-Rel |
| V$ETSF/ELK1.02 | Elk-1 |
| V$TBPF/TATA.01 | cellular and viral TATA box elements |
| V$MEIS/MEIS1.01 | Homeobox protein MEIS1 binding site |
| V$HOXF/HOXA9.01 | Member of the vertebrate HOX - cluster of homeobox factors |
| V$GATA/GATA1.03 | GATA-binding factor 1 |
| V$MEIS/MEIS1.01 | Homeobox protein MEIS1 binding site |
| V$NOLF/OLF1.01 | olfactory neuron-specific factor |
| V$AP4R/TAL1BETAE47.01 | Tal-1beta/E47 heterodimer |
| V$GATA/GATA1.02 | GATA-binding factor 1 |
| V$XBBF/RFX1.01 | X-box binding protein RFX1 |
| V$AHRR/AHRARNT.02 | aryl hydrocarbon/Arnt heterodimers, fixed core |
| V$PAX5/PAX9.01 | zebrafish PAX9 binding sites |
| V$CLOX/CDP.02 | transcriptional repressor CDP |
| V$GATA/GATA1.01 | GATA-binding factor 1 |
| V$IRFF/IRF1.01 | interferon regulatory factor 1 |
| V$E2FF/E2F.02 | E2F, involved in cell cycle regulation, interacts with Rb p107 protein TFBS in bla-3 |
| After removal of TFBS from bla-2 = before removal of TFBS from bla-3 = (16 matches) | |
| V$ETSF/NRF2.01 | nuclear respiratory factor 2 |
| V$E2FF/E2F.02 | E2F, involved in cell cycle regulation, interacts with Rb p107 protein |
| V$NFAT/NFAT.01 | Nuclear factor of activated T-cells |
| V$TBPF/TATA.02 | Mammalian C-type LTR TATA box |
| V$MYT1/MYT1.02 | MyT1 zinc finger transcription factor involved in primary neurogenesis |
| V$WHZF/WHN.01 | winged helix protein, involved in hair keratinization and thymus epithelium differentiation |
| V$SORY/SOX5.01 | Sox-5 |
| V$CEBP/CEBPB.01 | CCAAT/enhancer binding protein beta |
| V$CREB/HLF.01 | hepatic leukemia factor |
| V$VBPF/VBP.01 | PAR-type chicken vitellogenin promoter-binding protein |
| V$PAX5/PAX5.01 | B-cell-specific activating protein |
| V$XBBF/RFX1.02 | X-box binding protein RFX1 |
| V$CREB/HLF.01 | hepatic leukemia factor |
| V$GATA/GATA1.03 | GATA-binding factor 1 |
| V$MEIS/MEIS1.01 | Homeobox protein MEIS1 binding site |
| V$NOLF/OLF1.01 | olfactory neuron-specific factor TFBS in bla-4 |
| After removal of TFBS from bla-3 = before removal of TFBS from bla-4 = (14 matches) | |
| V$ETSF/NRF2.01 | nuclear respiratory factor 2 |
| V$NFAT/NFAT.01 | Nuclear factor of activated T-cells |
| V$WHZF/WHN.01 | winged helix protein, involved in hair keratinization and thymus epithelium differentiation |
| V$GATA/GATA3.01 | GATA-binding factor 3 |
| V$CEBP/CEBPB.01 | CCAAT/enhancer binding protein beta |
| V$EBOX/USF.02 | upstream stimulating factor |
| V$PAX5/PAX5.01 | B-cell-specific activating protein |
| V$XBBF/RFX1.02 | X-box binding protein RFX1 |
| V$GATA/GATA1.03 | GATA-binding factor 1 |
| V$MEIS/MEIS1.01 | Homeobox protein MEIS1 binding site |
| V$ZFIA/ZID.01 | zinc finger with interaction domain |
| V$WHZF/WHN.01 | winged helix protein, involved in hair keratinization and thymus epithelium differentiation |
| V$PAX1/PAX1.01 | Pax1 paired domain protein, expressed in the developing vertebral column of mouse embryos |
| V$GATA/LMO2COM.02 | complex of Lmo2 bound to Tal-1, E2A proteins, and GATA-1, half-site 2 TFBS in bla-5 |
| After removal of TFBS from bla-4 (5 matches) | |
| V$ETSF/NRF2.01 | nuclear respiratory factor 2 |
| V$WHZF/WHN.01 | winged helix protein, involved in hair keratinization and thymus epithelium differentiation |
| V$GATA/GATA3.01 | GATA-binding factor 3 |

TABLE 27-continued

Sequences in Synthetic NotI-SpeI Fragment of pGL4

| Name of family/matrix** | Further Information |
|---|---|
| V$CEBP/CEBPB.01 | CCAAT/enhancer binding protein beta |
| V$EBOX/USF.02 | upstream stimulating factor |

**matches are listed in order of occurrence in the corresponding sequence

TABLE 28

Sequences in Synthetic NotI-NcoI Fragment of pGL4

| Name of family/matrix** | Further Information |
|---|---|
| TFBS in pGL4B-4NN Before removal of TFBS from pGL4B-4NN = (11 matches) | |
| V$SMAD/FAST1.01 | FAST-1 SMAD interacting protein |
| V$SMAD/FAST1.01 | FAST-1 SMAD interacting protein |
| V$ETSF/FLI.01 | ETS family member FLI |
| V$RBPF/RBPJK.01 | Mammalian transcriptional repressor RBP-Jkappa/CBF1 |
| V$ETSF/FLI.01 | ETS family member FLI |
| V$EBOX/USF.02 | upstream stimulating factor |
| V$CEBP/CEBPB.01 | CCAAT/enhancer binding protein beta |
| V$GATA/GATA3.01 | GATA-binding factor 3 |
| V$WHZF/WHN.01 | winged helix protein, involved in hair keratinization and thymus epithelium differentiation |
| V$ETSF/NRF2.01 | nuclear respiratory factor 2 |
| V$TBPF/ATATA.01 | Avian C-type LTR TATA box |
| TFBS in pGL4B-4NN1 After removal of TFBS from pGL4B-4NN = before removal of TFBS from pGL4B-4NN1 (7 matches) | |
| V$ETSF/NRF2.01 | nuclear respiratory factor 2 |
| V$WHZF/WHN.01 | winged helix protein, involved in hair keratinization and thymus epithelium differentiation |
| V$CEBP/CEBPB.01 | CCAAT/enhancer binding protein beta |
| V$EBOX/USF.02 | upstream stimulating factor |
| V$ETSF/FLI.01 | ETS family member FLI |
| V$SMAD/FAST1.01 | FAST-1 SMAD interacting protein |
| TFBS in pGL4B-4NN2 After removal of TFBS from pGL4B-4NN1 = before removal of TFBS from pGL4B-4NN2 (4 matches) | |
| V$ETSF/NRF2.01 | nuclear respiratory factor 2 |
| V$WHZF/WHN.01 | winged helix protein, involved in hair keratinization and thymus epithelium differentiation |
| V$CEBP/CEBPB.01 | CCAAT/enhancer binding protein beta |
| V$EBOX/USF.02 | upstream stimulating factor |
| TFBS in pGL4B-4NN3 After removal of TFBS from pGLAB-4NN2 (3 matches) | |
| V$EBOX/USF.02 | upstream stimulating factor |
| V$WHZF/WHN.01 | winged helix protein, involved in hair keratinization and thymus epithelium differentiation |
| V$ETSF/NRF2.01 | nuclear respiratory factor 2 |

**matches are listed in order of occurrence in the corresponding sequence

TABLE 29

Sequences in Synthetic SpeI-NcoI section of pGL4

| Family/matrix** | Further Information |
|---|---|
| TFBS in SpeI-NcoI-Ver2-start Before removal of TFBS from SpeI-NcoI-Ver2-start (34 matches) | |
| V$PAX8/PAX8.01 | PAX 2/5/8 binding site |
| V$GATA/GATA1.02 | GATA-binding factor 1 |

TABLE 29-continued

Sequences in Synthetic SpeI-NcoI section of pGL4

| Family/matrix** | Further Information |
|---|---|
| V$CREB/E4BP4.01 | E4BP4, bZIP domain, transcriptional repressor |
| V$NKXH/NKX31.01 | Prostate-specific homeodomain protein NKX3.1 |
| V$TBPF/ATATA.01 | Avian C-type LTR TATA box |
| V$CREB/E4BP4.01 | E4BP4, bZIP domain, transcriptional repressor |
| V$NKXH/NKX31.01 | Prostate-specific homeodomain protein NKX3.1 |
| V$CART/CART1.01 | Cart-1 (cartilage homeoprotein 1) |
| V$NKXH/NKX25.02 | Homeo domain factor Nkx-2.5/Csx, tinman homolog low affinity sites |
| V$ETSF/ELK1.01 | Elk-1 |
| V$CDXF/CDX2.01 | Cdx-2 mammalian caudal related intestinal transcr. factor |
| V$BRNF/BRN3.01 | POU transcription factor Brn-3 |
| V$TBPF/TATA.02 | Mammalian C-type LTR TATA box |
| V$FKHD/FREAC3.01 | Fork head related activator-3 (FOXC1) |
| V$OCT1/OCT1.02 | Octamer-binding factor 1 |
| V$CART/CART1.01 | Cart-1 (cartilage homeoprotein 1) |
| V$PDX1/PDX1.01 | Pdx1 (IDX1/IPF1) pancreatic and intestinal homeodomain TF |
| V$PARF/DBP.01 | Albumin D-box binding protein |
| V$GATA/GATA3.02 | GATA-binding factor 3 |
| V$VBPF/VBP.01 | PAR-type chicken vitellogenin promoter-binding protein |
| V$AP4R/TAL1ALPHAE47.01 | Tal-1alpha/E47 heterodimer |
| V$RP58/RP58.01 | Zinc finger protein RP58 (ZNF238), associated preferentially with heterochromatin |
| V$COMP/COMP1.01 | COMP1, cooperates with myogenic proteins in multicomponent complex |
| V$CLOX/CLOX.01 | Clox |
| V$TBPF/ATATA.01 | Avian C-type LTR TATA box |
| V$PBXC/PBX1_MEIS1.02 | Binding site for a Pbx1/Meis1 heterodimer |
| V$PBXF/PBX1.01 | Homeo domain factor Pbx-1 |
| V$IRFF/IRF1.01 | Interferon regulatory factor 1 |
| V$TEAF/TEF1.01 | TEF-1 related muscle factor |
| V$EBOX/ATF6.01 | Member of b-zip family, induced by ER damage/stress, binds to the ERSE in association with NF-Y |
| V$NKXH/NKX32.01 | Homeodomain protein NKX3.2 (BAPX1, NKX3B, Bagpipe homolog) |
| V$E2TF/E2.02 | Papilloma virus regulator E2 |
| V$EVI1/EVI1.05 | Ecotropic viral integration site 1 encoded factor |
| V$GATA/GATA3.02 | GATA-binding factor 3 |
| TFBS in SpeI-NcoI-Ver2 After removal of TFBS from SpeI-NcoI-Ver2-start (28 matches) | |
| V$PAX8/PAX8.01 | PAX 2/5/8 binding site |
| Y$GATA/GATA1.02 | GATA-binding factor 1 |
| V$CREB/E4BP4.01 | E4BP4, bZIP domain, transcriptional repressor |
| V$NKXH/NKX31.01 | Prostate-specific homeodomain protein NKX3.1 |
| V$TBPF/ATATA.01 | Avian C-type LTR TATA box |
| V$CREB/E4BP4.01 | E4BP4, bZIP domain, transcriptional repressor |
| V$NKXH/NKX31.01 | Prostate-specific homeodomain protein NKX3.1 |
| V$CART/CART1.01 | Cart-1 (cartilage homeoprotein 1) |
| V$NKXH/NKX25.02 | Homeo domain factor Nkx-2.5/Csx, tinman homolog low affinity sites |
| V$CDXF/CDX2.01 | Cdx-2 mammalian caudal related intestinal transcr. factor |
| V$BRNF/BRN3.01 | POU transcription factor Brn-3 |
| V$TBPF/TATA.02 | Mammalian C-type LTR TATA box |
| V$FKHD/FREAC3.01 | Fork head related activator-3 (FOXC1) |
| V$OCT1/OCT1.02 | Octamer-binding factor 1 |
| V$CART/CART1.01 | Cart-1 (cartilage homeoprotein 1) |
| V$PDX1/PDX1.01 | Pdx1 (IDX1/IPF1) pancreatic and intestinal homeodomain TF |
| V$PARF/DBP.01 | Albumin D-box binding protein |
| V$GATA/GATA3.02 | GATA-binding factor 3 |

TABLE 29-continued

Sequences in Synthetic SpeI-NcoI section of pGL4

| Family/matrix** | Further Information |
| --- | --- |
| V$VBPF/VBP.01 | PAR-type chicken vitellogenin promoter-binding protein |
| V$AP4R/TAL1ALPHAE47.01 | Tal-1alpha/E47 heterodimer |
| V$RP58/RP58.01 | Zinc finger protein RP58 (ZNF238), associated preferentially with heterochromatin |
| V$COMP/COMP1.01 | COMP1, cooperates with myogenic proteins in multicomponent complex |
| V$CLOX/CLOX.01 | Clox |
| V$TBPF/ATATA.01 | Avian C-type LTR TATA box |
| V$PBXC/PBX1_MEIS1.02 | Binding site for a Pbx1/Meis1 heterodimer |
| V$PBXF/PBX1.01 | Homeo domain factor Pbx-1 |
| V$IRFF/IRF1.01 | Interferon regulatory factor 1 |
| V$TEAF/TEF1.01 | TEF-1 related muscle factor |

**matches are listed in order of occurrence in the corresponding sequence

The number of consensus transcription factor binding sites present in the vector backbone (including the ampicillin resistance gene) was reduced from 224 in pGL3 to 40 in pGL4, and the number of promoter modules was reduced from 10 in pGL3 to 4 for pGL4, using databases, search programs and the like as described herein. Other modifications in pGL4 relative to pGL3 include the removal of the f1 origin of replication and the redesign of the multiple cloning region. MCS-1 to MCS-4 have the following sequences (SEQ ID Nos:76-79)

```
MCS-1
ACTAGTCGTCTCTCTTGAGAGACCGCGATCGCCACCATGATAAGTAAGTA
ATATTAAATAAGTAAGGCCTGAGTGGCCCTCGAGCCAGCCTTGAGTTGGT
TGAGTCCAAGTCACGTCTGGAGATCTGGTACCTACGCGTGAGCTCTACGT
AGCTAGCGGCCTCGGCGGCCGAATTCTTGCGATCTAAGTAAGCTTGGCAT
TCCGGTACTGTTGGTAAAGCCACCATGG

MCS-2
ACTAGTACGTCTCTCTTGAGAGACCGCGATCGCCACCATGATAAGTAAGT
AATATTAAATAAGTAAGGCCTGAGTGGCCCTCGAGTCCAGCCTTGAGTTG
GTTGAGTCCAAGTCACGTCTGGAGATCTGGTACCTTACGCGTAGAGCTCT
ACGTAGCTAGCGGCCTCGGCGGCCGAATTCTTGCGATCTAAGCTTGGCAA
TCCGGTACTGTTGGTAAAGCCACCATGG

MCS-3
ACTAGTACGTCTCTCTTGAGAGACCGCGATCGCATGCCTAGGTAGGTAGT
ATTAGAGCATAGGTAGAGGCCTAAGTGGCCCTCGAGTCCAGCCTTGAGTT
GGTTGAGTCCAAGTCACGTCTGGAGATCTGGTACCTTACGCGTATGAGCT
CTACGTAGCTAGCGGCCTCGGCGGCCGAATTCTTGCGATCTAAGCTTGGC
AATCCGGTACTGTTGGTAAAGCCACCATGG

MCS-4
ACTAGTACGTCTCTCTTGAGAGACCGCGATCGCCACCATGTCTAGGTAGG
TAGTAAACGAAAGGGCTTAAAGGCCTAAGTGGCCCTCGAGTCCAGCCTTG
AGTTGGTTGAGTCCAAGTCACGTTTGGAGATCTGGTACCTTACGCGTATG
AGCTCTACGTAGCTAGCGGCCTCGGCGGCCGAATTCTTGCGATCTAAGCT
TGGCAATCCGGTACTGTTGGTAAAGCCACCATGG
``` bla has the following sequence:

```
(SEQ ID NO: 41)
ATGAGTATTCAACATTTCCGTGTCGCCCTTATTCCCTTTTTTGCGGCATT

TTGCCTTCCTGTTTTTGCTCACCCAGAAACGCTGGTGAAAGTAAAAGATG

CTGAAGATCAGTTGGGTGCACGAGTGGGTTACATCGAACTGGATCTCAAC

AGCGGTAAGATCCTTGAGAGTTTTCGCCCCGAAGAACGTTTTCCAATGAT

GAGCACTTTTAAAGTTCTGCTATGTGGCGCGGTATTATCCCGTATTGACG

CCGGGCAAGAGCAACTCGGTCGCCGCATACACTATTCTCAGAATGACTTG

GTTGAGTACTCACCAGTCACAGAAAAGCATCTTACGGATGGCATGACAGT

AAGAGAATTATGCAGTGCTGCCATAACCATGAGTGATAACACTGCGGCCA

ACTTACTTCTGACAACGATCGGAGGACCGAAGGAGCTAACCGCTTTTTTG

CACAACATGGGGGATCATGTAACTCGCCTTGATCGTTGGGAACCGGAGCT

GAATGAAGCCATACCAAACGACGAGCGTGACACCACGATGCCTGTAGCAA

TGGCAACAACGTTGCGCAAACTATTAACTGGCGAACTACTTACTCTAGCT

TCCCGGCAACAATTAATAGACTGGATGGAGGCGGATAAAGTTGCAGGACC

ACTTCTGCGCTCGGCCCTTCCGGCTGGCTGGTTTATTGCTGATAAATCTG

GAGCCGGTGAGCGTGGGTCTCGCGGTATCATTGCAGCACTGGGGCCAGAT

GGTAAGCCCTCCCGTATCGTAGTTATCTACACGACGGGGAGTCAGGCAAC

TATGGATGAACGAAATAGACAGATCGCTGAGATAGGTGCCTCACTGATTA

AGCATTGGTAA.
``` bla-1 to bla-5 have the following sequences (SEQ ID Nos:80-84):

```
bla-1
ACTAGTAACCCTGATAAATGCTTCAATAATATTGAAAAAGGAAGAGTATG

AGTATTCAACATTTCCGTGTCGCCCTTATTCCCTTTTTTGCGGCATTTTG

CCTTCCTGTTTTTGCTCACCCAGAAACGCTGGTGAAAGTAAAAGATGCTG

AAGATCAGTTGGGTGCACGAGTGGGTTACATCGAACTGGATCTCAACAGC

GGTAAGATCCTTGAGAGTTTTCGCCCCGAAGAACGTTTTCCAATGATGAG

CACTTTTAAAGTTCTGCTATGTGGCGCGGTATTATCCCGTATTGACGCCG

GGCAAGAGCAACTCGGTCGCCGCATACACTATTCTCAGAATGACTTGGTT

GAGTACTCACCAGTCACAGAAAAGCATCTTACGGATGGCATGACAGTAAG

AGAATTATGCAGTGCTGCCATAACCATGAGTGATAACACCGCGGCCAACT

TACTTCTGACAACGATCGGAGGACCGAAGGAGCTAACCGCTTTTTTGCAC

AACATGGGGGATCATGTAACTCGCCTTGATCGTTGGGAACCGGAGCTGAA

TGAAGCCATACCAAACGACGAGCGTGACACCACGATGCCTGTAGCAATGG

CAACAACGTTGCGCAAACTATTAACTGGCGAACTACTTACTCTAGCTTCC

CGGCAACAATTAATAGACTGGATGGAGGCGGATAAAGTTGCAGGACCACT

TCTGCGCTCGGCCCTTCCGGCTGGCTGGTTTATTGCTGATAAATCTGGAG

CCGGTGAGCGTGGCTCTCGCGGTATCATTGCAGCACTGGGCCAGATGGTA

AGCCCTCCCGTATCGTAGTTATCTACACGACGGGGAGTCAGGCAACTATG
```

GATGAACGAAATAGACAGATCGCTGAGATAGGTGCCTCACTGATTAAGCA

TTGGTAACCACTGCAGTGGTTTTCCTTTTGCGGCCGC bla-2
ACTAGTAACCCTGATAAATGCTGCAAACATATTGAAAAAGGAAGAGTATG

AGTATTCAACATTTCCGTGTCGCACTCATTCCCTTCTTTGCGGCATTTTG

CTTGCCTGTTTTTGCACACCCCGAAACGCTGGTGAAAGTAAAAGATGCTG

AAGATCAACTGGGTGCACGAGTGGGCTATATCGAACTGGATCTCAATAGC

GGTAAGATCCTTGAGAGTTTTCGCCCCGAAGAACGTTTTCCAATGATGAG

CACTTTTAAAGTTCTGCTATGTGGCGCGGTATTATCCCGTATTGACGCCG

GGCAAGAGCAGCTCGGTCGCCGCATACACTACTCACAGAACGACTTGGTT

GAGTACTCGCCGGTCACGGAAAAGCATCTTACGGATGGCATGACAGTAAG

AGAATTGTGTAGTGCTGCCATAACCATGAGTGATAACACCGCGGCCAACT

TACTTCTGACAACGATCGGAGGCCCTAAGGAGCTGACCGCATTTTTGCAC

AACATGGGGATCATGTAACCCGGCTTGATCGTTGGGAACCGGAGCTGAA

CGAAGCCATACCGAACGACGAGCGTGACACCACGATGCCTGTAGCAATGG

CAACAACGTTGCGCAAACTACTCACTGGCGAACTTCTCACTCTAGCATCA

CGACAGCAACTCATAGACTGGATGGAGGCGGATAAAGTTGCAGGACCACT

TCTGCGCTCGGCCCTTCCGGCTGGCTGGTTTATAGCTGATAAATCCGGTG

CCGGTGAACGCGGCTCTCGCGGGATCATTGCTGCGCTGGGGCCAGATGGT

AAGCCCTCACGAATCGTAGTTATCTACACGACGGGGAGTCAGGCAACTAT

GGATGAACGAAATAGACAGATCGCTGAGATAGGTGCCTCACTGATCAAGC

ACTGGTAGCCACTGCAGTGGTTTAGCTTTTGCGGCCGC bla-3
ACTAGTAACCCTGACAAATGCTGCAAACATATTGAAAAAGGAAGAGTATG

AGCATCCAACATTTTCGTGTCGCACTCATTCCCTTCTTTGCGGCATTTTG

CTTGCCTGTTTTTGCACACCCCGAAACGCTGGTGAAAGTAAAAGATGCTG

AAGATCAACTGGGTGCAAGAGTGGGCTATATCGAACTGGATCTCAATAGC

GGCAAGATCCTTGAGTCTTTTCGCCCCGAAGAACGTTTTCCGATGATGAG

CACTTTTAAAGTTCTGCTATGTGGCGCGGTGTTGTCCCGTATAGACGCCG

GGCAAGAGCAGCTTGGTCGCCGTATACACTACTCACAAAACGACTTGGTT

GAGTACTCGCCGGTCACGGAAAAGCATCTTACGGATGGCATGACGGTAAG

AGAATTGTGTAGTGCTGCCATTACCATGAGCGACAATACCGCGGCCAACT

TACTTCTGACAACGATCGGAGGCCCTAAGGAGCTGACCGCATTTTTGCAC

AACATGGGGATCATGTAACCCGGCTTGACCGCTGGGAACCGGAGCTGAA

CGAAGCCATACCGAACGACGAGCGTGACACCACGATGCCTGTAGCAATGG

CAACAACGTTGCGGAAACTACTCACTGGCGAACTTCTCACTCTAGCATCA

CGACAGCAGCTCATAGACTGGATGGAGGCGGACAAAGTAGCAGGACCACT

TCTTCGCTCGGCCCTCCCTGCTGGCTGGTTCATTGCTGATAAATCCGGTG

CCGGTGAACGCGGCTCTCGCGGGATCATTGCTGCGCTGGGGCCTGATGGT

AAGCCCTCACGAATCGTAGTAATCTACACGACGGGGAGTCAGGCCACTAT

GGACGAACGAAATAGACAGATCGCTGAGATCGGTGCCTCACTGATCAAGC

ACTGGTAACCACTGCAGTGGTTTAGCATTTGCGGCCGC bla-4
ACTAGTAACCCTGACAAATGCTGCAAACATATTGAAAAAGGAAGAGTATG

AGCATCCAACATTTTCGTGTCGCACTCATTCCCTTCTTTGCGGCATTTTG

CTTGCCTGTTTTTGCACACCCCGAAACGCTGGTGAAAGTAAAAGATGCTG

AAGATCAACTGGGTGCAAGAGTGGGCTATATCGAACTGGATCTCAATAGC

GGCAAGATCCTTGAGTCTTTCCGCCCCGAAGAACGTTTTCCGATGATGAG

CACTTTCAAGTACTGCTATGTGGCGCGGTGTTGTCCCGTATAGACGCCG

GCAAGAGCAGCTTGGTCGCCGTATACACTACTCACAAAACGACTTGGTTG

AGTACTCGCCGGTCACGGAAAAGCATCTTACGGATGGCATGACGGTAAGA

GAATTGTGTAGTGCTGCCATTACCATGAGCGATAATACCGCGGCCAACTT

ACTTCTGACAACGATCGGAGGCCCTAAGGAGCTGACCGCATTTTTGCACA

ACATGGGTGATCATGTGACCCGGCTTGACCGCTGGGAACCGGAGCTGAAC

GAAGCCATACCGAACGACGAGCGTGACACCACGATGCCTGTAGCAATGGC

AACAACTCTTCGGAAACTACTCACTGGCGAACTTCTCACTCTAGCATCAC

GACAGCAGCTCATAGACTGGATGGAGGCGGACAAAGTAGCAGGACCACTT

CTTCGCTCGGCCCTCCCTGCTGGCTGGTTCATTGCTGATAAATCTGGAGC

CGGTGAGCGTGGCTCTCGCGGTATCATTGCTGCGCTGGGGCCTGATGGTA

AGCCCTCACGAATCGTAGTAATCTACACGACGGGGAGTCAGGCCACTATG

GACGAACGAAATAGACAGATCGCTGAGATCGGTGCCTCACTGATCAAGCA

CTGGTAACCACTGCAGTGGTTTAGCATTTGCGGCCGC bla-5
ACTAGTAACCCTGACAAATGCTGCAAACATATTGAAAAAGGAAGAGTATG

AGCATCCAACATTTTCGTGTCGCACTCATTCCCTTCTTTGCGGCATTTTG

CTTGCCTGTTTTTGCACACCCCGAAACGCTGGTGAAAGTAAAAGATGCTG

AAGATCAACTGGGTGCAAGAGTGGGCTATATCGAACTGGATCTCAATAGC

GGCAAGATCCTTGAGTCTTTCCGCCCCGAAGAACGATTCCCGATGATGAG

CACTTTCAAAGTACTGCTATGTGGCGCGGTGTTGTCCCGTATAGACGCCG

GGCAAGAGCAGCTTGGTCGCCGTATACACTACTCACAAAACGACTTGGTT

GAGTACTCGCCGGTCACGGAAAAGCATCTTACGGATGGCATGACGGTAAG

AGAATTGTGTAGTGCTGCCATTACCATGAGCGATAATACCGCGGCCAACT

TACTTCTGACAACGATCGGAGGCCCTAAGGAGCTGACCGCATTTTTGCAC

AACATGGGTGATCATGTGACCCGGCTTGACCGCTGGGAACCGGAGCTGAA

CGAAGCCATACCGAACGACGAGCGTGATACCACGATGCCAGTAGCAATGG

CCACAACTCTTCGGAAACTACTCACTGGCGAACTTCTCACTCTAGCATCA

CGACAGCAGCTCATAGACTGGATGGAGGCGGACAAAGTAGCAGGACCACT

TCTTCGCTCGGCCCTCCCTGCTGGCTGGTTCATTGCTGACAAATCCGGTG

CCGGTGAACGCGGCTCTCGCGGCATCATTGCTGCGCTGGGGCCTGATGGT

AAGCCCTCACGAATCGTAGTAATCTACACGACGGGGAGTCAGGCCACTAT

GGACGAACGAAATAGACAGATCGCTGAGATCGGTGCCTCACTGATCAAGC

ACTGGTAACCACTGCAGTGGTTTAGCATTTGCGGCCGCNNN.

TABLE 30

Pairwise identity of different bla gene versions

| | bla | bla-1 | bla-2 | bla-3 | bla-4 | bla-5 | bla in pGL4 (SEQ ID NO: 74) |
|---|---|---|---|---|---|---|---|
| bla | — | 99 | 93 | 90 | 89 | 88 | 87 |
| bla-1 | | — | 94 | 90 | 90 | 89 | 88 |
| bla-2 | | | — | 96 | 94 | 94 | 93 |
| bla-3 | | | | — | 98 | 98 | 97 |
| bla-4 | | | | | — | 99 | 97 |
| bla-5 | | | | | | — | 98 | note:
sequence "bla" is bla gene from pGL3-Basic; ClustalW (Slow/Accurate, IUB); sequence comparisons were of ORF only SpeI-NcoI ver2 start has the following sequence:

(SEQ ID NO: 48)
ACTAGTACGTCTCTCAAGGATAAGTAAGTAATATTAAGGTACGGGAGGTA
CTTGGAGCGGCCGCAATAAAATATCTTTATTTTCATTACATCTGTGTGTT
GGTTTTTTGTGTGAATCGATAGTACTAACATACGCTCTCCATCAAAACAA
AACGAAACAAAACAAACTAGCAAAATAGGCTGTCCCCAGTGCAAGTGCAG
GTGCCAGAACATTTCTCTGGCCTAAGTGGCCGGTACCGAGCTCGCTAGCC
TCGAGGATATCAGATCTGGCCTCGGCGGCCAAGCTTGGCAATCCGGTACT
GTTGGTAAAGCCACCATGG;

and
SpeI-NcoI-Ver2 has the following sequence:

(SEQ ID NO: 49)
ACTAGTACGTCTCTCAAGGATAAGTAGTAATATTAAGGTACGGGAGGTAT
TGGACAGGCCGCAATAAAATATCTTTATTTTCATTACATCTGTGTGTTGG
TTTTTTGTGTGAATCGATAGTACTAACATACGCTCTCCATCAAAACAAAA
CGAAACAAAACAAACTAGCAAAATAGGCTGTCCCCAGTGCAAGTGCAGGT
GCCAGAACATTTCTCTGGCCTAACTGGCCGGTACCTGAGCTCGCTAGCCT
CGAGGATATCAAGATCTGGCCTCGGCGGCCAAGCTTGGCAATCCGGTACT
GTTGGTAAAGCCACCATGG pGL4 related sequences include (SEQ ID Nos. 95-97):

pGL4B-4NN
GCGGCCGCAAATGCTAAACCACTGCAGTGGTTACCAGTGCTTGATCAGTG
AGGCACCGATCTCAGCGATCTGTCTATTTCGTTCGTCCATAGTGGCCTGA
CTCCCCGTCGTGTAGATTACTACGATTCGTGAGGGCTTACCATCAGGCCC
CAGCGCAGCAATGATGCCGCGAGAGCCGCGTTCACCGGCACCGGATTTGT
CAGCAATGAACCAGCCAGCAGGGAGGGCCGAGCGAAGAAGTGGTCCTGCT
ACTTTGTCCGCCTCCATCCAGTCTATGAGCTGCTGTCGTGATGCTAGAGT
GAGAAGTTCGCCAGTGAGTAGTTTCCGAAGAGTTGTGGCCATTGCTACTG
GCATCGTGGTATCACGCTCGTCGTTCGGTATGGCTTCGTTCAGCTCCGGT
TCCCAGCGGTCAAGCCGGGTCACATGATCACCCATGTTGTGCAAAAATGC
GGTCAGCTCCTTAGGGCCTCCGATCGTTGTCAGAAGTAAGTTGGCCGCGG

TATTATCGCTCATGGTAATGGCAGCACTACACAATTCTCTTACCGTCATG
CCATCCGTAAGATGCTTTTCCGTGACCGGCGAGTACTCAACCAAGTCGTT
TTGTGAGTAGTGTATACGGCGACCAAGCTGCTCTTGCCCGGCGTCTATAC
GGGACAACACCGCGCCACATAGCAGTACTTTGAAAGTGCTCATCATCGGG
AATCGTTCTTCGGGGCGGAAAGACTCAAGGATCTTGCCGCTATTGAGATC
CAGTTCGATATAGCCCACTCTTGCACCCAGTTGATCTTCAGCATCTTTTA
CTTTCACCAGCGTTTCGGGGTGTGCAAAAACAGGCAAGCAAATGCCGCA
AAGAAGGGAATGAGTGCGACACGAAAATGTTGGATGCTCATACTCTTCCT
TTTTCAATATGTTTGCAGCATTTGTCAGGGTTACTAGTACGTCTCTCTTG
AGAGACCGCGATCGCCACCATGTCTAGGTAGGTAGTAAACGAAAGGGCTT
AAAGGCCTAAGTGGCCCTCGAGTCCAGCCTTGAGTTGGTTGAGTCCAAGT
CACGTTTGGAGATCTGGTACCTTACGCGTATGAGCTCTACGTAGCTAGCG
GCCTCGGCGGCCGAATTCTTGCGATCTAAGCTTGGCAATCCGGTACTGTT
GGTAAAGCCACCATGG pGL4B-4NN1
gcggccgcaaatgctaaaccactgcagtggttaccagtgcttgatcagtg
aggcaccgatctcagcgatctgtctatttcgttcgtccatagtggcctga
ctccccgtcgtgtagattactacgattcgtgagggcttaccatcaggccc
cagcgcagcaatgatgccgcgagagccgcgttcaccggcccccgatttgt
cagcaatgaaccagccagcagggagggccgagcgaagaagtggtcctgct
actttgtccgcctccatccagtctatgagctgctgtcgtgatgctagagt
aaagaagttcgccagtgagtagtttccgaagagttgtggccattgctact
ggcatcgtggtatcacgctcgtcgttcggtatggcttcgttcaactccgg
ttcccagcggtcaagccgggtcacatgatcacccatgttgtgcaaaaatg
cggtcagctccttagggcctccgatcgttgtcagaagtaagttggccgcg
gtgttgtcgctcatggtaatggcagcactacacaattctcttaccgtcat
gccatccgtaagatgcttttccgtgaccggcgagtactcaaccaagtcgt
tttgtgagtagtgtatacggcgaccaagctgctcttgcccggcgtctata
cgggacaacaccgcgccacatagcagtactttgaaagtgctcatcatcgg
gaatcgttcttcggggcggaaagactcaaggatcttgccgctattgagat
ccagttcgatatagcccactcttgcacccagttgatcttcagcatctttt
actttcaccagcgtttcggggtgtgcaaaaacaggcaagcaaatgccgc
aaagaagggaatgagtgcgacacgaaaatgttggatgctcatactcttcc
ttttcaatatgtttgcagcatttgtcagggttactagtacgtctctctt
gagagaccgcgatcgccaccatgtctaggtaggtagtaaacgaaagggct
taaaggcctaagtggccctcgagtccagccttgagttggttgagtccaag
tcacgtttggagatctggtaccttacgcgtatgagctctacgtagctagc
ggcctcggcggccgaattcttgcgttcgaagcttggcaatccggtactgt
tggtaaagccaccatgg;

and pGL4B-4NN2
GCGGCCGCAAATGCTAAACCACTGCAGTGGTTACCAGTGCTTGATCAGTG
AGGCACCGATCTCAGCGATCTGCCTATTTCGTTCGTCCATAGTGGCCTGA
CTCCCCGTCGTGTAGATCACTACGATTCGTGAGGGCTTACCATCAGGCCC
CAGCGCAGCAATGATGCCGCGAGAGCCGCGTTCACCGGCCCCCGATTTGT
CAGCAATGAACCAGCCAGCAGGGAGGGCCGAGCGAAGAAGTGGTCCTGCT
ACTTTGTCCGCCTCCATCCAGTCTATGAGCTGCTGTCGTGATGCTAGAGT
AAGAAGTTCGCCAGTGAGTAGTTTCCGAAGAGTTGTGGCCATTGCTACTG
GCATCGTGGTATCACGCTCGTCGTTCGGTATGGCTTCGTTCAACTCTGGT
TCCCAGCGGTCAAGCCGGGTCACATGATCACCCATGTTGTGCAAAAATGC
GGTCAGCTCCTTAGGGCCTCCGATCGTTGTCAGAAGTAAGTTGGCCGCGG
TGTTGTCGCTCATGGTAATGGCAGCACTACACAATTCTCTTACCGTCATG
CCATCCGTAAGATGCTTTTCCGTGACCGGCGAGTACTCAACCAAGTCGTT
TTGTGAGTAGTGTATACGGCGACCAAGCTGCTCTTGCCCGGCGTCTATAC
GGGACAACACCGCGCCACATAGCAGTACTTTGAAAGTGCTCATCATCGGG
AATCGTTCTTCGGGGCGGAAAGACTCAAGGATCTTGCCGCTATTGAGATC
CAGTTCGATATAGCCCACTCTTGCACCCAGTTGATCTTCAGCATCTTTTA
CTTTCACCAGCGTTTCGGGGTGTGCAAAAACAGGCAAGCAAAATGCCGCA
AAGAAGGGAATGAGTGCGACACGAAAATGTTGGATGCTCATACTCTTCCT
TTTTCAATATGTTTGCAGCATTTGTCAGGGTTACTAGTACGTCTCTCTTG
AGAGACCGCGATCGCCACCATGTCTAGGTAGGTAGTAAACGAAAGGGCTT
AAAGGCCTAAGTGGCCCTCGAGTCCAGCCTTGAGTTGGTTGAGTCCAAGT
CACGTTTGGAGATCTGGTACCTTACGCGTATGAGCTCTACGTAGCTAGCG
GCCTCGGCGGCCGAATTCTTGCGTTCGAAGCTTGGCAATCCGGTACTGTT
GGTAAAGCCACCATGG, as well as
pGL4B4NN3:

(SEQ ID NO: 45)
GCGGCCGCAAATGCTAAACCACTGCAGTGGTTACCAGTGCTTGATCAGTG
AGGCACCGATCTCAGCGATCTGCCTATTTCGTTCGTCCATAGTGGCCTGA
CTCCCCGTCGTGTAGATCACTACGATTCGTGAGGGCTTACCATCAGGCCC
CAGCGCAGCAATGATGCCGCGAGAGCCGCGTTCACCGGCCCCCGATTTGT
CAGCAATGAACCAGCCAGCAGGGAGGGCCGAGCGAAGAAGTGGTCCTGCT
ACTTTGTCCGCCTCCATCCAGTCTATGAGCTGCTGTCGTGATGCTAGAGT
AAGAAGTTCGCCAGTGAGTAGTTTCCGAAGAGTTGTGGCCATTGCTACTG
GCATCGTGGTATCACGCTCGTCGTTCGGTATGGCTTCGTTCAACTCTGGT
TCCCAGCGGTCAAGCCGGGTCACATGATCACCCATATTATGAAGAAATGC
AGTCAGCTCCTTAGGGCCTCCGATCGTTGTCAGAAGTAAGTTGGCCGCGG
TGTTGTCGCTCATGGTAATGGCAGCACTACACAATTCTCTTACCGTCATG
CCATCCGTAAGATGCTTTTCCGTGACCGGCGAGTACTCAACCAAGTCGTT
TTGTGAGTAGTGTATACGGCGACCAAGCTGCTCTTGCCCGGCGTCTATAC
GGGACAACACCGCGCCACATAGCAGTACTTTGAAAGTGCTCATCATCGGG
AATCGTTCTTCGGGGCGGAAAGACTCAAGGATCTTGCCGCTATTGAGATC
CAGTTCGATATAGCCCACTCTTGCACCCAGTTGATCTTCAGCATCTTTTA
CTTTCACCAGCGTTTCGGGGTGTGCAAAAACAGGCAAGCAAAATGCCGCA
AAGAAGGGAATGAGTGCGACACGAAAATGTTGGATGCTCATACTCTTCCT
TTTTCAATATGTTTGCAGCATTTGTCAGGGTTACTAGTACGTCTCTCTTG
AGAGACCGCGATCGCCACCATGTCTAGGTAGGTAGTAAACGAAAGGGCTT
AAAGGCCTAAGTGGCCCTCGAGTCCAGCCTTGAGTTGGTTGAGTCCAAGT
CACGTTTGGAGATCTGGTACCTTACGCGTATGAGGGTTGAGTCCAAGTCA
CGTTTGGAGATCTGGTACCTTACGCGTATGAGCTCTACGTAGCTAGCGGC
CTCGGCGGCCGAATTCTTGCGTTCGAAGCTTGGCAATCCGGTACTGTTGG
TAAAGCCACCATGG pGL4NN from Blue Heron:

(SEQ ID NO: 46)
GCGGCCGCAAATGCTAAACCACTGCAGTGGTTACCAGTGCTTGATCAGTG
AGGCACCGATCTCAGCGATCTGCCTATTTCGTTCGTCCATAGTGGCCTGA
CTCCCCGTCGTGTAGATCACTACGATTCGTGAGGGCTTACCATCAGGCCC
CAGCGCAGCAATGATGCCGCGAGAGCCGCGTTCACCGGCCCCCGATTTGT
CAGCAATGAACCAGCCAGCAGGGAGGGCCGAGCGAAGAAGTGGTCCTGCT
ACTTTGTCCGCCTCCATCCAGTCTATGAGCTGCTGTCGTGATGCTAGAGT
AAGAAGTTCGCCAGTGAGTAGTTTCCGAAGAGTTGTGGCCATTGCTACTG
GCATCGTGGTATCACGCTCGTCGTTCGGTATGGCTTCGTTCAACTCTGGT
TCCCAGCGGTCAAGCCGGGTCACATGATCACCCATATTATGAAGAAATGC
AGTCAGCTCCTTAGGGCCTCCGATCGTTGTCAGAAGTAAGTTGGCCGCGG
TGTTGTCGCTCATGGTAATGGCAGCACTACACAATTCTCTTACCGTCATG
CCATCCGTAAGATGCTTTTCCGTGACCGGCGAGTACTCAACCAAGTCGTT
TTGTGAGTAGTGTATACGGCGACCAAGCTGCTCTTGCCCGGCGTCTATAC
GGGACAACACCGCGCCACATAGCAGTACTTTGAAAGTGCTCATCATCGGG
AATCGTTCTTCGGGGCGGAAAGACTCAAGGATCTTGCCGCTATTGAGATC
CAGTTCGATATAGCCCACTCTTGCACCCAGTTGATCTTCAGCATCTTTTA
CTTTCACCAGCGTTTCGGGGTGTGCAAAAACAGGCAAGCAAAATGCCGCA
AAGAAGGGAATGAGTGCGACACGAAAATGTTGGATGCTCATACTCTTCCT
TTTTCAATATGTTTGCAGCATTTGTCAGGGTTACTAGTACGTCTCTCAAG
AGATTTGTGCATACACAGTGACTCATACTTTCACCAATACTTTGCATTTT
GGATAAATACTAGACAACTTTAGAAGTGAATTATTTATGAGGTTGTCTTA
AAATTAAAAATTACAAAGTAATAAATCACATTGTAATGTATTTTGTGTGA
TACCCAGAGGTTTAAGGCAACCTATTACTCTTATGCTCCTGAAGTCCACA
ATTCACAGTCCTGAACTATAATCTTATCTTTGTGATTGCTGAGCAAATTT
GCAGTATAATTTCAGTGCTTTTAAATTTTGTCCTGCTTACTATTTTCCTT

-continued

```
TTTTATTTGGGTTTGATATGCGTGCACAGAATGGGGCTTCTATTAAAATA
TTCTTGAGAGACCGCGATCGCCACCATGTCTAGGTAGGTAGTAAACGAAA
GGGCTTAAAGGCCTAAGTGGCCCTCGAGTCCAGCCTTGAGTTGGTTGAGT
CCAAGTCACGTTTGGAGATCTGGTACCTTACGCGTATGAGCTCTACGTAG
CTAGCGGCCTCGGCGGCCGAATTCTTGCGTTCGAAGCTTGGCAATCCGGT
ACTGTTGGTAAAGCCACCATGG,
``` pGL4 with promoter changes:

(SEQ ID NO: 47)
```
GCGGCCGCAAATGCTAAACCACTGCAGTGGTTACCAGTGCTTGATCAGTG
AGGCACCGATCTCAGCGATCTGCCTATTTCGTTCGTCCATAGTGGCCTGA
CTCCCCGTCGTGTAGATCACTACGATTCGTGAGGGCTTACCATCAGGCCC
CAGCGCAGCAATGATGCCGCGAGAGCCGCGTTCACCGGCCCCCGATTTGT
CAGCAATGAACCAGCCAGCAGGGAGGGCCGAGCGAAGAAGTGGTCCTGCT
ACTTTGTCCGCCTCCATCCAGTCTATGAGCTGCTGTCGTGATGCTAGAGT
AAGAAGTTCGCCAGTGAGTAGTTTCCGAAGAGTTGTGGCCATTGCTACTG
GCATCGTGGTATCACGCTCGTCGTTCGGTATGGCTTCGTTCAACTCTGGT
TCCCAGCGGTCAAGCCGGGTCACATGATCACCCATATTATGAAGAAATGC
AGTCAGCTCCTTAGGGCCTCCGATCGTTGTCAGAAGTAAGTTGGCCGCGG
TGTTGTCGCTCATGGTAATGGCAGCACTACACAATTCTCTTACCGTCATG
CCATCCGTAAGATGCTTTTCCGTGACCGGCGAGTACTCAACCAAGTCGTT
TTGTGAGTAGTGTATACGGCGACCAAGCTGCTCTTGCCCGGCGTCTATAC
GGGACAACACCGCGCCACATAGCAGTACTTTGAAAGTGCTCATCATCGGG
AATCGTTCTTCGGGGCGGAAAGACTCAAGGATCTTGCCGCTATTGAGATC
CAGTTCGATATAGCCCACTCTTGCACCCAGTTGATCTTCAGCATCTTTTA
CTTTTCACCAGCGTTTCGGGGTGTGCAAAAACAGGCAAGCAAAATGCCGCA
AAGAAGGGAATGAGTGCGACACGAAAATGTTGGATGCTCATACTCGTCCT
TTTTCAATATTATTGAAGCATTTATCAGGGTTACTAGTACGTCTCTCAAG
AGATTTGTGCATACACAGTGACTCATACTTTCACCAATACTTTGCATTTT
GGATAAATACTAGACAACTTTAGAAGTGAATTATTTATGAGGTTGTCTTA
AAATTAAAAATTACAAAGTAATAAATCACATTGTAATGTATTTTGTGTGA
TACCCAGAGGTTTAAGGCAACCTATTACTCTTAT,
```

A hygromycin gene in a pGL4 vector:

(SEQ ID NO: 88)
```
Atgaagaagcccgaactcaccgctaccagcgttgaaaaatttctcatcga
gaagttcgacagtgtgagcgacctgatgcagttgtcggagggcgaagaga
gccgagccttcagcttcgatgtcggcggacgcggctatgtactgcgggtg
aatagctgcgctgatggcttctacaaagaccgctacgtgtaccgccactt
cgccagcgctgcactacccatccccgaagtgttggacatcggcgagttca
gcgagagcctgacatactgcatcagtagacgcgcccaaggcgttactctc
caagacctccccgaaacagagctgcctgctgtgttacagcctgtcgccga
```

```
agctatggatgctattgccgccgccgacctcagtcaaaccagcggcttcg
gcccattcgggccccaaggcatcggccagtacacaacctggcgggatttc
atttgcgccattgctgatccccatgtctaccactggcagaccgtgatgga
cgacaccgtgtccgccagcgtagctcaagccctggacgaactgatgctgt
gggccgaagactgtcccgaggtgcgccacctcgtccatgccgacttcggc
agcaacaacaacgtcctgaccgacaacgccgcatcaccgccgtaatcga
ctggtccgaagctatgttcggggacagtcagtacgaggtggccaacatct
tcttctggcggccctggctggcttgcatggagcagcagactcgctacttc
gagcgccggcatcccgagctggccggcagccctcgtctgcgagcctacat
gctgcgcatcggcctggatcagctctaccagagcctcgtggacggcaact
tcgacgatgctgcctgggctcaaggccgctgcgatgccatcgtccgcagc
ggggccggcaccgtcgttcgcacacaaatcgctcgccggagcgcagccgt
atggaccgacggctgcgtcgaggtgctggccgacagcggcaaccgccggc
ccagtacacgaccgcgcgctaaggaggtaggtcgagtttaa,
``` pGL4.10

(SEQ ID NO: 89)
```
ggcctaactggccggtacctgagctcgctagcctcgaggatatcaagatc
tggcctcggcggccaagcttggcaatccggtactgttggtaaagccacca
tggaagatgccaaaaacattaagaagggcccagcgccattctacccactc
gaagacgggaccgccggcgagcagctgcacaaagccatgaagcgctacgc
cctggtgcccggcaccatcgcctttaccgacgcacatatcgaggtggaca
ttacctacgccgagtacttcgagatgagcgttcggctggcagaagctatg
aagcgctatgggctgaatacaaaccatcggatcgtggtgtgcagcgagaa
tagcttgcagttcttcatgcccgtgttgggtgccctgttcatcggtgtgg
ctgtggcccagctaacgacatctacaacgagcgcgagctgctgaacagc
atgggcatcagccagcccaccgtcgtattcgtgagcaagaaagggctgca
aaagatcctcaacgtgcaaaagaagctaccgatcatacaaaagatcatca
tcatggatagcaagaccgactaccagggcttccaaagcatgtacaccttc
gtgacttcccatttgccacccggcttcaacgagtacgacttcgtgcccga
gagcttcgaccgggacaaaaccatcgccctgatcatgaacagtagtggca
gtaccggattgcccaagggcgtagccctaccgcaccgcaccgcttgtgtc
cgattcagtcatgcccgcgaccccatcttcggcaaccagatcatccccga
caccgctatcctcagcgtggtgccatttcaccacggcttcggcatgttca
ccacgctgggctacttgatctgcggctttcgggtcgtgctcatgtaccgc
ttcgaggagagctattcttgcgcagcttgcaagactataagattcaatc
tgccctgctggtgcccacactatttagcttcttcgctaagagcactctca
tcgacaagtacgacctaagcaacttgcacgagatcgccagcggcggggcg
ccgctcagcaaggaggtaggtgaggccgtggccaaacgcttccacctacc
aggcatccgccagggctacggcctgacagaaacaaccagcgccattctga
tcaccccgaaggggacgacaagcctggcgcagtaggcaaggtggtgccc
ttcttcgaggctaaggtggtggacttggacaccggtaagacactgggtgt
gaaccagcgcggcgagctgtgcgtccgtggccccatgatcatgagcggct
```

-continued acgttaacaaccccgaggctacaaacgctctcatcgacaaggacggctgg
ctgcacagcggcgacatcgcctactgggacgaggacgagcacttcttcat
cgtggaccggctgaagagcctgatcaaatacaagggctaccaggtagccc
cagccgaactggagagcatcctgctgcaacaccccaacatcttcgacgcc
ggggtcgccggcctgcccgacgacgatgccggcgagctgcccgccgcagt
cgtcgtgctggaacacggtaaaaccatgaccgagaaggagatcgtggact
atgtggccagccaggttacaaccgccaagaagctgcgcggtggtgttgtg
ttcgtggacgaggtgcctaaaggactgaccggcaagttggacgcccgcaa
gatccgcgagattctcattaaggccaagaagggcggcaagatcgccgtgt
aataattctagagtcggggcggccggccgcttcgagcagacatgataaga
tacattgatgagtttggacaaaccacaactagaatgcagtgaaaaaaatg
ctttatttgtgaaatttgtgatgctattgctttatttgtaaccattataa
gctgcaataaacaagttaacaacaacaattgcattcattttatgtttcag
gttcaggggaggtgtgggaggttttttaaagcaagtaaaacctctacaa
atgtggtaaaatcgataaggatccgtcgaccgatgcccttgagagccttc
aacccagtcagctccttccggtgggcgcggggcatgactatcgtcgccgc
acttatgactgtcttctttatcatgcaactcgtaggacaggtgccggcag
cgctcttccgcttcctcgctcactgactcgctgcgctcggtcgttcggct
gcggcgagcggtatcagctcactcaaaggcggtaatacggttatccacag
aatcaggggataacgcaggaaagaacatgtgagcaaaaggccagcaaaag
gccaggaaccgtaaaaaggccgcgttgctggcgtttttccataggctccg
cccccctgacgagcatcacaaaaatcgacgctcaagtcagaggtggcgaa
acccgacaggactataaagataccaggcgtttccccctggaagctccctc
gtgcgctctcctgttccgaccctgccgcttaccggatacctgtccgcctt
tctcccttcgggaagcgtggcgctttctcatagctcacgctgtaggtatc
tcagttcggtgtaggtcgttcgctccaagctgggctgtgtgcacgaaccc
cccgttcagcccgaccgctgcgccttatccggtaactatcgtcttgagtc
caacccggtaagacacgacttatcgccactggcagcagccactggtaaca
ggattagcagagcgaggtatgtaggcggtgctacagagttcttgaagtgg
tggcctaactacggctacactagaagaacagtatttggtatctgcgctct
gctgaagccagttaccttcggaaaaagagttggtagctcttgatccggca
aacaaaccaccgctggtagcggtggtttttttgtttgcaagcagcagatt
acgcgcagaaaaaaaggatctcaagaagatcctttgatcttttctacggg
gtctgacgctcagtggaacgaaaactcacgttaagggattttggtcatga
gattatcaaaaaggatcttcacctagatccttttaaattaaaaatgaagt
tttaaatcaatctaaagtatatatgagtaaacttggtctgacagcggccg
caaatgctaaaccactgcagtggttaccagtgcttgatcagtgaggcacc
gatctcagcgatctgcctatttcgttcgtccatggcctgactcccgtcg
tgtagatcactacgattcgtgagggcttaccatcaggccccagcgcagca
atgatgccgcgagagccgcgttcaccggccccgatttgtcagcaatgaa ccagccagcagggaggggccgagcgaagaagtggtcctgctactttgtccg
cctccatccagtctatgagctgctgtcgtgatgctagagtaagaagttcg
ccagtgagtagtttccgaagagtgtggccattgctactggcatcgtggta
tcacgctcgtcgttcggtatggcttcgttcaactctggttcccagcggtc
aagccgggtcacatgatcacccatattatgaagaaatgcagtcagctcct
tagggcctccgatcgttgtcagaagtaagttggccgcggtgttgtcgctc
atggtaatggcagcactacacaattctcttaccgtcatgccatccgtaag
atgcttttccgtgaccggcgagtactcaaccaagtcgtttttgtgagtagt
gtatacggcgaccaagctgctcttgcccggcgtctatacgggacaacacc
gcgccacatagcagtactttgaaagtgctcatcatcgggaatcgttcttc
ggggcggaaagactcaaggatcttgccgctattgagatccagttcgatat
agcccactcttgcacccagttgatcttcagcatcttttactttcaccagc
gtttcggggtgtgcaaaaacaggcaagcaaaatgccgcaaagaagggaat
gagtgcgacacgaaaatgttggatgctcatactcgtccttttttcaatatt
attgaagcatttatcagggttactagtacgtctctcaaggataagtaagt
aatattaaggtacgggaggtattggacaggccgcaataaaatatctttat
tttcattacatctgtgtgttggttttttgtgtgaatcgatagtactaaca
tacgctctccatcaaaacaaaacgaaacaaaacaaactagcaaaataggc
tgtcccagtgcaagtgcaggtgccagaacatttctctaagtaatattaa
ggtacgggaggtattggacaggccgcaataaaatatctttattttcatta
catctgtgtgttggttttttgtgtgaatc,
and pGL4.70
(SEQ ID NO: 90)
ggcctaactggccggtacctgagctcgctagcctcgaggatatcaagatc
tggcctcggcggccaagcttggcaatccggtactgttggtaaagccacca
tggcttccaaggtgtacgaccccgagcaacgcaaacgcatgatcactggg
cctcagtggtgggctcgctgcaagcaaatgaacgtgctggactccttcat
caactactatgattccgagaagcacgccgagaacgccgtgatttttctgc
atggtaacgctgcctccagctacctgtggaggcacgtcgtgcctcacatc
gagcccgtggctagatgcatcatccctgatctgatcggaatgggtaagtc
cggcaagagcgggaatggctcatatcgcctcctggatcactacaagtacc
tcaccgcttggttcgagctgctgaaccttccaaagaaaatcatctttgtg
ggccacgactgggggcttgtctggcctttcactactcctacgagcacca
agacaagatcaaggccatcgtccatgctgagagtgcgtggacgtgatcga
gtcctgggacgagtggcctgacatcgaggaggatatcgccctgatcaaga
gcgaagagggcgagaaaatggtgcttgagaataacttcttcgtcgagacc
atgctcccaagcaagatcatgcggaaactggagcctgaggagttcgctgc
ctacctggagccattcaaggagaagggcgaggttagacggcctaccctct
cctggcctcgcgagatccctctcgttaagggaggcaagcccgacgtcgtc
cagattgtccgcaactacaacgcctaccttcgggccagcgacgatctgcc
taagatgttcatcgagtccgaccctgggttcttttccaacgctattgtcg -continued
```
agggagctaagaagttccctaacaccgagttcgtgaaggtgaagggcctc
cacttcagccaggaggacgctccagatgaaatgggtaagtacatcaagag
cttcgtggagcgcgtgctgaagaacgagcagtaattctagagtcggggcg
gccggccgcttcgagcagacatgataagatacattgatgagtttggacaa
accacaactagaatgcagtgaaaaaaatgctttatttgtgaaatttgtga
tgctattgctttatttgtaaccattataagctgcaataaacaagttaaca
acaacaattgcattcattttatgtttcaggttcaggggaggtgtgggag
gttttttaaagcaagtaaaacctctacaaatgtggtaaaatcgataagga
tccgtcgaccgatgcccttgagagccttcaacccagtcagctccttccgg
tgggcgcggggcatgactatcgtcgccgcacttatgactggtcttcttta
tcatgcaactcgtaggacaggtgccggcagcgctcttccgcttcctcgct
cactgactcgctgcgctcggtcgttcggctgcggcgagcggtatcagctc
actcaaaggcggtaatacggttatccacagaatcaggggataacgcagga
aagaacatgtgagcaaaaggccagcaaaaggccaggaaccgtaaaaaggc
cgcgttgctggcgtttttccataggctccgcccccctgacgagcatcaca
aaaatcgacgctcaagtcagaggtggcgaaacccgacaggactataaaga
taccaggcgtttccccctggaagctccctcgtgcgctctcctgttccgac
cctgccgcttaccggatacctgtccgcctttctcccttcgggaagcgtgg
cgctttctcatagctcacgctgtaggtatctcagttcggtgtaggtcgtt
cgctccaagctgggctgtgtgcacgaaccccccgttcagcccgaccgctg
cgccttatccggtaactatcgtcttgagtccaacccggtaagacacgact
tatcgccactggcagcagccactggtaacaggattagcagagcgaggtat
gtaggcggtgctacagagttcttgaagtggtggcctaactacggctacac
tagaagaacagtatttggtatctgcgctctgctgaagccagttaccttcg
gaaaaagagttggtagctcttgatccggcaaacaaaccaccgctggtagc
ggtggtttttttgtttgcaagcagcagattacgcgcagaaaaaaaggatc
tcaagaagatcctttgatcttttctacggggtctgacgctcagtggaacg
aaaactcacgttaagggattttggtcatgagattatcaaaaaggatcttc
acctagatccttttaaattaaaatgaagttttaaatcaatctaaagtatat
atgagtaaacttggtctgacagcggccgcaaatgctaaaccactgcagtgg
ttaccagtgcttgatcagtgaggcaccgatctcagcgatctgcctatttc
gttcgtccatagtggcctgactcccgtcgtgtagatcactacgattcgt
gagggcttaccatcaggccccagcgcagcaatgatgccgcgagagccgcg
ttcaccggccccgatttgtcagcaatgaaccagccagcagggagggccg
agcgaagaagtggtcctgctactttgtccgcctccatccagtctatgagc
tgctgtcgtgatgctagagtaagaagttcgccagtgagtagtttccgaag
agttgtggccattgctactggcatcgtggtatcacgctcgtcgttcggta
tggcttcgttcaactctggttcccagcggtcaagccgggtcacatgatca
cccatattatgaagaaatgcagtcagctccttagggcctccgatcgttgt
cagaagtaagttggccgcggtgttgtcgctcatggtaatggcagcactac
acaattctcttaccgtcatgccatccgtaagatgcttttccgtgaccggc
gagtactcaaccaagtcgttttgtgagtagtgtatacggcgaccaagctg
ctcttgcccggcgtctatacgggacaacaccgcgccacatagcagtactt
tgaaagtgctcatcatcgggaatcgttcttcggggcggaaagactcaagg
atcttgccgctattgagatccagttcgatatagcccactcttgcacccag
ttgatcttcagcatcttttactttcaccagcgtttcggggtgtgcaaaaa
caggcaagcaaaatgccgcaaagaagggaatgagtgcgacacgaaaatgt
tggatgctcatactcgtccttttcaatattattgaagcatttatcaggg
ttactagtacgtctctcaaggataagtaagtaatattaaggtacgggagg
tattggacaggccgcaataaaatatctttattttcattacatctgtgtgt
tggttttttgtgtgaatcgatagtactaacatacgctctccatcaaaaca
aaacgaaacaaaacaaactagcaaaataggctgtccccagtgcaagtgca
ggtgccagaacatttctct.
```

The pGL4 backbone (NotI-NcoI) has the following sequence:

(SEQ ID NO: 74)
```
gcggccgcaaatgctaaaccactgcagtggttaccagtgcttgatcagtg
aggcaccgatctcagcgatctgcctatttcgttcgtccatagtggcctga
ctcccgtcgtgtagatcactacgattcgtgagggcttaccatcaggccc
cagcgcagcaatgatgccgcgagagccgcgttcaccggccccgatttgt
cagcaatgaaccagccagcagggagggccgagcgaagaagtggtcctgct
acttttccgcctccatccagtctatgagctgctgtcgtgatgctagagta
agaagttcgccagtgagtgtttccgaagagttgtggccattgctactggc
atcgtggtatcacgctcgtcgttcggtatggcttcgttcaactctggttc
ccagcggtcaagccgggtcacatgatcacccatattatgaagaaatgcag
tcagctccttagggcctccgatcgttgtcagaagtaagttggccgcggtg
tttcgctcatggtaatggcagcactacacaattctcttaccgtcatgcca
tccgtaagatgcttttccgtgaccggcgagtactcaaccaagtcgttttg
tgagtagtgtatacggcgaccaagctgctcttgcccggcgtctatacggg
acaacaccgcgccacatagcagtactttgaaagtgctcatcatcgggaat
cgttcttcggggcggaaagactcaaggatcttgccgctattgagatccag
ttcgatatagcccactcttgcacccagttgatcttcagcatcttttactt
tcaccagcgtttcggggtgtgcaaaaacaggcaagcaaaatgccgcaaag
aagggaatgagtgcgacacgaaaatgttggatgctcatactcgtccttt
caatattattgaagcatttatcagggttactagtacgtctctcaaggata
agtaagtaatattaaggtacgggaggtattggacaggccgcaataaaata
tctttattttcattacatctgtgtgttggttttttgtgtgaatcgatagt
actaacatacgctctccatcaaaacaaaacgaaacaaaacaaactagcaa
aataggctgtccccagtgcaagtgcaggtgccagaacatttctctggcct
aactggccggtacctgagctcgctagcctcgaggatatcaagatctggcc
tcggcggccaagcttggcaatccggtactgttggtaaagccaccatgg.
```

EXAMPLE 10

Summary of Sequences Removed in Synthetic Genes

Search Parameters:

TFBS searches were limited to vertebrate TF binding sites. Searches were performed by matrix family, i.e., the results show only the best match from a family for each site. MatInspector default parameters were used for the core and matrix similarity values (core similarity=0.75, matrix similarity=optimized), except for sequence MCS-1 (core similarity=1.00, matrix similarity=optimized).

Promoter module searches included all available promoter modules (vertebrate and others) and were performed using default parameters (optimized threshold or 80% of maximum score).

Splice site searches were performed for splice acceptor or donor consensus sequences.

TABLE 31

| Sequence | Matrix Library | TFBS (family matches) | Promoter modules | Splice sites (+strand) |
|---|---|---|---|---|
| puro | (not applicable) | 62 | 5 | 0 |
| hpuro | (not applicable) | 68 | 4 | 1 |
| hpuro1 | Ver 4.1 February 2004 | 4 | 2 | 1 |
| hpuro2 | Ver 4.1 February 2004 | 2 | 0 | 1 |
| — | — | — | — | — |
| Neo | (not applicable) | 53 | 0 | No data |
| hneo | (not applicable) | 61 | 2 | 3 |
| hneo-1 | Ver 3.1.2 June 2003 | No data | No data | No data |
| hneo-2 | Ver 3.1.2 June 2003 | No data | No data | No data |
| hneo-3 | Ver 3.1.2 June 2003 | 0 | 0 | 0 |
| hneo-4 | Ver 4.1 February 2004 | 7 | 1 | 0 |
| hneo-5 | Ver 4.1 February 2004 | 0 | 0 | 0 |
| — | — | — | — | — |
| Hyg | (not applicable) | 74 | 3 | No data |
| hhyg | (not applicable) | 94 | 4 | 6 |
| hhyg-1 | Ver 3.1.2 June 2003 | No data | No data | No data |
| hhyg-2 | Ver 3.1.2 June 2003 | No data | No data | No data |
| hhyg-3 | Ver 3.1.2 June 2003 | 3 | 0 | 0 |
| hHygro | Ver 3.3 August 2003 | 5 | 0 | 0 |
| hhyg-4 | Ver 3.3 August 2003 | 4 | 0 | 0 |
| — | — | — | — | — |
| Luc | (not applicable) | 213 | 11 | No data |
| Luc+ | (not applicable) | 189 | 7 | No data |
| hluc + ver2A1 | Ver 3.0 November 2002 | 110 | 7 | 6 |
| hluc + ver2A2 | Ver 3.0 November 2002 | No data | No data | No data |
| hluc + ver2A3 | Ver 3.0 November 2002 | 8 | No data | 0 |
| hluc + ver2A4 | Ver 3.0 November 2002 | No data | No data | No data |
| hluc + ver2A5 | Ver 3.0 November 2002 | No data | No data | No data |
| hluc + ver2A6 | Ver 3.0 November 2002 | 2 | 0 | 0 |
| hluc + ver2A6 | Ver 3.1.1 April 2003 | 4 | 0 | 0 |
| hluc + ver2A7 | Ver 3.1.1 April 2003 | 1 | 0 | 0 |
| hluc + ver2A8 | Ver 3.1.1 April 2003 | 1 | 0 | 0 |
| hluc + ver2B1 | Ver 3.0 November 2002 | 187 | 2 | 8 |
| hluc + ver2B2 | Ver 3.0 November 2002 | No data | No data | No data |
| hluc + ver2B3 | Ver 3.0 November 2002 | 35 | No data | 0 |
| hluc + ver2B4 | Ver 3.0 November 2002 | No data | No data | No data |
| hluc + ver2B5 | Ver 3.0 November 2002 | No data | No data | No data |
| hluc + ver2B6 | Ver 3.0 November 2002 | 2 | 0 | 0 |
| hluc + ver2B6 | Ver 3.1.1 April 2003 | 6 | 0 | 0 |
| hluc + ver2B7 | Ver 3.1.1 April 2003 | 2 | 0 | 0 |
| hluc + ver2B8 | Ver 3.1.1 April 2003 | 1 | 0 | 0 |
| hluc + ver2B9 | Ver 3.1.1 April 2003 | 1 | 0 | 0 |
| hluc + ver2B10 | Ver 3.1.1 April 2003 | 1 | 0 | 0 |
| — | — | — | — | — |
| MCS-1 | Ver 2.2 September 2001 | 14 | No data | (not applicable) |
| MCS-2 | Ver 2.2 September 2001 | 12 | No data | (not applicable) |
| MCS-3 | Ver 2.2 September 2001 | 0 | No data | (not applicable) |
| MCS-4 | Ver 2.3 February 2001 | 0 | 0 | (not applicable) |
| — | — | — | — | — |
| Bla | (not applicable) | No data | No data | (not applicable) |
| bla-1 | Ver 2.2 September 2001 | 94 | 1 | (not applicable) |
| bla-2 | Ver 2.3 February 2001 | 51 | No data | (not applicable) |
| bla-3 | Ver 2.3 February 2001 | 16 | No data | (not applicable) |
| bla-4 | Ver 2.3 February 2001 | 14 | No data | (not applicable) |
| bla-5 | Ver 2.3 February 2001 | 5 | 0 | (not applicable) |
| — | — | — | — | — |
| pGL4B-4NN | Ver 2.4 May 2002 | 11 | 0 | (not applicable) |
| pGL4B-4NN1 | Ver 2.4 May 2002 | 7 | No data | (not applicable) |
| pGL4B-4NN2 | Ver 2.4 May 2002 | 4 | 0 | (not applicable) |
| pGL4B-4NN3 | Ver 2.4 May 2002 | 3 | 0 | (not applicable) |
| SpeI-NcoI-Ver2-Start | Ver 4.0 November 2003 | 34 | 1 | (not applicable) |
| SpeI-NcoI-Ver2 | Ver 4.0 November 2003 | 28 | 1 | (not applicable) |

Using the 5 sequences, i.e., hluc+ver2A1, bla-1, hneo-1, hpuro-1, hhyg-1 (humanized codon usage) for analysis, TTBS from the following families were found in 3 out 5 sequences:

V$AHRR (AHR-arnt heterodimers and AHR-related factors)

V$ETSF (Human and murine ETS1 factors)

V&NFKB (Nuclear Factor Kappa B/c-rel)
V$VMYB (AMV-viral myb oncogene)
V$CDEF (Cell cycle regulators: Cell cycle dependent element)
V$HAND (bHLH transcription factor dimer of HAND2 and E12)
V$NRSF (Neuron-Restrictive Silencer Factor)
V$WHZF (Winged Helix and ZF5 binding sites)
V$CMYB (C-myb, cellular transcriptional activator)
V$MINI (Muscle INItiator)
V$P53F (p53 tumor suppr.-neg. regulat. of the tumor suppr. Rb)
V$ZF5F (ZF5 POZ domain zinc finger)
V$DEAF (Homolog to deformed epidermal autoregulatory factor-1 from D. melanogaster)
V$MYOD (MYOblast Determining factor)
V$PAX5 (PAX-5/PAX-9 B-cell-specific activating protein)
V$EGRF (EGR/nerve growth Factor Induced protein C & rel. fact.)
V$NEUR (NeuroD, Beta2, HLH domain)
V$REBV (Epstein-Barr virus transcription factor R);
TFBS from the following families were found in 4 out of 5 sequences:
V$ETSF (Human and murine ETS1 factors)
V$CDEF (Cell cycle regulators: Cell cycle dependent element)
V$HAND (bHLH transcription factor dimer of HAND2 and E12)
V$NRSF (Neuron-Restrictive Silencer Factor)
V$PAX5 (PAX-5/PAX-9 B-cell-specific activating protein)
V$NEUR (NeuroD, Beta2, HLH domain); and
TFBS from the following families were found in 5 out of 5 sequences:
V$PAX5 (PAX-5/PAX-9 B-cell-specific activating protein).

References

Altschul et al., *Nucl. Acids Res.*, 25, 3389 (1997).
Aota et al., *Nucl. Acids Res.*, 16, 315 (1988).
Boshart et al., *Cell*, 41, 521 (1985).
Bronstein et al., *Cal. Biochem.*, 219, 169 (1994).
Corpet et al., *Nucl. Acids Res.*, 16, 881 (1988).
deWet et al., *Mol. Cell. Biol.*, 7, 725 (1987).
Dijkema et al., *EMBO J.*, 4, 761 (1985).
Faist and Meyer, *Nucl. Acids Res.*, 20, 26 (1992).
Gorman et al., *Proc. Natl. Acad. Sci. USA*, 79, 6777 (1982).
Higgins et al., *Gene*, 73, 237 (1985).
Higgins et al., *CABIOS*, 5, 151 (1989).
Huang et al., *CABIOS*, 8, 155 (1992).
Itolcik et al., *PNAS*, 94, 12410 (1997).
Johnson et al., *Mol. Reprod. Devel.*, 50, 377 (1998).
Jones et al., *Mol. Cell. Biol.*, 17, 6970 (1997).
Karlin and Altschul, *Proc. Natl. Acad. Sci. USA*, 87, 2264 (1990).
Karlin and Altschul, *Proc. Natl. Acad. Sci. USA*, 90, 5873 (1993).
Keller et al., *J. Cell Biol.*, 84, 3264 (1987).
Kim et al., *Gene*, 91, 217 (1990).
Lamb et al., *Mol. Reprod. Devel.*, 51, 218 (1998).
Mariatis et al., *Science*, 236, 1237 (1987).
Michael et al., *EMBO. J.*, 9, 481 (1990).
Mizushima and Nagata, *Nucl. Acids Res.*, 18, 5322 (1990).
Murray et al., *Nucl. Acids Res.*, 17, 477 (1989).
Myers and Miller, *CABIOS*, 4, 11 (1988).
Nakamura et al., *NAR*, 28:292 (2000).
Needleman and Wunsen, *J. Mol. Biol.*, 48, 443 (1970).
Pearson and Lipman, *Proc. Natl. Acad. Sci. USA*, 85, 2444 (1988).
Pearson et al., *Meth. Mol. Biol.*, 24, 307 (1994).
Sharp et al., *Nucl. Acids Res.*, 16, 8207 (1988).
Sharp et al., *Nucl. Acids Res.*, 15, 1281 (1987).
Smith and Waterman, *Adv. Appl. Math.*, 2, 482 (1981).
Stemmer et al., *Gene*, 164, 49 (1995).
Uetsuki et al., *J. Biol. Chem.*, 264, 5791 (1989).
Voss et al., *Trends Biochem. Sci.*, 11, 287 (1986).
Wada et al., *Nucl. Acids Res.*, 18, 2367 (1990).
Watson et al, eds. *Recombinant DNA: A Short Course*, Scientific American Books, W. H. Freeman and Company, New York (1983).
Wood, K. *Photochemistry and Photobiology*, 62, 662 (1995).
Wood, K. *Science* 244, 700 (1989)

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is

1. An isolated nucleic acid molecule comprising a synthetic nucleotide sequence encoding a firefly luciferase comprising a fragment of at least 300 nucleotides having 80% or less nucleic acid sequence identity to a parent nucleic acid sequence having SEQ ID NO:43 or 85% or less nucleic acid sequence identity to a parent nucleic acid sequence having SEQ ID NO:14 and having 99% or more nucleic acid sequence identity to SEQ ID NO:21, SEQ ID NO:22 or SEQ ID NO:23 or the complement thereof, wherein the decreased sequence identity is a result of different codons in the synthetic nucleotide sequence relative to the codons in the parent nucleic acid sequence, wherein the synthetic nucleotide sequence encodes a firefly luciferase which has at least 85% amino acid sequence identity to the corresponding luciferase encoded by the parent nucleic acid sequence, and wherein the synthetic nucleotide sequence has a reduced number of regulatory sequences relative to the parent nucleic acid sequence.

2. The isolated nucleic acid molecule of claim 1 wherein the regulatory sequences include transcription factor binding sequences, intron splice sites, poly(A) sites, promoter modules, and/or promoter sequences.

3. The isolated nucleic acid molecule of claim 1 wherein a majority of the codons of the synthetic nucleotide sequence which differ from the corresponding codons of the parent nucleic acid sequence are ones that are preferred codons of a desired host cell and/or are not low-usage codons in that host cell.

4. The isolated nucleic acid molecule of claim 3 wherein the majority of the codons of the synthetic nucleotide sequence which differ from the corresponding codons of the parent nucleic acid sequence are those which are employed more frequently in mammals.

5. The isolated nucleic acid molecule of claim 3 wherein the majority of the codons of the synthetic nucleotide sequence which differ from the corresponding codons of the parent nucleic acid sequence are those which are preferred codons in humans.

6. The isolated nucleic acid molecule of claim 3 wherein the majority of codons which differ are the codons CGC, CTG, AGC, ACC, CCC, GCC, GGC, GTG, ATC, AAG, AAC, GAG, CAC, GAC, TAC, TGC and TTC.

7. The isolated nucleic acid molecule of claim 1 wherein the synthetic nucleic acid molecule is expressed in a mammalian host cell at a level which is greater than that of the parent nucleic acid sequence.

8. The isolated nucleic acid molecule of claim 1 wherein the synthetic nucleic acid molecule has an increased number of AGC serine-encoding codons, an increased number of CCC proline-encoding codons, an increased number of ATC isoleucine-encoding codons and/or an increased number of ACC threonine-encoding codons relative to the number of these codons in the parent nucleic acid sequence.

9. The isolated acid molecule of claim 1 wherein the synthetic nucleotide sequence has at least 10% fewer transcription regulatory sequences relative to the parent nucleic acid sequence.

10. The isolated nucleic acid molecule of claim 1 wherein the codons in the synthetic nucleotide sequence which differ from the corresponding codons of the parent nucleic acid sequence encode the same amino acids as the corresponding codons in the parent nucleic acid sequence.

11. The isolated nucleic acid molecule of claim 1 wherein the nucleic acid molecule encodes a fusion of the luciferase with one or more other peptides or polypeptides, wherein at least the luciferase is encoded by the synthetic nucleic acid sequence.

12. The isolated nucleic acid molecule of claim 1 wherein one or more other peptides are peptides having protein destabilization sequences.

13. A plasmid comprising the nucleic acid molecule of claim 1.

14. The plasmid of claim 13 which further comprises a multiple cloning region.

15. The plasmid of claim 13 which further comprises a promoter operatively linked to the synthetic nucleotide sequence.

16. An expression vector comprising the nucleic acid molecule of claim 1 linked to a promoter functional in a cell.

17. The expression vector of claim 16 wherein the promoter is functional in a eukaryotic cell.

18. The expression vector of claim 16 wherein the expression vector further comprises a multiple cloning site.

19. The expression vector of claim 16 wherein the promoter is functional in a mammalian cell.

20. The expression vector of claim 16 wherein the synthetic nucleotide sequence is operatively linked to a Kozak consensus sequence.

21. An isolated host cell comprising the expression cassette of claim 16.

22. An isolated host cell comprising the plasmid of claim 13.

23. A kit comprising, in suitable container means, the plasmid of claim 13.

* * * * *